(12) United States Patent
Oestergaard et al.

(10) Patent No.: US 12,247,237 B2
(45) Date of Patent: Mar. 11, 2025

(54) POLYPEPTIDE VARIANTS

(71) Applicant: Novozymes A/S, Bagsvaerd (DK)

(72) Inventors: Lars Henrik Oestergaard, Charlottelund (DK); Annette Helle Johansen, Bronshoj (DK); Steffen Danielsen, Stenlose (DK); Roland Alexander Pache, Valby (DK); Johanne Moerch Jensen, Brighton (AU); Frank Winther Rasmussen, Roskilde (DK); Martin Gudmand, Holte (DK); Kasper Damgaard Tidemand, Copenhagen (DK)

(73) Assignee: Novozymes A/S, Bagsvaerd (DK)

( * ) Notice: Subject to any disclaimer, the term of this patent is extended or adjusted under 35 U.S.C. 154(b) by 682 days.

(21) Appl. No.: 17/437,114

(22) PCT Filed: Apr. 6, 2020

(86) PCT No.: PCT/EP2020/059712
§ 371 (c)(1),
(2) Date: Sep. 8, 2021

(87) PCT Pub. No.: WO2020/207944
PCT Pub. Date: Oct. 15, 2020

(65) Prior Publication Data
US 2022/0364138 A1    Nov. 17, 2022

(30) Foreign Application Priority Data

Apr. 10, 2019 (EP) .................................. 19168512

(51) Int. Cl.
*C12P 21/02* (2006.01)
*C11D 3/386* (2006.01)
*C12N 1/20* (2006.01)
*C12N 9/24* (2006.01)

(52) U.S. Cl.
CPC .......... *C12P 21/02* (2013.01); *C11D 3/38636* (2013.01); *C12N 1/20* (2013.01); *C12N 9/2402* (2013.01); *C12Y 302/01052* (2013.01)

(58) Field of Classification Search
CPC ....... C12P 21/02; C11D 3/38636; C12N 1/20; C12N 9/2402; C12Y 302/01052
See application file for complete search history.

(56) References Cited

U.S. PATENT DOCUMENTS

| 11,732,220 B2 * | 8/2023 | Weide ................ C11D 3/38636 435/193 |
| 2019/0169547 A1 * | 6/2019 | Ooehlenschlaeger ....................... C11D 3/38636 |

FOREIGN PATENT DOCUMENTS

| CN | 101180393 A | 5/2008 |
| CN | 106133135 A | 11/2016 |
| CN | 108368528 A | 8/2018 |
| CN | 108473974 A | 8/2018 |
| WO | 2006/072773 A1 | 7/2006 |
| WO | 2015/144824 A1 | 10/2015 |
| WO | 2017/066255 A1 | 4/2017 |
| WO | 2017/089366 A1 | 6/2017 |
| WO | 2017/186943 A1 | 11/2017 |
| WO | 2018/184873 A1 | 10/2018 |

OTHER PUBLICATIONS

Fagerlund et al (2016, Frontiers in Microbiology, doi: 10.3389/fmicb.2016.00856). (Year: 2016).*
Manuel et al., FEBS Journal, vol. 274, No. 22, pp. 5987-5999 (2007).
Sharma et al., Biochimica et Biophysica Acta, vol. 1637, No. 1, pp. 113-118 (2003).
Tews et al., 2015, NCBI Reference Sequence WP_049320289.1.

* cited by examiner

*Primary Examiner* — Paul J Holland
*Assistant Examiner* — Erica Nicole Jones-Foster
(74) *Attorney, Agent, or Firm* — Elias Lambiris

(57) ABSTRACT

The present invention relates to polypeptide variants and methods for obtaining variants. The present invention also relates to polynucleotides encoding the variants; nucleic acid constructs, vectors, and host cells comprising the polynucleotides; and methods of using the variants.

20 Claims, No Drawings
Specification includes a Sequence Listing.

POLYPEPTIDE VARIANTS

CROSS-REFERENCE TO RELATED APPLICATIONS

This application is a 35 U.S.C. 371 national application of international application no. PCT/EP2020/059712 filed Apr. 6, 2020, which claims priority or the benefit under 35 U.S.C. 119 of European application no. 19168512.2 filed Apr. 10, 2019. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to novel dispersin variants having improved properties relative to the parent dispersin, such properties may include one or more of the following; wash performance, stability e.g. detergent and/or storage stability. The variants of the invention are suitable for use in cleaning processes and detergent compositions, such as laundry compositions and dish wash compositions, including hand wash and automatic dish wash compositions. The present invention also relates to isolated DNA sequences encoding the variants, expression vectors, host cells, and methods for producing and using the dispersin variants of the invention.

Description of the Related Art

Enzymes have been used in detergents for decades most commercially relevant are the proteases and amylases effectively removing protein and starch related soiling, respectively. However, most household care related soiling is a complex mixture of various organic matters. Hard surfaces and fabrics are exposed to skin debris e.g. dead cells, sweat, sebum, pollution, as well as stains derived from microorganisms from the environment and from e.g. the body. Complex organic stains, such as biosoil from human skin e.g. dead skin cells, sweat, sebum in particular underarm soil, composes different substances such as of protein, starch, grease but also e.g. polysaccharides. Consequently, stain removal requires different enzyme activity, which vary depending on the specific stain targeted.

To be useful in cleaning processes such as laundry, an enzyme such as dispersin needs to be stable in detergent compositions and compatible with standard detergent components such as surfactants, builders, bleaches etc.

The present invention provides such enzymes, which are suitable for use in detergents for e.g. improving cleaning of laundry and washing/dish-washing machines.

SUMMARY OF THE INVENTION

The present invention relates to dispersin variants, which are particularly useful in detergents and cleaning processes, such as laundry and dish wash.

One aspect of the invention relates to a dispersin variant, comprising an alteration, preferably substitution at one or more position(s) corresponding to position(s): 2, 3, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 140, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 225, 227, 230, 232, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 or 323 of the polypeptide shown in SEQ ID NO: 1, wherein the dispersin variant has hexosaminidase activity preferably beta-1,6 N-acetylglucosaminidase activity, and wherein the variant has increased stability, preferably thermo stability measured as half-life improvement factor, HIF, compared to the dispersin with SEQ ID NO: 1

One aspect of the invention relates to a dispersin variant, comprising an alteration, preferably substitution at one or more positions corresponding to positions 2, 3, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 140, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 225, 227, 230, 232, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 and 323 of the polypeptide of SEQ ID NO: 1, wherein the dispersin variant has beta-1,6 N-acetylglucosaminidase activity, wherein the dispersin variant has at least 80%, at least 85%, at least 90%, at least 95%, at least 96%, at least 97%, at least 98%, or at least 99%, but less than 100% sequence identity to the polypeptide shown in SEQ ID NO: 1, and wherein the variant has increased stability, preferably thermo stability measured as half-life improvement factor, HIF, compared to the dispersin of SEQ ID NO: 1.

One aspect of the invention relates to a dispersin variant, comprising at least one alteration selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19N, E19P, K22A, K22M, K22V, S23C, S23E, S23I, S23L, S23R, S23T, S23V, V25R, D26M, Y30*, Y30D, Y30L, Y30M, Y30N, Y30R, Y30T, Y30V, G32L, G32M, G32R, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80V, K80W, D81A, D81G, D81L, D81R, D81S, D81T, D81V, D81W, I82V, L90F, E99Q, E99R, L100S, K103A, K103R, K104N, K104W, D105N, V106A, V106D, V106E, V106H, V106K, V106L, V106M, V106N, V106Q, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116N, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124I, Y124K, Y124L, Y124M, Y124Q, Y124R, Y124T, Y124V, Y124W, D125C, D125G, D125K, D125Q, D125R, N126V, R127D, R127H, R127K, R127L, R127M, R127Q, R127W, V128C, V128L, V128T, D131V, Q135*, Q135A, Q135D, Q135E, Q135K, Q135M, Q135Y, D138K, D138L, D138M, D138Q, D138R, D138S, D138V, D138W, E139W, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150D, E150H, E150K, E150L, E150M, E150N, E150R, E150V, E150W, E150Y, G151A, G151C, G151D, G151L, G151N, G151P, G151S, G151W, K152D, K152L, K152R, G164D, G164E, G164H, G164S, G164V, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181N, S181P, S181Q, S181T, S181V, S181W, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203R, A203S, A203T, A203V, A203W, N204L, N204M, N204V, N204W, N204Y, L205I, D207A, D207C, D207E, D207G, D207N, D207Q, D207S, D207V, D207W, S208A, S208C, S208D, S208G, S208L, S208Q, S208T, S208V, S208W, S210T, Q215R, Q215M, Q215L, Q215*, S217V, T218A, T218L, T218Q, T218R, T218V, G222D, E224A, E224P, N227A, N227Q, N227R, N227S, N227T, N227K, D230*, D230R, D230T, D230W, E232D, E232V, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251L, S251N, S251R, S251W, N252P, N252C, N252G, N252H, F254I, F254L, F254M, F254Y, Q256E, Q256R, N260*, N260A, N260C, N260E, N260I, N260K, N260L, N260M, N260Q, N260R, N260V, N260W, N260Y, E261*, E261A, E261D, E261R, E261W, Q262*, Q262F, Q262H, Q262W, Q262Y, M263K, M263L, M263Q, D264*, D264C, D264E, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y282E, Y282N, Y281R, H283I, A284I, A284L, A284N, A284P, A284T, A284V, T287N, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308G, K308I, K308L, K308Q, K308S, K308T, K308V, K308Y, K309A, K309C, K309D, K309H, K309L, K309M, K309N, K309Q, K309S, K309T, K309I, K312A, K312L, K312M, K312N, K312Q, K312S, K312W, E314I, E314L, E314V, L315I, L315V, R319A, and N323R, wherein the positions correspond to the positions of the polypeptide shown in SEQ ID NO: 1, wherein the dispersin variant has hexosaminidase activity preferably beta-1,6 N-acetylglucosaminidase activity, preferably wherein the alteration at the one or more position(s) produces a dispersin variant having increased stability, preferably thermo-stability measured as improvement factor, HIF, of at least 1.1 compared to the polypeptide shown in SEQ ID NO: 1 and preferably wherein dispersin variant has at least 60%, at least 65%, at least 70%, at least 75%, at least 80%, at least 85%, at least 90%, at least 95%, at least 96%, at least 97%, at least 98%, or at least 99%, but less than 100% sequence identity to the polypeptide shown in SEQ ID NO: 1.

One aspect of the invention relates to a method for obtaining a dispersin variant, comprising;

a) introducing into a dispersin parent having hexosaminidase, preferably beta-1,6-N-acetyl glycosaminidase activity, an alteration, preferably a substitution at one or more positions corresponding to positions 2, 3, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 140, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 225, 227, 230, 232, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 or 323 of the polypeptide of SEQ ID NO: 1, b) and recovering the variant.

One aspect of the invention relates to a method for obtaining a dispersin variant, comprising;

a) introducing into a dispersin parent having 1,6-N-acetyl glycosaminidase activity, an alteration, preferably a substitution at one or more positions corresponding to positions 2, 3, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 140, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 225, 227, 230, 232, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 and 323 of the polypeptide of SEQ ID NO: 1, b) and recovering the variant.

One aspect of the invention relates to a composition, preferably a cleaning composition comprising a variant according to the invention.

One aspect of the invention relates to a method of cleaning an item comprising a) adding a dispersin variant according to the invention to a cleaning composition and b) washing item with the composition, wherein the item is a textile or a hard surface.

One aspect of the invention relates to a method for finding improved polypeptide variants, comprising the steps of:

a) generate diversity in selected, preferably all, positions of a polypeptide, thereby preparing libraries of polypeptide variants ($V_L$), and
b) select subset library ($V_{LSub}$) with improved variants.

The method above preferably comprises subjecting some subset of variants to one or more stress condition and then leave a reference dispersin variants unstressed. In that way the subset can be compared, and improved variants selected.

One aspect of the invention relates to a method for finding improved polypeptide variants, comprising the steps of:
a) generate diversity in selected, preferably all, positions of a polypeptide, thereby preparing a library of polypeptide variants ($V_L$),
b) expose part of the library of polypeptide variants ($V_L$) to one or more stress conditions suitable for measuring a property of interest, thereby generating a stressed $V_{LS+n}$ and an unstressed $V_{LUS}$ library;
c) compare the stressed $V_{LS}$ and the unstressed $V_{LUS}$ library; and
d) select subset library ($V_{LSub}$) with improved variants.

Definitions

The term "adjunct materials" means any liquid, solid or gaseous material selected for the particular type of detergent composition desired and the form of the product (e.g., liquid, granule, powder, bar, paste, spray, tablet, gel, or foam composition), which materials are also preferably compatible with the dispersin variant enzyme used in the composition. In some aspects, granular compositions are in "compact" form, while in other aspects, the liquid compositions are in a "concentrated" form.

The term "allelic variant" means any of two or more alternative forms of a gene occupying the same chromosomal locus. Allelic variation arises naturally through mutation and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "biofilm" means any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from free-floating bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community. On laundry biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp.

The term "biosoil" mean a stain composed of several types of organic material such as protein, starch, grease but also e.g. polysaccharides.

The term "cDNA" means a DNA molecule that can be prepared by reverse transcription from a mature, spliced, mRNA molecule obtained from a prokaryotic or eukaryotic cell. A cDNA lacks intron sequences that may be present in the corresponding genomic DNA. The initial, primary RNA transcript is a precursor to mRNA that is processed through a series of steps, including splicing, before appearing as mature spliced mRNA.

The term "clade" means a group of polypeptides clustered together based on homologous features traced to a common ancestor. Polypeptide clades can be visualized as phylogenetic trees and a clade is a group of polypeptides that consists of a common ancestor and all its lineal descendants. Polypeptides forming a group e.g. a clade as shown in a phylogenetic tree may often share common properties and are also functionally more closely related than other polypeptides not in the clade.

The term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

The term "control sequences" means all components necessary for the expression of a polynucleotide encoding a variant of the present invention. Each control sequence may be native or foreign to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for introducing specific restriction sites facilitating ligation of the control sequences with the coding region of the polynucleotide encoding a variant.

By the term "deep-cleaning" is meant disruption or removal of components of organic matter, e.g. biosoil or biofilm and EPS, such as polysaccharides, PNAG, proteins, DNA, soil or other components present in the organic matter.

The term "detergent composition", includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, soap bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types. The terms "detergent composition" and "detergent formulation" are used in reference to mixtures which are intended for use in a wash medium for the cleaning of soiled objects. In some aspects, the term is used in reference to laundering fabrics and/or garments (e.g., "laundry detergents"). In alternative aspects, the term refers to other detergents, such as those used to clean dishes, cutlery, etc. (e.g., "dishwashing detergents"). It is not intended that the present invention be limited to any particular detergent formulation or composition. The term "detergent composition" is not intended to be limited to compositions that contain surfactants. It is intended that in addition to the variants according to the invention, the term encompasses detergents that may contain, e.g., surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "dispersin" and the abbreviations "Dsp" or "Disp" are polypeptides having hexosaminidase activity, EC 3.2.1.—that catalyzes the hydrolysis of β-1,6-glycosidic linkages of N-acetyl-glucosamine polymers (poly-N-acetyl-glucosamine, PNAG) found e.g. in biofilm, EPS, cell debris and other biosoils. Thus, dispersins are enzymes having beta-1,6 N-acetylglucosaminidase activity or poly-beta-1,6-N-actylglucosamin (PNAG) activity. For purposes of the present invention, dispersin activity i.e. beta-1,6 N-acetylglucosaminidase activity is determined according to the procedure described in the activity assay of Example 3. In some aspects, the dispersin variants of the present invention have improved dispersin activity compared to the parent dispersin. In some aspects, the dispersin variants of the present invention have at least 100%, e.g., at least 110%, at least 120%, at least 130%, at least 140%, at least 150%, at least 160%, at least 170%, at least 180%, at least 190%, or at least 200% dispersin activity compared to the polypeptide shown in SEQ ID NO: 1 or such as from 100% to 200% dispersin activity compared to the polypeptide shown in SEQ ID NO: 1.

The term "effective amount of enzyme" refers to the quantity of enzyme necessary to achieve the enzymatic activity required in the specific application, e.g., in a defined detergent composition. Such effective amounts are readily ascertained by one of ordinary skill in the art and are based on many factors, such as the particular enzyme used, the cleaning application, the specific composition of the detergent composition, and whether a liquid or dry (e.g., granular, bar) composition is required, and the like. The term "effective amount" of a dispersin variant refers to the quantity of dispersin variant described hereinbefore that achieves a desired level of enzymatic activity, e.g., in a defined detergent composition.

The term "expression" includes any step involved in the production of the variant including, but not limited to, transcription, post-transcriptional modification, translation, post-translational modification, and secretion.

The term "expression vector" means a linear or circular DNA molecule that comprises a polynucleotide encoding a variant and is operably linked to additional nucleotides that provide for its expression.

The term "fabric" encompasses any textile material. Thus, it is intended that the term encompass garments, as well as fabrics, yarns, fibers, non-woven materials, natural materials, synthetic materials, and any other textile material.

The term "high detergent concentration" system includes detergents wherein greater than about 2000 ppm of detergent components is present in the wash water. European detergents are generally considered to be high detergent concentration systems.

The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

The term "improved property" means a characteristic associated with a variant that is improved compared to the parent and/or compared to a dispersin with SEQ ID NO: 1 or compared to a dispersin having the identical amino acid sequence of said variant but not having the alterations at two or more of said specified positions. Such improved properties include, but are not limited to, stability, such as detergent stability, wash performance e.g. deep cleaning effect and the deep-cleaning effect may include but is not limited to de-gluing effect (some organic materials such as EPS is sticky i.e. glue-like and courses dirt to stick to the material), improved whiteness, reduction of malodor and re-deposition. Improved property also includes improved stability in presence of certain enzymes e.g. proteases (protease stability) or substances e.g. stability in presence of sulfite e.g. sulfite stability.

The term "improved dispersin activity" is defined herein as an altered dispersin activity e.g. by increased catalyse of β-1,6-glycosidic linkages of N-acetyl-glucosamine polymers (poly-N-acetylglucosamine, PNAG) i.e. the dispersin variant displaying an alteration of the activity relative (or compared) to the activity of the parent dispersin, such as compared to a dispersin with SEQ ID NO: 1 or compared to a dispersin having the identical amino acid sequence of said variant but not having the alterations at one or more of said specified positions.

The term "low detergent concentration" system includes detergents where less than about 800 ppm of detergent components is present in the wash water. Asian, e.g., Japanese detergents are typically considered low detergent concentration systems.

The term "improved wash performance" includes but is not limited to the term "deep cleaning effect". Improved performance e.g. deep cleaning performance of a dispersin variant according to the invention is measured compared to the dispersin parent e.g. the dispersin shown in SEQ ID NO: 1 or compared to a dispersin having the identical amino acid sequence of said variant but not having the alterations at one or more of said specified positions. The improved performance e.g. deep cleaning performance may be expressed as a Remission value of the stained swatches. After washing and rinsing the swatches are spread out flat and allowed to air dry at room temperature overnight. All washed swatches are evaluated the day after the wash. Light reflectance evaluations of the swatches are done using a Macbeth Color Eye 7000 reflectance spectrophotometer with very small aperture. The measurements are made without UV in the incident light and remission at 460 nm is extracted. Positive responses indicate that soil is removed.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

The term "mature polypeptide" means a polypeptide in its final form following translation and any post-translational modifications, such as N-terminal processing, C-terminal truncation, glycosylation, phosphorylation, etc. In some aspects, the mature polypeptide is amino acids 1 to 324 of SEQ ID NO: 1. The N-terminals of the mature polypeptide used according to the present invention may be experimentally confirmed based on EDMAN N-terminal sequencing data and Intact MS data. It is known in the art that a host cell may produce a mixture of two of more different mature polypeptides (i.e., with a different C-terminal and/or N-terminal amino acid) expressed by the same polynucleotide.

The term "medium detergent concentration" system includes detergents wherein between about 800 ppm and about 2000 ppm of detergent components is present in the wash water. North American detergents are generally considered to be medium detergent concentration systems.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

The term "non-fabric detergent compositions" include non-textile surface detergent compositions, including but not limited to compositions for hard surface cleaning, such as dishwashing detergent compositions including manual dish wash compositions, oral compositions, denture compositions, and personal cleansing compositions.

The term "operably linked" means a configuration in which a control sequence is placed at an appropriate position relative to the coding sequence of a polynucleotide such that the control sequence directs the expression of the coding sequence.

The term "parent" dispersin, dispersin parent or precursor dispersin may be used interchangeably. In context of the present invention "parent dispersin" is to be understood as a dispersin into which at least one alteration is made in the amino acid sequence to produce a dispersin variant having an amino acid sequence which is less than 100% identical to the dispersin sequence into which the alteration was made i.e. the parent dispersin. Thus, the parent is a dispersin having identical amino acid sequence compared to the variant but not having the alterations at one or more of the specified positions. It will be understood, that in the present context the expression "having identical amino acid sequence" relates to 100% sequence identity. In a particular aspect the dispersin parent is a dispersin having at least 60%, at least 61%, at least 62%, at least 63%, at least 64%, at least 65%, at least 66%, at least 67%, at least 68%, at least 69%, at least 70%, at least 72%, at least 73%, at least 74%, at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, e. g. at least 99.1%, at least 99.2%, at least 99.3%, at least 99.4%, at least 99.5%, at least 99.6 or 100% identity to a polypeptide shown in SEQ ID NO: 1.

The term "relevant washing conditions" is used herein to indicate the conditions, particularly washing temperature, time, washing mechanics, detergent concentration, type of detergent and water hardness, actually used in households in a detergent market segment.

The term "stability" includes storage stability and stability during use, e.g. during a wash process and reflects the stability of the dispersin variant according to the invention as a function of time e.g. how much activity is retained when the dispersin variant is kept in solution in particular in a detergent solution. The stability is influenced by many factors e.g. pH, temperature, detergent composition e.g. amounts of builder, surfactants etc. The dispersin stability may be measured as improved RA (residual activity), $T_m$ (melting temperature) or $T_{1/2}$ (half-life) as described in Examples 2a, 2b, 3, 4, 5 and 6. The term "improved stability" or "increased stability" is defined herein as a variant dispersin displaying an increased stability in solutions, relative to the stability of the parent dispersin and/or relative to SEQ ID NO: 1. "Improved stability" and "increased stability" includes detergent stability. The term "detergent stability" or "improved detergent stability is defined as improved stability in a detergent (e.g. cleaning composition) compared to the parent dispersin. The dispersin variant improvement may be measured by RAR (residual activity ratio), HIF (Half-life improvement factor) o $T_m$, described in Example 2a, 2b, 3, 4, 5 and 6.

The term "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers. The term, "textile materials" is a general term for fibers, yarn intermediates, yarn, fabrics, and products made from fabrics (e.g., garments and other articles).

The term "transcription terminator" is used for a section of the genetic sequence that marks the end of gene or operon on genomic DNA for transcription.

The term "variant" means a polypeptide which comprises an alteration at one or more (e.g., several) positions compared to the parent or reference polypeptide. The alteration may be a substitution, insertion or deletion. A substitution means replacement of the amino acid occupying a position with a different amino acid, a deletion means removal of an amino acid occupying a position and an insertion means adding amino acids e.g. 1 to 10 amino acids, preferably 1-3 amino acids adjacent to an amino acid occupying a position. The term "dispersin variant" means a polypeptide having hexosaminidase, preferably beta-1,6 N-acetylglucosaminidase activity or is active topoly-beta-1,6-N-actylglucosamin (PNAG) and which comprise an alteration, i.e., a substitution, insertion, and/or deletion at one or more (or one or several) positions compared to the parent dispersin e.g. compared to SEQ ID NO: 1. The term "dispersin activity" means a polypeptide having hexosaminidase, preferably beta-1,6 N-acetylglucosaminidase activity or is active topoly-beta-1,6-N-actylglucosamin (PNAG). The variants e.g. dispersin variants of the present invention preferably have at least 20%, e.g., at least 40%, at least 50%, at least 60%, at least 70%, at least 80%, at least 90%, at least 95%, or at least 100% of the dispersin activity of the polypeptide shown in SEQ ID NO: 1.

The term "water hardness" or "degree of hardness" or "dH" or "° dH" as used herein refers to German degrees of hardness. One degree is defined as 10 milligrams of calcium oxide per liter of water.

The term "wild-type dispersin" means a dispersin expressed by a naturally occurring organism, such as a fungal, bacterium, archaea, yeast, plant or animal found in nature.

Conventions for Designation of Variants

For purposes of the present invention, the polypeptide disclosed in SEQ ID NO: 1 is used to determine the corresponding amino acid residue in another dispersin. The amino acid sequence of another dispersin is aligned with the polypeptide disclosed in SEQ ID NO: 1, and based on the alignment, the amino acid position number corresponding to any amino acid residue in the polypeptide disclosed in SEQ ID NO: 1 is determined using e.g. the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another dispersin can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When another enzyme has diverged from e.g. the polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example, the SCOP super families of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

As different amino acids may be present at a given position depending on the selected parent for the variants the amino acid positions are indicated with $\#_1$, $\#_2$, etc. in the definitions below. In describing the variants of the present invention, the nomenclature described below is adapted for ease of reference. The accepted IUPAC single letter or three letters amino acid abbreviations are employed.

Substitutions

For an amino acid substitution, the following nomenclature is used: Original amino acid, position, substituted amino acid. Accordingly, the substitution of valine at position $\#_1$ with alanine is designated as "Val $\#_1$Ala" or "V $\#_1$A". Multiple mutations may be separated by addition marks ("+") or by commas (,), e.g., "Val $\#_1$Ala+"Pro $\#_2$Gly" or V $\#_1$A, P $\#_2$G, representing substitutions at positions $\#_1$ and $\#_2$ of valine (V) and proline (P) with alanine (A) and glycine (G), respectively. If more than one amino acid may be substituted in a given position these may be listed in brackets, such as [X] or {X}. Thus, if both Trp and Lys may be substituted instead of the amino acid occupying at position $\#_1$ this may be indicated as X $\#_1$ {W, K}, X $\#_1$ [W, K] or X $\#_1$ [W/K], where the X indicate the amino acid residue present at the position of the parent dispersin e.g. such as a dispersin shown in SEQ ID NO: 1 or a dispersin having at least 60% identity hereto. In some cases, the variants may be represented as $\#_1$ {W, K} or X $\#_2$P emphasizing that the amino acids to be substituted vary depending on the parent. For convenience, as SEQ ID NO: 1 is used for numbering, the amino acid in the corresponding position in SEQ ID NO: 1 is indicated, e.g. D2V. However, it will be clear to the skilled artisan that a dispersin variant comprising D2V is not limited to parent dispersins having a "D" (aspartic acid) at a position corresponding to position 2 of SEQ ID NO: 1. In a parent dispersin having e.g. asparagine in position 2, the skilled person would translate the mutation specified as D2V to N2V. In the event the parent dispersin has valine in position 1, the skilled person would recognize that the parent dispersin is not changed at this position. The same applies for deletions and insertions described below.

Deletions

For an amino acid deletion, the following nomenclature is used: Original amino acid, position, *. Accordingly, the deletion of valine at position $\#_1$ is designated as "Val $\#_1$*" or "V $\#_1$*". Multiple deletions may be separated by addition marks ("+") or commas, e.g., "Val $\#_1$*+Pro $\#_2$*" or "V $\#_1$*, P $\#_2$*".

Insertions

The insertion of an additional amino acid residue such as e.g. a lysine after Val $\#_1$ may be indicated by: Val $\#_1$ValLys or V $\#_1$VK. Alternatively, insertion of an additional amino acid residue such as lysine after V $\#_1$ may be indicated by: *$\#_1$aK. When more than one amino acid residue is inserted, such as e.g. a Lys, and Gly after $\#_1$ this may be indicated as: Val $\#_1$ValLysGly or V $\#_1$VKG. In such cases, the inserted amino acid residue(s) may also be numbered by the addition of lower case letters to the position number of the amino acid residue preceding the inserted amino acid residue(s), in this example: *$\#_1$aK *$\#_1$bG.

Multiple Alterations

Variants comprising multiple alterations may be separated by addition marks ("+") or by commas (,), e.g., "Val $\#_1$Trp+Pro $\#_2$Gly" or "V $\#_1$W, P $\#_2$G" representing a substitution of valine and proline at positions $\#_1$ and $\#_2$ with tryptophan and glycine, respectively as described above.

Different Alterations

Where different alterations can be introduced at a position, the different alterations may be separated by a comma, e.g., "Val $\#_1$Trp, Lys" or V $\#_1$W, K representing a substitution of valine at position $\#_1$ with tryptophan or lysine. Thus, "Val $\#_1$Trp, Lys+Pro $\#_2$Asp" designates the following variants: "Val $\#_1$Trp+Pro $\#_2$Asp", "Val $\#_1$Lys+Pro $\#_2$Asp" or V $\#_1$W, K+P $\#_2$D. The term "substitution set" is in the context of the present invention a variant comprising more than one mutation compared to the parent or reference enzyme e.g. the substitution set D2V+Q3L (compared to SEQ ID NO: 1) is a variant of SEQ ID NO: 1 comprising the two mutations D2V+Q3L compared to SEQ ID NO: 1.

When mutations in alteration e.g. substitution sets are separated by comas or plusses "+" this means that all the alterations in the set are present and the selection is between the lists of alterations (alteration sets). E.g. "comprises one or more of the following substitution sets: Q3I+A49W, Q3I+N59E, Q3I+S163P, Q3I+S186R, Q3I+Q215K, Q3I+S225G, Q3I+N227T, Q3I+N252P, Q3I+N267T, Q3I+F276A, Q3I+Y281P, Q3I+K308Q, Q3I+K308E, Q3I+K309E, Q3I+K312Q, Q3I+K312E . . . .

means the selection is made between each of the substitution sets separated by commas.

The terms parent enzyme includes terms such as reference enzyme, back bone or starting enzyme and is used to denote the enzyme into which to mutations e.g. substitutions are made. The terms may be used interchangeably Specific for Nomenclature of Clades For purposes of the present invention, the nomenclature [IV] or [I/V] means that the amino acid at this position may be isoleucine (Ile, I) or valine (Val, V). Likewise, the nomenclature [LVI] and [L/V/I] means that the amino acid at this position may be a leucine (Leu, L), valine (Val, V) or isoleucine (Ile, I), and so forth for other combinations as described herein. Unless otherwise limited further, the amino acid X is defined such that it may be any of the 20 naturally-occurring amino acids.

DETAILED DESCRIPTION OF THE INVENTION

The present invention provides novel dispersins preferably obtained from *Terribacillus*, in particular, *Terribacillus saccharophilus*. The dispersins of the invention preferably comprise at least 60% sequence identity to a polypeptide with SEQ ID NO: 1 and comprise an alteration of at least one amino acid positions compared to the dispersin with SEQ ID NO: 1. In some aspects, a dispersin variant of the invention comprise an amino acid sequence comprising at least two substitutions of an amino acid made at positions equivalent to the positions in SEQ ID NO: 1. The present invention also relates to methods for producing dispersin variants. The dispersin variants of the present invention preferably have at least one improved property compared to the parent dispersin or compared to SEQ ID NO: 1. Properties include but are not limited to: stability such as; stability in detergents, storage stability, in wash stability and thermo-stability, wash performance in particular deep-cleaning performance, increased expression level and malodor reduction. Preferably the improved property is improved stability e.g. stability in detergent (e.g. cleaning compositions). When household care surfaces such as textiles are soiled the stain is often a complex mixture of various organic matters such as skin debris e.g. dead cells, sweat and sebum, pollution from outside and from e.g. the body. Such biosoil composes different organic stains, such as protein, starch, grease but also e.g. polysaccharides. Complex stains, which are often stubborn and difficult to remove. The use of dispersins in laundry processes and in detergents has been described in WO2017/186943 (Novozymes A/S), which disclose the dispersins from *Terribacillus* such as dispersins with SEQ ID NO: 1. Dispersins have shown very effective in removing e.g. PNAG (Poly-N-Acetyl Glucosamine) related stains from textiles under laundry conditions. However, when enzymes are formulated into cleaning compositions, such as detergents, they may be less active over time, particularly in liquid detergents. Obviously, its preferable that enzymes are stable in cleaning and detergent compositions during storage (storage stability) and during the wash process (in-wash stability). The former may be measured in accelerated stability tests where the dispersin variants are tested under stressed (e.g. increased heating) and non-stressed conditions, residual activity (RA) or Half-life ($T_{1/2}$) are measured and compared to the values of the parent (or another reference). The residual activity ratio (RAR) or Half-life improvement factor (HIF) of the reference or parent dispersin may be assigned the value 1. Thus, dispersin variants having RAR or HIF above 1 have improved stability under the measured conditions compared to the parent or reference dispersin. In a preferred embodiment of the invention the dispersin variants have improved stability compared to the parent dispersin and are therefore advantageous over state-of-the-art dispersins.

Dispersin Variants

Some aspects of the invention relate to dispersin variants of SEQ ID NO: 1 or variants of a dispersin having at least 60% identity hereto and to methods for production of a dispersin variant of SEQ ID NO: 1 or a dispersin having at least 60% identity hereto.

In one aspect the present invention relates to a dispersin comprising an alteration at one or more position selected from the list consisting of positions 2, 3, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 140, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 225, 227, 230, 232, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 and 323, wherein each position corresponds to the position of the polypeptide of SEQ ID NO: 1, wherein the variant has dispersin activity and preferably wherein the variant has improved stability compared to the parent e.g. compared to SEQ ID NO: 1.

In one aspect the present invention relates to a dispersin comprising an alteration at one or more position selected from the list consisting of positions 31, 33, 36, 73, 75, 94, 141, 144, 241, 277, 294, 297, 299, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising an alteration at one or more positions selected from the list consisting of positions 2, 3, 12, 15, 18, 22, 23, 24, 25, 30, 49, 56, 57, 59, 62, 63, 68, 72, 74, 77, 82, 90, 99, 100, 106, 114, 123, 124, 125, 135, 138, 163, 167, 170, 171, 173, 174, 175, 178, 179, 181, 185, 186, 187, 188, 189, 199, 203, 204, 205, 207, 210, 215, 221, 225, 227, 232, 235, 244, 252, 256, 260, 262, 263, 264, 265, 267, 270, 272, 273, 274, 276, 278, 279, 280, 281, 282, 283, 284, 288, 290, 291, 296, 303, 304, 305, 306, 308, 309, 312, 314, 315, 319, 321, 322 and 323, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising an alteration at one or more positions selected from the list consisting of positions 3, 15, 49, 59, 140, 163, 186, 207, 215, 218, 225, 227, 232, 235, 237, 252, 260, 267, 272, 276, 279, 281, 288, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at one or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at two or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at three or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at four or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at five or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at six or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at seven or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at eight or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at nine or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at ten or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at eleven or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at twelve or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at thirteen or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at fourteen or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at fifteen or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at sixteen or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at seventeen or more positions selected from the list consisting of positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

In one preferred aspect the present invention relates to a dispersin comprising a substitution at all the positions 3, 15, 49, 59, 163, 186, 225, 227, 232, 235, 252, 260, 272, 279, 281, 308, 309 and 312, wherein each position corresponds to the position of the polypeptide of SEQ ID NO: 1, wherein the variant has dispersin activity and preferably wherein the variant has improved stability compared to the parent e.g. compared to SEQ ID NO: 1.

The term "comprising a substitution" is in the present context meant comprising a substitution compared to the starting dispersin or the parent. The thus, dispersin have a replacement of the amino acid in e.g. position 3 with another amino acid.

In some aspects the variant has a sequence identity of at least 60%, at least 65%, at least 70%, at least 75%, at least 80%, at least 85%, at least 90%, at least 95%, such as at least 96%, at least 97%, at least 98%, or at least 99%, but less than 100%, to the amino acid sequence of the mature parent dispersin e.g. the dispersin shown in SEQ ID NO: 1.

In some preferred aspects, the dispersin variant comprises an alteration selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19N, E19P, K22A, K22M, K22V, S23C, S23E, S23I, S23L, S23R, S23T, S23V, V25R, D26M, Y30*, Y30D, Y30L, Y30M, Y30N, Y30R, Y30T, Y30V, G32L, G32M, G32R, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80V, K80W, D81A, D81G, D81L, D81R, D81S, D81T, D81V, D81W, I82V, L90F, E99Q, E99R, L100S, K103A, K103R, K104N, K104W, D105N, V106A, V106D, V106E, V106H, V106K, V106L, V106M, V106N, V106Q, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116N, Y116K, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124I, Y124K, Y124L, Y124M, Y124Q, Y124R, Y124T, Y124V, Y124W, D125C, D125G, D125K, D125Q, D125R, N126V, R127D, R127H, R127K, R127L, R127M, R127Q, R127W, V128C, V128L, V128T, D131V, Q135*, Q135A, Q135D, Q135E, Q135K, Q135M, Q135Y, D138K, D138L, D138M, D138Q, D138R, D138S, D138V, D138W, E139W, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150D, E150H, E150K, E150L, E150M, E150N, E150R, E150V, E150W, E150Y, G151A, G151C, G151D, G151L, G151N, G151P, G151S, G151W, K152D, K152L, K152R, G164D, G164E, G164H, G164S, G164V, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181N, S181P, S181Q, S181T, S181V, S181W, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203R, A203S, A203T, A203V, A203W, N204L, N204M, N204V, N204W, N204Y, L205I, D207A, D207C, D207E, D207G, D207N, D207Q, D207S, D207V, D207W, S208A, S208C, S208D, S208G, S208L, S208Q, S208T, S208V, S208W, S210T, Q215R, Q215M, Q215L, Q215*, S217V, T218A, T218L, T218Q, T218R, T218V, G222D, E224A, E224P, N227A, N227Q, N227R, N227S, N227T, N227K, D230*, D230R, D230T, D230W, E232D, E232V, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251L, S251N, S251R, S251W, N252P, N252C, G253D, G253W, F254I, F254L, F254M, F254Y, Q256E, Q256R, N260*, N260A, N260C, N260E, N260I, N260K, N260L, N260M, N260Q, N260R, N260V, N260W, N260Y, E261*, E261A, E261D, E261R, E261W, Q262*, Q262F, Q262H, Q262W, Q262Y, M263K, M263L, M263Q, D264*, D264C, D264E, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y281R, Y282E, Y282N, H283I, A284I, A284L, A284N, A284P, A284T, A284V, T287N, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308G, K308I, K308L, K308Q, K308S, K308T, K308V, K308Y, K309A, K309C, K309D, K309H, K309L, K309M, K309N, K309Q, K309S, K309T, K309I, K312A, K312L, K312M, K312N, K312Q, K312S, K312W, E314I, E314L, E314V, L315I, L315V, R319A, and N323R, wherein the variant has dispersin activity and wherein each position corresponds to the position of the polypeptide shown in SEQ ID NO: 1 (numbering according to SEQ ID NO: 1).

In some preferred aspects the alteration is a substitution and the dispersin variant comprises one or more substitution(s) selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19N, E19P, K22A, K22M, K22V, S23C, S23E, S23I, S23L, S23R, S23T, S23V, V25R, D26M, Y30D, Y30L, Y30M, Y30N, Y30R, Y30T, Y30V, G32L, G32M, G32R, N43H, N43L, N45D, N45L, N45V, A49W, A49Y, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72C, S72D, S72E, S72F, S72G, S72I, S72M, S72N, S72R, S72T, S72Y, I74L, S77A, D79V, K80E, K80H, K80L, K80N, K80Q, K80V, K80W, D81A, D81G, D81L, D81R, D81S, D81T, D81V, D81W, I82V, L90F, E99Q, E99R, L100S, K103A, K103R, K104N, K104W, D105N, V106A, V106D, V106E, V106H, V106K, V106L, V106M, V106N, V106Q, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116N, Y116R, S117D, S117H, S117N, S117P, E118A, E118D, E118G, E118L, E119G, E119W, T120I, T120L, T120M, T120V, T120W, D122H, D122R, Y123W, Y124C, Y124I, Y124K, Y124L, Y124M, Y124Q, Y124R, Y124T, Y124V, Y124W, D125C, D125G, D125K, D125Q, D125R, N126V, R127D, R127H, R127K, R127L, R127M, R127Q, R127W, V128C, V128L, V128T, D131V, Q135A, Q135D, Q135E, Q135K, Q135M, Q135Y, D138K, D138L, D138M, D138Q, D138R, D138S, D138V, D138W, E139W, D142R, D142W, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150D, E150H, E150K, E150L, E150M, E150N, E150R, E150V, E150W, E150Y, G151A, G151C, G151D, G151L, G151N, G151P, G151S, G151W, K152D, K152L, K152R, G164D, G164E, G164H, G164S, G164V, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178A, Q178K, Q178R, Q178W, I179T, S181C, S181D, S181F, S181G, S181N, S181P, S181Q, S181T, S181V, S181W, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203R, A203S, A203T, A203V, A203W, N204L, N204M, N204V, N204W, N204Y, L205I, D207A, D207C, D207E, D207G, D207N, D207Q, D207S, D207V, D207W, S208A, S208C, S208D, S208G, S208L, S208Q, S208T, S208V, S208W, S210T, Q215R, Q215M, Q215L, S217V, T218A, T218L, T218Q, T218R, T218V, G222D, E224A, E224P, N227A, N227Q, N227R, N227S, N227T, N227K, D230R, D230T, D230W, E232D, E232V, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251L, S251N, S251R, S251W, N252P, N252C, G253D, G253W, F254I, F254L, F254M, F254Y, Q256E, Q256R, N260A, N260C, N260E, N260I, N260K, N260L, N260M, N260Q, N260R, N260V, N260W, N260Y, E261A, E261D, E261R, E261W, Q262F, Q262H, Q262W, Q262Y, M263K, M263L, M263Q, D264C, D264E, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281A, Y281C, Y281H, Y281K, Y281N, Y281P, Y281R, Y282E, Y282N, H283I, A284I, A284L, A284N, A284P, A284T, A284V, T287N, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308G, K308I, K308L, K308Q, K308S, K308T, K308V, K308Y, K309A, K309C, K309D, K309H, K309L, K309M, K309N, K309Q, K309S, K309T, K309I, K312A, K312L, K312M, K312N, K312Q, K312S, K312W, E314I, E314L, E314V, L315I, L315V, R319A, and N323R, wherein the variant has dispersin activity and wherein each position corresponds to the position of the polypeptide shown in SEQ ID NO: 1 (numbering according to SEQ ID NO: 1).

One aspect relates to a dispersin variant, which compared to a dispersin with SEQ ID NO: 1, comprises one or more substitutions selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19K, E19N, E19P, K22A, K22M, K22V, S23A, S23C, S23E, S23I, S23L, S23R, S23T, S23V, L24I, V25R, D26M, Y30A, Y30D, Y30L, Y30M, Y30N, Y30R, Y30T, Y30V, G32L, G32M, G32R, N34D, N43H, N43L, N45D, N45L, N45V, A49W, A49Y, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72C, S72D, S72E, S72F, S72G, S72I, S72M, S72N, S72R, S72T, S72Y, I74L, S77A, D79V, K80E, K80H, K80L, K80N, K80Q, K80R, K80V, K80W, D81A, D81G, D81L, D81N, D81R, D81S, D81T, D81V, D81W, I82V, L90F, E99Q, E99R, L100S, K103A, K103R, K103V, K104N, K104W, D105N, V106A, V106D, V106E, V106H, V106K, V106L, V106M, V106N, V106Q, V106R, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116N, Y116R, S117D, S117H, S117N, S117P, E118A, E118D, E118G, E118L, E119G, E119W, T120I, T120L, T120M, T120V, T120W, D122H, D122R, Y123W, Y124C, Y124H, Y124I, Y124K, Y124L, Y124M, Y124N, Y124Q, Y124R, Y124T, Y124V, Y124W, D125C, D125G, D125H, D125K, D125Q, D125R, N126V, R127D, R127H, R127K, R127L, R127M, R127Q, R127W, V128A, V128C, V128D, V128L, V128T, D131V, Q135A, Q135D, Q135E, Q135K, Q135M, Q135Y, D138K, D138L, D138M, D138N, D138Q, D138R, D138S, D138V, D138W, E139W, V140I, D142R, D142W, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150A, E150D, E150H, E150K, E150L, E150M, E150N, E150R, E150V, E150W, E150Y, G151A, G151C, G151D, G151L, G151N, G151P, G151S, G151W, K152D, K152L, K152R, S163P, G164D, G164E, G164H, G164S, G164V, V167A, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178A, Q178K, Q178R, Q178W, I179T, S181C, S181D, S181F, S181G, S181K, S181N, S181P, S181Q, S181T, S181V, S181W, E185A, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203Q, A203R, A203S, A203T, A203V, A203W, N204L, N204M, N204V, N204W, N204Y, L205I, D207A, D207C, D207E, D207G, D207K, D207N, D207Q, D207R, D207S, D207V, D207W, S208A, S208C, S208D, S208G, S208L, S208Q, S208T, S208V, S208W, S210T, Q215K, Q215R, Q215M, Q215L, S217V, T218A, T218L, T218Q, T218R, T218V, S221N, G222D, E224A, E224P, S225G, N227A, N227Q, N227R, N227S, N227T, N227K, D230N, D230R, D230T, D230W, E232D, E232V, N233D, N233E, N233H, N233Q, N233R, N233W, W234R, G235A, G235W, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251A, S251L, S251N, S251R, S251W, N252P, N252C, G253D, G253W, F254I, F254L, F254M, F254Y, Q256D, Q256E, Q256R, N260A, N260C, N260E, N260I, N260K, N260L, N260M, N260Q, N260R, N260T, N260V, N260W, N260Y, E261A, E261D, E261R, E261W, Q262F, Q262H, Q262Q, Q262Y, M263K, M263L, M263Q, D264C, D264E, D264N, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281A, Y281C, Y281H, Y281K, Y281N, Y281P, Y281R, Y282E, Y282N, H283I, A284I, A284L, A284N, A284P, A284T, A284V, T287N, S288P, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308E, K308G, K308I, K308L, K308Q, K308S, K308T, K308V, K308Y, K309A, K309C, K309D, K309E, K309G, K309H, K309L, K309M, K309N, K309Q, K309S, K309T, K309I, K312A, K312E, K312L, K312M, K312N, K312Q, K312S, K312W, E314I, E314L, E314V, L315I, L315N, R319A, Y321F and N323R, wherein the positions correspond to the positions of SEQ ID NO: 1 (numbering according to SEQ ID NO: 1) wherein the variant has a sequence identity to the polypeptide shown in SEQ ID NO: of at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to SEQ ID NO: 1, and wherein the variant has dispersin, preferably beta-1,6 N-acetylglucosaminidase activity.

One aspect relates to a dispersin variant, which compared to a dispersin with SEQ ID NO: 1, comprises one or more substitutions selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19N, E19P, K22A, K22M, K22V, S23C, S23E, S23I, S23L, S23R, S23T, S23V, V25R, D26M, Y30D, Y30L, Y30M, Y30N, Y30R, Y30T, Y30V, G32L, G32M, G32R, N43H, N43L, N45D, N45L, N45V, A49W, A49Y, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72C, S72D, S72E, S72F, S72G, S72I, S72M, S72N, S72R, S72T, S72Y, I74L, S77A, D79V, K80E, K80H, K80L, K80N, K80Q, K80V, K80W, D81A, D81G, D81L, D81R, D81S, D81T, D81V, D81W, I82V, L90F, E99Q, E99R, L100S, K103A, K103R, K104N, K104W, D105N, V106A, V106D, V106E, V106H, V106K, V106L, V106M, V106N, V106Q, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116N, Y116R, S117D, S117H, S117N, S117P, E118A, E118D, E118G, E118L, E119G, E119W, T120I, T120L, T120M, T120V, T120W, D122H, D122R, Y123W, Y124C, Y124I, Y124K, Y124L, Y124M, Y124Q, Y124R, Y124T, Y124V, Y124W, D125C, D125G, D125K, D125Q, D125R, N126V, R127D, R127H, R127K, R127L, R127M, R127Q, R127W, V128C, V128L, V128T, D131V, Q135A, Q135D, Q135E, Q135K, Q135M, Q135Y, D138K, D138L, D138M, D138Q, D138R, D138S, D138V, D138W, E139W, D142R, D142W, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150D, E150H, E150K, E150L, E150M, E150N, E150R, E150V, E150W, E150Y, G151A, G151C, G151D, G151L, G151N, G151P, G151S, G151W, K152D, K152L, K152R, G164D, G164E, G164H, G164S, G164V, V167D, V167E, V167L, V167P, V167Q, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174R, D174W, F175Y, N177M, Q178A, Q178K, Q178R, Q178W, I179T, S181C, S181D, S181F, S181G, S181N, S181P, S181Q, S181T, S181V, S181W, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203R, A203S, A203T, A203V, A203W, N204L, N204M, N204V, N204W, N204Y, L205I, D207A, D207C, D207E, D207G, D207N, D207Q, D207S, D207V, D207W, S208A, S208C, S208D, S208G, S208L, S208Q, S208T, S208V, S208W, S210T, Q215R, Q215M, Q215L, S217V, T218A, T218L, T218Q, T218R, T218V, G222D, E224A, E224P, N227A, N227Q, N227R, N227S, N227T, N227K, D230R, D230T, D230W, E232D, E232V, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251L, S251N, S251R, S251W, N252P, N252C, G253D, G253W, F254I, F254L, F254M, F254Y, Q256E, Q256R, N260A, N260C, N260E, N260I, N260K, N260L, N260M, N260Q, N260R, N260V, N260W, N260Y, E261A, E261D, E261R, E261W, Q262F, Q262H, Q262W, Q262Y, M263K, M263L, M263Q, D264C, D264E, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281A, Y281C, Y281H, Y281K, Y281N, Y281P, Y281R, Y282E, Y282N, H283I, A284I, A284L, A284N, A284P, A284T, A284V, T287N, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308G, K308I, K308L, K308Q, K308S, K308T, K308V, K308Y, K309A, K309C, K309D, K309H, K309L, K309M, K309N, K309Q, K309S, K309T, K309I, K312A, K312L, K312M, K312N, K312Q, K312S, K312W, E314I, E314L, E314V, L315I, L315V, R319A, and N323R, wherein the positions correspond to the positions of SEQ ID NO: 1 (numbering according to SEQ ID NO: 1) wherein the variant has a sequence identity to the polypeptide shown in SEQ ID NO: 1 of at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to SEQ ID NO: 1, and wherein the variant has dispersin, preferably beta-1,6 N-acetylglucosaminidase activity.

In some preferred aspects the alteration is a substitution and the dispersin variant comprises one or more substitutions selected from the group consisting of: D2V, Q3F, Q3I, S12A, H15Y, T17W, T17E, V18L, K22M, S23I, S23C, S23T, S23L, S23V, S23E, V25R, Y30L, A49W, A49Y, S56T, N59D, N59C, N59E, N59R, N59F, N59W, N59V, N62C, N62D, T63C, N68Q, S72D, S72E, I74L, S77A, I82V, L90F, E99Q, L100S, T114S, T114C, Y123W, Y123W, Y124I, Y124M, Y124R, Y124V, Y124Q, Y124T, Y124K, D125R, D125C, D125G, D125K, D125Q, Q135M, D138R, D138K, D138Q, L170D, L170K, L170S, L170H, D171E, D171K, D171Y, D171M, D171Q, D171L, I173C, D174W, D174H, D174M, D174N, F175Y, Q178K, I179T, S181T, S181F, S181Q, S181G, S181N, S181C, E185R, E185M, E185V, S186K, S186M, S186R, S186H, K187G, Y188P, E189V, S199C, S199L, A203G, A203E, N227T, N227K, E232D, G235W, S237W, Y244M, Y244C, N252P, N252C, Q256E, N260Q, Q262H, M263Q, D264E, Y265F, N267T, N267S, Y270F, H272M, H272P, H272I, H272V, N273W, K274H, F276A, F276N, F276K, F276C, I278V, S279N, S279D, S279G, D280E, D280C, Y281P, Y282N, H283I, A284T, A284L, A284I, S288K, V290I, K291R, T296C, T303Q, D304M, D304C, L305M, L305N, S306C, K308D, K308A, K308V, K308Q, K308S, K308Y, K308G, K308L, K308T, K308I, K309C, K309L, K309D, K309Q, K309N, K309T, K309A, K309S, K309M, K309H, K312A, K312Q, K312S, K312W, K312L, K312N, E314L, E314V, E314I, L315I, R319A and N323R, wherein the variant has dispersin activity, preferably beta-1,6 N-acetylglucosaminidase activity and wherein each position corresponds to the position of the polypeptide shown in SEQ ID NO: 1 (numbering according to SEQ ID NO: 1).

In some aspects the variant has a sequence identity of at least 60%, at least 65%, at least 70%, at least 75%, at least 80%, at least 85%, at least 90%, at least 95%, such as at least 96%, at least 97%, at least 98%, or at least 99%, but less than 100%, to the amino acid sequence of the mature parent dispersin e.g. the dispersin shown in SEQ ID NO: 1.

In some aspects, the number of substitutions in the variants of the present invention is 2-20, e.g., 2-10 and 2-5, such as 2, 3, 4, 5, 6, 7, 8, 9, 10, 11, 12, 13, 14, 15, 16, 17, 18, 19 or 20 substitutions. In one aspect the total number of substitutions compared to SEQ ID NO: 1 is 3-20, e.g. at least 5 to 20, at least 10 to 20 or such as at least 15 to 20 substitutions compared to the dispersin comprising the amino acid sequence shown in SEQ ID NO: 1.

In another aspect, the dispersin variant comprises or consists of a substitution at a position corresponding to position 2 of SEQ ID NO: 1. In another aspect, the amino acid at a position corresponding to position 2 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val, Leu, Ala, Trp, Arg or Asn. In another aspect, the dispersin variant comprises or consists of a substitution selected from the group consisting of D2V, D2L, D2A, D2W, D2R and D2N, wherein the position corresponds to the positions of SEQ ID NO: 1 and wherein the variant has at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 3 of SEQ ID NO: 1. In another aspect, the amino acid at a position corresponding to position 3 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe, Leu, Val, Tyr, Met, Ile, Pro or Thr. In another aspect, the dispersin variant comprises or consists of a substitution selected from the group consisting of Q3F, Q3L, Q3V, Q3Y, Q3M, Q3I, Q3P and Q3T, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 12 of SEQ ID NO: 1. In another aspect, the amino acid at a position corresponding to position 12 of SEQ ID NO: 1 is substituted with Ala, Ar, Asn, Asp, Cys, Gln, Glu, Gly, His, Ile, Leu, Lys, Met, Phe, Pro, Ser, Thr, Trp, Tyr, or Val, preferably with Ala. In another aspect, the dispersin variant comprises or consists of the substitution S12A, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 15 of SEQ ID NO: 1. In another aspect, the amino acid at a position corresponding to position 15 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Tyr or Phe. In another aspect, the dispersin variant comprises or consists of the substitution H15Y or H15F, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 17 of SEQ ID NO: 1. In another aspect, the amino acid at a position corresponding to position 17 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp, Val, Arg, Met, Phe, Cys or Glu. In another aspect, the dispersin variant comprises or consists of a substitution selected from the group consisting of T17W, T17V, T17R, T17M, T17F, T17C and T17E, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 18 of SEQ ID NO: 1. In another aspect, the amino acid at a position corresponding to position 18 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the dispersin variant comprises or consists of the substitution V18L, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 19 of SEQ ID NO: 1. In another aspect, the amino acid at a position corresponding to position 19 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro, Asn, Lys or Asp. In another aspect, the dispersin variant comprises or consists of a substitution selected from the group consisting of E19P, E19N, E19K and E19D, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 22 of SEQ ID NO: 1. In another aspect, the amino acid at a position corresponding to position 22 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Val or Met. In another aspect, the dispersin variant comprises or consists of a substitution selected from the group consisting of K22A, K22V and K22M, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 23 of SEQ ID NO: 1. In another aspect, the amino acid at a position corresponding to position 23 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Cys, Glu, Ile, Leu, Arg, Thr or Val. In another aspect, the dispersin variant comprises or consists of the substitution selected from the group consisting of S23A, S23C, S23E, S23I, S23L, S23R, S23T and S23V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 24 of SEQ ID NO: 1. In another aspect, the amino acid at a position corresponding to position 24 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the dispersin variant comprises or consists of the substitution L24I, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 25 of SEQ ID NO: 1. In another aspect, the amino acid at a position corresponding to position 25 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg. In another aspect, the dispersin variant comprises or consists of the substitution V25R, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 26 of SEQ ID NO: 1. In another aspect, the amino acid at a position corresponding to position 26 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Met. In another aspect, the dispersin variant comprises or consists of the substitution D26M, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 30 of SEQ ID NO: 1. In another aspect, the dispersin variant comprises or consists of a substitution at a position corresponding to position 30 of SEQ ID NO: 1. In another aspect, the amino acid at a position corresponding to position 30 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg, Val, Asp, Thr, Asn, Met, Ala or Leu. In another aspect, the dispersin variant comprises or consists of a substitution selected from the group consisting of Y30R, Y30V, Y30D, Y30T, Y30N, Y30M, Y30A and Y30L, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 32 of SEQ ID NO: 1. In another aspect, the amino acid at a position corresponding to position 32 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg, Met or Leu. In another aspect, the dispersin variant comprises or consists of a substitution selected from the group consisting of G32R, G32M and G32L, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 34 of SEQ ID NO: 1. In another aspect, the amino acid at a position corresponding to position 34 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the dispersin variant comprises or consists of the substitution N34D, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 43 of SEQ ID NO: 1. In another aspect, the dispersin variant comprises or consists of a substitution at a position corresponding to position 43 of SEQ ID NO: 1. In another aspect, the amino acid at a position corresponding to position 43 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu or His. In another aspect, the dispersin variant comprises or consists of the substitution N43L or N43H, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 44 of SEQ ID NO: 1.

In another aspect, the dispersin variant comprises or consists of a substitution at a position corresponding to position 45 of SEQ ID NO: 1. In another aspect, the amino acid at a position corresponding to position 45 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp, Leu or Val. In another aspect, the dispersin variant comprises or consists of a substitution selected from the group consisting of N45D, N45L and N45V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 49 of SEQ ID NO: 1. In another aspect, the amino acid at a position corresponding to position 49 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp or Tyr. In another aspect, the dispersin variant comprises or consists of the substitution A49W, A49Y, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 52 of SEQ ID NO: 1. In another aspect, the dispersin variant comprises or consists of a substitution at a position corresponding to position 52 of SEQ ID NO: 1. In another aspect, the amino acid at a position corresponding to position 52 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Met. In another aspect, the dispersin variant comprises or consists of the substitution Y52M, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 54 of SEQ ID NO: 1. In another aspect, the amino acid at a position corresponding to position 54 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn, Leu or Met. In another aspect, the dispersin variant comprises or consists of a substitution selected from the group consisting of G54N, G54L and G54M, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 56 of SEQ ID NO: 1. In another aspect, the amino acid at a position corresponding to position 56 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp or Thr. In another aspect, the dispersin variant comprises or consists of the substitution S56W or S56T, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 57 of SEQ ID NO: 1. In another aspect, the amino acid at a position corresponding to position 57 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp. In another aspect, the dispersin variant comprises or consists of the substitution S57W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 58 of SEQ ID NO: 1. In another aspect, the amino acid at a position corresponding to position 58 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn. In another aspect, the dispersin variant comprises or consists of the substitution E58N, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 59 of SEQ ID NO: 1. In another aspect, the amino acid at a position corresponding to position 59 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Cys, Asp, Glu, Phe, Met, Arg, Val or Trp. In another aspect, the dispersin variant comprises or consists of a substitution selected from the group consisting of N59A, N59C, N59D, N59E, N59F, N59M, N59R, N59V, N59W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 60 of SEQ ID NO: 1. In another aspect, the amino acid at a position corresponding to position 60 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the dispersin variant comprises or consists of the substitution T60V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 62 of SEQ ID NO: 1. In another aspect, the amino acid at a position corresponding to position 62 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp, Gln, His, Cys or Asp. In another aspect, the dispersin variant comprises or consists of a substitution selected from the group consisting of N62W, N62Q, N62H, N62C and N62D, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 63 of SEQ ID NO: 1. In another aspect, the amino acid at a position corresponding to position 63 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val, Leu, Asn, Arg, Asp or Cys. In another aspect, the dispersin variant comprises or consists of a substitution selected from the group consisting of T63V, T63L, T63N, T63R, T63D and T63C, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 67 of SEQ ID NO: 1. In another aspect, the amino acid at a position corresponding to position 67 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu or Ala. In another aspect, the dispersin variant comprises or consists of the substitution K67L or K67A, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 68 of SEQ ID NO: 1. In another aspect, the amino acid at a position corresponding to position 68 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu or Gln. In another aspect, the dispersin variant comprises or consists of the substitution N68L or N68Q, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 71 of SEQ ID NO: 1. In another aspect, the amino acid at a position corresponding to position 71 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg, His, Asn, Trp, or Val. In another aspect, the dispersin variant comprises or consists of a substitution selected from the group consisting of L71R, L71H, L71N, L71W and L71V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 72 of SEQ ID NO: 1. In another aspect, the dispersin variant comprises or consists of a substitution at a position corresponding to position 72 of SEQ ID NO: 1. In another aspect, the amino acid at a position corresponding to position 72 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr, Gly, Cys, Met, Phe, Asn, Tyr, Arg, Ile, Asp or Glu. In another aspect, the dispersin variant comprises or consists of a substitution selected from the group consisting of S72T, S72G, S72C, S72M, S72F, S72N, S72Y, S72R, S72I, S72D and S72E, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 74 of SEQ ID NO: 1. In another aspect, the amino acid at a position corresponding to position 74 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the dispersin variant comprises or consists of the substitution I74L, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 77 of SEQ ID NO: 1. In another aspect, the amino acid at a position corresponding to position 77 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the dispersin variant comprises or consists of the substitution S77A, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 79 of SEQ ID NO: 1. In another aspect, the amino acid at a position corresponding to position 79 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the dispersin variant comprises or consists of the substitution D79V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 80 of SEQ ID NO: 1. In another aspect, the dispersin variant comprises or consists of a substitution at a position corresponding to position 80 of SEQ ID NO: 1. In another aspect, the amino acid at a position corresponding to position 80 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn, Arg, Trp, Leu, Val, Gln or His. In another aspect, the dispersin variant comprises or consists of a substitution selected from the group consisting of K80N, K80R, K80W, K80E, K80L, K80V, K80Q and K80H, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 81 of SEQ ID NO: 1. In another aspect, the amino acid at a position corresponding to position 81 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly, Ala, Trp, Leu, Trp, Thr, Val, Arg, Ser or Asn. In another aspect, the dispersin variant comprises or consists of a substitution selected from the group consisting of D81G, D81A, D81L, D81W, D81T, D81V, D81R, D81S and D81N, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 82 of SEQ ID NO: 1. In another aspect, the amino acid at a position corresponding to position 82 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the dispersin variant comprises or consists of the substitution I82V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 90 of SEQ ID NO: 1. In another aspect, the amino acid at a position corresponding to position 90 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe. In another aspect, the dispersin variant comprises or consists of the substitution L90F, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 99 of SEQ ID NO: 1. In another aspect, the amino acid at a position corresponding to position 99 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln or Arg. In another aspect, the dispersin variant comprises or consists of the substitution E99Q or E99R, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 100 of SEQ ID NO: 1. In another aspect, the amino acid at a position corresponding to position 100 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser. In another aspect, the dispersin variant comprises or consists of the substitution L100S, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 103 of SEQ ID NO: 1. In another aspect, the amino acid at a position corresponding to position 103 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg, Val or Ala. In another aspect, the dispersin variant comprises or consists of a substitution selected from the group consisting of K103R, K103V and K103A, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 104 of SEQ ID NO: 1. In another aspect, the amino acid at a position corresponding to position 104 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn or Trp. In another aspect, the dispersin variant comprises or consists of the substitution K104N or K104W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 105 of SEQ ID NO: 1. In another aspect, the amino acid at a position corresponding to position 105 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn. In another aspect, the dispersin variant comprises or consists of the substitution D105N, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 106 of SEQ ID NO: 1. In another aspect, the amino acid at a position corresponding to position 106 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Tyr, Leu, His, Glu, Trp, Asn, Arg, Met, Asp, Lys, Ala or Gln. In another aspect, the dispersin variant comprises or consists of a substitution selected from the group consisting of V106Y, V106L, V106H, V106E, V106W, V106N, V106R, V106M, V106D, V106K, V106A and V106Q, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 107 of SEQ ID NO: 1. In another aspect, the amino acid at a position corresponding to position 107 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Met, Trp, Leu, Cys, Val, Ala or Thr. In another aspect, the dispersin variant comprises or consists of a substitution selected from the group consisting of K107M, K107W, K107L, K107C, K107V, K107A and K107T, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 110 of SEQ ID NO: 1. In another aspect, the amino acid at a position corresponding to position 110 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg, Val or Met. In another aspect, the dispersin variant comprises or consists of a substitution selected from the group consisting of: N110R, N110V and N110M, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 111 of SEQ ID NO: 1. In another aspect, the amino acid at a position corresponding to position 111 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val, Ala, Arg, Asn, Trp, Met, Gln or Glu. In another aspect, the dispersin variant comprises or consists of a substitution selected from the group consisting of: D111V, D111A, D111R, D111N, D111W, D111M, D111Q and D111E, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 113 of SEQ ID NO: 1. In another aspect, the amino acid at a position corresponding to position 113 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr. In another aspect, the dispersin variant comprises or consists of the substitution V113T, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 114 of SEQ ID NO: 1. In another aspect, the amino acid at a position corresponding to position 114 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser or Cys. In another aspect, the dispersin variant comprises or consists of the substitution T114S or T114C, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 116 of SEQ ID NO: 1. In another aspect, the amino acid at a position corresponding to position 116 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp, Asn or Arg. In another aspect, the dispersin variant comprises or consists of the substitution Y116D, Y116N or Y116R, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 117 of SEQ ID NO: 1. In another aspect, the dispersin variant comprises or consists of a substitution at a position corresponding to position 117 of SEQ ID NO: 1. In another aspect, the amino acid at a position corresponding to position 117 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp, His, Asn or Pro. In another aspect, the dispersin variant comprises or consists of the substitution S117D, S117H, S117N or S117P, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 118 of SEQ ID NO: 1. In another aspect, the dispersin variant comprises or consists of a substitution at a position corresponding to position 118 of SEQ ID NO: 1. In another aspect, the amino acid at a position corresponding to position 118 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Asp, Gly or Leu. In another aspect, the dispersin variant comprises or consists of the substitution E118A, E118D, E118G or E118L, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 119 of SEQ ID NO: 1. In another aspect, the amino acid at a position corresponding to position 119 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly or Trp. In another aspect, the dispersin variant comprises or consists of the substitution E119G or E119W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 120 of SEQ ID NO: 1. In another aspect, the amino acid at a position corresponding to position 120 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile, Leu, Met, Val or Trp. In another aspect, the dispersin variant comprises or consists of the substitution T120I, T120L, T120M, T120V or T120W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 122 of SEQ ID NO: 1. In another aspect, the dispersin variant comprises or consists of a substitution at a position corresponding to position 122 of SEQ ID NO: 1. In another aspect, the amino acid at a position corresponding to position 122 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg or His. In another aspect, the dispersin variant comprises or consists of the substitution D122R or D122H, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 123 of SEQ ID NO: 1. In another aspect, the amino acid at a position corresponding to position 123 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp. In another aspect, the dispersin variant comprises or consists of the substitution Y123W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 124 of SEQ ID NO: 1. In another aspect, the amino acid at a position corresponding to position 124 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile, Met, His, Arg, Val, Gln, Thr, Lys, Leu, Asn, Trp or Cys. In another aspect, the dispersin variant comprises or consists of a substitution selected from the group consisting of: Y124I, Y124M, Y124H, Y124R, Y124V, Y124Q, Y124T, Y124K, Y124L, Y124N, Y124W and Y124C, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 125 of SEQ ID NO: 1. In another aspect, the amino acid at a position corresponding to position 125 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg, Cys, Gly, His, Lys or Gln. In another aspect, the dispersin variant comprises or consists of a substitution selected from the group consisting of: D125R, D125C, D125G, D125H, D125K and D125Q, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 126 of SEQ ID NO: 1. In another aspect, the amino acid at a position corresponding to position 126 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the dispersin variant comprises or consists of the substitution N126V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 127 of SEQ ID NO: 1. In another aspect, the amino acid at a position corresponding to position 127 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu, Trp, Gln, Met, Asp, His or Lys. In another aspect, the dispersin variant comprises or consists of a substitution selected from the group consisting of: R127L, R127W, R127Q, R127M, R127D, R127H and R127K, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 128 of SEQ ID NO: 1. In another aspect, the amino acid at a position corresponding to position 128 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu, Asp, Ala, Cys, or Thr. In another aspect, the dispersin variant comprises or consists of a substitution selected from the group consisting of: V128L, V128D, V128A, V128C and V128T, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 131 of SEQ ID NO: 1. In another aspect, the amino acid at a position corresponding to position 131 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the dispersin variant comprises or consists of the substitution D131V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 135 of SEQ ID NO: 1. In another aspect, the dispersin variant comprises or consists of a substitution at a position corresponding to position 135 of SEQ ID NO: 1. In another aspect, the amino acid at a position corresponding to position 135 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Met, Tyr, Ala, Asp, Glu or Lys. In another aspect, the dispersin variant comprises or consists of a substitution selected from the group consisting of: Q135M, Q135Y, Q135A, Q135D, Q135E and Q135K, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 138 of SEQ ID NO: 1. In another aspect, the amino acid at a position corresponding to position 138 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Met, Val, Leu, Trp, Ser, Arg, Lys, Asn or Gln. In another aspect, the dispersin variant comprises or consists of a substitution selected from the group consisting of: D138M, D138V, D138L, D138W, D138S, D138R, D138K, D138N and D138Q, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 139 of SEQ ID NO: 1. In another aspect, the amino acid at a position corresponding to position 139 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp. In another aspect, the dispersin variant comprises or consists of the substitution E139W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 140 of SEQ ID NO: 1. In another aspect, the amino acid at a position corresponding to position 140 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the dispersin variant comprises or consists of the substitution V140I, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 142 of SEQ ID NO: 1. In another aspect, the amino acid at a position corresponding to position 142 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp or Arg. In another aspect, the dispersin variant comprises or consists of the substitution D142W or D142R, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1

In another aspect, the dispersin variant comprises or consists of a deletion of the amino acid at a position corresponding to position 145 of SEQ ID NO: 1. In another aspect, the dispersin variant comprises or consists of a substitution at a position corresponding to position 145 of SEQ ID NO: 1. In another aspect, the amino acid at a position corresponding to position 145 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val, Asn, His or Leu. In another aspect, the dispersin variant comprises or consists of a substitution selected from the group consisting of: Y145V, Y145N, Y145H and Y145L, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 147 of SEQ ID NO: 1. In another aspect, the amino acid at a position corresponding to position 147 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu, Asp, Ala, Val, Gly, Arg, Ser, Met, Thr, Cys or Phe. In another aspect, the dispersin variant comprises or consists of a substitution selected from the group consisting of: P147L, P147D, P147A, P147V, P147G, P147R, P147S, P147M, P147T, P147C and P147F, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 148 of SEQ ID NO: 1. In another aspect, the amino acid at a position corresponding to position 148 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu, Asp, Ala or Val. In another aspect, the dispersin variant comprises or consists of a substitution selected from the group consisting of: K148L, K148D, K148A and K148V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 149 of SEQ ID NO: 1. In another aspect, the amino acid at a position corresponding to position 149 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn, Met or Leu. In another aspect, the dispersin variant comprises or consists of a substitution selected from the group consisting of: F149N, F149M and F149L, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 150 of SEQ ID NO: 1. In another aspect, the amino acid at a position corresponding to position 150 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn, Arg, Asp, Lys, Mat, His, Trp, Val, Gly, Leu or Ala. In another aspect, the dispersin variant comprises or consists of a substitution selected from the group consisting of: E150N, E150R, E150D, E150K, E150M, E150H, E150W, E150V, E150Y, E150L and E150A, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 151 of SEQ ID NO: 1. In another aspect, the amino acid at a position corresponding to position 151 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Pro, Trp, Asp, Leu, Ser, Asn or Cys. In another aspect, the dispersin variant comprises or consists of a substitution selected from the group consisting of: G151A, G151P, G151W, G151D, G151L, G151S, G151N and G151C, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 152 of SEQ ID NO: 1. In another aspect, the amino acid at a position corresponding to position 152 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp, Leu or Arg. In another aspect, the dispersin variant comprises or consists of a substitution selected from the group consisting of: K152D, K152L and K152R, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 163 of SEQ ID NO: 1. In another aspect, the amino acid at a position corresponding to position 163 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro. In another aspect, the dispersin variant comprises or consists of the substitution S163P, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1

In another aspect, the dispersin variant comprises or consists of a substitution at a position corresponding to position 164 of SEQ ID NO: 1. In another aspect, the amino acid at a position corresponding to position 164 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp, His, Ser, Glu or Val. In another aspect, the dispersin variant comprises or consists of a substitution selected from the group consisting of: G164D, G164H, G164S, G164E and G164V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 167 of SEQ ID NO: 1. In another aspect, the amino acid at a position corresponding to position 167 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln, Ala, Trp, Pro, Asp, Leu, Arg or Glu. In another aspect, the dispersin variant comprises or consists of a substitution selected from the group consisting of: V167Q, V167A, V167W, V167P, V167D, V167L, V167R and V167E, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 168 of SEQ ID NO: 1. In another aspect, the amino acid at a position corresponding to position 168 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn. In another aspect, the dispersin variant comprises or consists of the substitution H168N, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1

In another aspect, the dispersin variant comprises or consists of a substitution at a position corresponding to position 170 of SEQ ID NO: 1. In another aspect, the amino acid at a position corresponding to position 170 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp, Lys, Ser, His, Asn, Arg, Glu, Phe, Met, Ala, Trp, Tyr, Val, Gln or Pro. In another aspect, the dispersin variant comprises or consists of a substitution selected from the group consisting of: L170D, L170K, L170S, L170H, L170N, L170R, L170E, L170F, L170M, L170A, L170W, L170Y, L170V, L170Q and L170P, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 171 of SEQ ID NO: 1. In another aspect, the amino acid at a position corresponding to position 171 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val, Ala, Trp, Arg, Cys, Glu, Lys, Tyr, Met, Gln or Leu. In another aspect, the dispersin variant comprises or consists of a substitution selected from the group consisting of: D171V, D171A, D171W, D171R, D171C, D171E, D171K, D171Y, D171M, D171Q and D171L, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 173 of SEQ ID NO: 1. In another aspect, the amino acid at a position corresponding to position 173 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys. In another aspect, the dispersin variant comprises or consists of the substitution I173C, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1

In another aspect, the dispersin variant comprises or consists of a substitution at a position corresponding to position 174 of SEQ ID NO: 1. In another aspect, the amino acid at a position corresponding to position 174 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp, His, Met, Asn or Val. In another aspect, the dispersin variant comprises or consists of a substitution selected from the group consisting of: D174W, D174H, D174M, D174N and D174V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 175 of SEQ ID NO: 1. In another aspect, the amino acid at a position corresponding to position 175 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Tyr. In another aspect, the dispersin variant comprises or consists of the substitution F175Y, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 177 of SEQ ID NO: 1. In another aspect, the amino acid at a position corresponding to position 177 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Met. In another aspect, the dispersin variant comprises or consists of the substitution N177M, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 178 of SEQ ID NO: 1. In another aspect, the dispersin variant comprises or consists of a substitution at a position corresponding to position 178 of SEQ ID NO: 1. In another aspect, the amino acid at a position corresponding to position 178 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg, Trp, Ala or Lys. In another aspect, the dispersin variant comprises or consists of a substitution selected from the group consisting of: Q178R, Q178W, Q178A and Q178K, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 179 of SEQ ID NO: 1. In another aspect, the amino acid at a position corresponding to position 179 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr. In another aspect, the dispersin variant comprises or consists of the substitution I179T, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 181 of SEQ ID NO: 1. In another aspect, the amino acid at a position corresponding to position 181 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr, Phe, Gln, Gly, Asn, Cys, Lys, Trp, Val, Asp, Thr or Pro. In another aspect, the dispersin variant comprises or consists of a substitution selected from the group consisting of: S181T, S181F, S181Q, S181G, S181N, S181C, S181K, S181W, S181V, S181D, S181T and S181P, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 185 of SEQ ID NO: 1. In another aspect, the amino acid at a position corresponding to position 185 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Arg, Met, Val or Trp. In another aspect, the dispersin variant comprises or consists of a substitution selected from the group consisting of: E185A, E185R, E185M, E185V and E185W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 186 of SEQ ID NO: 1. In another aspect, the amino acid at a position corresponding to position 186 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp, Glu, Asn, Gln, Leu, Trp, Val, Ile, Lys, Met, Arg or His. In another aspect, the dispersin variant comprises or consists of a substitution selected from the group consisting of: S186D, S186E, S186N, S186Q, S186L, S186W, S186V, S186I, S186K, S186M, S186R and S186H, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 187 of SEQ ID NO: 1. In another aspect, the amino acid at a position corresponding to position 187 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly, Arg, Trp, Val, Cys, Asp or Ser. In another aspect, the dispersin variant comprises or consists of a substitution selected from the group consisting of: K187G, K187R, K187W, K187V, K187C, K187D and K187S, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 188 of SEQ ID NO: 1. In another aspect, the amino acid at a position corresponding to position 188 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro. In another aspect, the dispersin variant comprises or consists of the substitution Y188P, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 189 of SEQ ID NO: 1. In another aspect, the amino acid at a position corresponding to position 189 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with, Leu, Val or Trp. In another aspect, the dispersin variant comprises or consists of a substitution selected from the group consisting of: E189V, E189L and E189W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 199 of SEQ ID NO: 1. In another aspect, the amino acid at a position corresponding to position 199 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Tyr, Met, Cys or Leu. In another aspect, the dispersin variant comprises or consists of a substitution selected from the group consisting of: S199Y, S199M, S199C and S199L, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 200 of SEQ ID NO: 1. In another aspect, the amino acid at a position corresponding to position 200 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp, Asp, Lys, Arg, Met, Phe, Asn or Leu. In another aspect, the dispersin variant comprises or consists of a substitution selected from the group consisting of: E200W, E200D, E200K, E200R, E200M, E200F, E200N and E200L, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 203 of SEQ ID NO: 1. In another aspect, the amino acid at a position corresponding to position 203 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg, Thr, Pro, Cys, Leu, Ser, Met, Gln, Thr, Asp, Gly, Glu or Val. In another aspect, the dispersin variant comprises or consists of a substitution selected from the group consisting of: A203R, A203W, A203P, A203C, A203L, A203S, A203M, A203Q, A203T, A203D, A203G, A203E and A203V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 204 of SEQ ID NO: 1. In another aspect, the amino acid at a position corresponding to position 204 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu, Tyr, Val, Trp or Met. In another aspect, the dispersin variant comprises or consists of a substitution selected from the group consisting of: N204L, N204Y, N204V, N204W and N204M, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 205 of SEQ ID NO: 1. In another aspect, the amino acid at a position corresponding to position 205 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the dispersin variant comprises or consists of the substitution L205I, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 207 of SEQ ID NO: 1. In another aspect, the amino acid at a position corresponding to position 207 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Lys, Ser, Cys, Gly, Asn, Val, Arg, Gln, Glu, Trp or Ala. In another aspect, the dispersin variant comprises or consists of a substitution selected from the group consisting of: D207S, D207C, D207G, D207N, D207V, D207R, D207Q, D207E, D207W, D207K and D207A, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 208 of SEQ ID NO: 1. In another aspect, the amino acid at a position corresponding to position 208 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Val, Cys, Trp, Asp, Thr, Gln, Gly or Leu. In another aspect, the dispersin variant comprises or consists of a substitution selected from the group consisting of: S208A, S208V, S208C, S208W, S208D, S208T, S208Q, S208G and S208L, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 210 of SEQ ID NO: 1. In another aspect, the amino acid at a position corresponding to position 210 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr. In another aspect, the dispersin variant comprises or consists of the substitution S210T, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 215 of SEQ ID NO: 1. In another aspect, the dispersin variant comprises or consists of a substitution at a position corresponding to position 215 of SEQ ID NO: 1. In another aspect, the amino acid at a position corresponding to position 215 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Lys, Arg, Leu or Met. In another aspect, the dispersin variant comprises or consists of a substitution selected from the group consisting of: Q215K, Q215R, Q215L and Q215M, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 217 of SEQ ID NO: 1. In another aspect, the amino acid at a position corresponding to position 217 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val. In another aspect, the dispersin variant comprises or consists of the substitution S217V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 218 of SEQ ID NO: 1. In another aspect, the amino acid at a position corresponding to position 218 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln, Arg, Ala, Val or Leu. In another aspect, the dispersin variant comprises or consists of a substitution selected from the group consisting of: T218Q, T218R, T218A, T218V and T218L, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 221 of SEQ ID NO: 1. In another aspect, the amino acid at a position corresponding to position 221 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn. In another aspect, the dispersin variant comprises or consists of the substitution S221N, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 222 of SEQ ID NO: 1. In another aspect, the amino acid at a position corresponding to position 222 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the dispersin variant comprises or consists of the substitution G222D, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 224 of SEQ ID NO: 1. In another aspect, the amino acid at a position corresponding to position 224 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala or Pro. In another aspect, the dispersin variant comprises or consists of the substitution E224A or E224P, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 225 of SEQ ID NO: 1. In another aspect, the amino acid at a position corresponding to position 225 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly. In another aspect, the dispersin variant comprises or consists of the substitution S225G, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 227 of SEQ ID NO: 1. In another aspect, the amino acid at a position corresponding to position 227 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Gln, Arg, Ser, Thr or Lys. In another aspect, the dispersin variant comprises or consists of the substitution N227A, N227Q, N227R, N227S, N227T or N227K, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of an amino acid at a position corresponding to position 230 of SEQ ID NO: 1. In another aspect, the dispersin variant comprises or consists of a substitution at a position corresponding to position 230 of SEQ ID NO: 1. In another aspect, the amino acid at a position corresponding to position 230 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn, Arg, Trp or Thr. In another aspect, the dispersin variant comprises or consists of a substitution selected from the group consisting of: D230N, D230R, D230W and D230T, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 232 of SEQ ID NO: 1. In another aspect, the amino acid at a position corresponding to position 232 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp or Val. In another aspect, the dispersin variant comprises or consists of the substitution E232D or E232V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 233 of SEQ ID NO: 1. In another aspect, the amino acid at a position corresponding to position 233 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Asp, His, Gln, Arg or Trp. In another aspect, the dispersin variant comprises or consists of a substitution selected from the group consisting of: N233E, N233D, N233H, N233Q, N233R and N233W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 234 of SEQ ID NO: 1. In another aspect, the amino acid at a position corresponding to position 234 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg. In another aspect, the dispersin variant comprises or consists of the substitution W234R, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 235 of SEQ ID NO: 1. In another aspect, the amino acid at a position corresponding to position 235 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp, Ala, Ser, Val, Leu, Met, Asn, His, Glu, Phe, Pro or Ile. In another aspect, the dispersin variant comprises or consists of a substitution selected from the group consisting of: G235W, G235A, G235S, G235V, G235L, G235M, G235N, G235H, G235E, G235F, G235P and G235I, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 237 of SEQ ID NO: 1. In another aspect, the amino acid at a position corresponding to position 237 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp, Tyr, Gly, Met, Asn or Cys. In another aspect, the dispersin variant comprises or consists of a substitution selected from the group consisting of: S237W, S237Y, S237G, S237M, S237N and S237C, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 244 of SEQ ID NO: 1. In another aspect, the amino acid at a position corresponding to position 244 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Met or Cys. In another aspect, the dispersin variant comprises or consists of a substitution selected from the group consisting of: Y244E, Y244M and Y244C, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 249 of SEQ ID NO: 1. In another aspect, the amino acid at a position corresponding to position 249 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln, Arg, Trp, His, Lys or Tyr. In another aspect, the dispersin variant comprises or consists of a substitution selected from the group consisting of: L249Q, L249R, L249W, L249H, L249K and L249Y, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 251 of SEQ ID NO: 1. In another aspect, the amino acid at a position corresponding to position 251 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Leu, Arg, Trp or Asn. In another aspect, the dispersin variant comprises or consists of a substitution selected from the group consisting of S251A, S251L, S251R, S251W and S251N, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 252 of SEQ ID NO: 1. In another aspect, the amino acid at a position corresponding to position 252 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro or Cys. In another aspect, the dispersin variant comprises or consists of the substitution N252P or N252C, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 253 of SEQ ID NO: 1. In another aspect, the amino acid at a position corresponding to position 253 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp or Trp. In another aspect, the dispersin variant comprises or consists of the substitution G253D, or G253W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 254 of SEQ ID NO: 1. In another aspect, the amino acid at a position corresponding to position 254 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile, Leu, Met or Tyr. In another aspect, the dispersin variant comprises or consists of a substitution selected from the group consisting of F254I, F254L, F254M and F254Y, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 256 of SEQ ID NO: 1. In another aspect, the amino acid at a position corresponding to position 256 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Arg or Asp. In another aspect, the dispersin variant comprises or consists of the substitution Q256E, Q256R or Q256D, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 260 of SEQ ID NO: 1. In another aspect, the dispersin variant comprises or consists of a substitution at a position corresponding to position 260 of SEQ ID NO: 1. In another aspect, the amino acid at a position corresponding to position 260 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln, Leu, Cys, Arg, Met, Lys, Ala, Val, Ile, Thr, Glu, Trp or Tyr. In another aspect, the dispersin variant comprises or consists of a substitution selected from the group consisting of N260Q, N260L, N260C, N260R, N260M, N260K, N260A, N260V, N260I, N260T, N260E, N260W and N260Y, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 261 of SEQ ID NO: 1. In another aspect, the amino acid at a position corresponding to position 261 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Asp, Arg or Trp. In another aspect, the dispersin variant comprises or consists of a substitution selected from the group consisting of E261A, E261D, E261R and E261W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 262 of SEQ ID NO: 1. In another aspect, the dispersin variant comprises or consists of a substitution at a position corresponding to position 262 of SEQ ID NO: 1. In another aspect, the amino acid at a position corresponding to position 262 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with His, Phe, Trp or Tyr. In another aspect, the dispersin variant comprises or consists of a substitution selected from the group consisting of Q262H, Q262F, Q262W and Q262Y, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 263 of SEQ ID NO: 1. In another aspect, the amino acid at a position corresponding to position 263 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln, Leu or Lys. In another aspect, the dispersin variant comprises or consists of a substitution selected from the group consisting of M263Q, M263L and M263K, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 264 of SEQ ID NO: 1. In another aspect, the dispersin variant comprises or consists of a substitution at a position corresponding to position 264 of SEQ ID NO: 1. In another aspect, the amino acid at a position corresponding to position 264 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Cys or Asn. In another aspect, the dispersin variant comprises or consists of a substitution selected from the group consisting of D264E, D264C and D264N, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 265 of SEQ ID NO: 1. In another aspect, the amino acid at a position corresponding to position 265 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe. In another aspect, the dispersin variant comprises or consists of the substitution Y265F, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 267 of SEQ ID NO: 1. In another aspect, the amino acid at a position corresponding to position 267 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr or Ser. In another aspect, the dispersin variant comprises or consists of the substitution N267T or N267S, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 268 of SEQ ID NO: 1. In another aspect, the amino acid at a position corresponding to position 268 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Arg, Cys or Met. In another aspect, the dispersin variant comprises or consists of a substitution selected from the group consisting of W268E, W268R, W268C and W268M, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 270 of SEQ ID NO: 1. In another aspect, the amino acid at a position corresponding to position 270 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe. In another aspect, the dispersin variant comprises or consists of the substitution Y270F, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 271 of SEQ ID NO: 1. In another aspect, the amino acid at a position corresponding to position 271 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly or Asp. In another aspect, the dispersin variant comprises or consists of the substitution A271G or A271D, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 272 of SEQ ID NO: 1. In another aspect, the amino acid at a position corresponding to position 272 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp, Met, Pro, Ile, Val or Trp. In another aspect, the dispersin variant comprises or consists of a substitution selected from the group consisting of H272D, H272M, H272P, H272I, H272V and H272W wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 273 of SEQ ID NO: 1. In another aspect, the amino acid at a position corresponding to position 273 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Trp. In another aspect, the dispersin variant comprises or consists of the substitution N273W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 274 of SEQ ID NO: 1. In another aspect, the amino acid at a position corresponding to position 274 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with His, Arg or Ala. In another aspect, the dispersin variant comprises or consists of a substitution selected from the group consisting of K274H, K274R and K274A, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 276 of SEQ ID NO: 1. In another aspect, the amino acid at a position corresponding to position 276 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala, Asn, Lys, Cys, Gly, Leu, Met, Pro, Ser, Val or Trp. In another aspect, the dispersin variant comprises or consists of a substitution selected from the group consisting of F276A, F276N, F276K, F276C, F276G, F276L, F276M, F276P, F276S, F276V and F276W, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 278 of SEQ ID NO: 1. In another aspect, the amino acid at a position corresponding to position 278 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Val, Gln, Ala, Asn or Lys. In another aspect, the dispersin variant comprises or consists of a substitution selected from the group consisting of I278V, I278Q, I278A, I278N and I278K, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 279 of SEQ ID NO: 1. In another aspect, the amino acid at a position corresponding to position 279 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys, Glu, Asn, Asp or Gly. In another aspect, the dispersin variant comprises or consists of a substitution selected from the group consisting of S279C, S279E, S279N, S279D and S279G, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 280 of SEQ ID NO: 1. In another aspect, the amino acid at a position corresponding to position 280 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu or Cys. In another aspect, the dispersin variant comprises or consists of the substitution D280E or D280C, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a deletion of the amino acid at a position corresponding to position 281 of SEQ ID NO: 1. In another aspect, the dispersin variant comprises or consists of a substitution at a position corresponding to position 281 of SEQ ID NO: 1. In another aspect, the amino acid at a position corresponding to position 281 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with His, Ala, Lys, Asn, Cys, Pro or Arg. In another aspect, the dispersin variant comprises or consists of a substitution selected from the group consisting of Y281H, Y281A, Y281K, Y281N, Y281C, Y281P and Y281R, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 282 of SEQ ID NO: 1. In another aspect, the amino acid at a position corresponding to position 282 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn or Glu. In another aspect, the dispersin variant comprises or consists of a substitution selected from the group consisting of Y282N and Y282E, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 283 of SEQ ID NO: 1. In another aspect, the amino acid at a position corresponding to position 283 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the dispersin variant comprises or consists of the substitution H283I, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 284 of SEQ ID NO: 1. In another aspect, the amino acid at a position corresponding to position 284 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu, Ile, Val, Asn, Pro or Thr. In another aspect, the dispersin variant comprises or consists of a substitution selected from the group consisting of A284L, A284I, A284V, A284N, A284P and A284T, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 287 of SEQ ID NO: 1. In another aspect, the amino acid at a position corresponding to position 287 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn. In another aspect, the dispersin variant comprises or consists of the substitution T287N, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 288 of SEQ ID NO: 1. In another aspect, the amino acid at a position corresponding to position 288 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro, Asp, Asn or Lys. In another aspect, the dispersin variant comprises or consists of a substitution selected from the group consisting of S288P, S288D, S288N and S288K, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 290 of SEQ ID NO: 1. In another aspect, the amino acid at a position corresponding to position 290 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the dispersin variant comprises or consists of the substitution V290I, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 291 of SEQ ID NO: 1. In another aspect, the amino acid at a position corresponding to position 291 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg, Leu or Val. In another aspect, the dispersin variant comprises or consists of a substitution selected from the group consisting of K291R, K291L and K291V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 296 of SEQ ID NO: 1. In another aspect, the amino acid at a position corresponding to position 296 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys. In another aspect, the dispersin variant comprises or consists of the substitution T296C, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 300 of SEQ ID NO: 1. In another aspect, the amino acid at a position corresponding to position 300 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp or Ala. In another aspect, the dispersin variant comprises or consists of the substitution E300D or E300A, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 301 of SEQ ID NO: 1. In another aspect, the amino acid at a position corresponding to position 301 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn, Cys or Arg. In another aspect, the dispersin variant comprises or consists of a substitution selected from the group consisting of H301N, H301C and H301R, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 303 of SEQ ID NO: 1. In another aspect, the amino acid at a position corresponding to position 303 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln, Ala, Cys, Lys, Gly, Trp or Arg. In another aspect, the dispersin variant comprises or consists of a substitution selected from the group consisting of T303Q, T303A, T303C, T303K, T303G, T303W and T303R, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 304 of SEQ ID NO: 1. In another aspect, the amino acid at a position corresponding to position 304 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Met or Cys. In another aspect, the dispersin variant comprises or consists of a substitution selected from the group consisting of D304M and D304C, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 305 of SEQ ID NO: 1. In another aspect, the amino acid at a position corresponding to position 305 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Met or Asn. In another aspect, the dispersin variant comprises or consists of the L305M or L305N, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 306 of SEQ ID NO: 1. In another aspect, the amino acid at a position corresponding to position 306 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys. In another aspect, the dispersin variant comprises or consists of the S306C, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 308 of SEQ ID NO: 1. In another aspect, the amino acid at a position corresponding to position 308 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp, Glu, Ala, Val, Gln, Ser, Tyr, Gly, Leu, Thr or Ile. In another aspect, the dispersin variant comprises or consists of a substitution selected from the group consisting of K308D, K308E, K308A, K308V, K308Q, K308S, K308Y, K308G, K308L, K308T and K308I, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 309 of SEQ ID NO: 1. In another aspect, the amino acid at a position corresponding to position 309 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Gly, Cys, Leu, Asp, Gln, Asn, Thr, Ala, Ser, Met, His or Ile. In another aspect, the dispersin variant comprises or consists of a substitution selected from the group consisting of K309E, K309G, K309C, K309L, K309D, K309Q, K309N, K309T, K309A, K309S, K309M, K309H and K309I, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 312 of SEQ ID NO: 1. In another aspect, the amino acid at a position corresponding to position 312 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu, Ala, Gln, Ser, Trp, Leu, Asn or Met. In another aspect, the dispersin variant comprises or consists of a substitution selected from the group consisting of K312E, K312A, K312Q, K312S, K312W, K312L, K312N and K312M, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 314 of SEQ ID NO: 1. In another aspect, the amino acid at a position corresponding to position 314 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu, Val or Ile. In another aspect, the dispersin variant comprises or consists of a substitution selected from the group consisting of E314L, E314V and E314I, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 315 of SEQ ID NO: 1. In another aspect, the amino acid at a position corresponding to position 315 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile or Val. In another aspect, the dispersin variant comprises or consists of the L315I or L315V, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 319 of SEQ ID NO: 1. In another aspect, the amino acid at a position corresponding to position 319 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the dispersin variant comprises or consists of the R319A, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 321 of SEQ ID NO: 1. In another aspect, the amino acid at a position corresponding to position 321 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe. In another aspect, the dispersin variant comprises or consists of the Y321F, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In another aspect, the dispersin variant comprises or consists of a substitution at a position corresponding to position 323 of SEQ ID NO: 1. In another aspect, the amino acid at a position corresponding to position 323 of SEQ ID NO: 1 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg. In another aspect, the dispersin variant comprises or consists of the N323R, wherein the position corresponds to the positions of SEQ ID NO: 1 and wherein the variant has at least at least 60%, at least 65%, at least 70%, at least 75%, at least 80%, at least 85%, at least 90%, at least 95%, such as at least 96%, at least 97%, at least 98%, or at least 99%, but less than 100%, sequence identity to the amino acid sequence shown in SEQ ID NO: 1.

In one aspect, the variant comprises or consists of one or more the substitutions at a position selected from the group consisting of: 2, 3, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 140, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 225, 227, 230, 232, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 and 323, wherein the position corresponds to the positions of SEQ ID NO: 1, wherein the variant has at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide shown in SEQ ID NO: 1 which has dispersin, preferably beta-1,6 N-acetylglucosaminidase activity, and further the variant has at least one improved property compared to a reference enzyme e.g. compared to SEQ ID NO: 1.

In one aspect, the variant comprises or consists of one or more the substitutions at a position selected from the group consisting of: 2, 3, 12, 15, 17, 18, 22, 23, 24, 25, 30, 49, 56, 57, 59, 62, 63, 68, 72, 74, 77, 82, 90, 99, 100, 106, 114, 123, 124, 125, 135, 138, 140, 163, 167, 170, 171, 173, 174, 175, 178, 179, 181, 185, 186, 187, 188, 189, 199, 203, 204, 205, 207, 210, 215, 218, 221, 225, 227, 227, 232, 235, 237, 244, 252, 256, 260, 262, 263, 264, 265, 267, 270, 272, 273, 274, 276, 278, 279, 280, 281, 282, 283, 284, 288, 290, 291, 296, 303, 304, 305, 306, 308, 309, 312, 314, 315, 319, 321, 322 and 323, wherein the position corresponds to the positions of SEQ ID NO: 1, wherein the variant has at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide shown in SEQ ID NO: 1 which has dispersin, preferably beta-1,6 N-acetylglucosaminidase activity, and further the variant has at least one improved property compared to a reference enzyme e.g. compared to SEQ ID NO: 1.

In one aspect, the variant comprises or consists of one or more the substitutions at a position selected from the group consisting of: 31, 33, 36, 73, 75, 94, 141, 144, 241, 277, 294, 297, 299, wherein the position corresponds to the positions of SEQ ID NO: 1, wherein the variant has at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide shown in SEQ ID NO: 1 which has dispersin, preferably beta-1,6 N-acetylglucosaminidase activity, and further the variant has at least one improved property compared to a reference enzyme e.g. compared to SEQ ID NO: 1.

In one aspect, the variant comprises or consists of one or more of the alterations selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19K, E19N, E19P, K22A, K22M, K22V, S23A, S23C, S23E, S23I, S23L, S23R, S23T, S23V, L24I, V25R, D26M, Y30*, Y30A, Y30D, Y30L, Y30M, Y30N, Y30R, Y30T, Y30V, G32L, G32M, G32R, N34D, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80R, K80V, K80W, D81A, D81G, D81L, D81N, D81R, D81S, D81T, D81V, D81W, I82V, L90F, E99Q, E99R, L100S, K103A, K103R, K103V, K104N, K104W, D105N, V106A, V106D, V106E, V106H, V106K, V106L, V106M, V106N, V106Q, V106R, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116N, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124H, Y124I, Y124K, Y124L, Y124M, Y124N, Y124Q, Y124R, Y124T, Y124V, Y124W, D125C, D125G, D125H, D125K, D125Q, D125R, N126V, R127D, R127H, R127K, R127L, R127M, R127Q, R127W, V128A, V128C, V128D, V128L, V128T, D131V, Q135*, Q135A, Q135D, Q135E, Q135K, Q135M, Q135Y, D138K, D138L, D138M, D138N, D138Q, D138R, D138S, D138V, D138W, E139W, V140I, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150A, E150D, E150H, E150K, E150L, E150M, E150N, E150R, E150V, E150W, E150Y, G151A, G151C, G151D, G151L, G151N, G151P, G151S, G151W, K152D, K152L, K152R, S163P, G164D, G164E, G164H, G164S, G164V, V167A, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181K, S181N, S181P, S181Q, S181T, S181V, S181W, E185A, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203Q, A203R, A203S, A203T, A203V, A203W, N204L, N204M, N204V, N204W, N204Y, L205I, D207A, D207C, D207E, D207G, D207K, D207N, D207Q, D207R, D207S, D207V, D207W, S208A, S208C, S208D, S208G, S208L, S208Q, S208T, S208V, S208W, S210T, Q215K, Q215R, Q215M, Q215L, Q215*, S217V, T218A, T218L, T218Q, T218R, T218V, S221N, G222D, E224A, E224P, S225G, N227A, N227Q, N227R, N227S, N227T, N227K, D230*, D230N, D230R, D230T, D230W, E232D, E232V, N233D, N233E, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251A, S251L, S251N, S251R, S251W, N252P, N252C, G253D, G253W, F254I, F254L, F254M, F254Y, Q256D, Q256E, Q256R, N260*, N260A, N260C, N260E, N260I, N260K, N260L, N260M, N260Q, N260R, N260T, N260V, N260W, N260Y, E261*, E261A, E261D, E261R, E261W, Q262*, Q262F, Q262H, Q262W, Q262Y, M263K, M263L, M263Q, D264*, D264C, D264E, D264N, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y281R, Y282E, Y282N, H283I, A284I, A284L, A284N, A284P, A284T, A284V, T287N, S288P, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308E, K308G, K308I, K308L, K308Q, K308S, K308T, K308V, K308Y, K309A, K309C, K309D, K309E, K309G, K309H, K309L, K309M, K309N, K309Q, K309S, K309T, K309I, K312A, K312E, K312L, K312M, K312N, K312Q, K312S, K312W, E314I, E314L, E314V, L315I, L315V, R319A, Y321F and N323R, wherein the position corresponds to the positions of SEQ ID NO: 1, wherein the variant has at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide shown in SEQ ID NO: 1 which has dispersin, preferably beta-1,6 N-acetylglucosaminidase activity, and further the variant has at least one improved property compared to a reference enzyme e.g. compared to SEQ ID NO: 1.

In one aspect, the variant comprises or consists of one or more of the substitutions selected from the group consisting of: D2V, Q3F, Q3I, S12A, H15Y, T17W, T17E, V18L, K22M, S23I, S23C, S23T, S23L, S23V, S23E, V25R, Y30L, A49W, A49Y, S56T, N59D, N59C, N59E, N59R, N59F, N59W, N59V, N62C, N62D, T63C, N68Q, S72D, S72E, I74L, S77A, I82V, L90F, E99Q, L100S, T114S, T114C, Y123W, Y124I, Y124M, Y124R, Y124V, Y124Q, Y124T, Y124K, D125R, D125C, D125G, D125K, D125Q, Q135M, D138R, D138K, D138Q, L170D, L170K, L170S, L170H, D171E, D171K, D171Y, D171M, D171Q, D171L, I173C, D174W, D174H, D174M, D174N, F175Y, Q178K, I179T, S181T, S181F, S181Q, S181G, S181N, S181C, E185R, E185M, E185V, S186K, S186M, S186R, S186H, K187G, Y188P, E189V, S199C, S199L, A203G, A203E, A203V, N204L, N204Y, N204V, L205I, D207N, D207S, D207C, D207G, S210T, Q215R, T218Q, N227T, N227K, E232D, G235W, S237W, Y244M, Y244C, N252P, N252C, Q256E, Q262H, N260Q, M263Q, D264E, Y265F, N267T, N267S, Y270F, H272M, H272P, H272I, H272V, N273W, K274H, F276A, F276N, F276K, F276C, I278V, S279N, S279D, S279G, D280E, D280C, Y281P, Y282N, H283I, A284T, A284L, A284I, S288K, V290I, K291R, T296C, T303Q, D304M, D304C, L305M, L305N, S306C, K308D, K308A, K308V, K308Q, K308S, K308Y, K308G, K308L, K308T, K308I, K309C, K309L, K309D, K309Q, K309N, K309T, K309A, K309S, K309M, K309H, K312A, K312Q, K312S, K312W, K312L, K312N, E314L, E314V, E314I, L315I, R319A and N323R, wherein the position corresponds to the positions of SEQ ID NO: 1, wherein the variant has at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the polypeptide shown in SEQ ID NO: 1 which has dispersin, preferably beta-1,6 N-acetylglucosaminidase activity, and further the variant has at least one improved property compared to a reference enzyme e.g. compared to SEQ ID NO: 1 or compared to SEQ ID NO: 15.

In some aspects, the improved property is increased stability e.g. improved detergent stability, improved in-wash stability and improved thermostability. Some aspects of the invention relate to dispersin variants having an improvement factor above 1 (e.g. measured as HIF), when the dispersin variants are tested for a property of interest in a relevant assay, wherein the property of the reference dispersin is given a value of 1. In some aspects, the property is stability, such as storage stability. Some aspects of the invention relate to dispersin variants having an improvement factor above 1 (e.g. measured as HIF), when the dispersin variants are tested for a property of interest in the assay described in Example 2, 3, 4, 5 or 6, wherein the property of the reference dispersin is given a value of 1. In some aspects, the property is stability, such as storage stability.

In some aspects, the improved property is increased stability e.g. improved detergent stability, improved in-wash stability and improved thermostability. Some aspects of the invention relate to dispersin variants having an improvement factor above 1 when the dispersin variants are tested for a property of interest in a relevant assay, wherein the property of the reference dispersin is given a value of 1. In some aspects, the property is stability, such as storage stability.

In some aspects, the improved property is improved detergent stability.

In some aspects, the improved property is improved protease stability.

In some aspects a variant according to the invention is improved under the measured conditions when the residual activity ratio, defined as $$\text{Residual Activity Ratio}(RAR) = \frac{RA_{variant}}{RA_{reference}}$$

is above 1 compared to the reference dispersin, as shown in Examples 2a and 3. In some aspects, the variant is improved compared to the reference dispersin.

In some aspects, the variants according to the invention have improved stability relative to a reference dispersin measured as a residual activity ratio (RAR) that is greater than 1.0.

The Residual Activity Ratio (RAR) for the dispersin variants of the invention may be calculated as $RA_{variant}/RA_{reference}$. Improved variants were identified as variants having residual activity ratio (RAR) larger than 1.0 compared to the reference dispersin, as shown in Example 2a and 3.

In some aspects, the variants according to the invention have improved stability relative to a reference dispersin measured as an Half-life Improvement Factor (HIF) that is greater than 1.0.

The Half-life Improvement Factor (HIF) for the dispersin variants of the invention may be calculated as $T_{1/2variant}/T_{1/2reference}$. Improved variants were identified as variants having a Half-life Improvement Factor HIF larger than 1.0 compared to the reference dispersin, as shown in Example 2b. Improved alterations e.g. substitutions according to the invention are those which result in an improvement factor e.g. HIF or RAR above 1 or is a variant which have at least one improved property compared to the starting molecule i.e. the precursor, reference parent polypeptide etc. In a particular preferred aspect, dispersin variants comprising the alterations according to the invention results in dispersin variants having improved stability where HIF>1.0. In some aspects, the variants according to the invention have a Half-life Improvement Factor (HIF) which is at least 1.1; 1.2; 1.3; 1.4; 1.5; 1.6; 1.7; 1.8; 1.9; 2.0; 2.1; 2.2; 2.3; 2.4; 2.5; 2.6; 2.7, 2.8; 2.9; 3.0, 3.1; 3.2; 3.3; 3.4; 3.5, 3.6, 3.7, 3.8, 3.9; 4.0, 4.1; 4.2; 4.3; 4.4; 4.5, 4.6, 4.7, 4.8, 4.9, 5.0, 5.1; 5.2; 5.3; 5.4; 5.5, 5.6, 5.7, 5.8, 5.9; 3.0, 6.1; 6.2; 6.3; 6.4; 6.5, 6.6, 6.7, 6.8, 6.9; 7.0, 7.1; 7.2; 7.3; 7.4; 7.5, 7.6, 7.7, 7.8, 7.9; 8.0, 8.1; 8.2; 8.3; 8.4; 8.5, 8.6, 8.7, 8.8, 8.9; 9.0, 9.1; 9.2; 9.3; 9.4; 9.5, 9.6, 9.7, 9.8, 9.9; 10.0, 10.1; 10.2; 10.3; 10.4; 10.5, 10.6, 10.7, 10.8, 10.9; 12, 15, 16, 20, 25 or 30 compared to a reference dispersin e.g. SEQ ID NO: 1 or compared to SEQ ID NO: 15.

In a preferred aspect, the combination of mutations according to the invention results in dispersin variants having improved stability, where RAR>1.0. In some aspects, the variants according to the invention have a Residual Activity Ratio (RAR) which is at least 1.1; 1.2; 1.3; 1.4; 1.5; 1.6; 1.7; 1.8; 1.9; 2.0; 2.1; 2.2; 2.3; 2.4; 2.5; 2.6; 2.7, 2.8; 2.9; 3.0, 3.1; 3.2; 3.3; 3.4; 3.5, 3.6, 3.7, 3.8, 3.9; 4.0, 4.1; 4.2; 4.3; 4.4; 4.5, 4.6, 4.7, 4.8, 4.9, 5.0, 5.1; 5.2; 5.3; 5.4; 5.5, 5.6, 5.7, 5.8, 5.9; 3.0, 6.1; 6.2; 6.3; 6.4; 6.5, 6.6, 6.7, 6.8, 6.9; 7.0, 7.1; 7.2; 7.3; 7.4; 7.5, 7.6, 7.7, 7.8, 7.9; 8.0, 8.1; 8.2; 8.3; 8.4; 8.5, 8.6, 8.7, 8.8, 8.9; 9.0, 9.1; 9.2; 9.3; 9.4; 9.5, 9.6, 9.7, 9.8, 9.9; 10.0, 10.1; 10.2; 10.3; 10.4; 10.5, 10.6, 10.7, 10.8, 10.9; 12, 15, 16, 20, 25 or 30 compared to a reference dispersin e.g. SEQ ID NO: 1 or compared to SEQ ID NO: 15.

One preferred embodiment relates to a dispersin variant having improved stability, wherein HIF>1.0, compared to SEQ ID NO: 1 or compared to SEQ ID NO: 15. One preferred embodiment relates to a dispersin variant having improved stability, wherein the Half-life Improvement Factor is at least 1.5, compared to SEQ ID NO: 1 or compared to SEQ ID NO: 15, when measured as described in Example 2a.

One preferred embodiment relates to a dispersin variant having improved stability, wherein RAR>1.0, compared to SEQ ID NO: 1 or compared to SEQ ID NO: 15. One preferred embodiment relates to a dispersin variant having improved stability, wherein the residual activity ratio (RAR) is at least 1.5, compared to SEQ ID NO: 1 or compared to SEQ ID NO: 15, when measured as described in Example 2a and 3.

One preferred embodiment relates to a dispersin variant having improved stability, wherein HIF>1.0 compared to SEQ ID NO: 1. One preferred embodiment relates to a dispersin variant having improved stability, wherein the Half-life Improvement Factor (HIF) is at least 1.2 e.g. 1.5, compared to SEQ ID NO: 1 or compared to SEQ ID NO: 15, wherein HIF is calculated as $T_{1/2dispersinvariant}/T_{1/2reference}$ and the half-life ($T_{1/2}$ in minutes) for the dispersin variants and the dispersin reference (e.g. SEQ ID NO: 1 or 15) is calculated as: 20 minutes×LN(0.5)/LN(RA) and the residual activity (RA) for each dispersin variant and the reference dispersin (e.g. SEQ ID NO: 1 or 15) is calculated as: slope (stress sample, 56° C. for 60 min)/slope(unstressed sample, 21° C. for 60 min), e.g. as described in Example 2b.

One preferred embodiment relates to a dispersin variant having improved stability, wherein residual activity ratio (RAR)>1.0 compared to SEQ ID NO: 1 or compared to SEQ ID NO: 15. One preferred embodiment relates to a dispersin variant having improved stability, wherein the residual activity ratio (RAR) is at least 1.2 e.g. 1.5, compared to SEQ ID NO: 1 or compared to SEQ ID NO: 15, wherein RAR is calculated as, $$\text{Residual Activity Ratio } (RAR) = \frac{RA_{variant}}{RA_{reference}}$$

as described in 2a and 3, in the Example section.

One preferred aspect of the invention relates to a dispersin variant, which compared to a dispersin with SEQ ID NO: 1, comprises an alteration e.g. substitution at a position selected from the group consisting of: 2, 3, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 140, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 225, 227, 230, 232, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 and 323, wherein the positions correspond to the positions of SEQ ID NO: 1 (numbering according to SEQ ID NO: 1), wherein the variant has a sequence identity to the polypeptide shown in SEQ ID NO: 1 or the polypeptide sequence shown in SEQ ID NO: 15 of at least 65%, at least 70%, at least 75%, at least 80%, at least 85%, at least 90%, at least 91%, at least 92%, at least 93%, at least 94%, at least 95%, at least 96%, at least 97%, at least 98% or at least 99% but less than 100%, wherein the variant has hexosaminidase e.g. beta-1,6 N-acetylglucosaminidase activity and wherein the variant has improved stability, measured as having an improvement factor e.g. RAR or HIF>1.0, compared to the polypeptide sequence shown in SEQ ID NO: 1 or compared to the polypeptide sequence shown in SEQ ID NO: 15.

One preferred aspect of the invention relates to a dispersin variant, which compared to a dispersin with SEQ ID NO: 1, comprises an alteration e.g. substitution at a position selected from the group consisting of: 2, 3, 12, 15, 17, 18, 22, 23, 24, 25, 30, 49, 56, 57, 59, 62, 63, 68, 72, 74, 77, 82, 90, 99, 100, 106, 114, 123, 124, 125, 135, 138, 140, 163, 167, 170, 171, 173, 174, 175, 178, 179, 181, 185, 186, 187, 188, 189, 199, 203, 204, 205, 207, 210, 215, 218, 221, 225, 227, 227, 232, 235, 237, 244, 252, 256, 260, 262, 263, 264, 265, 267, 270, 272, 273, 274, 276, 278, 279, 280, 281, 282, 283, 284, 288, 290, 291, 296, 303, 304, 305, 306, 308, 309, 312, 314, 315, 319, 321, 322 and 323, wherein the positions correspond to the positions of SEQ ID NO: 1 (numbering according to SEQ ID NO: 1), wherein the variant has a sequence identity to the polypeptide shown in SEQ ID NO: 1 or the polypeptide sequence shown in SEQ ID NO: 15 of at least 65%, at least 70%, at least 75%, at least 80%, at least 85%, at least 90%, at least 91%, at least 92%, at least 93%, at least 94%, at least 95%, at least 96%, at least 97%, at least 98% or at least 99% but less than 100%, wherein the variant has hexosaminidase e.g. beta-1,6 N-acetylglucosaminidase activity and wherein the variant has improved stability, measured as having an improvement factor e.g. RAR or HIF>1.0, compared to the polypeptide sequence shown in SEQ ID NO: 1 or compared to the polypeptide sequence shown in SEQ ID NO: 15.

One preferred aspect of the invention relates to a dispersin variant, which compared to a dispersin with SEQ ID NO: 1, comprises an alteration e.g. substitution at a position selected from the group consisting of: 31, 33, 36, 73, 75, 94, 141, 144, 241, 277, 294, 297, 299, wherein the positions correspond to the positions of SEQ ID NO: 1 (numbering according to SEQ ID NO: 1), wherein the variant has a sequence identity to the polypeptide shown in SEQ ID NO: 1 or the polypeptide sequence shown in SEQ ID NO: 15 of at least 65%, at least 70%, at least 75%, at least 80%, at least 85%, at least 90%, at least 91%, at least 92%, at least 93%, at least 94%, at least 95%, at least 96%, at least 97%, at least 98% or at least 99% but less than 100%, wherein the variant has hexosaminidase e.g. beta-1,6 N-acetylglucosaminidase activity and wherein the variant has improved stability, measured as having an improvement factor e.g. RAR or HIF>1.0, compared to the polypeptide sequence shown in SEQ ID NO: 1 or compared to the polypeptide sequence shown in SEQ ID NO: 15.

One preferred aspect of the invention relates to a dispersin variant, which compared to a dispersin with SEQ ID NO: 1, comprises one or more alteration e.g. substitution selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19K, E19N, E19P, K22A, K22M, K22V, S23A, S23C, S23E, S23I, S23L, S23R, S23T, S23V, L24I, V25R, D26M, Y30*, Y30A, Y30D, Y30L, Y30M, Y30N, Y30R, Y30T, Y30V, G32L, G32M, G32R, N34D, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68K, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80R, K80V, K80W, D81A, D81G, D81L, D81N, D81R, D81S, D81T, D81V, D81W, I82V, L90F, E99Q, E99R, L100S, K103A, K103R, K103V, K104N, K104W, D105N, V106A, V106D, V106E, V106H, V106K, V106L, V106M, V106N, V106Q, V106R, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116N, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124H, Y124I, Y124K, Y124L, Y124M, Y124N, Y124Q, Y124R, Y124T, Y124V, Y124W, D125C, D125G, D125H, D125K, D125Q, D125R, N126V, R127D, R127H, R127K, R127L, R127M, R127Q, R127W, V128A, V128C, V128D, V128L, V128T, D131V, Q135*, Q135A, Q135D, Q135E, Q135K, Q135M, Q135Y, D138K, D138L, D138M, D138N, D138Q, D138R, D138S, D138V, D138W, E139W, V140I, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150A, E150D, E150H, E150K, E150L, E150M, E150N, E150R, E150V, E150W, E150Y, G151A, G151C, G151D, G151L, G151N, G151P, G151S, G151W, K152D, K152L, K152R, S163P, G164D, G164E, G164H, G164S, G164V, V167A, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181K, S181N, S181P, S181Q, S181T, S181V, S181W, E185A, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203Q, A203R, A203S, A203T, A203V, A203W, N204L, N204M, N204V, N204W, N204Y, L205I, D207A, D207C, D207E, D207G, D207K, D207N, D207Q, D207R, D207S, D207V, D207W, S208A, S208C, S208D, S208G, S208L, S208Q, S208T, S208V, S208W, S210T, Q215K, Q215R, Q215M, Q215L, Q215*, S217V, T218A, T218L, T218Q, T218R, T218V, S221N, G222D, E224A, E224P, S225G, N227A, N227Q, N227R, N227S, N227T, N227K, D230*, D230N, D230R, D230T, D230W, E232D, E232V, N233D, N233E, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251A, S251L, S251N, S251R, S251W, N252P, N252C, G253D, G253W, F254I, F254L, F254M, F254Y, Q256D, Q256E, Q256R, N260*, N260A, N260C, N260E, N260I, N260K, N260L, N260M, N260Q, N260R, N260T, N260V, N260W, N260Y, E261*, E261A, E261D, E261R, E261W, Q262*, Q262F, Q262H, Q262W, Q262Y, M263K, M263L, M263Q, D264*, D264C, D264E, D264N, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y281R, Y282E, Y282N, H283I, A284I, A284L, A284N, A284P, A284T, A284V, T287N, S288P, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308E, K308G, K308I, K308L, K308Q, K308S, K308T, K308V, K308Y, K309A, K309C, K309D, K309E, K309G, K309H, K309L, K309M, K309N, K309Q, K309S, K309T, K309I, K312A, K312E, K312L, K312M, K312N, K312Q, K312S, K312W, E314I, E314L, E314V, L315I, L315V, R319A, Y321F and N323R, wherein the positions correspond to the positions of SEQ ID NO: 1 (numbering according to SEQ ID NO: 1), wherein the variant has a sequence identity to the polypeptide shown in SEQ ID NO: 1 or to the polypeptide sequence shown in SEQ ID NO: 15 of at least 65%, at least 70%, at least 75%, at least 80%, at least 85%, at least 90%, at least 91%, at least 92%, at least 93%, at least 94%, at least 95%, at least 96%, at least 97%, at least 98% or at least 99% but less than 100%, wherein the variant has hexosaminidase e.g. beta-1,6 N-acetylglucosaminidase activity and wherein the variant has improved stability, measured as having an improvement factor e.g. RAR or HIF>1.0, compared to the polypeptide sequence shown in SEQ ID NO: 1 or compared to the polypeptide sequence shown in SEQ ID NO: 15.

One preferred aspect of the invention relates to a dispersin variant, which compared to a dispersin with SEQ ID NO: 1, comprises one or more alteration e.g. substitution selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19N, E19P, K22A, K22M, K22V, S23C, S23E, S23I, S23L, S23R, S23T, S23V, V25R, D26M, Y30*, Y30D, Y30L, Y30M, Y30N, Y30R, Y30T, Y30V, G32L, G32M, G32R, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80V, K80W, D81A, D81G, D81L, D81R, D81S, D81T, D81V, D81W, I82V, L90F, E99Q, E99R, L100S, K103A, K103R, K104N, K104W, D105N, V106A, V106D, V106E, V106H, V106K, V106L, V106M, V106N, V106Q, V106W, V106Y, K107A, K107C, K107L, K107M, K107T, K107V, K107W, N110M, N110R, N110V, D111A, D111E, D111N, D111Q, D111R, D111V, D111W, V113T, T114C, T114S, Y116D, Y116N, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124I, Y124K, Y124L, Y124M, Y124Q, Y124R, Y124T, Y124V, Y124W, D125C, D125G, D125K, D125Q, D125R, N126V, R127D, R127H, R127K, R127L, R127M, R127Q, R127W, V128C, V128L, V128T, D131V, Q135*, Q135A, Q135D, Q135E, Q135K, Q135M, Q135Y, D138K, D138L, D138M, D138Q, D138R, D138S, D138V, D138W, E139W, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150D, E150H, E150K, E150L, E150M, E150N, E150R, E150V, E150W, E150Y, G151A, G151C, G151D, G151L, G151N, G151P, G151S, G151W, K152D, K152L, K152R, G164D, G164E, G164H, G164S, G164V, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181N, S181P, S181Q, S181T, S181V, S181W, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203R, A203S, A203T, A203V, A203W, N204L, N204M, N204V, N204W, N204Y, L205I, D207A, D207C, D207E, D207G, D207N, D207Q, D207S, D207V, D207W, S208A, S208C, S208D, S208G, S208L, S208Q, S208T, S208V, S208W, S210T, Q215R, Q215M, Q215L, Q215*, S217V, T218A, T218L, T218Q, T218R, T218V, G222D, E224A, E224P, N227A, N227Q, N227R, N227S, N227T, N227K, D230*, D230R, D230T, D230W, E232D, E232V, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251L, S251N, S251R, S251W, N252P, N252C, G253D, G253W, F254I, F254L, F254M, F254Y, Q256E, Q256R, N260*, N260A, N260C, N260E, N260I, N260K, N260L, N260M, N260Q, N260R, N260V, N260W, N260Y, E261*, E261A, E261D, E261R, E261W, Q262*, Q262F, Q262H, Q262W, Q262Y, M263K, M263L, M263Q, D264*, D264C, D264E, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y281R, Y282E, Y282N, H283I, A284I, A284L, A284N, A284P, A284T, A284V, T287N, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308G, K308I, K308L, K308Q, K308S, K308T, K308V, K308Y, K309A, K309C, K309D, K309E, K309G, K309L, K309M, K309Q, K309S, K309T, K309I, K312A, K312E, K312L, K312M, K312N, K312Q, K312S, K312W, E314I, E314L, E314V, L315I, L315V, R319A, and N323R, wherein the positions correspond to the positions of SEQ ID NO: 1 (numbering according to SEQ ID NO: 1), wherein the variant has a sequence identity to the polypeptide shown in SEQ ID NO: 1 or to the polypeptide sequence shown in SEQ ID NO: 15 of at least 65%, at least 70%, at least 75%, at least 80%, at least 85%, at least 90%, at least 91%, at least 92%, at least 93%, at least 94%, at least 95%, at least 96%, at least 97%, at least 98% or at least 99% but less than 100%, wherein the variant has hexosaminidase e.g. beta-1,6 N-acetylglucosaminidase activity and wherein the variant has improved stability, measured as having an improvement factor e.g. RAR or HIF>1.0, compared to the polypeptide sequence shown in SEQ ID NO: 1 or compared to the polypeptide sequence shown in SEQ ID NO: 15.

One preferred aspect of the invention relates to a dispersin variant, which compared to a dispersin with SEQ ID NO: 1, comprises one or more alteration e.g. substitution selected from the group consisting of: D2V, Q3F, Q3I, S12A, H15Y, T17W, T17E, V18L, K22M, S23I, S23C, S23T, S23L, S23V, S23E, V25R, Y30L, A49W, A49Y, S56T, N59D, N59C, N59E, N59R, N59F, N59W, N59V, N62C, N62D, T63C, N68Q, S72D, S72E, I74L, S77A, I82V, L90F, E99Q, L100S, T114S, T114C, Y123W, Y124I, Y124M, Y124R, Y124V, Y124Q, Y124T, Y124K, D125R, D125C, D125G, D125K, D125Q, Q135M, D138R, D138K, D138Q, L170D, L170K, L170S, L170H, D171E, D171K, D171Y, D171M, D171Q, D171L, I173C, D174W, D174H, D174M, D174N, F175Y, Q178K, I179T, S181T, S181F, S181Q, S181G, S181N, S181C, E185R, E185M, E185V, S186K, S186M, S186R, S186H, K187G, Y188P, E189V, S199C, S199L, A203G, A203E, A203V, N204L, N204Y, N204V, L205I, D207N, D207S, D207C, D207G, S210T, Q215R, T218Q, N227T, N227K, E232D, G235W, S237W, Y244M, Y244C, N252P, N252C, Q256E, N260Q, Q262H, M263Q, D264E, Y265F, N267T, N267S, Y270F, H272M, H272P, H272I, H272V, N273W, K274H, F276A, F276N, F276K, F276C, I278V, S279N, S279D, S279G, D280E, D280C, Y281P, Y282N, H283I, A284T, A284L, A284I, S288K, V290I, K291R, T296C, T303Q, D304M, D304C, L305M, L305N, S306C, K308D, K308A, K308V, K308Q, K308S, K308Y, K308G, K308L, K308T, K308I, K309C, K309L, K309D, K309Q, K309N, K309T, K309A, K309S, K309M, K309H, K312A, K312Q, K312S, K312W, K312L, K312N, E314L, E314V, E314I, L315I, R319A and N323R, wherein the positions correspond to the positions of SEQ ID NO: 1 (numbering according to SEQ ID NO: 1), wherein the variant has a sequence identity to the polypeptide shown in SEQ ID NO: 1 the polypeptide sequence shown in SEQ ID NO: 15 of at least 65%, at least 70%, at least 75%, at least 80%, at least 85%, at least 90%, at least 91%, at least 92%, at least 93%, at least 94%, at least 95%, at least 96%, at least 97%, at least 98% or at least 99% but less than 100%, wherein the variant has hexosaminidase e.g. beta-1,6 N-acetylglucosaminidase activity and wherein the variant has improved stability, measured as having an improvement factor e.g. RAR or HIF>1.0, compared to the polypeptide sequence shown in SEQ ID NO: 1 or compared to the polypeptide sequence shown in SEQ ID NO: 15.

In some preferred aspects, a dispersin variant of the invention comprise an alteration at one or more positions selected from the group consisting of 2, 3, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 140, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 225, 227, 230, 232, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 and 323, wherein the variant has at least 60%, at least 65%, at least 70%, at least 75%, at least 80%, at least 85%, at least 90%, at least 95%, such as at least 96%, at least 97%, at least 98%, or at least 99%, but less than 100%, sequence identity to the polypeptide shown in SEQ ID NO: 1, wherein each position corresponds to the position of the polypeptide shown in SEQ ID NO: 1 (numbering according to SEQ ID NO: 1) and wherein the variant has at least one improved property compared to the parent dispersin e.g. a dispersin comprising the polypeptide having the amino acid sequence shown in SEQ ID NO: 1, preferably the improved property is improved stability, wherein stability is tested as described in example 2a, 2b or 3.

In some preferred aspects, a dispersin variant of the invention comprise an alteration at one or more positions selected from the group consisting of 2, 3, 12, 15, 17, 18, 22, 23, 24, 25, 30, 49, 56, 57, 59, 62, 63, 68, 72, 74, 77, 82, 90, 99, 100, 106, 114, 123, 124, 125, 135, 138, 140, 163, 167, 170, 171, 173, 174, 175, 178, 179, 181, 185, 186, 187, 188, 189, 199, 203, 204, 205, 207, 210, 215, 218, 221, 225, 227, 232, 235, 237, 244, 252, 256, 260, 262, 263, 264, 265, 267, 270, 272, 273, 274, 276, 278, 279, 280, 281, 282, 283, 284, 288, 290, 291, 296, 303, 304, 305, 306, 308, 309, 312, 314, 315, 319, 321, 322 and 323, wherein the variant has at least 60%, at least 65%, at least 70%, at least 75%, at least 80%, at least 85%, at least 90%, at least 95%, such as at least 96%, at least 97%, at least 98%, or at least 99%, but less than 100%, sequence identity to the polypeptide shown in SEQ ID NO: 1, wherein each position corresponds to the position of the polypeptide shown in SEQ ID NO: 1 (numbering according to SEQ ID NO: 1) and wherein the variant has at least one improved property compared to the parent dispersin e.g. a dispersin comprising the polypeptide having the amino acid sequence shown in SEQ ID NO: 1, preferably the improved property is improved stability, wherein stability is tested as described in example 2a, 2b or 3.

In some preferred aspects, a dispersin variant of the invention comprise an alteration at one or more positions selected from the group consisting of: 31, 33, 36, 73, 75, 94, 141, 144, 241, 277, 294, 297, 299, wherein the variant has at least 60%, at least 65%, at least 70%, at least 75%, at least 80%, at least 85%, at least 90%, at least 95%, such as at least 96%, at least 97%, at least 98%, or at least 99%, but less than 100%, sequence identity to the polypeptide shown in SEQ ID NO: 1, wherein each position corresponds to the position of the polypeptide shown in SEQ ID NO: 1 (numbering according to SEQ ID NO: 1) and wherein the variant has at least one improved property compared to the parent dispersin e.g. a dispersin comprising the polypeptide having the amino acid sequence shown in SEQ ID NO: 1, preferably the improved property is improved stability, wherein stability is tested as described in example 2a, 2b or 3.

In some preferred aspects, a dispersin variant of the invention comprise one or more alteration selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19K, E19N, E19P, K22A, K22M, K22V, S23A, S23C, S23E, S23I, S23L, S23R, S23T, S23V, L24I, V25R, D26M, Y30*, Y30A, Y30D, Y30L, Y30M, Y30N, Y30R, Y30T, Y30V, G32L, G32M, G32R, N34D, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80R, K80V, K80W, D81A, D81G, D81L, D81N, D81R, D81S, D81T, D81V, D81W, I82V, L90F, E99Q, E99R, L100S, K103A, K103R, K103V, K104N, K104W, D105N, V106A, V106D, V106E, V106H, V106K, V106L, V106M, V106N, V106Q, V106R, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116N, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124H, Y124I, Y124K, Y124L, Y124M, Y124N, Y124Q, Y124R, Y124T, Y124V, Y124W, D125C, D125G, D125H, D125K, D125Q, D125R, N126V, R127D, R127H, R127K, R127L, R127M, R127Q, R127W, V128A, V128C, V128D, V128L, V128T, D131V, Q135*, Q135A, Q135D, Q135E, Q135K, Q135M, Q135Y, D138K, D138L, D138M, D138N, D138Q, D138R, D138S, D138V, D138W, E139W, V140I, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150A, E150D, E150H, E150K, E150L, E150M, E150N, E150R, E150V, E150W, E150Y, G151A, G151C, G151D, G151L, G151N, G151P, G151S, G151W, K152D, K152L, K152R, S163P, G164D, G164E, G164H, G164S, G164V, V167A, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181K, S181N, S181P, S181Q, S181T, S181V, S181W, E185A, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203Q, A203R, A203S, A203T, A203V, A203W, N204L, N204M, N204V, N204W, N204Y, L205I, D207A, D207C, D207E, D207G, D207K, D207N, D207Q, D207R, D207S, D207V, D207W, S208A, S208C, S208D, S208G, S208L, S208Q, S208T, S208V, S208W, S210T, Q215K, Q215R, Q215M, Q215L, Q215*, S217V, T218A, T218L, T218Q, T218R, T218V, S221N, G222D, E224A, E224P, S225G, N227A, N227Q, N227R, N227S, N227T, N227K, D230*, D230N, D230R, D230T, D230W, E232D, E232V, N233D, N233E, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251A, S251L, S251N, S251R, S251W, N252P, N252C, G253D, G253W, F254L, F254M, F254Y, Q256D, Q256E, Q256R, N260*, N260A, N260C, N260E, N260I, N260K, N260L, N260M, N260Q, N260R, N260T, N260V, N260W, N260Y, E261*, E261A, E261D, E261R, E261W, Q262*, Q262F, Q262H, Q262W, Q262Y, M263K, M263L, M263Q, D264*, D264C, D264E, D264N, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y281R, Y282E, Y282N, H283I, A284I, A284L, A284N, A284P, A284T, A284V, T287N, S288P, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308E, K308G, K308I, K308L, K308Q, K308S, K308T, K308V, K308Y, K309A, K309C, K309D, K309E, K309G, K309H, K309L, K309M, K309N, K309Q, K309S, K309T, K309I, K312A, K312E, K312L, K312M, K312N, K312Q, K312S, K312W, E314I, E314L, E314V, L315I, L315V, R319A, Y321F and N323R, wherein the variant has at least 60%, at least 65%, at least 70%, at least 75%, at least 80%, at least 85%, at least 90%, at least 95%, such as at least 96%, at least 97%, at least 98%, or at least 99%, but less than 100%, sequence identity to the polypeptide shown in SEQ ID NO: 1, wherein each position corresponds to the position of the polypeptide shown in SEQ ID NO: 1 (numbering according to SEQ ID NO: 1) and wherein the variant has at least one improved property compared to the parent dispersin e.g. a dispersin comprising the polypeptide having the amino acid sequence shown in SEQ ID NO: 1, preferably the improved property is improved stability, wherein stability is tested as described in example 2a, 2b or 3.

In some preferred aspects, a dispersin variant of the invention comprise one or more alteration selected from the group consisting of D2V, Q3F, Q3I, S12A, H15Y, T17W, T17E, V18L, K22M, S23I, S23C, S23T, S23L, S23V, S23E, V25R, Y30L, A49W, A49Y, S56T, N59D, N59C, N59E, N59R, N59F, N59W, N59V, N62C, N62D, T63C, N68Q, S72D, S72E, I74L, S77A, I82V, L90F, E99Q, L100S, T114S, T114C, Y123W, Y124I, Y124M, Y124R, Y124V, Y124Q, Y124T, Y124K, D125R, D125C, D125G, D125K, D125Q, Q135M, D138R, D138K, D138Q, L170D, L170K, L170S, L170H, D171E, D171K, D171Y, D171M, D171Q, D171L, I173C, D174W, D174H, D174N, F175Y, Q178K, I179T, S181T, S181F, S181Q, S181G, S181N, S181C, E185R, E185M, E185V, S186K, S186M, S186R, S186H, K187G, Y188P, E189V, S199C, S199L, A203G, A203E, A203V, N204L, N204Y, N204V, L205I, D207N, D207S, D207C, D207G, S210T, Q215R, T218K, T218Q, N227T, N227K, E232D, G235W, S237W, Y244M, Y244C, N252P, N252C, Q256E, N260Q, Q262H, M263Q, D264E, Y265F, N267T, N267S, Y270F, H272M, H272P, H272I, H272V, N273W, K274H, F276A, F276N, F276K, F276C, I278V, S279N, S279D, S279G, D280E, D280C, Y281P, Y282N, H283I, A284T, A284L, A284I, S288K, V290I, K291R, T296C, T303Q, D304M, D304C, L305M, L305N, S306C, K308D, K308A, K308V, K308Q, K308S, K308Y, K308G, K308L, K308T, K308I, K309C, K309L, K309D, K309Q, K309N, K309T, K309A, K309S, K309M, K309H, K312A, K312Q, K312S, K312W, K312L, K312N, E314L, E314V, E314I, L315I, R319A and N323R, wherein the variant has at least 60%, at least 65%, at least 70%, at least 75%, at least 80%, at least 85%, at least 90%, at least 95%, such as at least 96%, at least 97%, at least 98%, or at least 99%, but less than 100%, sequence identity to the polypeptide shown in SEQ ID NO: 1, wherein each position corresponds to the position of the polypeptide shown in SEQ ID NO: 1 (numbering according to SEQ ID NO: 1), and wherein the variant has at least one improved property compared to the parent dispersin e.g. a dispersin comprising the polypeptide having the amino acid sequence shown in SEQ ID NO: 1, preferably the improved property is improved stability, wherein stability is tested as described in example 2a, 2b or 3.

In some preferred aspects, a dispersin variant of the invention comprise an alteration at one or more positions selected from the group consisting of 2, 3, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 140, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 225, 227, 230, 232, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 and 323, wherein each position corresponds to the position of the polypeptide of SEQ ID NO: 1, wherein each alteration provides a dispersin variant having an increase in stability measured as half-life improvement factor, HIF or residual activity ratio, RAR, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent dispersin e.g. a dispersin comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In some preferred aspects, a dispersin variant of the invention comprise an alteration at one or more positions selected from the group consisting of: 2, 3, 12, 15, 17, 18, 22, 23, 24, 25, 30, 49, 56, 57, 59, 62, 63, 68, 72, 74, 77, 82, 90, 99, 100, 106, 114, 123, 124, 125, 135, 138, 140, 163, 167, 170, 171, 173, 174, 175, 178, 179, 181, 185, 186, 187, 188, 189, 199, 203, 204, 205, 207, 210, 215, 218, 221, 225, 227, 232, 235, 237, 244, 252, 256, 260, 262, 263, 264, 265, 267, 270, 272, 273, 274, 276, 278, 279, 280, 281, 282, 283, 284, 288, 290, 291, 296, 303, 304, 305, 306, 308, 309, 312, 314, 315, 319, 321, 322 and 323, wherein each substitution provides a dispersin variant having an increase in stability measured as half-life improvement factor, HIF or residual activity ratio, RAR, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent dispersin e.g. a dispersin comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1) and preferably wherein the variant has hexosaminidase e.g. beta-1,6 N-acetylglucosaminidase activity.

In some preferred aspects, a dispersin variant of the invention comprise an alteration at one or more positions selected from the group consisting of: 31, 33, 36, 73, 75, 94, 141, 144, 241, 277, 294, 297, 299, wherein each substitution provides a dispersin variant having an increase in stability measured as half-life improvement factor, HIF or residual activity ratio, RAR, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent dispersin e.g. a dispersin comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1) and preferably wherein the variant has hexosaminidase e.g. beta-1,6 N-acetylglucosaminidase activity.

In some preferred aspects, a dispersin variant of the invention comprises one or more alteration (compared to SEQ ID NO: 1), wherein the alteration is selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19K, E19N, E19P, K22A, K22M, K22V, S23A, S23C, S23E, S23I, S23L, S23R, S23T, S23V, L24I, V25R, D26M, Y30*, Y30A, Y30D, Y30L, Y30M, Y30N, Y30R, Y30T, Y30V, G32L, G32M, G32R, N34D, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80R, K80V, K80W, D81A, D81G, D81L, D81N, D81R, D81S, D81T, D81V, D81W, I82V, L90F, E99Q, E99R, L100S, K103A, K103R, K103V, K104N, K104W, D105N, V106A, V106D, V106E, V106H, V106K, V106L, V106M, V106N, V106Q, V106R, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116N, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124H, Y124I, Y124K, Y124L, Y124M, Y124N, Y124Q, Y124R, Y124T, Y124V, Y124W, D125C, D125G, D125H, D125K, D125Q, D125R, N126V, R127D, R127H, R127K, R127L, R127M, R127Q, R127W, V128A, V128C, V128D, V128L, V128T, D131V, Q135*, Q135A, Q135D, Q135E, Q135K, Q135M, Q135Y, D138K, D138L, D138M, D138N, D138Q, D138R, D138S, D138V, D138W, E139W, V140I, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148W, F149L, F149M, F149N, E150A, E150D, E150H, E150K, E150L, E150M, E150N, E150R, E150V, E150W, E150Y, G151A, G151C, G151D, G151L, G151N, G151P, G151S, G151W, K152D, K152L, K152R, S163P, G164D, G164E, G164H, G164S, G164V, V167A, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181K, S181N, S181P, S181Q, S181T, S181V, S181W, E185A, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203Q, A203R, A203S, A203T, A203V, A203W, N204L, N204M, N204V, N204W, N204Y, L205I, D207A, D207C, D207E, D207G, D207K, D207N, D207Q, D207R, D207S, D207V, D207W, S208A, S208C, S208D, S208G, S208L, S208Q, S208T, S208V, S208W, S210T, Q215K, Q215R, Q215M, Q215L, Q215*, S217V, T218A, T218L, T218Q, T218R, T218V, S221N, G222D, E224A, E224P, S225G, N227A, N227Q, N227R, N227S, N227T, N227K, D230*, D230N, D230R, D230T, D230W, E232D, E232V, N233D, N233E, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251A, S251L, S251N, S251R, S251W, N252P, N252C, G253D, G253W, F254I, F254L, F254M, F254Y, Q256D, Q256E, Q256R, N260*, N260A, N260C, N260E, N260I, N260K, N260L, N260M, N260Q, N260R, N260T, N260V, N260W, N260Y, E261*, E261A, E261D, E261R, E261W, Q262*, Q262F, Q262H, Q262W, Q262Y, M263K, M263L, M263Q, D264*, D264C, D264E, D264N, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y281R, Y282E, Y282N, H283I, A284I, A284L, A284N, A284P, A284T, A284V, T287N, S288P, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308E, K308G, K308I, K308L, K308Q, K308S, K308T, K308V, K308Y, K309A, K309C, K309D, K309E, K309G, K309H, K309L, K309M, K309N, K309Q, K309S, K309T, K309I, K312A, K312E, K312L, K312M, K312N, K312Q, K312S, K312W, E314I, E314L, E314V, L315I, L315V, R319A, Y321F and N323R, wherein each substitution provides a dispersin variant having an increase in stability measured as half-life improvement factor, HIF, or residual activity, RAR, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent dispersin e.g. a dispersin comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In some preferred aspects, a dispersin variant of the invention comprises one or more substitutions (compared to SEQ ID NO: 1), wherein the substitutions are selected from the group consisting of: D2V, Q3F, Q3I, S12A, H15Y, T17W, T17E, V18L, K22M, S23I, S23C, S23T, S23L, S23V, S23E, V25R, Y30L, A49W, A49Y, S56T, N59D, N59C, N59E, N59R, N59F, N59W, N59V, N62C, N62D, T63C, N68Q, S72D, S72E, I74L, S77A, I82V, L90F, E99Q, L100S, T114S, T114C, Y123W, Y124I, Y124M, Y124R, Y124V, Y124Q, Y124T, Y124K, D125R, D125C, D125G, D125K, D125Q, Q135M, D138R, D138K, D138Q, L170D, L170K, L170S, L170H, D171E, D171K, D171Y, D171M, D171Q, D171L, I173D, D174W, D174H, D174M, D174N, F175Y, Q178K, I179T, S181T, S181F, S181Q, S181G, S181N, S181C, E185R, E185M, E185V, S186K, S186M, S186R, S186H, K187G, Y188P, E189V, S199C, S199L, A203G, A203E, A203V, N204L, N204Y, N204V, L205I, D207N, D207S, D207C, D207G, S210T, Q215R, T218Q, S225G, N227T, N227K, E232D, G235W, S237W, Y244M, Y244C, N252P, N252C, Q256E, N260Q, Q262H, M263Q, D264E, Y265F, N267T, N267S, Y270F, H272M, H272P, H272I, H272V, N273W, K274H, F276A, F276N, F276K, F276C, I278V, S279N, S279D, S279G, D280E, D280C, Y281P, Y282N, H283I, A284T, A284L, A284I, S288K, V290I, K291R, T296C, T303Q, D304M, D304C, L305M, L305N, S306C, K308D, K308A, K308V, K308Q, K308S, K308Y, K308G, K308L, K308T, K308I, K309C, K309L, K309D, K309Q, K309N, K309T, K309A, K309S, K309M, K309H, K312A, K312Q, K312S, K312W, K312L, K312N, E314L, E314V, E314I, L315I, R319A and N323R, wherein each substitution provides a dispersin variant having an increase in stability measured as half-life improvement factor, HIF or residual activity ratio, RAR, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent dispersin e.g. a dispersin comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In some preferred embodiment of the invention, the dispersin variant of the invention comprises one or more of the following substitutions: Q3F, Q3I, H15Y, T17W, A49W, N59E, V140I, S163P, S186R, D207N, Q215K, T218Q, S225G, N227T, E232D, G235W, S237W, N252P, N260Q, N267T, H272V, H272P, F276A, S279D, Y281P, S288P, K308Q, K308E, K309E, K312Q, K312E, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

The variants of the invention preferably comprise one or more of the conservative motifs GXDE (SEQ ID NO:8), [EQ][NRSHA][YVFL][AGSTC][IVLF][EAQYN][SN] (SEQ ID NO:9),[VIM][LIV]G[GAV]DE[VI][PSA] SEQ ID NO: 10), WND[SQR][IVL][TLVM] (SEQ ID NO: 11), QSTL (SEQ ID NO: 12), NKFFY (SEQ ID NO: 13) or NLD[DR]S (SEQ ID NO: 14), which are shared among dispersins of the *Terribacillus* clade as described below. As explained in "Definitions" a clade comprises a group of polypeptides clustered together based on homologous features traced to a common ancestor. Polypeptides forming a group e.g. a clade as shown in a phylogenetic tree often share common properties and are more closely related than other polypeptides not in the clade.

One preferred aspect of the invention relates to a variant of a dispersin parent, wherein the variant comprises one or more motifs GXDE (SEQ ID NO:8), [EQ][NRSHA][YVFL] [AGSTC][IVLF][EAQYN][SN] (SEQ ID NO:9),[VIM] [LIV]G[GAV]DE[VI][PSA] (SEQ ID NO: 10), WND[SQR] [IVL][TLVM] (SEQ ID NO: 11), QSTL (SEQ ID NO: 12), NKFFY (SEQ ID NO: 13) or NLD[DR]S (SEQ ID NO: 14), and wherein the variant comprise an alteration at one or more positions selected from the list consisting of positions: 2, 3, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 140, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 225, 227, 230, 232, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 and 323, wherein each position corresponds to the position of the polypeptide of SEQ ID NO: 1, wherein each alteration provides a dispersin variant with at least one improved property compared to the polypeptide shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and wherein each position corresponds to the position of the polypeptide shown in SEQ ID NO: 1 (numbering according to SEQ ID NO: 1) and preferably wherein the variant has hexosaminidase e.g. beta-1,6 N-acetylglucosaminidase activity.

one preferred aspect of the invention relates to a variant of a dispersin parent, wherein the variant comprises one or more motifs GXDE (SEQ ID NO:8), [EQ][NRSHA][YVFL][AGSTC][IVLF][EAQYN][SN] (SEQ ID NO:9),[VIM][LIV]G[GAV]DE[VI][PSA] SEQ ID NO: 10), [WND[SQR][IVL][TLVM] (SEQ ID NO: 11), QSTL (SEQ ID NO: 12), NKFFY (SEQ ID NO: 13) or NLD[DR]S (SEQ ID NO: 14), and wherein the variant comprise an alteration at one or more positions selected from the list consisting of positions: 2, 3, 12, 15, 17, 18, 22, 23, 24, 25, 30, 49, 56, 57, 59, 62, 63, 68, 72, 74, 77, 82, 90, 99, 100, 106, 114, 123, 124, 125, 135, 138, 140, 163, 167, 170, 171, 173, 174, 175, 178, 179, 181, 185, 186, 187, 188, 189, 199, 203, 204, 205, 207, 210, 215, 218, 221, 225, 227, 232, 235, 237,244, 252, 256, 260, 262, 263, 264, 265, 267, 270, 272, 273, 274, 276, 278, 279, 280, 281, 282, 283, 284, 288, 290, 291, 296, 303, 304, 305, 306, 308, 309, 312, 314, 315, 319, 321, 322 and 323, wherein each position corresponds to the position of the polypeptide of SEQ ID NO: 1, wherein each alteration provides a dispersin variant with at least one improved property compared to the polypeptide shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and wherein each position corresponds to the position of the polypeptide shown in SEQ ID NO: 1 (numbering according to SEQ ID NO: 1) and preferably wherein the variant has hexosaminidase e.g. beta-1,6 N-acetylglucosaminidase activity.

one preferred aspect of the invention relates to a variant of a dispersin parent, wherein the variant comprises one or more motifs GXDE (SEQ ID NO:8), [EQ][NRSHA][YVFL][AGSTC][IVLF][EAQYN][SN] (SEQ ID NO:9),[VIM][LIV]G[GAV]DE[VI][PSA] SEQ ID NO: 10), [WND[SQR][IVL][TLVM] (SEQ ID NO: 11), QSTL (SEQ ID NO: 12), NKFFY (SEQ ID NO: 13) or NLD[DR]S (SEQ ID NO: 14), and wherein the variant comprise an alteration at one or more positions selected from the list consisting of positions: 31, 33, 36, 73, 75, 94, 141, 144, 241, 277, 294, 297, 299, wherein each position corresponds to the position of the polypeptide of SEQ ID NO: 1, wherein each alteration provides a dispersin variant with at least one improved property compared to the polypeptide shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and wherein each position corresponds to the position of the polypeptide shown in SEQ ID NO: 1 (numbering according to SEQ ID NO: 1) and preferably wherein the variant has hexosaminidase e.g. beta-1,6 N-acetylglucosaminidase activity.

One preferred aspect of the invention relates to a variant of a dispersin parent, wherein the variant comprises one or more motifs GXDE (SEQ ID NO:8), [EQ][NRSHA][YVFL][AGSTC][IVLF][EAQYN][SN] (SEQ ID NO:9),[VIM][LIV]G[GAV]DE[VI][PSA] SEQ ID NO: 10), [WND[SQR][IVL][TLVM] (SEQ ID NO: 11), QSTL (SEQ ID NO: 12), NKFFY (SEQ ID NO: 13) or NLD[DR]S (SEQ ID NO: 14), wherein the variant comprises one or more alterations (compared to SEQ ID NO: 1), wherein the alterations are selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19K, E19N, E19P, K22A, K22M, K22V, S23A, S23C, S23E, S23I, S23L, S23R, S23T, S23V, L24I, V25R, D26M, Y30*, Y30A, Y30D, Y30L, Y30M, Y30N, Y30R, Y30T, Y30V, G32L, G32M, G32R, N34D, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80R, K80V, K80W, D81A, D81G, D81L, D81N, D81R, D81S, D81T, D81V, D81W, I82V, L90F, E99Q, E99R, L100S, K103A, K103R, K103V, K104N, K104W, D105N, V106A, V106D, V106E, V106H, V106K, V106L, V106M, V106N, V106Q, V106R, V106W, V106Y, K107A, K107C, K107L, K107M, K107T, K107V, K107W, N110M, N110N, N110V, D111A, D111E, D111M, D111N, D111Q, D111R, D111V, D111W, V113T, T114C, T114S, Y116D, Y116N, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124H, Y124I, Y124K, Y124L, Y124M, Y124N, Y124Q, Y124R, Y124T, Y124V, Y124W, D125C, D125G, D125H, D125K, D125Q, D125R, N126V, R127D, R127H, R127K, R127L, R127M, R127Q, R127W, V128A, V128C, V128D, V128L, V128T, D131V, Q135*, Q135A, Q135D, Q135E, Q135K, Q135M, Q135Y, D138K, D138L, D138M, D138N, D138Q, D138R, D138S, D138V, D138W, E139W, V140I, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150A, E150D, E150H, E150K, E150L, E150M, E150N, E150R, E150V, E150W, E150Y, G151A, G151C, G151D, G151L, G151N, G151P, G151S, G151W, K152D, K152L, K152R, S163P, G164D, G164E, G164H, G164S, G164V, V167A, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181K, S181N, S181P, S181Q, S181T, S181V, S181W, E185A, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203Q, A203R, A203S, A203T, A203V, A203W, N204L, N204M, N204V, N204W, N204Y, L205I, D207A, D207C, D207E, D207G, D207K, D207N, D207Q, D207R, D207S, D207V, D207W, S208A, S208C, S208D, S208G, S208L, S208Q, S208T, S208V, S208W, S210T, Q215K, Q215R, Q215M, Q215L, Q215*, S217V, T218A, T218L, T218Q, T218R, T218V, S221N, G222D, E224A, E224P, S225G, N227A, N227Q, N227R, N227S, N227T, N227K, D230*, D230N, D230R, D230T, D230W, E232D, E232V, N233D, N233E, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251A, S251L, S251N, S251R, S251W, N252P, N252C, G253D, G253W, F254I, F254L, F254M, F254Y, Q256D, Q256E, Q256R, N260*, N260A, N260C, N260E, N260I, N260K, N260L, N260M, N260Q, N260R, N260T, N260V, N260W, N260Y, E261*, E261A, E261D, E261R, E261W, Q262*, Q262F, Q262H, Q262W, Q262Y, M263K, M263L, M263Q, D264*, D264C, D264E, D264N, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y281R, Y282E, Y282N, H283I, A284I, A284L, A284N, A284P, A284T, A284V, T287N, S288P, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308E, K308G, K308I, K308L, K308Q, K308S, K308T, K308V, K308Y, K309A, K309C, K309D, K309E, K309G, K309H, K309L, K309M, K309N, K309Q, K309S, K309T, K309I, K312A, K312E, K312L, K312M, K312N, K312Q, K312S, K312W, E314I, E314L, E314V, L315I, L315V, R319A, Y321F and N323R, wherein each substitution provides a dispersin variant with at least one improved property compared to the polypeptide shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and wherein each position corresponds to the position of the polypeptide shown in SEQ ID NO: 1 (numbering according to SEQ ID NO: 1) and preferably wherein the variant has hexosaminidase e.g. beta-1,6 N-acetylglucosaminidase activity.

One preferred aspect of the invention relates to a variant of a dispersin parent, wherein the variant comprises one or more motifs GXDE (SEQ ID NO:8), [EQ][NRSHA][YVFL] [AGSTC][IVLF][EAQYN][SN] (SEQ ID NO:9),[VIM] [LIV]G[GAV]DE[VI][PSA] SEQ ID NO: 10), [WND[SQR] [IVL][TLVM] (SEQ ID NO: 11), QSTL (SEQ ID NO: 12), NKFFY (SEQ ID NO: 13) or NLD[DR]S (SEQ ID NO: 14), wherein the variant comprises one or more alterations (compared to SEQ ID NO: 1), wherein the alterations are selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19N, E19P, K22A, K22M, K22V, S23C, S23E, S23I, S23L, S23R, S23T, S23V, V25R, D26M, Y30*, Y30D, Y30L, Y30M, Y30N, Y30R, Y30T, Y30V, G32L, G32M, G32R, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72O, S72D, S72E, S72F, S72G, S72I, S72M, S72N, S72R, S72T, S72Y, I74L, S77A, D79V, K80*, K80E, K80H, K80L, K80N, K80Q, K80V, K80W, D81A, D81G, D81L, D81R, D81S, D81T, D81V, D81W, I82V, L90F, E99Q, E99R, L100S, K103A, K103R, K104N, K104W, D105N, V106A, V106D, V106E, V106H, V106K, V106L, V106M, V106N, V106Q, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116N, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124I, Y124K, Y124L, Y124M, Y124Q, Y124R, Y124T, Y124V, Y124W, D125C, D125G, D125K, D125Q, D125R, N126V, R127D, R127H, R127K, R127L, R127M, R127Q, R127W, V128C, V128L, V128T, D131V, Q135*, Q135A, Q135D, Q135E, Q135K, Q135M, Q135Y, D138K, D138L, D138M, D138Q, D138R, D138S, D138V, D138W, E139W, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150D, E150H, E150K, E150L, E150M, E150N, E150R, E150V, E150W, E150Y, G151A, G151C, G151D, G151L, G151N, G151P, G151S, G151W, K152D, K152L, K152R, G164D, G164E, G164H, G164S, G164V, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181N, S181P, S181Q, S181T, S181V, S181W, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203R, A203S, A203T, A203V, A203W, N204L, N204M, N204V, N204W, N204Y, L205I, D207A, D207C, D207E, D207G, D207N, D207Q, D207S, D207V, D207W, S208A, S208C, S208D, S208G, S208L, S208Q, S208T, S208V, S208W, S210T, Q215R, Q215M, Q215L, Q215*, S217V, T218A, T218L, T218Q, T218V, G222D, E224A, E224P, N227A, N227Q, N227R, N227S, N227T, N227K, D230*, D230T, D230W, E232D, E232V, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251L, S251N, S251R, S251W, N252P, N252C, G253D, G253W, F254I, F254L, F254M, F254Y, Q256E, Q256R, N260*, N260A, N260C, N260E, N260I, N260K, N260L, N260M, N260Q, N260R, N260V, N260W, N260Y, E261*, E261A, E261D, E261R, E261W, Q262*, Q262F, Q262H, Q262W, Q262Y, M263K, M263L, M263Q, D264*, D264C, D264E, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y281R, Y282E, Y282N, H283I, A284I, A284L, A284N, A284P, A284T, A284V, T287N, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308G, K308I, K308L, K308Q, K308S, K308T, K308V, K308Y, K309A, K309C, K309D, K309H, K309L, K309M, K309N, K309Q, K309S, K309T, K309I, K312A, K312L, K312M, K312N, K312Q, K312S, K312W, E314I, E314L, E314V, L315I, L315V, R319A, and N323R, wherein each substitution provides a dispersin variant with at least one improved property compared to the polypeptide shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and wherein each position corresponds to the position of the polypeptide shown in SEQ ID NO: 1 (numbering according to SEQ ID NO: 1) and preferably wherein the variant has hexosaminidase e.g. beta-1,6 N-acetylglucosaminidase activity.

One preferred aspect of the invention relates to a variant of a dispersin parent, wherein the variant comprises one or more substitution(s) (compared to SEQ ID NO: 1), wherein the variant comprises one or more motifs GXDE (SEQ ID NO:8), [EQ][NRSHA][YVFL][AGSTC][IVLF][EAQYN][SN] (SEQ ID NO:9),[VIM][LIV]G[GAV]DE[VI][PSA] SEQ ID NO: 10), [WND[SQR][IVL][TLVM] (SEQ ID NO: 11), QSTL (SEQ ID NO: 12), NKFFY (SEQ ID NO: 13) or NLD[DR]S (SEQ ID NO: 14), wherein the substitution(s) are selected from the group consisting of: D2V, Q3I, Q3F, S12A, H15Y, T17W, T17E, V18L, K22M, S23I, S23C, S23T, S23L, S23V, S23E, V25R, Y30L, A49W, A49Y, S56T, N59D, N59C, N59E, N59R, N59F, N59W, N59V, N62C, N62D, T63C, N68Q, S72D, S72E, I74L, S77A, I82V, L90F, E99Q, L100S, T114S, T114C, Y123W, Y124I, Y124M, Y124R, Y124V, Y124Q, Y124T, Y124K, D125R, D125C, D125G, D125K, D125Q, Q135M, D138R, D138K, D138Q, L170D, L170K, L170S, L170H, D171E, D171K, D171Y, D171M, D171Q, D171L, I173C, D174W, D174H, D174M, D174N, F175Y, Q178K, I179T, S181T, S181F, S181Q, S181G, S181N, S181C, E185R, E185M, E185V, S186K, S186M, S186R, S186H, K187G, Y188P, E189V, S199C, S199L, A203G, A203E, A203V, N204L, N204Y, N204V, L205I, D207N, D207S, D207C, D207G, S210T, Q215R, T218Q, N227T, N227K, E232D, G235W, S237W, Y244M, Y244C, N252P, N252C, Q256E, N260Q, Q262H, M263Q, D264E, Y265F, N267T, N267S, Y270F, H272M, H272P, H272I, H272V, N273W, K274H, F276A, F276N, F276K, F276C, I278V, S279N, S279D, S279G, D280E, D280C, Y281P, Y282N, H283I, A284T, A284L, A284I, S288K, V290I, K291R, T296C, T303Q, D304M, D304C, L305M, L305N, S306C, K308D, K308A, K308V, K308Q, K308S, K308Y, K308G, K308L, K308T, K308I, K309C, K309L, K309D, K309Q, K309N, K309T, K309A, K309S, K309M, K309H, K312A, K312Q, K312S, K312W, K312L, K312N, E314L, E314V, E314I, L315I, R319A and N323R, wherein each substitution provides a dispersin variant with at least one improved property compared to the polypeptide shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and wherein each position corresponds to the position of the polypeptide shown in SEQ ID NO: 1 (numbering according to SEQ ID NO: 1) and preferably wherein the variant has hexosaminidase e.g. beta-1,6 N-acetylglucosaminidase activity.

One preferred aspect of the invention relates to a variant of a dispersin parent, wherein the variant comprises one or more motifs GXDE (SEQ ID NO:8), [EQ][NRSHA][YVFL][AGSTC][IVLF][EAQYN][SN] (SEQ ID NO:9),[VIM][LIV]G[GAV]DE[VI][PSA] SEQ ID NO: 10), [WND[SQR][IVL][TLVM] (SEQ ID NO: 11), QSTL (SEQ ID NO: 12), NKFFY (SEQ ID NO: 13) or NLD[DR]S (SEQ ID NO: 14), and wherein the variant comprise an alteration at one or more positions selected from the list consisting of positions: 2, 3, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 140, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 225, 227, 230, 232, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 and 323, wherein each position corresponds to the position of the polypeptide of SEQ ID NO: 1, wherein each substitution provides a dispersin variant having an increase in stability measured as half-life improvement factor, HIF or residual activity ratio, RAR, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent dispersin e.g. a dispersin comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and preferably wherein the variant has hexosaminidase e.g. beta-1,6 N-acetylglucosaminidase activity.

One preferred aspect of the invention relates to a variant of a dispersin parent, wherein the variant comprises one or more motifs GXDE (SEQ ID NO:8), [EQ][NRSHA][YVFL][AGSTC][IVLF][EAQYN][SN] (SEQ ID NO:9),[VIM][LIV]G[GAV]DE[VI][PSA] SEQ ID NO: 10), [WND[SQR][IVL][TLVM] (SEQ ID NO: 11), QSTL (SEQ ID NO: 12), NKFFY (SEQ ID NO: 13) or NLD[DR]S (SEQ ID NO: 14), and wherein the variant comprise an alteration at one or more positions selected from the list consisting of positions:

2, 3, 12, 15, 17, 18, 22, 23, 24, 25, 30, 49, 56, 57, 59, 62, 63, 68, 72, 74, 77, 82, 90, 99, 100, 106, 114, 123, 124, 125, 135, 138, 140, 163, 167, 170, 171, 173, 174, 175, 178, 179, 181, 185, 186, 187, 188, 189, 199, 203, 204, 205, 207, 210, 215, 218, 221, 225, 227, 232, 235, 237, 244, 252, 256, 260, 262, 263, 264, 265, 267, 270, 272, 273, 274, 276, 278, 279, 280, 281, 282, 283, 284, 288, 290, 291, 296, 303, 304, 305, 306, 308, 309, 312, 314, 315, 319, 321, 322 and 323, wherein each position corresponds to the position of the polypeptide of SEQ ID NO: 1, wherein each substitution provides a dispersin variant having an increase in stability measured as half-life improvement factor, HIF or residual activity ratio, RAR, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent dispersin e.g. a dispersin comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and preferably wherein the variant has hexosaminidase e.g. beta-1,6 N-acetylglucosaminidase activity.

One preferred aspect of the invention relates to a variant of a dispersin parent, wherein the variant comprises one or more motifs GXDE (SEQ ID NO:8), [EQ][NRSHA][YVFL][AGSTC][IVLF][EAQYN][SN] (SEQ ID NO:9),[VIM][LIV]G[GAV]DE[VI][PSA] SEQ ID NO: 10), [WND[SQR][IVL][TLVM] (SEQ ID NO: 11), QSTL (SEQ ID NO: 12), NKFFY (SEQ ID NO: 13) or NLD[DR]S (SEQ ID NO: 14), and wherein the variant comprise an alteration at one or more positions selected from the list consisting of positions: 31, 33, 36, 73, 75, 94, 141, 144, 241, 277, 294, 297, 299, wherein each position corresponds to the position of the polypeptide of SEQ ID NO: 1, wherein each substitution provides a dispersin variant having an increase in stability measured as half-life improvement factor, HIF or residual activity ratio, RAR, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent dispersin e.g. a dispersin comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and preferably wherein the variant has hexosaminidase e.g. beta-1,6 N-acetylglucosaminidase activity.

One preferred aspect of the invention relates to a variant of a dispersin parent, wherein the variant comprises one or more motifs GXDE (SEQ ID NO:8), [EQ][NRSHA][YVFL][AGSTC][IVLF][EAQYN][SN] (SEQ ID NO:9),[VIM][LIV]G[GAV]DE[VI][PSA] SEQ ID NO: 10), [WND[SQR][IVL][TLVM] (SEQ ID NO: 11), QSTL (SEQ ID NO: 12), NKFFY (SEQ ID NO: 13) or NLD[DR]S (SEQ ID NO: 14), wherein the variant comprises one or more alterations (compared to SEQ ID NO: 1), wherein the alterations are selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19K, E19N, E19P, K22A, K22M, K22V, S23A, S23C, S23E, S23I, S23L, S23R, S23T, S23V, L24I, V25R, D26M, Y30*, Y30A, Y30D, Y30L, Y30M, Y30N, Y30R, Y30T, Y30V, G32L, G32M, G32R, N34D, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80R, K80V, K80W, D81A, D81G, D81L, D81N, D81R, D81S, D81T, D81V, D81W, I82V, L90F, E99Q, E99R, L100S, K103A, K103R, K103V, K104N, K104W, D105N, V106A, V106D, V106E, V106H, V106K, V106L, V106M, V106N, V106Q, V106R, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116N, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124H, Y124I, Y124K, Y124L, Y124M, Y124N, Y124Q, Y124R, Y124T, Y124V, Y124W, D125C, D125G, D125H, D125K, D125Q, D125R, N126V, R127D, R127H, R127K, R127L, R127M, R127Q, R127W, V128A, V128C, V128D, V128L, V128T, D131V, Q135*, Q135A, Q135D, Q135E, Q135K, Q135M, Q135Y, D138K, D138L, D138M, D138N, D138Q, D138R, D138S, D138V, D138W, E139W, V140I, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150A, E150D, E150H, E150K, E150L, E150M, E150N, E150R, E150V, E150W, E150Y, G151A, G151C, G151D, G151L, G151N, G151P, G151S, G151W, K152D, K152L, K152V, S163P, G164D, G164E, G164H, G164S, G164V, V167A, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181K, S181N, S181P, S181Q, S181T, S181V, S181W, E185A, E185M, E185R, E185V, E185W, S186A, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203Q, A203R, A203S, A203T, A203V, A203W, N204L, N204M, N204V, N204W, N204Y, L205I, D207A, D207C, D207E, D207G, D207K, D207N, D207Q, D207R, D207S, D207V, D207W, S208A, S208C, S208D, S208G, S208L, S208Q, S208T, S208V, S208W, S210T, Q215K, Q215R, Q215M, Q215L, Q215*, S217V, T218A, T218L, T218Q, T218R, T218V, S221N, G222D, E224A, E224P, S225G, N227A, N227Q, N227R, N227S, N227T, N227K, D230*, D230N, D230R, D230T, D230W, E232D, E232V, N233D, N233E, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251A, S251L, S251N, S251R, S251W, N252P, N252C, G253D, G253W, F254I, F254L, F254M, F254Y, Q256D, Q256E, Q256R, N260*, N260A, N260C, N260E, N260I, N260K, N260L, N260M, N260Q, N260R, N260T, N260V, N260W, N260Y, E261*, E261A, E261D, E261R, E261W, Q262*, Q262F, Q262H, Q262W, Q262Y, M263K, M263L, M263Q, D264*, D264C, D264E, D264N, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y281R, Y282E, Y282N, H283I, A284I, A284L, A284N, A284P, A284T, A284V, T287N, S288P, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308E, K308G, K308I, K308L, K308Q, K308S, K308T, K308V, K308Y, K309A, K309C, K309D, K309E, K309G, K309H, K309L, K309M, K309N, K309Q, K309S, K309T, K309I, K312A, K312E, K312L, K312M, K312N, K312Q, K312S, K312W, E314I, E314L, E314V, L315I, L315V, R319A, Y321F and N323R, wherein each position corresponds to the position of the polypeptide of SEQ ID NO: 1, wherein each substitution provides a dispersin variant having an increase in stability measured as half-life improvement factor, HIF or residual activity ratio, RAR, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent dispersin e.g. a dispersin comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and preferably wherein the variant has hexosaminidase e.g. beta-1,6 N-acetylglucosaminidase activity.

One preferred aspect of the invention relates to a variant of a dispersin parent, wherein the variant comprises one or more motifs GXDE (SEQ ID NO:8), [EQ][NRSHA][YVFL][AGSTC][IVLF][EAQYN][SN] (SEQ ID NO:9),[VIM][LIV]G[GAV]DE[VI][PSA] SEQ ID NO: 10), [WND[SQR][IVL][TLVM] (SEQ ID NO: 11), QSTL (SEQ ID NO: 12), NKFFY (SEQ ID NO: 13) or NLD[DR]S (SEQ ID NO: 14), wherein the variant comprises one or more alterations (compared to SEQ ID NO: 1), wherein the alterations are selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19N, E19P, K22A, K22M, K22V, S23C, S23E, S23I, S23L, S23R, S23T, S23V, V25R, D26M, Y30*, Y30D, Y30L, Y30M, Y30N, Y30R, Y30T, Y30V, G32L, G32M, G32R, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80V, K80W, D81A, D81G, D81L, D81R, D81S, D81T, D81V, D81W, I82V, L90F, E99Q, E99R, L100S, K103A, K103R, K104N, K104W, D105V, V106A, V106D, V106E, V106H, V106K, V106L, V106M, V106N, V106Q, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116N, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124I, Y124K, Y124L, Y124M, Y124Q, Y124R, Y124T, Y124V, Y124W, D125C, D125G, D125K, D125Q, D125R, N126V, R127D, R127H, R127K, R127L, R127M, R127Q, R127W, V128C, V128L, V128T, D131V, Q135*, Q135A, Q135D, Q135E, Q135K, Q135M, Q135Y, D138K, D138L, D138M, D138Q, D138R, D138S, D138V, D138W, E139W, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150D, E150H, E150K, E150L, E150M, E150N, E150R, E150V, E150W, E150Y, G151A, G151C, G151D, G151L, G151N, G151P, G151S, G151W, K152D, K152L, K152R, G164D, G164E, G164H, G164S, G164V, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181N, S181P, S181Q, S181T, S181V, S181W, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203R, A203S, A203T, A203V, A203W, N204L, N204M, N204V, N204W, N204Y, L205I, D207A, D207C, D207E, D207G, D207N, D207Q, D207S, D207V, D207W, S208A, S208C, S208D, S208G, S208L, S208Q, S208T, S208V, S208W, S210T, Q215R, Q215M, Q215L, Q215*, S217V, T218A, T218L, T218Q, T218R, T218V, G222D, E224A, E224P, N227A, N227Q, N227R, N227S, N227T, N227K, D230*, D230R, D230T, D230W, E232D, E232V, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251L, S251N, S251R, S251W, N252P, N252C, G253D, G253W, F254I, F254L, F254M, F254Y, Q256E, Q256R, N260*, N260A, N260C, N260E, N260I, N260K, N260L, N260M, N260Q, N260R, N260V, N260W, N260Y, E261*, E261A, E261D, E261R, E261W, Q262*, Q262F, Q262H, Q262W, Q262Y, M263K, M263L, M263Q, D264*, D264C, D264E, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y281R, Y282E, Y282N, H283I, A284I, A284L, A284N, A284P, A284T, A284V, T287N, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308G, K308I, K308L, K308Q, K308S, K308T, K308V, K308Y, K309A, K309C, K309D, K309H, K309L, K309M, K309N, K309Q, K309S, K309T, K309I, K312A, K312L, K312M, K312N, K312Q, K312S, K312W, E314I, E314L, E314V, L315I, L315V, R319A, and N323R, wherein each position corresponds to the position of the polypeptide of SEQ ID NO: 1, wherein each substitution provides a dispersin variant having an increase in stability measured as half-life improvement factor, HIF or residual activity ratio, RAR, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent dispersin e.g. a dispersin comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and preferably wherein the variant has hexosaminidase e.g. beta-1,6 N-acetylglucosaminidase activity.

One preferred aspect of the invention relates to a variant of a dispersin parent, wherein the variant comprises one or more motifs GXDE (SEQ ID NO:8), [EQ][NRSHA][YVFL][AGSTC][IVLF][EAQYN][SN] (SEQ ID NO:9),[VIM][LIV]G[GAV]DE[VI][PSA] SEQ ID NO: 10), [WND[SQR][IVL][TLVM] (SEQ ID NO: 11), QSTL (SEQ ID NO: 12), NKFFY (SEQ ID NO: 13) or NLD[DR]S (SEQ ID NO: 14), wherein the variant comprises one or more alterations (compared to SEQ ID NO: 1), wherein the alterations are selected from the group consisting of: D2V, Q3F, Q3I, S12A, H15Y, T17W, T17E, V18L, K22M, S23I, S23C, S23T, S23L, S23V, S23E, V25R, Y30L, A49W, A49Y, S56T, N59D, N59C, N59E, N59R, N59F, N59W, N59V, N62C, N62D, T63C, N68Q, S72D, S72E, I74L, S77A, I82V, L90F, E99Q, L100S, T114S, T114C, Y123W, Y124I, Y124M, Y124R, Y124V, Y124Q, Y124T, Y124K, D125R, D125C, D125G, D125K, D125Q, Q135M, D138R, D138K, D138Q, L170D, L170K, L170S, L170H, D171E, D171K, D171Y, D171M, D171Q, D171L, I173C, D174W, D174H, D174M, D174N, F175Y, Q178K, I179T, S181T, S181F, S181Q, S181G, S181N, S181C, E185R, E185M, E185V, S186K, S186M, S186R, S186H, K187G, Y188P, E189V, S199C, S199L, A203G, A203E, A203V, N204L, N204Y, N204V, L205I, D207N, D207S, D207C, D207G, S210T, Q215R, T218Q, N227T, N227K, E232D, G235W, S237W, Y244M, Y244C, N252C, Q256E, N260Q, Q262H, M263Q, D264E, Y265F, N267T, N267S, Y270F, H272M, H272P, H272I, H272V, N273W, K274H, F276A, F276N, F276K, F276C, I278V, S279N, S279D, S279G, D280E, D280C, Y281P, Y282N, H283I, A284T, A284L, A284I, S288K, V290I, K291R, T296C, T303Q, D304M, D304C, L305M, L305N, S306C, K308D, K308A, K308V, K308Q, K308S, K308Y, K308G, K308L, K308T, K308I, K309C, K309L, K309D, K309Q, K309N, K309T, K309A, K309S, K309M, K309H, K312A, K312Q, K312S, K312W, K312L, K312N, E314L, E314V, E314I, L315I, R319A and N323R, wherein each position corresponds to the position of the polypeptide of SEQ ID NO: 1, wherein each substitution provides a dispersin variant having an increase in stability measured as half-life improvement factor, HIF or residual activity ratio, RAR, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent dispersin e.g. a dispersin comprising the polypeptide having the amino acid sequence shown in SEQ ID NO: 1, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1 and preferably wherein the variant has hexosaminidase e.g. beta-1,6 N-acetylglucosaminidase activity.

Addition of any one of the mutations of the invention, have shown to improve stability.

In some preferred aspects, a dispersin variant of the invention comprises 2, 3, 4, 5, 6, 7, 8 or 9 or more substitutions (compared to SEQ ID NO: 1), wherein the substitutions are selected from the group consisting of: D2V, Q3F, Q3I, S12A, H15Y, T17W, T17E, V18L, K22M, S23I, S23C, S23T, S23L, S23V, S23E, V25R, Y30L, A49W, A49Y, S56T, N59D, N59C, N59E, N59R, N59F, N59W, N59V, N62C, N62D, T63C, N68Q, S72D, S72E, I74L, S77A, I82V, L90F, E99Q, L100S, T114S, T114C, Y123W, Y124I, Y124M, Y124R, Y124V, Y124Q, Y124T, Y124K, D125R, D125C, D125G, D125K, D125Q, Q135M, D138R, D138K, D138Q, L170D, L170K, L170S, L170H, D171E, D171K, D171Y, D171M, D171Q, D171L, I173C, D174W, D174H, D174M, D174N, F175Y, Q178K, I179T, S181T, S181F, S181Q, S181G, S181N, S181C, E185R, E185M, E185V, S186K, S186M, S186R, S186H, K187G, Y188P, E189V, S199C, S199L, A203G, A203E, A203V, N204L, N204Y, N204V, L205I, D207N, D207S, D207C, D207G, S210T, Q215R, T218Q, S225G, N227T, N227K, E232D, G235W, S237W, Y244M, Y244C, N252C, Q256E, N260Q, Q262H, M263Q, D264E, Y265F, N267T, N267S, Y270F, H272M, H272P, H272I, H272V, N273W, K274H, F276A, F276N, F276K, F276C, I278V, S279N, S279D, S279G, D280E, D280C, Y281P, Y282N, H283I, A284T, A284L, A284I, S288K, V290I, K291R, T296C, T303Q, D304M, D304C, L305M, L305N, S306C, K308D, K308A, K308V, K308Q, K308S, K308Y, K308G, K308L, K308T, K308I, K309C, K309L, K309D, K309Q, K309N, K309T, K309A, K309S, K309M, K309H, K312A, K312Q, K312S, K312W, K312L, K312N, E314L, E314V, E314I, L315I, R319A and N323R, wherein the variant has at least 60%, at least 65%, at least 70%, at least 75%, at least 80%, at least 85%, at least 90%, at least 95%, such as at least 96%, at least 97%, at least 98%, or at least 99%, but less than 100%, sequence identity to the polypeptide shown in SEQ ID NO: 1, wherein each position corresponds to the position of the polypeptide shown in SEQ ID NO: 1 (numbering according to SEQ ID NO: 1) and wherein the variant has at least one improved property compared to the parent dispersin e.g. a dispersin comprising the polypeptide having the amino acid sequence shown in SEQ ID NO: 1, preferably the improved property is, improved stability, wherein stability is tested as described in Example 4 and Example 5, preferably wherein the variant has hexosaminidase e.g. beta-1,6 N-acetylglucosaminidase activity.

In some aspects, the dispersin variant of the invention has an improved stability, measured as Half-life Improvement Factor, HIF, compared to the parent or compared to the dispersin having the polypeptide shown in SEQ ID NO: 1 or compared to a dispersin having the identical amino acid sequence of the dispersin variant but not having the alterations at 2, 3, 4, 5, 6, 7, 8 or 9 or more of the specified positions.

In some aspects, the dispersin variant of the invention has an improved stability, measured as residual activity ratio, RAR, compared to the parent or compared to the dispersin having the polypeptide shown in SEQ ID NO: 1 or compared to a dispersin having the identical amino acid sequence of the dispersin variant but not having the alterations at 2, 3, 4, 5, 6, 7, 8 or 9 or more of the specified positions.

In one preferred embodiment of the invention the dispersin variant of the invention comprises one or more of the following substitution(s), Q3F, Q3I, H15Y, T17W, A49W, N59E, V140I, S163P, S186R, D207N, Q215K, T218Q, S225G, N227T, E232D, G235W, S237W, N252P, N260Q, N267T, H272V, H272P, S279D, Y281P, S288P, K308Q, K309E or K312Q, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In one preferred embodiment of the invention the dispersin variant of the invention comprises one or more of the following substitution(s), Q3I, H15Y, A49W, N59E, S163P, S186R, S225G, N227T, E232D, G235W, N252P, N260Q, H272V, S279D, Y281P, K308Q, K309E or K312Q, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In some preferred embodiment of the invention the dispersin variant of the invention comprises one or more of the following substitution sets: Q3I+A49W, Q3I+N59E, Q3I+S163P, Q3I+S186R, Q3I+Q215K, Q3I+S225G, Q3I+N227T, Q3I+N252P, Q3I+N267T, Q3I+F276A, Q3I+Y281P, Q3I+K308Q, Q3I+K308E, Q3I+K309E, Q3I+K312Q, Q3I+K312E, Q3F+A49W, Q3F+N59E, Q3F+S163P, Q3F+S186R, Q3F+Q215K, Q3F+S225G, Q3F+N227T, Q3F+N252P, Q3F+N267T, Q3F+F276A, Q3F+Y281P, Q3F+K308Q, Q3F+K308E, Q3F+K309E, Q3F+K312E, Q3F+K312Q, A49W+N59E, A49W+S163P, A49W+S186R, A49W+Q215K, A49W+S225G, A49W+N227T, A49W+N252P, A49W+N267T, A49W+F276A, A49W+Y281P, A49W+K308Q, A49W+K308E, A49W+K309E, A49W+K312Q, A49W+K312E, N59E+S163P, N59E+S186R, N59E+Q215K, N59E+S225G, N59E+N227T, N59E+N252P, N59E+N267T, N59E+F276A, N59E+Y281P, N59E+K308Q, N59E+K308E, N59E+K309E, N59E+K312Q, N59E+K312E, S163P+S186R, S163P+Q215K, S163P+S225G, S163P+N227T, S163P+N252P, S163P+N267T, S163P+F276A, S163P+Y281P, S163P+K308E, S163P+K308Q, S163P+K309E, S163P+K312Q, S163P+K312E, S186R+Q215K, S186R+S225G, S186R+N227T, S186R+N252P, S186R+N267T, S186R+F276A, S186R+Y281P, S186R+K308E, S186R+K308Q, S186R+K309E, S186R+K312Q, S186R+K312E, Q215K+S225G, Q215K+N227T, Q215K+N252P, Q215K+N267T, Q215K+F276A, Q215K+Y281P, Q215K+K308E, Q215K+K308Q, Q215K+K309E, Q215K+K312Q, Q215K+K312E, S225G+N227T, S225G+N252P, S225G+N267T, S225G+F276A, S225G+Y281P, S225G+K308E, S225G+K308Q, S225G+K309E, S225G+K312Q, S225G+K312E, N227T+N252P, N227T+N267T, N227T+F276A, N227T+Y281P, N227T+K308Q, N227T+K308E, N227T+K309E, N227T+K312Q N227T+K312E, N252P+N267T, N252P+F276A, N252P+Y281P, N252P+K308Q, N252P+K308E, N252P+K309E, N252P+K312Q, N252P+K312E, N267T+F276A, N267T+Y281P, N267T+K308E, N267T+K309E, N267T+K312Q, N267T+K312E, F276A+Y281P, F276A+K308Q, F276A+K308E, F276A+K309E, F276A+K312Q, F276A+K312E, Y281P+K308Q, Y281P+K308E, Y281P+K309E, Y281P+K312Q, Y281P+K312E, K308E+K312Q, K308E+K312E, K308Q+K312Q, K309E+K312Q or K309E+K312E, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In one preferred embodiment the dispersin variant of the invention comprises at least two substitutions wherein the substitutions or substitution sets are selected from the group consisting of:
F276A+K308E, F276A+K309E, K308E+K309E, K308E+K312E, K309E+K312E, N227T+F276A, N227T+K308E, N227T+K312E, N227T+N252P, N227T+N267T, N252P+F276A, N252P+K308E, N252P+K309E, N252P+N267T, N267T+F276A, N267T+K308E, N267T+K309E, N267T+K312E, Q215K+F276A, Q215K+K308E, Q215K+K309E, Q215K+K312E, Q215K+N227T, Q215K+N252P, Q215K+N267T, S163P+F276A, S163P+K308E, S163P+K309E, S163P+K312E, S163P+N252P, S163P+N267T and S163P+Q215K.

In one preferred embodiment the dispersin variant of the invention comprises at least two substitutions, wherein the substitution sets are selected from the group consisting of: Q3I+H15Y, Q3I+A49W, Q3I+N59E, Q3I+S163P, Q3I+S186R, Q3I+S225G, Q3I+N227T, Q3I+E232D, Q3I+G235W, Q3I+N252P, Q3I+N260Q, Q3I+H272V, Q3I+S279D, Q3I+Y281P, Q3I+K308Q, Q3I+K309E, Q3I+K312Q, H15Y+A49W, H15Y+N59E, H15Y+S163P, H15Y+S186R, H15Y+S225G, H15Y+N227T, H15Y+E232D, H15Y+G235W, H15Y+N252P, H15Y+N260Q, H15Y+H272V, H15Y+S279D, H15Y+Y281P, H15Y+K308Q, H15Y+K309E, H15Y+K312Q, A49W+N59E, A49W+S163P, A49W+S186R, A49W+S225G, A49W+N227T, A49W+E232D, A49W+G235W, A49W+N252P, A49W+N260Q, A49W+H272V, A49W+S279D, A49W+Y281P, A49W+K308Q, A49W+K309E, A49W+K312Q, N59E+S163P, N59E+S186R, N59E+S225G, N59E+N227T, N59E+E232D, N59E+G235W, N59E+N252P, N59E+N260Q, N59E+H272V, N59E+S279D, N59E+Y281P, N59E+K308Q, N59E+K309E, N59E+K312Q, S163P+S186R, S163P+S225G, S163P+N227T, S163P+E232D, S163P+G235W, S163P+N252P, S163P+N260Q, S163P+H272V, S163P+S279D, S163P+Y281P, S163P+K308Q, S163P+K309E, S163P+K312Q, S186R+S225G, S186R+N227T, S186R+E232D, S186R+G235W, S186R+N252P, S186R+N260Q, S186R+H272V, S186R+S279D, S186R+Y281P, S186R+K308Q, S186R+K309E, S186R+K312Q, S225G+N227T, S225G+E232D, S225G+G235W, S225G+N252P, S225G+N260Q, S225G+H272V, S225G+S279D, S225G+Y281P, S225G+K308Q, S225G+K309E, S225G+K312Q, N227T+E232D, N227T+G235W, N227T+N252P, N227T+N260Q, N227T+H272V, N227T+S279D, N227T+Y281P, N227T+K308Q, N227T+K309E, N227T+K312Q, E232D+G235W, E232D+N252P, E232D+N260Q, E232D+H272V, E232D+S279D, E232D+Y281P, E232D+K308Q, E232D+K309E, E232D+K312Q, G235W+N252P, G235W+N260Q, G235W+H272V, G235W+S279D, G235W+Y281P, G235W+K308Q, G235W+K309E, G235W+K312Q, N252P+N260Q, N252P+H272V, N252P+S279D, N252P+Y281P, N252P+K308Q, N252P+K309E, N252P+K312Q, N260Q+H272V, N260Q+S279D, N260Q+Y281P, N260Q+

K308Q, N260Q+K309E, N260Q+K312Q, H272V+S279D, H272V+Y281P, H272V+K308Q, H272V+K309E, H272V+ K312Q, S279D+Y281P, S279D+K308Q, S279D+K309E, S279D+K312Q, Y281P+K308Q, Y281P+K309E, Y281P+ K312Q, K308Q+K309E, K308Q+K312Q and K309E+ K312Q.

In one preferred embodiment the dispersin variant of the invention comprises at least three substitutions, wherein the substitutions or substitution sets are selected from the group consisting of:

K312E+N227T+F276A, K312E+N227T+K308E, K312E+N227T+K309E, K312E+N227T+K312E, K312E+ F276A+K308E, K312E+F276A+K309E, K312E+F276A+ K312E, K312E+K308E+K309E, K312E+K308E+K312E, K312E+K309E+K312E, N227T+F276A+K308E, N227T+ F276A+K309E, N227T+F276A+K312E, N227T+K308E+ K309E, N227T+K308E+K312E, N227T+K309E+K312E, F276A+K308E+K309E, F276A+K308E+K312E, F276A+ K309E+K312E, and K308E+K309E+K312E.

In one preferred embodiment the dispersin variant of the invention comprises at least three substitutions, wherein the substitution sets are selected from the group consisting of: Q3I+H15Y+A49W, Q3I+H15Y+N59E, Q3I+H15Y+ S163P, Q3I+H15Y+S186R, Q3I+H15Y+S225G, Q3I+ H15Y+N227T, Q3I+H15Y+E232D, Q3I+H15Y+G235W, Q3I+H15Y+N252P, Q3I+H15Y+N260Q, Q3I+H15Y+ H272V, Q3I+H15Y+S279D, Q3I+H15Y+Y281P, Q3I+ H15Y+K308Q, Q3I+H15Y+K309E, Q3I+H15Y+K312Q, Q3I+A49W+N59E, Q3I+A49W+S163P, Q3I+A49W+ S186R, Q3I+A49W+S225G, Q3I+A49W+N227T, Q3I+ A49W+E232D, Q3I+A49W+G235W, Q3I+A49W+N252P, Q3I+A49W+N260Q, Q3I+A49W+H272V, Q3I+A49W+ S279D, Q3I+A49W+Y281P, Q3I+A49W+K308Q, Q3I+ A49W+K309E, Q3I+A49W+K312Q, Q3I+N59E+S163P, Q3I+N59E+S186R, Q3I+N59E+S225G, Q3I+N59E+ N227T, Q3I+N59E+E232D, Q3I+N59E+G235W, Q3I+ N59E+N252P, Q3I+N59E+N260Q, Q3I+N59E+H272V, Q3I+N59E+S279D, Q3I+N59E+Y281P, Q3I+N59E+ K308Q, Q3I+N59E+K309E, Q3I+N59E+K312Q, Q3I+ S163P+S186R, Q3I+S163P+S225G, Q3I+S163P+N227T, Q3I+S163P+E232D, Q3I+S163P+G235W, Q3I+S163P+ N252P, Q3I+S163P+N260Q, Q3I+S163P+H272V, Q3I+ S163P+S279D, Q3I+S163P+Y281P, Q3I+S163P+K308Q, Q3I+S163P+K309E, Q3I+S163P+K312Q, Q3I+S186R+ S225G, Q3I+S186R+N227T, Q3I+S186R+E232D, Q3I+ S186R+G235W, Q3I+S186R+N252P, Q3I+S186R+N260Q, Q3I+S186R+H272V, Q3I+S186R+S279D, Q3I+S186R+ Y281P, Q3I+S186R+K308Q, Q3I+S186R+K309E, Q3I+ S186R+K312Q, Q3I+S225G+N227T, Q3I+S225G+E232D, Q3I+S225G+G235W, Q3I+S225G+N252P, Q3I+S225G+ N260Q, Q3I+S225G+H272V, Q3I+S225G+S279D, Q3I+ S225G+Y281P, Q3I+S225G+K308Q, Q3I+S225G+K309E, Q3I+S225G+K312Q, Q3I+N227T+E232D, Q3I+N227T+ G235W, Q3I+N227T+N252P, Q3I+N227T+N260Q, Q3I+ N227T+H272V, Q3I+N227T+S279D, Q3I+N227T+Y281P, Q3I+N227T+K308Q, Q3I+N227T+K309E, Q3I+N227T+ K312Q, Q3I+E232D+G235W, Q3I+E232D+N252P, Q3I+ E232D+N260Q, Q3I+E232D+H272V, Q3I+E232D+ S279D, Q3I+E232D+Y281P, Q3I+E232D+K308Q, Q3I+ E232D+K309E, Q3I+E232D+K312Q, Q3I+G235W+ N252P, Q3I+G235W+N260Q, Q3I+G235W+H272V, Q3I+ G235W+S279D, Q3I+G235W+Y281P, Q3I+G235W+ K308Q, Q3I+G235W+K309E, Q3I+G235W+K312Q, Q3I+ N252P+N260Q, Q3I+N252P+H272V, Q3I+N252P+S279D, Q3I+N252P+Y281P, Q3I+N252P+K308Q, Q3I+N252P+ K309E, Q3I+N252P+K312Q, Q3I+N260Q+H272V, Q3I+ N260Q+S279D, Q3I+N260Q+Y281P, Q3I+N260Q+ K308Q, Q3I+N260Q+K309E, Q3I+N260Q+K312Q, Q3I+ H272V+S279D, Q3I+H272V+Y281P, Q3I+H272V+ K308Q, Q3I+H272V+K309E, Q3I+H272V+K312Q, Q3I+ S279D+Y281P, Q3I+S279D+K308Q, Q3I+S279D+K309E, Q3I+S279D+K312Q, Q3I+Y281P+K308Q, Q3I+Y281P+ K309E, Q3I+Y281P+K312Q, Q3I+K308Q+K309E, Q3I+ K308Q+K312Q, Q3I+K309E+K312Q, H15Y+A49W+ N59E, H15Y+A49W+S163P, H15Y+A49W+S186R, H15Y+A49W+S225G, H15Y+A49W+N227T, H15Y+ A49W+E232D, H15Y+A49W+G235W, H15Y+A49W+ N252P, H15Y+A49W+N260Q, H15Y+A49W+H272V, H15Y+A49W+S279D, H15Y+A49W+Y281P, H15Y+ A49W+K308Q, H15Y+A49W+K309E, H15Y+A49W+ K312Q, H15Y+N59E+S163P, H15Y+N59E+S186R, H15Y+N59E+S225G, H15Y+N59E+N227T, H15Y+ N59E+E232D, H15Y+N59E+G235W, H15Y+N59E+ N252P, H15Y+N59E+N260Q, H15Y+N59E+H272V, H15Y+N59E+S279D, H15Y+N59E+Y281P, H15Y+N59E+ K308Q, H15Y+N59E+K309E, H15Y+N59E+K312Q, H15Y+S163P+S186R, H15Y+S163P+S225G, H15Y+ S163P+N227T, H15Y+S163P+E232D, H15Y+S163P+ G235W, H15Y+S163P+N252P, H15Y+S163P+N260Q, H15Y+S163P+H272V, H15Y+S163P+S279D, H15Y+ S163P+Y281P, H15Y+S163P+K308Q, H15Y+S163P+ K309E, H15Y+S163P+K312Q, H15Y+S186R+S225G, H15Y+S186R+N227T, H15Y+S186R+E232D, H15Y+ S186R+G235W, H15Y+S186R+N252P, H15Y+S186R+ N260Q, H15Y+S186R+H272V, H15Y+S186R+S279D, H15Y+S186R+Y281P, H15Y+S186R+K308Q, H15Y+ S186R+K309E, H15Y+S186R+K312Q, H15Y+S225G+ N227T, H15Y+S225G+E232D, H15Y+S225G+G235W, H15Y+S225G+N252P, H15Y+S225G+N260Q, H15Y+ S225G+H272V, H15Y+S225G+S279D, H15Y+S225G+ Y281P, H15Y+S225G+K308Q, H15Y+S225G+K309E, H15Y+S225G+K312Q, H15Y+N227T+E232 D, H15Y+ N227T+G235W, H15Y+N227T+N252P, H15Y+N227T+ N260Q, H15Y+N227T+H272V, H15Y+N227T+S279D, H15Y+N227T+Y281P, H15Y+N227T+K308Q, H15Y+ N227T+K309E, H15Y+N227T+K312Q, H15Y+E232 D+G235W, H15Y+E232 D+N252P, H15Y+E232D+ N260Q, H15Y+E232D+H272V, H15Y+E232 D+S279D, H15Y+E232 D+Y281P, H15Y+E232D+K308Q, H15Y+ E232 D+K309E, H15Y+E232D+K312Q, H15Y+G235W+ N252P, H15Y+G235W+N260Q, H15Y+G235W+H272V, H15Y+G235W+S279D, H15Y+G235W+Y281P, H15Y+ G235W+K308Q, H15Y+G235W+K309E, H15Y+G235W+ K312Q, H15Y+N252P+N260Q, H15Y+N252P+H272V, H15Y+N252P+S279D, H15Y+N252P+Y281P, H15Y+ N252P+K308Q, H15Y+N252P+K309E, H15Y+N252P+ K312Q, H15Y+N260Q+H272V, H15Y+N260Q+S279D, H15Y+N260Q+Y281P, H15Y+N260Q+K308Q, H15Y+ N260Q+K309E, H15Y+N260Q+K312Q, H15Y+H272V+ S279D, H15Y+H272V+Y281P, H15Y+H272V+K308Q, H15Y+H272V+K309E, H15Y+H272V+K312Q, H15Y+ S279D+Y281P, H15Y+S279D+K308Q, H15Y+S279D+ K309E, H15Y+S279D+K312Q, H15Y+Y281P+K308Q, H15Y+Y281P+K309E, H15Y+Y281P+K312Q, H15Y+ K308Q+K309E, H15Y+K308Q+K312Q, H15Y+K309E+ K312Q, A49W+N59E+S163P, A49W+N59E+S186R, A49W+N59E+S225G, A49W+N59E+N227T, A49W+ N59E+E232D, A49W+N59E+G235W, A49W+N59E+ N252P, A49W+N59E+N260Q, A49W+N59E+H272V, A49W+N59E+S279D, A49W+N59E+Y281P, A49W+ N59E+K308Q, A49W+N59E+K309E, A49W+N59E+ K312Q, A49W+S163P+S186R, A49W+S163P+S225G, A49W+S163P+N227T, A49W+S163P+E232D, A49W+ S163P+G235W, A49W+S163P+N252P, A49W+S163P+

N260Q, A49W+S163P+H272V, A49W+S163P+S279D, A49W+S163P+Y281P, A49W+S163P+K308Q, A49W+S163P+K309E, A49W+S163P+K312Q, A49W+S186R+S225G, A49W+S186R+N227T, A49W+S186R+E232D, A49W+S186R+G235W, A49W+S186R+N252P, A49W+S186R+N260Q, A49W+S186R+H272V, A49W+S186R+S279D, A49W+S186R+Y281P, A49W+S186R+K308Q, A49W+S186R+K309E, A49W+S186R+K312Q, A49W+S225G+N227T, A49W+S225G+E232D, A49W+S225G+G235W, A49W+S225G+N252P, A49W+S225G+N260Q, A49W+S225G+H272V, A49W+S225G+S279D, A49W+S225G+Y281P, A49W+S225G+K308Q, A49W+S225G+K309E, A49W+S225G+K312Q, A49W+N227T+E232D, A49W+N227T+G235W, A49W+N227T+N252P, A49W+N227T+N260Q, A49W+N227T+H272V, A49W+N227T+S279D, A49W+N227T+Y281P, A49W+N227T+K308Q, A49W+N227T+K309E, A49W+N227T+K312Q, A49W+E232D+G235W, A49W+E232D+N252P, A49W+E232D+N260Q, A49W+E232D+H272V, A49W+E232D+S279D, A49W+E232D+Y281P, A49W+E232D+K308Q, A49W+E232 D+K309E, A49W+E232D+K312Q, A49W+G235W+N252P, A49W+G235W+N260Q, A49W+G235W+H272V, A49W+G235W+S279D, A49W+G235W+Y281P, A49W+G235W+K308Q, A49W+G235W+K309E, A49W+G235W+K312Q, A49W+N252P+N260Q, A49W+N252P+H272V, A49W+N252P+S279D, A49W+N252P+Y281P, A49W+N252P+K308Q, A49W+N252P+K309E, A49W+N252P+K312Q, A49W+N260Q+H272V, A49W+N260Q+S279D, A49W+N260Q+Y281P, A49W+N260Q+K308Q, A49W+N260Q+K309E, A49W+N260Q+K312Q, A49W+H272V+S279D, A49W+H272V+Y281P, A49W+H272V+K308Q, A49W+H272V+K309E, A49W+H272V+K312Q, A49W+S279D+Y281P, A49W+S279D+K308Q, A49W+S279D+K309E, A49W+S279D+K312Q, A49W+Y281P+K308Q, A49W+Y281P+K309E, A49W+Y281P+K312Q, A49W+K308Q+K309E, A49W+K308Q+K312Q, A49W+K309E+K312Q, N59E+S163P+S186R, N59E+S163P+S225G, N59E+S163P+N227T, N59E+S163P+E232D, N59E+S163P+G235W, N59E+S163P+N252P, N59E+S163P+N260Q, N59E+S163P+H272V, N59E+S163P+S279D, N59E+S163P+Y281P, N59E+S163P+K308Q, N59E+S163P+K309E, N59E+S163P+K312Q, N59E+S186R+S225G, N59E+S186R+N227T, N59E+S186R+E232D, N59E+S186R+G235W, N59E+S186R+N252P, N59E+S186R+N260Q, N59E+S186R+H272V, N59E+S186R+S279D, N59E+S186R+Y281P, N59E+S186R+K308Q, N59E+S186R+K309E, N59E+S186R+K312Q, N59E+S225G+N227T, N59E+S225G+E232D, N59E+S225G+G235W, N59E+S225G+N252P, N59E+S225G+N260Q, N59E+S225G+H272V, N59E+S225G+S279D, N59E+S225G+Y281P, N59E+S225G+K308Q, N59E+S225G+K309E, N59E+S225G+K312Q, N59E+N227T+E232 D, N59E+N227T+G235W, N59E+N227T+N252P, N59E+N227T+N260Q, N59E+N227T+H272V, N59E+N227T+S279D, N59E+N227T+Y281P, N59E+N227T+K308Q, N59E+N227T+K309E, N59E+N227T+K312Q, N59E+E232 D+G235W, N59E+E232 D+N252P, N59E+E232D+N260Q, N59E+E232D+H272V, N59E+E232 D+S279D, N59E+E232 D+Y281P, N59E+E232D+K308Q, N59E+E232 D+K309E, N59E+E232D+K312Q, N59E+G235W+N252P, N59E+G235W+N260Q, N59E+G235W+H272V, N59E+G235W+S279D, N59E+G235W+Y281P, N59E+G235W+K308Q, N59E+G235W+K309E, N59E+G235W+K312Q, N59E+N252P+N260Q, N59E+N252P+H272V, N59E+N252P+S279D, N59E+N252P+Y281P, N59E+N252P+K308Q, N59E+N252P+K309E, N59E+N252P+K312Q, N59E+N260Q+H272V, N59E+N260Q+S279D, N59E+N260Q+Y281P, N59E+N260Q+K308Q, N59E+N260Q+K309E, N59E+N260Q+K312Q, N59E+H272V+S279D, N59E+H272V+Y281P, N59E+H272V+K308Q, N59E+H272V+K309E, N59E+H272V+K312Q, N59E+S279D+Y281P, N59E+S279D+K308Q, N59E+S279D+K309E, N59E+S279D+K312Q, N59E+Y281P+K308Q, N59E+Y281P+K309E, N59E+Y281P+K312Q, N59E+K308Q+K309E, N59E+K308Q+K312Q, N59E+K309E+K312Q, S163P+S186R+S225G, S163P+S186R+N227T, S163P+S186R+E232D, S163P+S186R+G235W, S163P+S186R+N252P, S163P+S186R+N260Q, S163P+S186R+H272V, S163P+S186R+S279D, S163P+S186R+Y281P, S163P+S186R+K308Q, S163P+S186R+K309E, S163P+S186R+K312Q, S163P+S225G+N227T, S163P+S225G+E232D, S163P+S225G+G235W, S163P+S225G+N252P, S163P+S225G+N260Q, S163P+S225G+H272V, S163P+S225G+S279D, S163P+S225G+Y281P, S163P+S225G+K308Q, S163P+S225G+K309E, S163P+S225G+K312Q, S163P+N227T+E232D, S163P+N227T+G235W, S163P+N227T+N252P, S163P+N227T+N260Q, S163P+N227T+H272V, S163P+N227T+S279D, S163P+N227T+Y281P, S163P+N227T+K308Q, S163P+N227T+K309E, S163P+N227T+K312Q, S163P+E232D+G235W, S163P+E232D+N252P, S163P+E232D+N260Q, S163P+E232D+H272V, S163P+E232D+S279D, S163P+E232D+Y281P, S163P+E232D+K308Q, S163P+E232D+K309E, S163P+E232D+K312Q, S163P+G235W+N252P, S163P+G235W+N260Q, S163P+G235W+H272V, S163P+G235W+S279D, S163P+G235W+Y281P, S163P+G235W+K308Q, S163P+G235W+K309E, S163P+G235W+K312Q, S163P+N252P+N260Q, S163P+N252P+H272V, S163P+N252P+S279D, S163P+N252P+Y281P, S163P+N252P+K308Q, S163P+N252P+K309E, S163P+N252P+K312Q, S163P+N260Q+H272V, S163P+N260Q+S279D, S163P+N260Q+Y281P, S163P+N260Q+K308Q, S163P+N260Q+K309E, S163P+N260Q+K312Q, S163P+H272V+S279D, S163P+H272V+Y281P, S163P+H272V+K308Q, S163P+H272V+K309E, S163P+H272V+K312Q, S163P+S279D+Y281P, S163P+S279D+K308Q, S163P+S279D+K309E, S163P+S279D+K312Q, S163P+Y281P+K308Q, S163P+Y281P+K309E, S163P+Y281P+K312Q, S163P+K308Q+K309E, S163P+K308Q+K312Q, S163P+K309E+K312Q, S186R+S225G+N227T, S186R+S225G+E232D, S186R+S225G+G235W, S186R+S225G+N252P, S186R+S225G+N260Q, S186R+S225G+H272V, S186R+S225G+S279D, S186R+S225G+Y281P, S186R+S225G+K308Q, S186R+S225G+K309E, S186R+S225G+K312Q, S186R+N227T+E232D, S186R+N227T+G235W, S186R+N227T+N252P, S186R+N227T+N260Q, S186R+N227T+H272V, S186R+N227T+S279D, S186R+N227T+Y281P, S186R+N227T+K308Q, S186R+N227T+K309E, S186R+N227T+K312Q, S186R+E232D+G235W, S186R+E232D+N252P, S186R+E232D+N260Q, S186R+E232D+H272V, S186R+E232D+S279D, S186R+E232D+Y281P, S186R+E232D+K308Q, S186R+E232D+K309E, S186R+E232D+K312Q, S186R+G235W+N252P, S186R+G235W+N260Q, S186R+G235W+H272V, S186R+G235W+S279D, S186R+G235W+Y281P, S186R+G235W+K308Q, S186R+G235W+K309E, S186R+G235W+K312Q, S186R+N252P+N260Q, S186R+N252P+H272V, S186R+N252P+S279D, S186R+N252P+Y281P, S186R+N252P+K308Q, S186R+N252P+K309E, S186R+N252P+K312Q, S186R+N260Q+H272V, S186R+N260Q+S279D, S186R+N260Q+Y281P, S186R+N260Q+K308Q, S186R+N260Q+K309E, S186R+N260Q+K312Q, S186R+H272V+S279D, S186R+H272V+Y281P, S186R+H272V+K308Q, S186R+H272V+K309E, S186R+H272V+K312Q, S186R+S279D+Y281P, S186R+S279D+K308Q, S186R+

S279D+K309E, S186R+S279D+K312Q, S186R+Y281P+ K308Q, S186R+Y281P+K309E, S186R+Y281P+K312Q, S186R+K308Q+K309E, S186R+K308Q+K312Q, S186R+ K309E+K312Q, S225G+N227T+E232D, S225G+N227T+ G235W, S225G+N227T+N252P, S225G+N227T+N260Q, S225G+N227T+H272V, S225G+N227T+S279D, S225G+ N227T+Y281P, S225G+N227T+K308Q, S225G+N227T+ K309E, S225G+N227T+K312Q, S225G+E232D+G235W, S225G+E232D+N252P, S225G+E232D+N260Q, S225G+ E232D+H272V, S225G+E232D+S279D, S225G+E232D+ Y281P, S225G+E232D+K308Q, S225G+E232D+K309E, S225G+E232D+K312Q, S225G+G235W+N252P, S225G+ G235W+N260Q, S225G+G235W+H272V, S225G+ G235W+S279D, S225G+G235W+Y281P, S225G+ G235W+K308Q, S225G+G235W+K309E, S225G+ G235W+K312Q, S225G+N252P+N260Q, S225G+N252P+ H272V, S225G+N252P+S279D, S225G+N252P+Y281P, S225G+N252P+K308Q, S225G+N252P+K309E, S225G+ N252P+K312Q, S225G+N260Q+H272V, S225G+N260Q+ S279D, S225G+N260Q+Y281P, S225G+N260Q+K308Q, S225G+N260Q+K309E, S225G+N260Q+K312Q, S225G+ H272V+S279D, S225G+H272V+Y281P, S225G+H272V+ K308Q, S225G+H272V+K309E, S225G+H272V+K312Q, S225G+S279D+Y281P, S225G+S279D+K308Q, S225G+ S279D+K309E, S225G+S279D+K312Q, S225G+Y281P+ K308Q, S225G+Y281P+K309E, S225G+Y281P+K312Q, S225G+K308Q+K309E, S225G+K308Q+K312Q, S225G+ K309E+K312Q, N227T+E232D+G235W, N227T+E232D+ N252P, N227T+E232D+N260Q, N227T+E232D+H272V, N227T+E232D+S279D, N227T+E232D+Y281P, N227T+ E232D+K308Q, N227T+E232D+K309E, N227T+E232D+ K312Q, N227T+G235W+N252P, N227T+G235W+N260Q, N227T+G235W+H272V, N227T+G235W+S279D, N227T+G235W+Y281P, N227T+G235W+K308Q, N227T+G235W+K309E, N227T+G235W+K312Q, N227T+N252P+N260Q, N227T+N252P+H272V, N227T+ N252P+S279D, N227T+N252P+Y281P, N227T+N252P+ K308Q, N227T+N252P+K309E, N227T+N252P+K312Q, N227T+N260Q+H272V, N227T+N260Q+S279D, N227T+ N260Q+Y281P, N227T+N260Q+K308Q, N227T+N260Q+ K309E, N227T+N260Q+K312Q, N227T+H272V+S279D, N227T+H272V+Y281P, N227T+H272V+K308Q, N227T+ H272V+K309E, N227T+H272V+K312Q, N227T+S279D+ Y281P, N227T+S279D+K308Q, N227T+S279D+K309E, N227T+S279D+K312Q, N227T+Y281P+K308Q, N227T+ Y281P+K309E, N227T+Y281P+K312Q, N227T+K308Q+ K309E, N227T+K308Q+K312Q, N227T+K309E+K312Q, E232 D+G235W+N252P, E232D+G235W+N260Q, E232D+G235W+H272V, E232D+G235W+S279D, E232D+G235W+Y281P, E232D+G235W+K308Q, E232D+G235W+K309E, E232D+G235W+K312Q, E232D+N252P+N260Q, E232D+N252P+H272V, E232D+ N252P+S279D, E232D+N252P+Y281P, E232D+N252P+ K308Q, E232D+N252P+K309E, E232D+N252P+K312Q, E232D+N260Q+H272V, E232D+N260Q+S279D, E232D+ N260Q+Y281P, E232D+N260Q+K308Q, E232D+N260Q+ K309E, E232D+N260Q+K312Q, E232D+H272V+S279D, E232D+H272V+Y281P, E232D+H272V+K308Q, E232D+ H272V+K309E, E232D+H272V+K312Q, E232D+S279D+ Y281P, E232D+S279D+K308Q, E232D+S279D+K309E, E232D+S279D+K312Q, E232D+Y281P+K308Q, E232D+ Y281P+K309E, E232D+Y281P+K312Q, E232D+K308Q+ K309E, E232D+K308Q+K312Q, E232 D+K309E+K312Q, G235W+N252P+N260Q, G235W+N252P+H272V, G235W+N252P+S279D, G235W+N252P+Y281P, G235W+N252P+K308Q, G235W+N252P+K309E, G235W+N252P+K312Q, G235W+N260Q+H272V, G235W+N260Q+S279D, G235W+N260Q+Y281P, G235W+N260Q+K308Q, G235W+N260Q+K309E, G235W+N260Q+K312Q, G235W+H272V+S279D, G235W+H272V+Y281P, G235W+H272V+K308Q, G235W+H272V+K309E, G235W+H272V+K312Q, G235W+S279D+Y281P, G235W+S279D+K308Q, G235W+S279D+K309E, G235W+S279D+K312Q, G235W+Y281P+K308Q, G235W+Y281P+K309E, G235W+Y281P+K312Q, G235W+K308Q+K309E, G235W+K308Q+K312Q, G235W+K309E+K312Q, N252P+N260Q+H272V, N252P+N260Q+S279D, N252P+ N260Q+Y281P, N252P+N260Q+K308Q, N252P+N260Q+ K309E, N252P+N260Q+K312Q, N252P+H272V+S279D, N252P+H272V+Y281P, N252P+H272V+K308Q, N252P+ H272V+K309E, N252P+H272V+K312Q, N252P+S279D+ Y281P, N252P+S279D+K308Q, N252P+S279D+K309E, N252P+S279D+K312Q, N252P+Y281P+K308Q, N252P+ Y281P+K309E, N252P+Y281P+K312Q, N252P+K308Q+ K309E, N252P+K308Q+K312Q, N252P+K309E+K312Q, N260Q+H272V+S279D, N260Q+H272V+Y281P, N260Q+ H272V+K308Q, N260Q+H272V+K309E, N260Q+ H272V+K312Q, N260Q+S279D+Y281P, N260Q+S279D+ K308Q, N260Q+S279D+K309E, N260Q+S279D+K312Q, N260Q+Y281P+K308Q, N260Q+Y281P+K309E, N260Q+ Y281P+K312Q, N260Q+K308Q+K309E, N260Q+K308Q+ K312Q, N260Q+K309E+K312Q, H272V+S279D+Y281P, H272V+S279D+K308Q, H272V+S279D+K309E, H272V+ S279D+K312Q, H272V+Y281P+K308Q, H272V+Y281P+ K309E, H272V+Y281P+K312Q, H272V+K308Q+K309E, H272V+K308Q+K312Q, H272V+K309E+K312Q, S279D+ Y281P+K308Q, S279D+Y281P+K309E, S279D+Y281P+ K312Q, S279D+K308Q+K309E, S279D+K308Q+K312Q, S279D+K309E+K312Q, Y281P+K308Q+K309E, Y281P+ K308Q+K312Q, Y281P+K309E+K312Q and K308Q+ K309E+K312Q.

In one preferred embodiment the dispersin variant of the invention comprises at least three substitutions wherein the substitutions or substitution sets are selected from the group consisting of:

F276A+K308E+K309E, F276A+K308E+K312E, F276A+K309E+K312E, K308E+K309E+K312E, N227T+ F276A+K309E, N227T+F276A+K312E, N227T+K308E+ K309E, N227T+K308E+K312E, N227T+K309E+K312E, N227T+N252P+K308E, N227T+N252P+K309E, N227T+ N252P+K312E, N227T+N252P+N267T, N227T+N267T+ F276A, N227T+N267T+K308E, N227T+N267T+K309E, N227T+N267T+K312E, N252P+F276A+K308E, N252P+ F276A+K309E, N252P+F276A+K312E, N252P+K308E+ K309E, N252P+K308E+K312E, N252P+N267T+F276A, N252P+N267T+K308E, N252P+N267T+K309E, N252P+ N267T+K312E, N267T+F276A+K308E, N267T+F276A+ K309E, N267T+F276A+K312E, N267T+K308E+K309E, N267T+K308E+K312E, N267T+K309E+K312E, Q215K+ F276A+K308E, Q215K+F276A+K312E, Q215K+K308E+ K312E, Q215K+K309E+K312E, Q215K+N227T+F276A, Q215K+N227T+K308E, Q215K+N227T+K309E, Q215K+ N227T+K312E, Q215K+N227T+N252P, Q215K+N227T+ N267T, Q215K+N252P+F276A, Q215K+N252P+K309E, Q215K+N252P+K312E, Q215K+N252P+N267T, Q215K+ N267T+F276A, Q215K+N267T+K312E, S163P+F276A+ K308E, S163P+F276A+K312E, S163P+K308E+K309E, S163P+K308E+K312E, S163P+K309E+K312E, S163P+ N227T+F276A, S163P+N227T+K309E, S163P+N227T+ N252P, S163P+N227T+N267T, S163P+N252P+F276A, S163P+N252P+K308E, S163P+N252P+K309E, S163P+ N252P+K312E, S163P+N252P+N267T, S163P+N267T+ K308E, S163P+N267T+K309E, S163P+N267T+K312E,

S163P+Q215K+F276A, S163P+Q215K+K308E, S163P+Q215K+K309E, S163P+Q215K+K312E, S163P+Q215K+N227T and S163P+Q215K+N252P.

In one preferred embodiment the dispersin variant of the invention comprises at least four substitutions wherein the substitutions or substitution sets are selected from the group consisting of: K312E+N227T+F276A+K308E, K312E+N227T+F276A+K309E, K312E+N227T+F276A+K312E, K312E+N227T+K308E+K309E, K312E+N227T+K308E+K312E, K312E+N227T+K309E+K312E, K312E+F276A+K308E+K309E, K312E+F276A+K308E+K312E, K312E+F276A+K309E+K312E, K312E+K308E+K309E+K312E, N227T+F276A+K308E+K309E, N227T+F276A+K308E+K312E, N227T+F276A+K309E+K312E, N227T+K308E+K309E+K312E, F276A+K308E+K309E+K312E, F276A+K308E+K309E+K312E, N227T+K308E+K309E+K312E and N227T+F276A+K308E+K309E.

In one preferred embodiment the dispersin variant of the invention comprises at least four substitutions wherein the substitution sets are selected from the group consisting of: K312Q+N227T+S225G+K308Q, K312Q+N227T+S225G+K309E, K312Q+N227T+S225G+K312Q, K312Q+N227T+K308Q+K309E, K312Q+N227T+K308Q+K312Q, K312Q+N227T+K309E+K312Q, K312Q+S225G+K308Q+K309E, K312Q+S225G+K308Q+K312Q, K312Q+S225G+K309E+K312Q, K312Q+K308Q+K309E+K312Q, N227T+S225G+K308Q+K309E, N227T+S225G+K308Q+K312Q, N227T+S225G+K309E+K312Q, N227T+K308Q+K309E+K312Q, S225G+K308Q+K309E+K312Q, S225G+K308Q+K309E+K312Q, N227T+K308Q+K309E+K312Q and N227T+S225G+K308Q+K309E.

In one preferred embodiment the dispersin variant of the invention comprises at least four substitutions wherein the substitutions or substitution sets are selected from the group consisting of: N227T+F276A+K308E+K309E, N227T+F276A+K308E+K312E, N227T+F276A+K309E+K312E, N227T+N267T+F276A+K308E, N227T+N267T+F276A+K309E, N227T+N267T+F276A+K312E, and S163P+N227T+F276A+K308E, In one preferred embodiment the dispersin variant of the invention comprises at least four substitutions wherein the substitution sets are selected from the group consisting of: N227T+S225G+K308Q+K309E, N227T+S225G+K308Q+K312Q, N227T+S225G+K309E+K312Q, N227T+N267T+S225G+K308Q, N227T+N267T+S225G+K309E, N227T+N267T+S225G+K312Q, and S163P+N227T+S225G+K308Q, In one preferred embodiment the dispersin variant of the invention comprises at least five substitutions wherein the substitutions or substitution sets are selected from the group consisting of: S163P+Q215K+N227T+N252P+N267T, S163P+Q215K+N227T+N252P+F276A, S163P+Q215K+N227T+N252P+K308E, S163P+Q215K+N227T+N252P+K309E, S163P+Q215K+N227T+N267T+F276A, S163P+Q215K+N227T+N267T+K308E, S163P+Q215K+N227T+N267T+K309E, S163P+Q215K+N227T+F276A+K308E, S163P+Q215K+N227T+F276A+K309E, S163P+Q215K+N227T+K308E+K309E, S163P+Q215K+N252P+N267T+F276A, S163P+Q215K+N252P+N267T+K308E, S163P+Q215K+N252P+N267T+K309E, S163P+Q215K+N252P+F276A+K308E, S163P+Q215K+N252P+F276A+K309E, S163P+Q215K+N252P+K308E+K309E, S163P+Q215K+N267T+F276A+K308E, S163P+Q215K+N267T+F276A+K309E, S163P+Q215K+N267T+K308E+K309E, S163P+Q215K+F276A+K308E+K309E, S163P+N227T+N252P+N267T+F276A, S163P+N227T+N252P+N267T+K308E, S163P+N227T+N252P+N267T+K309E, S163P+N227T+N252P+F276A+K308E, S163P+N227T+N252P+F276A+K309E, S163P+N227T+N252P+K308E+K309E, S163P+N227T+N267T+F276A+K308E, S163P+N227T+N267T+F276A+K309E, S163P+N227T+N267T+K308E+K309E, S163P+N227T+F276A+K308E+K309E, S163P+N252P+N267T+F276A+K308E, S163P+N252P+N267T+F276A+K309E, S163P+N252P+N267T+K308E+K309E, S163P+N252P+F276A+K308E+K309E, S163P+N267T+F276A+K308E+K309E, Q215K+N227T+N252P+N267T+F276A, Q215K+N227T+N252P+N267T+K308E, Q215K+N227T+N252P+N267T+K309E, Q215K+N227T+N252P+F276A+K308E, Q215K+N227T+N252P+F276A+K309E, Q215K+N227T+N252P+K308E+K309E, Q215K+N227T+N267T+F276A+K308E, Q215K+N227T+N267T+F276A+K309E, Q215K+N227T+N267T+K308E+K309E, Q215K+N227T+F276A+K308E+K309E, Q215K+N252P+N267T+F276A+K308E, Q215K+N252P+N267T+F276A+K309E, Q215K+N252P+N267T+K308E+K309E, Q215K+N252P+F276A+K308E+K309E, Q215K+N267T+F276A+K308E+K309E, N227T+N252P+N267T+F276A+K308E, N227T+N252P+N267T+F276A+K309E, N227T+N252P+N267T+K308E+K309E, N227T+N252P+F276A+K308E+K309E, N227T+N267T+F276A+K308E+K309E N252P+N267T+F276A+K308E+K309E, Q215K+N227T+F276A+K308E+K309E, Q215K+N227T+F276A+K308E+K312E, Q215K+N227T+F276A+K309E+K312E, Q215K+N227T+K308E+K309E+K312E, Q215K+F276A+K308E+K309E+K312E, and N227T+F276A+K308E+K309E+K312E.

In one preferred embodiment the dispersin variant of the invention comprises at least five substitutions wherein the substitution sets are selected from the group consisting of: S163P+N59E+N227T+N252P+E232D, S163P+N59E+N227T+N252P+S225G, S163P+N59E+N227T+N252P+K308Q, S163P+N59E+N227T+N252P+K309E, S163P+N59E+N227T+E232D+S225G, S163P+N59E+N227T+E232D+K308Q, S163P+N59E+N227T+E232D+K309E, S163P+N59E+N227T+S225G+K308Q, S163P+N59E+N227T+S225G+K309E, S163P+N59E+N227T+K308Q+K309E, S163P+N59E+N252P+E232D+S225G, S163P+N59E+N252P+E232D+K308Q, S163P+N59E+N252P+E232D+K309E, S163P+N59E+N252P+S225G+K308Q, S163P+N59E+N252P+S225G+K309E, S163P+N59E+N252P+K308Q+K309E, S163P+N59E+E232 D+S225G+K308Q, S163P+N59E+E232D+S225G+K309E, S163P+N59E+E232 D+K308Q+K309E, S163P+N59E+S225G+K308Q+K309E, S163P+N227T+N252P+E232D+S225G, S163P+N227T+N252P+E232D+K308Q, S163P+N227T+N252P+E232D+K309E, S163P+N227T+N252P+S225G+K308Q, S163P+N227T+N252P+S225G+K309E, S163P+N227T+N252P+K308Q+K309E, S163P+N227T+E232D+S225G+K308Q, S163P+N227T+E232D+S225G+K309E, S163P+N227T+E232D+K308Q+K309E, S163P+N227T+S225G+K308Q+K309E, S163P+N252P+E232D+S225G+K308Q, S163P+N252P+E232 D+S225G+K309E, S163P+N252P+E232D+K308Q+K309E, S163P+N252P+S225G+K308Q+K309E, S163P+E232D+S225G+K308Q+K309E, N59E+N227T+N252P+E232D+S225G, N59E+N227T+N252P+E232D+K308Q, N59E+N227T+N252P+E232D+K309E, N59E+N227T+N252P+S225G+K308Q, N59E+N227T+N252P+S225G+K309E, N59E+N227T+N252P+K308Q+K309E, N59E+N227T+E232D+S225G+K308Q, N59E+N227T+E232 D+S225G+K309E, N59E+N227T+E232D+K308Q+K309E, N59E+N227T+S225G+K308Q+K309E, N59E+N252P+E232D+S225G+K308Q, N59E+N252P+E232D+S225G+K309E, N59E+N252P+E232D+K308Q+K309E, N59E+N252P+S225G+K308Q+K309E, N59E+E232D+S225G+K308Q+K309E, N227T+N252P+

E232D+S225G+K308Q, N227T+N252P+E232D+S225G+ K309E, N227T+N252P+E232D+K308Q+K309E, N227T+ N252P+S225G+K308Q+K309E, N227T+E232D+S225G+ K308Q+K309E N252P+E232D+S225G+K308Q+K309E, N59E+N227T+S225G+K308Q+K309E, N59E+N227T+ S225G+K308Q+K312Q, N59E+N227T+S225G+K309E+ K312Q, N59E+N227T+K308Q+K309E+K312Q, N59E+ S225G+K308Q+K309E+K312Q, and N227T+S225G+ K308Q+K309E+K312Q.

In one preferred embodiment the dispersin variant of the invention comprises at least five substitutions wherein the substitutions or substitution sets are selected from the group consisting of: N227T+N267T+F276A+K308E+K309E, N227T+N267T+F276A+K308E+K312E, N227T+N267T+F276A+K309E+K312E, S163P+N227T+F276A+K308E+K312E, N227T+F276A+K308E+K309E+K312E, N227T+F276A+K308E+K309E+K312E, and N227T+F276A+K308E+K309E+K312E.

In one preferred embodiment the dispersin variant of the invention comprises at least five substitutions wherein the substitution sets are selected from the group consisting of: N227T+E232D+S225G+K308Q+K309E, N227T+E232D+S225G+K308Q+K312Q, N227T+E232D+S225G+K309E+K312Q, S163P+N227T+S225G+K308Q+K309E, N227T+S225G+K308Q+K309E+K312Q, N227T+S225G+K308Q+K309E+K312Q, and N227T+S225G+K308Q+K309E+K312Q.

In one preferred embodiment the dispersin variant of the invention comprises at least six substitutions wherein the substitutions or substitution sets are selected from the group consisting of: N227T+N267T+F276A+K308E+K309E+K312E, N227T+N267T+F276A+K308E+K309E+K312E, N227T+N252P+F276A+K308E+K309E+K312E, Q215K+N227T+F276A+K308E+K309E+K312E, S163P+N227T+F276A+K308E+K309E+K312E, N227T+N267T+F276A+K308E+K309E+K312E, N227T+N252P+F276A+K308E+K309E+K312E, Q215K+N227T+F276A+K308E+K309E+K312E and S163P+N227T+F276A+K308E+K309E+K312E.

In one preferred embodiment the dispersin variant of the invention comprises at least six substitutions wherein the substitution sets are selected from the group consisting of: N227T+S225G+S186R+K308Q+K309E+K312Q, N227T+S225G+S186R+K308Q+K309E+K312Q, N227T+N252P+S186R+K308Q+K309E+K312Q, G235W+N227T+S186R+K308Q+K309E+K312Q, S163P+N227T+S186R+K308Q+K309E+K312Q, N227T+S225G+S186R+K308Q+K309E+K312Q, N227T+N252P+S186R+K308Q+K309E+K312Q, G235W+N227T+S186R+K308Q+K309E+K312Q and S163P+N227T+S186R+K308Q+K309E+K312Q.

In one preferred embodiment the dispersin variant of the invention comprises at least seven substitutions wherein the substitutions or substitution sets are selected from the group consisting of: N227T+N252P+N267T+F276A+K308E+K309E+K312E, Q215K+N227T+N252P+F276A+K308E+K309E+K312E, Q215K+N227T+N267T+F276A+K308E+K309E+K312E, S163P+N227T+N252P+F276A+K308E+K309E+K312E, S163P+N227T+N267T+F276A+K308E+K309E+K312E, S163P+Q215K+N227T+F276A+K308E+K309E+K312E, N227T+N252P+N267T+F276A+K308E+K309E+K312E, Q215K+N227T+N252P+F276A+K308E+K309E+K312E, Q215K+N227T+N267T+F276A+K308E+K309E+K312E, S163P+N227T+N252P+F276A+K308E+K309E+K312E, S163P+N227T+N267T+F276A+K308E+K309E+K312E, and S163P+Q215K+N227T+F276A+K308E+K309E+K312E.

In one preferred embodiment the dispersin variant of the invention comprises at least seven substitutions wherein the substitution sets are selected from the group consisting of: N227T+N252P+S225G+S186R+K308Q+K309E+K312Q, S186R+N227T+N252P+S186R+K308Q+K309E+K312Q, S186R+N227T+S225G+S186R+K308Q+K309E+K312Q, S163P+N227T+N252P+S186R+K308Q+K309E+K312Q, S163P+N227T+S225G+S186R+K308Q+K309E+K312Q, S163P+S186R+N227T+S186R+K308Q+K309E+K312Q, N227T+N252P+S225G+S186R+K308Q+K309E+K312Q, S186R+N227T+N252P+S186R+K308Q+K309E+K312Q, S186R+N227T+S225G+S186R+K308Q+K309E+K312Q, S163P+N227T+N252P+S186R+K308Q+K309E+K312Q, S163P+N227T+S225G+S186R+K308Q+K309E+K312Q, and S163P+S186R+N227T+S186R+K308Q+K309E+K312Q.

In one preferred embodiment the dispersin variant of the invention comprises at least eight substitutions wherein the substitutions are selected from the group consisting of: S163P+Q215K+N227T+N252P+N267T+F276A+K308E+K309E, S163P+Q215K+N227T+N252P+N267T+F276A+K308E+K312E, S163P+Q215K+N227T+N252P+N267T+F276A+K309E+K312E, S163P+Q215K+N227T+N252P+N267T+K308E+K309E+K312E, S163P+Q215K+N227T+N252P+F276A+K308E+K309E+K312E, S163P+Q215K+N227T+N267T+F276A+K308E+K309E+K312E, S163P+Q215K+N252P+N267T+F276A+K308E+K309E+K312E, S163P+N227T+N252P+N267T+F276A+K308E+K309E+K312E, and Q215K+N227T+N252P+N267T+F276A+K308E+K309E+K312E.

In one preferred embodiment the dispersin variant of the invention comprises at least eight substitutions wherein the substitution sets are selected from the group consisting of: S163P+G235W+N227T+N252P+S186R+N260Q+K308Q+K309E, S163P+G235W+N227T+N252P+S186R+N260Q+K308Q+K312Q, S163P+G235W+N227T+N252P+S186R+N260Q+K309E+K312Q, S163P+G235W+N227T+N252P+S186R+K308Q+K309E+K312Q, S163P+G235W+N227T+N252P+N260Q+K308Q+K309E+K312Q, S163P+G235W+N227T+S186R+N260Q+K308Q+K309E+K312Q, S163P+G235W+N252P+S186R+N260Q+K308Q+K309E+K312Q, S163P+N227T+N252P+S186R+N260Q+K308Q+K309E+K312Q, and G235W+N227T+N252P+S186R+N260Q+K308Q+K309E+K312Q.

In one preferred embodiment the dispersin variant of the invention comprises at least eight substitutions wherein the substitutions or substitution sets are selected from the group consisting of: Q215K+N227T+N252P+N267T+F276A+K308E+K309E+K312E, S163P+N227T+N252P+N267T+F276A+K308E+K309E+K312E, S163P+Q215K+N227T+N252P+F276A+K308E+K309E+K312E, S163P+Q215K+N227T+N267T+F276A+K308E+K309E+K312E, Q215K+N227T+N252P+N267T+F276A+K308E+K309E+K312E, S163P+N227T+N252P+N267T+F276A+K308E+K309E+K312E, S163P+Q215K+N227T+N252P+F276A+K308E+K309E+K312E and S163P+Q215K+N227T+N267T+F276A+K308E+K309E+K312E.

In one preferred embodiment the dispersin variant of the invention comprises at least eight substitutions wherein the substitution sets are selected from the group consisting of: S225G+N227T+N252P+S186R+N260Q+K308E+K309E+K312E, S163P+N227T+N252P+S186R+N260Q+K308E+K309E+K312E, S163P+S225G+N227T+N252P+N260Q+K308E+K309E+K312E, S163P+S225G+N227T+S186R+N260Q+K308E+K309E+K312E, S225G+N227T+N252P+S186R+N260Q+K308E+K309E+K312E, S163P+N227T+N252P+S186R+N260Q+K308E+K309E+K312E, S163P+

S225G+N227T+N252P+N260Q+K308E+K309E+K312E and S163P+S225G+N227T+S186R+N260Q+K308E+K309E+K312E.

In one preferred embodiment the dispersin variant of the invention comprises at least nine substitutions wherein the substitutions or substitution sets are selected from the group consisting of: S163P+Q215K+N227T+N252P+N267T+F276A+K308E+K309E+K312E, Q3F+Q215K+N227T+N252P+N267T+F276A+K308E+K309E+K312E, A49W+S163P+Q215K+N227T+N252P+N267T+F276A+K309E+K312E, Q3F+S163P+Q215K+N227T+N252P+N267T+K308E+K309E+K312E, and A49W+Q215K+N227T+N252P+N267T+F276A+K308E+K309E+K312E.

In one preferred embodiment the dispersin variant of the invention comprises at least nine substitutions wherein the substitution sets are selected from the group consisting of: S163P+S225G+N227T+N252P+N260Q+S186R+K308Q+K309E+K312Q, Q3I+S225G+N227T+N252P+N260Q+S186R+K308Q+K309E+K312Q, A49W+S163P+S225G+N227T+N252P+N260Q+S186R+K309E+K312Q, Q3I+S163P+S225G+N227T+N252P+N260Q+K308Q+K309E+K312Q, and A49W+S225G+N227T+N252P+N260Q+S186R+K308Q+K309E+K312Q.

In one preferred embodiment the dispersin variant of the invention comprises at least nine substitutions wherein the substitutions or substitution sets are selected from the group consisting of: S163P+Q215K+N227T+N252P+N267T+F276A+K308E+K309E+K312E and S163P+Q215K+N227T+N252P+N267T+F276A+K308E+K309E+K312E.

In one preferred embodiment the dispersin variant of the invention comprises at least nine substitutions wherein the substitution sets are selected from the group consisting of: S163P+S186R+S225G+N227T+G235W+N252P+K308Q+K309E+K312Q and S163P+S186R+S225G+N227T+G235W+N252P+K308Q+K309E+K312Q.

In one preferred embodiment the dispersin variant of the invention comprises at least eight, at least nine, at least ten or at least eleven substitutions wherein the substitutions or substitution sets are selected from the group consisting of: Q3F+A49W+Q215K+F276A+K308E+K309E+K312E+N227T+N267T, Q3F+A49W+Q215K+F276A+K308E+K309E+K312E+N227T+N267T, Q3F+A49W+Q215K+F276A+K308E+K309E+K312E+N227T+N267T, Q3F+A49W+Q215K+F276A+K308E+K309E+K312E+N227T+, Q3F+A49W+Q215K+F276A+K308E+K309E+K312E+N267T+, Q3F+A49W+Q215K+F276A+K308E+K309E+N227T+N267T+, Q3F+A49W+Q215K+F276A+K308E+K312E+N227T+N267T+, Q3F+A49W+Q215K+F276A+K309E+K312E+N227T+N267T+, Q3F+A49W+Q215K+K308E+K309E+K312E+N227T+N267T+, Q3F+A49W+F276A+K308E+K309E+K312E+N227T+N267T+, Q3F+Q215K+F276A+K308E+K309E+K312E+N227T+N267T+, A49W+Q215K+F276A+K308E+K309E+K312E+N227T+N267T and Q3F+A49W+Q215K+F276A+K308E+K309E+K312E+N227T+N267T.

In one preferred embodiment the dispersin variant of the invention comprises at least eleven substitutions wherein the substitution sets are selected from the group consisting of: Q3I+A49W+N59E+S163P+S186R+S225G+N227T+Y281P+K308Q+K309E+K312Q, Q3I+A49W+N59E+S163P+S186R+S225G+E232D+Y281P+K308Q+K309E+K312Q, Q3I+A49W+N59E+S163P+S186R+S225G+G235W+Y281P+K308Q+K309E+K312Q, Q3I+A49W+N59E+S163P+S186R+S225G+N252P+Y281P+K308Q+K309E+K312Q, Q3I+A49W+N59E+S163P+S186R+S225G+N260Q+Y281P+K308Q+K309E+K312Q, Q3I+A49W+N59E+S163P+S186R+S225G+N227T+H272V+Y281P+K308Q+K309E, Q3I+A49W+N59E+S163P+S186R+S225G+N227T+S279D+Y281P+K308Q+K312Q, H15Y+A49W+N59E+S163P+S186R+S225G+N227T+E232D+Y281P+K309E+K312Q, H15Y+A49W+N59E+S163P+S186R+S225G+N227T+G235W+K308Q+K309E+K312Q, H15Y+A49W+S163P+S186R+S225G+N227T+Y281P+S288P+K308Q+K309E+K312Q, H15Y+A49W+S163P+S186R+S225G+N227T+N252P+Y281P+K308Q+K309E+K312Q, H15Y+A49W+S163P+S186R+S225G+N227T+H272P+Y281P+K308Q+K309E+K312Q, H15Y+A49W+S163P+S186R+S225G+N227T+S279D+Y281P+K308Q+K309E+K312Q, and H15Y+A49W+N59E+S163P+S186R+S225G+N227T+E232D+Y281P+K308Q+K312Q.

In one preferred embodiment of the invention the dispersin variant of the invention comprises one of the substitution sets selected from the group consisting of:
Q3F+A49W+N59E+S163P+S186R+S225G+N227T+N252P+F276A+Y281P+K308E+K309E+K312E;
Q3I+H15Y+A49W+N59E+S163P+S186R+S225G+N227T+E232D+N252P+N260Q+N267T+H272V+S279D+Y281P+K308Q+K309E+K312Q;
Q3I+H15Y+A49W+N59E+S163P+S186R+S225G+N227T+E232D+N252P+N260Q+N267T+H272P+S279D+Y281P+K308Q+K309E+K312Q;
Q3I+H15Y+A49W+N59E+S163P+S186R+S225G+N227T+E232D+G235W+N252P+N260Q+H272V+S279D+Y281P+K308Q+K309E+K312E;
Q3I+H15Y+A49W+N59E+S163P+S186R+S225G+N227T+E232D+G235W+N252P+N260Q+H272V+S279D+Y281P+K308E+K309E+K312Q;
Q3F+H15Y+V140I+S163P+S186R+Q215K+S225G+N227T+E232D+G235W+N252P+N260Q+N267T+H272V+S279D+Y281P+K308Q+K309E+K312Q;
Q3F+H15Y+S163P+S186R+Q215K+S225G+N227T+E232D+N252P+N260Q+N267T+H272V+S279D+Y281P+K308Q+K309E+K312Q; Q3F+H15Y+T17W+A49W+N59E+S163P+S186R+T218Q+S225G+N227T+G235W+S237W+N252P+H272P+K308Q+K309E+K312Q; H15Y+A49W+N59E+S163P+S186R+S225G+N227T+E232D+G235W+N252P+N260Q+H272V+S279D+Y281P+K309E+K312Q; Q3F+H15Y+T17W+A49W+N59E+S163P+S186R+D207N+T218Q+S225G+N227T+G235W+S237W+N252P+H272P+Y281P+K308Q+K309E+K312Q; Q3I+H15Y+A49W+N59E+S163P+S186R+S225G+N227T+E232 D+G235W+N252P+N260Q+H272V+S279D+Y281P+K308Q+K309E+K312Q; H15Y+A49W+N59E+S163P+S186R+S225G+N227T+E232D+N252P+N260Q+H272P+S279D+Y281P+S288P+K308Q+K309E+K312Q; and H15Y+A49W+N59E+S163P+S186R+S225G+N227T+E232D+N252P+N260Q+H272P+S279D+Y281P+K308Q+K309E+K312Q, wherein the variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In one preferred embodiment of the invention the dispersin variant of the invention comprises one of the substitution sets selected from the group consisting of: S186R+N227T+E232D+K308E, S163P+Q215K+N227T+N252P+

N267T+F276A+K308Q+K309E+K312E, S163P+Q215K+
N227T+N252P+N267T+F276A+K308E+K309E+K312Q,
Q3F+A49W+N59E+S163P+S186R+N227T+E232
　　D+N252P+F276A+S279G+K308E+K309E+K312E,
A49W+N59E+S163P+S186R+S225G+N227T+E232D+
　　N252P+F276A+S279G+K308E+K309E+K312E,
Q3F+T17W+A49W+N59E+S163P+S186R+S225G+
　　N227T+G235W+N252P+H272P+Y281P+K308Q+
　　K309E+K312Q,
A49W+N59E+S163P+S186R+N227T+E232D+N252P+
　　H272V+F276A+S279G+K308E+K309E+K312E,
Q3F+A49W+N59E+S163P+S186R+S225G+N227T+
　　N252P+F276A+S279G+K308E+K309E+K312E,
A49W+N59E+S163P+S186R+N227T+E232D+N252P+
　　F276A+S279G+Y281P+K308E+K309E+K312E,
A49W+N59E+S163P+S186R+S225G+N227T+N252P+
　　F276A+S279G+Y281P+K308E+K309E+K312E,
Q3F+A49W+N59E+S163P+S186R+S225G+N227T+
　　E232　　D+N252P+F276A+S279G+K308E+K309E+
　　K312E,
Q3F+S163P+S186R+Q215K+N227T+E232D+N252P+
　　N267T+F276A+S279G+K308E+K309E+K312E,
H15Y+A49W+N59E+S163P+S186R+S225G+N227T+
　　E232D+G235W+N252P+N260Q+H272P+S279D+
　　Y281P+K308Q+K309E+K312Q,
Q3F+S163P+S186R+Q215K+S225G+N227T+N252P+
　　N267T+F276A+S279G+K308E+K309E+K312E,
H15Y+A49W+N59E+S163P+S186R+S225G+N227T+
　　E232D+N252P+N260Q+H272P+S279D+Y281P+
　　S288P+K308Q+K309E+K312Q,
A49W+N59E+S163P+S186R+S225G+N227T+E232D+
　　N252P+H272V+F276A+S279G+K308E+K309E+
　　K312E,
H15Y+A49W+N59E+S163P+S186R+S225G+N227T+
　　E232D+G235W+N252P+N260Q+H272V+S279D+
　　Y281P+K308Q+K309E+K312Q,
S163P+S186R+Q215K+N227T+E232　　D+N252P+
　　N267T+F276A+S279G+Y281P+K308E+K309E+
　　K312E,
Q3F+A49W+N59E+S163P+S186R+N227T+E232
　　D+N252P+F276A+S279G+Y281P+K308E+K309E+
　　K312E,
H15Y+A49W+N59E+S163P+S186R+S225G+N227T+
　　E232D+N252P+N260Q+H272P+S279D+Y281P+
　　K308Q+K309E+K312Q,
A49W+N59E+S163P+S186R+S225G+N227T+E232D+
　　N252P+F276A+S279G+Y281P+K308E+K309E+
　　K312E,
H15Y+A49W+N59E+S163P+S186R+S225G+N227T+
　　E232D+N252P+N260Q+H272V+Y281P+K308Q+
　　K309E+K312Q,
Q3F+T17W+A49W+N59E+S163P+S186R+D207N+
　　T218Q+S225G+N227T+G235W+N252P+H272P+
　　Y281P+K308Q+K309E+K312Q,
H15Y+T17W+A49W+N59E+S163P+S186R+S225G+
　　N227T+E232D+G235W+N252P+N260Q+H272V+
　　S279D+Y281P+K308Q+K309E+K312Q,
Q3F+A49W+N59E+S163P+S186R+S225G+N227T+
　　N252P+F276A+S279G+Y281P+K308E+K309E+
　　K312E,
Q3F+A49W+N59E+S163P+S186R+S225G+N227T+
　　E232D+N252P+H272V+F276A+S279G+K308E+
　　K309E+K312E,
A49W+N59E+S163P+S186R+N227T+E232D+N252P+
　　H272V+F276A+S279G+Y281P+K308E+K309E+
　　K312E,
S163P+S186R+S225G+N227T+E232　　D+N252P+
　　N267T+F276A+S279G+Y281P+K308E+K309E+
　　K312E,
H15Y+T17W+A49W+N59E+S163P+S186R+S225G+
　　N227T+E232D+N252P+N260Q+H272V+S279D+
　　Y281P+K308Q+K309E+K312Q,
Q3F+S163P+S186R+Q215K+N227T+E232　　D+N252P+
　　N267T+H272V+F276A+S279G+K308E+K309E+
　　K312E,
Q3I+H15Y+A49W+N59E+S163P+S186R+S225G+
　　N227T+E232D+G235W+N252P+N260Q+H272V+
　　S279D+Y281P+K308Q+K309E+K312Q,
S163P+S186R+Q215K+S225G+N227T+E232D+
　　N252P+N267T+F276A+S279G+Y281P+K308E+
　　K309E+K312E,
S163P+Q215K+S225G+N227T+E232D+N252P+
　　N267T+F276A+S279G+Y281P+K308E+K309E+
　　K312E,
S163P+S186R+Q215K+S225G+N227T+E232D+
　　N252P+N267T+H272V+F276A+S279G+K308E+
　　K309E+K312E,
S163P+Q215K+S225G+N227T+E232D+N252P+
　　N267T+H272V+F276A+S279G+K308E+K309E+
　　K312E,
A49W+N59E+S163P+S186R+S225G+N227T+N252P+
　　H272V+F276A+S279G+Y281P+K308E+K309E+
　　K312E,
Q3F+S163P+S186R+Q215K+N227T+E232　　D+N252P+
　　N267T+F276A+S279G+Y281P+K308E+K309E+
　　K312E,
Q3F+S163P+Q215K+N227T+E232　　D+N252P+N267T+
　　F276A+S279G+Y281P+K308E+K309E+K312E,
Q3F+H15Y+T17W+A49W+N59E+S163P+S186R+
　　T218Q+S225G+N227T+G235W+S237W+N252P+
　　H272P+Y281P+K308Q+K309E+K312Q,
S163P+Q215K+N227T+E232D+N252P+N267T+
　　H272V+F276A+S279G+Y281P+K308E+K309E+
　　K312E,
Q3F+S163P+Q215K+S225G+N227T+E232　　D+N252P+
　　N267T+H272V+F276A+S279G+K308E+K309E+
　　K312E,
Q3F+A49W+N59E+S163P+S186R+N227T+E232D+
　　N252P+H272V+F276A+S279G+Y281P+K308E+
　　K309E+K312E,
Q3F+S163P+S186R+Q215K+S225G+N227T+N252P+
　　N267T+F276A+S279G+Y281P+K308E+K309E+
　　K312E,
Q3F+H15Y+T17W+A49W+N59E+S163P+S186R+
　　D207N+T218Q+S225G+N227T+G235W+S237W+
　　N252P+H272P+Y281P+K308Q+K309E+K312Q,
S163P+S186R+Q215K+S225G+N227T+N252P+
　　N267T+H272V+F276A+S279G+Y281P+K308E+
　　K309E+K312E,
S163P+Q215K+S225G+N227T+N252P+N267T+
　　H272V+F276A+S279G+Y281P+K308E+K309E+
　　K312E,
Q3F+S163P+Q215K+N227T+E232D+N252P+N267T+
　　H272V+F276A+S279G+Y281P+K308E+K309E+
　　K312E,
Q3F+A49W+N59E+S163P+S186R+S225G+N227T+
　　E232D+N252P+F276A+S279G+Y281P+K308E+
　　K309E+K312E,
Q3F+A49W+N59E+S163P+S186R+S225G+N227T+
　　N252P+H272V+F276A+S279G+Y281P+K308E+
　　K309E+K312E,

A49W+N59E+S163P+S186R+S225G+N227T+E232D+
   N252P+H272V+F276A+S279G+Y281P+K308E+
   K309E+K312E,
S163P+Q215K+S225G+N227T+E232D+N252P+
   N267T+H272V+F276A+S279G+Y281P+K308E+
   K309E+K312E,
Q3F+S163P+S186R+Q215K+S225G+N227T+E232D+
   N252P+N260Q+N267T+H272P+S279D+Y281P+
   K308Q+K309E+K312Q,
Q3F+S163P+S186R+Q215K+N227T+E232 D+N252P+
   N267T+H272V+F276A+S279G+Y281P+K308E+
   K309E+K312E,
S163P+S186R+Q215K+S225G+N227T+E232D+
   N252P+N267T+H272V+F276A+S279G+Y281P+
   K308E+K309E+K312E,
Q3F+S163P+S186R+Q215K+S225G+N227T+N252P+
   N267T+H272V+F276A+S279G+Y281P+K308E+
   K309E+K312E,
Q3F+H15Y+V140I+S163P+S186R+Q215K+S225G+
   N227T+E232D+G235W+N252P+N260Q+N267T+
   H272V+S279D+Y281P+K308Q+K309E+K312Q,
Q3F+T17W+S163P+S186R+Q215K+S225G+N227T+
   E232D+G235W+N252P+N267T+H272V+F276A+
   S279G+Y281P+K308E+K309E+K312Q,
Q3F+S163P+S186R+Q215K+S225G+N227T+E232D+
   N252P+N267T+H272V+F276A+S279G+Y281P+
   K308E+K309E+K312Q,
Q3F+A49W+N59E+S163P+S186R+S225G+N227T+
   E232D+N252P+H272V+F276A+S279G+Y281P+
   K308E+K309E+K312E,
Q3F+S163P+S186R+Q215K+S225G+N227T+E232D+
   N252P+N267T+H272V+F276A+S279G+Y281P+
   K308E+K309E+K312E,
Q3F+H15Y+T17W+S163P+S186R+Q215K+S225G+
   N227T+E232D+G235W+N252P+N260Q+N267T+
   H272V+S279D+Y281P+K308Q+K309E+K312Q,
Q3F+S163P+Q215K+S225G+N227T+E232 D+N252P+
   N267T+H272V+F276A+S279G+Y281P+K308E+
   K309E+K312E,
Q3F+H15Y+S163P+S186R+Q215K+S225G+N227T+
   E232D+G235W+N252P+N260Q+N267T+H272P+
   S279D+Y281P+K308Q+K309E+K312Q,
Q3F+A49W+N59E+S163P+S186R+S225G+N227T+
   E232 D+G235W+N252P+N260Q+H272P+F276A+
   S279D+Y281P+K308E+K309E+K312Q,
Q3F+H15Y+T17W+S163P+S186R+Q215K+S225G+
   N227T+E232D+N252P+N260Q+N267T+H272V+
   S279D+Y281P+K308Q+K309E+K312Q,
Q3F+H15Y+S163P+S186R+Q215K+S225G+N227T+
   E232D+N252P+N260Q+N267T+H272P+S279D+
   Y281P+K308Q+K309E+K312Q,
Q3F+H15Y+S163P+S186R+Q215K+S225G+N227T+
   E232D+G235W+N252P+N267T+H272V+F276A+
   S279G+Y281P+K308Q+K309E+K312Q,
Q3F+H15Y+T17W+S163P+S186R+Q215K+S225G+
   N227T+E232D+N252P+N267T+H272V+F276A+
   S279G+Y281P+K308Q+K309E+K312Q and Q3F+
   H15Y+A49W+N59E+V140I+S163P+S186R+
   Q215K+S225G+N227T+E232D+G235W+N252P+
   N260Q+N267T+H272V+S279D+Y281P+K308Q+
   K309E+K312Q, wherein the variant has at least 60%,
   at least 65%, at least 70%, at least 75%, at least 80%,
   at least 85%, at least 90%, at least 95%, such as at least
   96%, at least 97%, at least 98%, or at least 99%, but less
   than 100% sequence identity to the polypeptide shown
   in SEQ ID NO: 1, wherein each position corresponds to
the position of the polypeptide shown in SEQ ID NO:
   1 (numbering according to SEQ ID NO: 1).

In one preferred embodiment of the invention the dispersin variant of the invention comprises one of the substitution sets selected from the group consisting of:
   A49W+F276A+K308E;
   A49W+N227T+A269C+Y282C+K308E;
   A49W+N227T+F276A;
   A49W+N227T+F276A+K308E;
   A49W+S186R+N227T+F276A;
   A49W+S186R+N227T+F276A+K308E;
   A49W+S186R+N227T+K308E;
   A49W+Y124R+N227T+F276A+K308E;
   A49W+Y124R+S186R+N227T+F276A;
   A49W+Y124R+S186R+N227T+F276A+K308E;
   A49W+Y124R+S186R+N227T+K308E;
   S163P+N227T+F276A+K308E;
   S163P+Q215K+N227T+N252P+N267T+F276A;
   S163P+Q215K+N227T+N252P+N267T+F276A+
      K308E;
   S163P+Q215K+N227T+N252P+N267T+F276A+
      K309E;
   S163P+Q215K+N227T+N252P+N267T+F276A+
      K312E;
   S163P+Q215K+N252P;
   S186R+F276A+K308E;
   S186R+N227T+F276A;
   S186R+N227T+K308E;
   Y124R+S186R+N227T+A269C+F276A+Y282C+
      K308E; and Y124R+S186R+N227T+F276A+K308E,
   wherein the variant has at least 60%, at least 65%, at
   least 70%, at least 75%, at least 80%, at least 85%, at
   least 90%, at least 95%, such as at least 96%, at least
   97%, at least 98%, or at least 99%, but less than 100%
   sequence identity to the polypeptide shown in SEQ ID
   NO: 1, wherein each position corresponds to the position of the polypeptide shown in SEQ ID NO: 1
   (numbering according to SEQ ID NO: 1).

The dispersin variants above preferably has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1.

In one preferred embodiment the dispersin comprises the polypeptide shown in SEQ ID NO: 17 or a polypeptide having at least at least 60%, at least 65%, at least 70%, at least 75%, at least 80%, at least 85%, at least 90%, at least 95%, such as at least 96%, at least 97%, at least 98%, or at least 99%, but less than 100% sequence identity hereto.

In some aspects, the dispersin variant comprises one or more substitution sets selected from the group consisting of: Q3F+A49W, Q3F+N59E, Q3F+S163P, Q3F+S186R, Q3F+Q215K, Q3F+S225G, Q3F+N227T, Q3F+N252P, Q3F+N267T, Q3F+F276A, Q3F+Y281P, Q3F+K308E, Q3F+K309E, Q3F+K312E, A49W+N59E, A49W+S163P, A49W+S186R, A49W+Q215K, A49W+S225G, A49W+N227T, A49W+N252P, A49W+N267T, A49W+F276A, A49W+Y281P, A49W+K308E, A49W+K309E, A49W+K312E, N59E+S163P, N59E+S186R, N59E+Q215K, N59E+S225G, N59E+N227T, N59E+N252P, N59E+N267T, N59E+F276A, N59E+Y281P, N59E+K308E, N59E+K309E, N59E+K312E, S163P+S186R, S163P+Q215K, S163P+S225G, S163P+N227T, S163P+N252P, S163P+N267T, S163P+F276A, S163P+Y281P, S163P+K308E, S163P+K309E, S163P+K312E, S186R+Q215K, S186R+S225G, S186R+N227T, S186R+N252P, S186R+

N267T, S186R+F276A, S186R+Y281P, S186R+K308E, S186R+K309E, S186R+K312E, Q215K+S225G, Q215K+N227T, Q215K+N252P, Q215K+N267T, Q215K+F276A, Q215K+Y281P, Q215K+K308E, Q215K+K309E, Q215K+K312E, S225G+N227T, S225G+N252P, S225G+N267T, S225G+F276A, S225G+Y281P, S225G+K308E, S225G+K309E, S225G+K312E, N227T+N252P, N227T+N267T, N227T+F276A, N227T+Y281P, N227T+K308E, N227T+K309E, N227T+K312E, N252P+N267T, N252P+F276A, N252P+Y281P, N252P+K308E, N252P+K309E, N252P+K312E, N267T+F276A, N267T+Y281P, N267T+K308E, N267T+K309E, N267T+K312E, F276A+Y281P, F276A+K308E, F276A+K309E, F276A+K312E, Y281P+K308E, Y281P+K309E, Y281P+K312E, K308E+K309E, K308E+K312E and K309E+K312E, wherein each substitution provides a dispersin variant having an increase in stability measured as half-life improvement factor, HIF or residual activity ratio, RAR, of at least 1.05, such as 1.08, such as 1.1, such as 1.15, such as 1.2, such as 1.25, such as 1.3, such as 1.4, such as 1.5, such as 1.6, such as 1.7, such as 1.8, such as 1.9, such as 2, such as 3, such as 4, such as 5 or such as at least 10 compared to the parent dispersin e.g. a dispersin comprising the polypeptide having the amino acid sequence shown in SEQ ID NO: 1, wherein the dispersin variant has at least 60%, at least 65%, at least 70%, at least 75%, at least 80%, at least 85%, at least 90%, at least 95%, such as at least 96%, at least 97%, at least 98%, or at least 99%, but less than 100% sequence identity to the polypeptide shown in SEQ ID NO: 1, wherein each position corresponds to the position of the polypeptide shown in SEQ ID NO: 1 (numbering according to SEQ ID NO: 1).

In one particular embodiment, the dispersin variant of the invention comprises at least one di-sulfide bridge. In one embodiment, the dispersin variant of the invention comprises at least one of the disulfide bridge: A269C-Y282C.

In one embodiment the dispersin variant comprises any of the following substitutions and disulfide bridges:
A49W+A269C+F276A+Y282C+K308E,
A49W+N227T+A269C+F276A+Y282C,
A49W+N227T+A269C+F276A+Y282C+K308E,
A49W+S186R+N227T+A269C+F276A+Y282C,
A49W+S186R+N227T+A269C+F276A+Y282C+K308E,
A49W+S186R+N227T+A269C+Y282C+K308E,
A49W+Y124R+N227T+A269C+F276A+Y282C+K308E,
A49W+Y124R+S186R+N227T+A269C+F276A+Y282C,
A49W+Y124R+S186R+N227T+A269C+F276A+Y282C+K308E,
A49W+Y124R+S186R+N227T+A269C+Y282C+K308E,
N227T+A269C+F276A+Y282C+K308E,
S186R+A269C+F276A+Y282C+K308E,
S186R+N227T+A269C+F276A+Y282C,
S186R+N227T+A269C+F276A+Y282C+K308E,
S186R+N227T+A269C+Y282C+K308E or
Y124R+S186R+N227T+A269C+F276A+Y282C+K308E.

Preferably the dispersin variants have at least 60%, at least 65%, at least 70%, at least 75%, at least 80%, at least 85%, at least 90%, at least 95%, such as at least 96%, at least 97%, at least 98% or 100% sequence identity to SEQ ID NO: 1.

The dispersin variant may also comprise any of the following alterations: D2E, D2S, D2T, Q3A, Q3*, T17A, E19T, E19H, E19W, E19L, K22R, K22N, K22M, K22S, D26*, S29G, Y30C, Y30S, Y30E, Y30G, N31W, N31G, G32N, N34*, N34M, N43D, N43F, E44N, E44S, E44I, S50C, E51D, Y52F, G54D, G54R, S56D, S56A, S57N, S57L, E58R, E58K, E58W, E58P, N59Q, N59K, N59I, N59G, T60I, T60M, T60R, T60A, N61E, N62K, N62M, N62V, N62G, T63Y, T63I, T63K, K67W, N68M, N68A, L71K, L71Q, L71E, L71D, S72P, A75R, A75W, A75G, A75N, A75M, D79R, D79L, D79N, D79E, D79W, K80I, K80D, K80Y, D81M, D81I, D81*, D81E, K95M, G96A, E99V, E99M, K102A, K102Q, K103D, K103C, K103P, K103T, K103N, K103I, K103S, K104A, K104V, K104*, D105*, V106I, V106P, V106*, V106S, V106F, K107R, K107G, K107N, K107H, K107Q, L108M, N110W, D111L, D111K, D111H, V113*, V113R, D115V, Y116*, Y116E, S117W, S117V, S117R, E118C, E118F, E118H, E119*, E119T, E119Y, E119M, E119H, Y124A, Y124S, Y124K, Y124I, Y124F, D125G, R127V, R127G, V128W, V128L, D131R, D131*, N134R, N134M, Q135H, Q135W, D138A, D138C, D138I, D138E, D138K, D142M, D142L, D142T, D142V, D142*, Y145A, Y145K, Y145R, Y145G, P147I, P147*, P147N, P147E, K148M, K148R, K148G, K148P, K148N, F149Y, F149E, E150I, G151M, G151R, G151V, G151T, G151E, G151F, K152V, K152W, K152S, G164F, G164Q, G164L, G164W, G164R, G164A, G164C, V167N, H168M, H168A, H168W, H168S, L170I, D171F, D171N, D171M, D174L, D174T, D174A, D174R, N177D, N177*, Q178E, Q178H, S181H, S181M, S181R, S181G, S181F, K184P, K184M, K184D, E185R, E185D, E185N, E185M, S186A, S186H, S186P, K187N, K187F, K187Y, E189M, S199I, S199E, S199N, S199A, S199R, E200Q, E200H, E200I, E200Y, A203N, A203I, N204A, N204Y, D207M, D207L, D207P, D207H, S208M, S208N, S208P, S208R, S217L, S217A, S217R, T218E, T218C, T218K, G222N, G222K, E224G, E224L, D230M, N233I, W234K, W234N, W234F, G235D, S237A, S237T, S237P, Y244V, L249D, L249I, L249T, S251Q, S251K, S251D, S251T, N252T, N252W, N252Y, G253E, G253*, G253R, G253I, G253A, F254T, F254K, F254N, F254V, F254A, F254*, T255E, Q256V, E257D, N260D, N260H, E261N, Q262L, Q262W, Q262H, N267V, W268Q, W268V, A271F, H272*, H272N, H272T, H272S, I278T, D280M, Y282P, Y282D, H283K, A284L, E286D, S288F, S288W, S288A, S288Q, S288E, E300N, E300L, H301L, H301V, H301M, T303D, T303M, T303E, T303N, Q307L, K308A, K308D, K309V, L311M, R319A or R319L, preferably wherein the dispersin variants have at least 60%, at least 65%, at least 70%, at least 75%, at least 80%, at least 85%, at least 90%, at least 95%, such as at least 96%, at least 97%, at least 98% or 100% sequence identity to SEQ ID NO: 1.

The dispersin variant may also comprise any of the following alterations: N31W N31G, S50C, N59I, N59Q, G96A, Y124A, V128L, D138A, F149Y, S181H, K184P, K184M, E189M, N204A, D207N, S208A, Q262L, Q262W, H283K, E300N, T303G, T303C or K309V, preferably the dispersin variants have at least 60%, at least 65%, at least 70%, at least 75%, at least 80%, at least 85%, at least 90%, at least 95%, such as at least 96%, at least 97%, at least 98% or 100% sequence identity to SEQ ID NO: 1.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for dispersin activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64.

Parent Dispersin

Preferably, the dispersin parent is obtained from a microorganism and the dispersin is a microbial enzyme. The dispersin is preferably of fungal or bacterial origin. The dispersin parent is preferably obtainable from *Terribacillus* e.g. *Terribacillus saccharophilus, Terribacillus goriensis* or *Terribacillus saccharophilus*.

The parent dispersin is preferably selected from the group consisting of:
a) a polypeptide comprising the amino acid sequence shown in SEQ ID NO: 1 or is a polypeptide having at least 60%, at least 65%, at least 70%, at least 75%, at least 80%, at least 85%, at least 90%, at least 95%, such as at least 96%, at least 97%, at least 98% or 100% sequence identity hereto,
b) a polypeptide comprising the amino acid sequence shown in SEQ ID NO:2 or is a polypeptide having at least 60%, at least 65%, at least 70%, at least 75%, at least 80%, at least 85%, at least 90%, at least 95%, such as at least 96%, at least 97%, at least 98% or 100% sequence identity hereto,
c) a polypeptide comprising the amino acid sequence shown in SEQ ID NO:3 or is a polypeptide having at least 60%, at least 65%, at least 70%, at least 75%, at least 80%, at least 85%, at least 90%, at least 95%, such as at least 96%, at least 97%, at least 98% or 100% sequence identity hereto,
d) a polypeptide comprising the amino acid sequence shown in SEQ ID NO:4 or is a polypeptide having at least 60%, at least 65%, at least 70%, at least 75%, at least 80%, at least 85%, at least 90%, at least 95%, such as at least 96%, at least 97%, at least 98% or 100% sequence identity hereto, and
e) a polypeptide comprising the amino acid sequence shown in SEQ ID NO:5 or is a polypeptide having at least 60%, at least 65%, at least 70%, at least 75%, at least 80%, at least 85%, at least 90%, at least 95%, such as at least 96%, at least 97%, at least 98% or 100% sequence identity hereto.

The parent dispersins preferably belong to the *Terribacillus* clade and comprises one or more of the conserved motifs: GXDE (SEQ ID NO:8), [EQ][NRSHA][YVFL][AGSTC][IVLF][EAQYN][SN] (SEQ ID NO:9),[VIM][LIV]G[GAV]DE[VI][PSA] SEQ ID NO: 10), [WND[SQR][IVL][TLVM] (SEQ ID NO: 11), QSTL (SEQ ID NO: 12), NKFFY (SEQ ID NO: 13) or NLD[DR]S (SEQ ID NO: 14), An overview of the *Terribacillus* clade is provided in the table below. The *Terribacillus* clade comprises homologous sequences. The polypeptides with hexosaminidase activity of the present invention having the mature amino acid sequences SEQ ID Nos 1-5 can be pairwise aligned using the Needleman-Wunsch algorithm (Needleman and Wunsch, 1970, *J. Mol. Biol.* 48: 443-453). The percent identities resulting from such alignments are shown below.

| SEQ ID NO: 5 | SEQ ID NO: 4 | SEQ ID NO: 3 | SEQ ID NO: 2 | SEQ ID NO: 1 | |
|---|---|---|---|---|---|
| 100 | 75.9 | 81.8 | 82.4 | 81.2 | SEQ ID NO: 5 |
| 75.9 | 100 | 77.5 | 76.5 | 77.5 | SEQ ID NO: 4 |
| 81.8 | 77.5 | 100 | 95.1 | 95.7 | SEQ ID NO: 3 |
| 82.4 | 76.5 | 95.1 | 100 | 93.5 | SEQ ID NO: 2 |
| 81.2 | 77.5 | 95.7 | 93.5 | 100 | SEQ ID NO: 1 |

The table shows that the polypeptides of the invention share close sequence relatedness. The polypeptides comprising the amino acids sequences of SEQ ID NO: 1, SEQ ID NO:2, SEQ ID NO:3, SEQ ID NO:4 and SEQ ID NO:5 belongs to a subclade of the Dispersin clade. These polypeptides share more than 90% pairwise sequence identity and are close related to each other.

The polypeptides of the invention all lie within the same clade, the *Terribacillus* clade, and all have common functional features including cleaning properties in the presence of detergents. In one aspect the parent dispersins belongs to the *Terribacillus* clade and comprises one or more of the motif(s) GXDE (SEQ ID NO:8), [EQ][NRSHA][YVFL][AGSTC][IVLF][EAQYN][SN] (SEQ ID NO:9), [VIM][LIV]G[GAV]DE[VI][PSA] (SEQ ID NO: 10), WND[SQR][IVL][TLVM] (SEQ ID NO: 11), QSTL (SEQ ID NO: 12), NKFFY (SEQ ID NO: 13) or NLD[DR]S (SEQ ID NO: 14).

Use and Methods

The dispersin variants of the present invention may be added to and thus become a component of a cleaning e.g. detergent composition.

The cleaning composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a dispersin variant of the present invention as described herein.

The cleaning compositions may be used for cleaning an item such as a textile or a hard surface in e.g. laundry and dish wash processes.

One aspect relates to a method of cleaning an item comprising a) adding a dispersin variant according to invention to a cleaning composition and b) washing item with the composition, wherein the item is a textile or a hard surface.

One aspect relates to a method of cleaning an item comprising;
a) adding a dispersin variant, comprising an alteration, preferably substitution at one or more positions corresponding to positions 2, 3, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 140, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 225, 227, 230, 232, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 or 323 of the polypeptide of SEQ ID NO: 1, wherein the dispersin variant has beta-1,6 N-acetylglucosaminidase activity, wherein the dispersin variant has at least 80%, at least 85%, at least 90%, at least 95%, at least 96%, at least 97%, at least 98%, or at least 99%, but less than 100% sequence identity to the polypeptide shown in SEQ ID NO: 1, to a cleaning composition and b) washing item with the composition, wherein the item is a textile or a hard surface.

One aspect relates to a method of cleaning an item comprising;

a) adding a dispersin variant, comprising an alteration, preferably substitution at one or more positions corresponding to positions 31, 33, 36, 73, 75, 94, 141, 144, 241, 277, 294, 297 or 299 of the polypeptide of SEQ ID NO: 1, wherein the dispersin variant has beta-1,6 N-acetylglucosaminidase activity, wherein the dispersin variant has at least 80%, at least 85%, at least 90%, at least 95%, at least 96%, at least 97%, at least 98%, or at least 99%, but less than 100% sequence identity to the polypeptide shown in SEQ ID NO: 1, to a cleaning composition and b) washing item with the composition, wherein the item is a textile or a hard surface.

One aspect relates to a method of cleaning an item comprising a) adding a dispersin variant, wherein the variant comprises any of the alterations selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19K, E19N, E19P, K22A, K22M, K22V, S23A, S23C, S23E, S23I, S23L, S23R, S23T, S23V, L24I, V25R, D26M, Y30*, Y30A, Y30D, Y30L, Y30M, Y30N, Y30R, Y30T, Y30V, G32L, G32M, G32R, N34D, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80R, K80V, K80W, D81A, D81G, D81L, D81N, D81R, D81S, D81T, D81V, D81W, I82V, L90F, E99Q, E99R, L100S, K103A, K103R, K103V, K104N, K104W, D105N, V106A, V106D, V106E, V106H, V106K, V106L, V106M, V106N, V106Q, V106R, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116M, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124H, Y124I, Y124K, Y124L, Y124M, Y124N, Y124Q, Y124R, Y124T, Y124V, Y124W, D125C, D125G, D125H, D125K, D125Q, D125R, N126V, R127D, R127H, R127K, R127L, R127M, R127Q, R127W, V128A, V128C, V128D, V128L, V128T, D131V, Q135*, Q135A, Q135D, Q135E, Q135K, Q135M, Q135Y, D138K, D138L, D138M, D138N, D138Q, D138R, D138S, D138V, D138W, E139W, V140I, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148W, F149L, F149M, F149N, E150A, E150D, E150H, E150K, E150L, E150M, E150N, E150R, E150V, E150W, E150Y, G151A, G151C, G151D, G151L, G151N, G151P, G151S, G151W, K152D, K152L, K152S, S163P, G164D, G164E, G164H, G164S, G164V, V167A, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181K, S181N, S181P, S181Q, S181T, S181V, S181W, E185A, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203Q, A203R, A203S, A203T, A203V, A203W, N204L, N204M, N204V, N204W, N204Y, L205I, D207A, D207C, D207E, D207G, D207K, D207N, D207Q, D207R, D207S, D207V, D207W, S208A, S208C, S208D, S208G, S208L, S208Q, S208T, S208V, S208W, S210T, Q215K, Q215R, Q215M, Q215L, Q215*, S217V, T218A, T218L, T218Q, T218R, T218V, S221N, G222D, E224A, E224P, S225G, N227A, N227Q, N227R, N227S, N227T, N227K, D230*, D230N, D230R, D230T, D230W, E232D, E232V, N233D, N233E, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251A, S251L, S251N, S251R, S251W, N252P, N252C, Q253D, Q253W, F254I, F254L, F254M, F254Y, Q256D, Q256E, Q256R, N260*, N260A, N260C, N260E, N260I, N260K, N260L, N260M, N260Q, N260R, N260T, N260V, N260W, N260Y, E261*, E261A, E261D, E261R, E261W, Q262*, Q262F, Q262H, Q262W, Q262Y, M263K, M263L, M263Q, D264*, D264C, D264E, D264N, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y281R, Y282E, Y282N, H283I, A284I, A284L, A284N, A284P, A284T, A284V, T287N, S288P, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308E, K308G, K308I, K308L, K308Q, K308S, K308T, K308V, K308Y, K309A, K309C, K309D, K309E, K309G, K309H, K309L, K309M, K309N, K309Q, K309S, K309T, K309I, K312A, K312E, K312L, K312M, K312N, K312Q, K312S, K312W, E314I, E314L, E314V, L315I, L315V, R319A, Y321F and N323R compared to the dispersin shown in SEQ ID NO: 1 to a cleaning composition and b) washing item with the composition, wherein the item is a textile or a hard surface.

The dispersin variants of the invention are suitable for use in cleaning such as laundry. Thus, some aspect of the invention relates to a method for laundering an item, wherein the method comprises the steps of:
a. Exposing an item to a wash liquor comprising a dispersin variant of the invention;
b. Completing at least one wash cycle; and
c. Optionally rinsing the item,
wherein the item is a textile or a hard surface.

The pH of the liquid solution is in the range of 1 to 11, such as in the range 5.5 to 11, such as in the range of 7 to 9, in the range of 7 to 8 or in the range of 7 to 8.5.

The wash liquor may have a temperature in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C. In some aspects the temperature of the wash liquor is 30° C.

The dispersin variants of the invention may be added to a wash liquor.

The concentration of the dispersin variant enzyme in the wash liquor is typically in the range of 0.00001-1000 ppm enzyme protein, such as in the range of 0.00004-100 ppm enzyme protein, such as in the range of 0.00008-100 enzyme protein, in the range of 0.0001-100 enzyme protein, in the range of 0.0002-100 enzyme protein, in the range of 0.0004-100 enzyme protein, in the range of 0.0008-100 enzyme protein, in the range of 0.001-100 ppm enzyme protein, in the range of 0.01-100 ppm enzyme protein, in the range of 1-1000 ppm enzyme protein, preferably in the range of 0.05-50 ppm enzyme protein, more preferably in the range of 0.1-50 ppm enzyme protein, more preferably in the range of 0.1-30 ppm enzyme protein, more preferably in the range of 0.5-20 ppm enzyme protein, and most preferably in the range of 0.5-10 ppm enzyme protein.

In some aspects the dispersin variants of the present invention are effective in preventing and/or reducing the malodor. The presence of complex organic stains such as body soil e.g. cell debris, sebum or EPS attach to e.g. laundry items which become sticky and therefore soil adheres to the sticky areas. This soil s to the laundry has shown difficult to reduce by commercially available detergent compositions. Further, when dirty laundry items are washed together with less dirty laundry items the dirt present in the wash liquor tend to adhere to the laundry (e.g. by re-deposition) in particular if the laundry is sticky as described above. As a result, hereof, the laundry item is more "soiled" after wash than before wash. In some aspects, the dispersin variants of the invention have improved cleaning properties compared to the parent dispersin and in some aspects, the dispersin variants of the invention reduce stickiness and/or re-deposition.

In some aspects, the invention relates to the use of a dispersin variant according to the invention for cleaning of an item, wherein the item is a fabric or a hard surface.

Further, the invention relates to the use of a dispersin variant according to the invention for preventing and/or reducing the adherence of soil to an item. In some aspect, the item is textile. When the soil does not adhere to the item, the item appears cleaner. Thus, the invention further relates to the use of a dispersin variant according to the invention for maintaining or improving the whiteness of the item.

The present invention further relates to detergent compositions comprising a dispersin variant according to the invention preferably with a detergent adjunct ingredient. The detergent composition comprising a dispersin variant according to the invention may be used for deep cleaning of an item, for preventing and/or reducing the stickiness of an item, for pretreating stains on the item, for preventing and/or reducing redeposition of soil during a wash cycle, for preventing and/or reducing adherence of soil to an item, for maintaining or improving the whiteness of an item and/or for preventing and/or reducing malodor from an item.

Preparation of Variants

The present invention also relates to a method for obtaining a dispersin variant having at least one improved property compared to the parent dispersin e.g. compared to the polypeptide shown in SEQ ID NO: 1.

One aspect of the invention relates to method for obtaining a dispersin variant, comprising;
a) introducing into a parent dispersin one or more alterations at a position selected from the group consisting of: 2, 3, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 140, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 225, 227, 230, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 and 323; and
b) recovering the variant, wherein the variant has hexosaminidase, preferably beta-1,6 N-acetylglucosaminidase activity.

One aspect of the invention relates to method for obtaining a dispersin variant, comprising;
a) introducing into a parent dispersin one or more alterations at a position selected from the group consisting of: 2, 3, 12, 15, 17, 18, 22, 23, 24, 25, 30, 49, 56, 57, 59, 62, 63, 68, 72, 74, 77, 82, 90, 99, 100, 106, 114, 123, 124, 125, 135, 138, 140, 163, 167, 170, 171, 173, 174, 175, 178, 179, 181, 185, 186, 187, 188, 189, 199, 203, 204, 205, 207, 210, 215, 218, 221, 225, 227, 235, 237, 244, 252, 256, 260, 262, 263, 264, 265, 267, 270, 272, 273, 274, 276, 278, 279, 280, 281, 282, 283, 284, 288, 290, 291, 296, 303, 304, 305, 306, 308, 309, 312, 314, 315, 319, 321, 322 and 323; and
b) recovering the variant, wherein the variant has hexosaminidase, preferably beta-1,6 N-acetylglucosaminidase activity.

One aspect of the invention relates to method for obtaining a dispersin variant, comprising;
a) introducing into a parent dispersin one or more alterations at a position selected from the group consisting of: 31, 33, 36, 73, 75, 94, 141, 144, 241, 277, 294, 297, 299 and
b) recovering the variant, wherein the variant has hexosaminidase, preferably beta-1,6 N-acetylglucosaminidase activity.

One aspect of the invention relates to method for obtaining a dispersin variant, comprising;
a) introducing into a parent dispersin one or more alterations selected from the group consisting of: D2A, D2L, D2N, D2R, D2V, D2W, Q3F, Q3I, Q3L, Q3M, Q3P, Q3V, Q3Y, Q3T, S12A, H15F, H15Y, T17W, T17C, T17E, T17F, T17M, T17R, T17V, V18L, E19D, E19K, E19N, E19P, K22A, K22M, K22V, S23A, S23C, S23E, S23I, S23L, S23R, S23T, S23V, L24I, V25R, D26M, Y30*, Y30A, Y30D, Y30L, Y30M, Y30N, Y30R, Y30T, Y30V, G32L, G32M, G32R, N34D, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80R, K80V, K80W, D81A, D81G, D81L, D81N, D81R, D81S, D81T, D81V, D81W, I82V, L90F, E99Q, E99R, L100S, K103A, K103R, K103V, K104N, K104W, D105N, V106A, V106D, V106E, V106H, V106K, V106L, V106M, V106N, V106Q, V106R, V106W, V106Y, K107A, K107C, K107L, K107M, K107T, K107V, K107W, N110M, N110R, N110V, D111A, D111E, D111M, D111N, D111Q, D111R, D111V, D111W, V113T, T114C, T114S, Y116D, Y116N, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124H, Y124I, Y124K, Y124L, Y124M, Y124N, Y124Q, Y124R, Y124T, Y124V, Y124W, D125C, D125G, D125H, D125K, D125Q, D125R, N126V, R127D, R127H, R127K, R127L, R127M, R127Q, R127W, V128A, V128C, V128D, V128L, V128T, D131V, Q135*, Q135A, Q135D, Q135E, Q135K, Q135M, Q135Y, D138K, D138L, D138M, D138N, D138Q, D138R, D138S, D138V, D138W, E139W, V140I, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150A, E150D, E150H, E150K, E150L, E150M, E150N, E150R, E150V, E150W, E150Y, G151A, G151C, G151D, G151L, G151N, G151P, G151S, G151W, K152D, K152L, K152R, S163P, G164D, G164E, G164H, G164S, G164V, V167A, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181K, S181N, S181P, S181Q, S181T, S181V, S181W, E185A, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203Q, A203R, A203S, A203T, A203V, A203W, N204L, N204M, N204V, N204W, N204Y, L205I, D207A, D207C, D207E, D207G, D207K, D207N, D207Q, D207R, D207S, D207V, D207W, S208A, S208C, S208D, S208G, S208L, S208Q, S208T, S208V, S208W, S210T, Q215K, Q215R, Q215M, Q215L, Q215*, S217V, T218A, T218L, T218Q, T218R, T218V, S221N, G222D, E224A, E224P, S225G, N227A, N227Q, N227R, N227S, N227T, N227K, D230*, D230N, D230R, D230T, D230W, E232D, E232V, N233D, N233E, N233H, N233Q, N233R, N233W, W234R, G235W, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251A, S251L, S251N, S251R, S251W, N252P, N252C, G253D, G253W, F254I, F254L, F254M, F254Y, Q256D, Q256E, Q256R, N260*, N260A, N260C, N260E, N260I, N260K, N260L, N260M, N260Q, N260R, N260T, N260V, N260W, N260Y, E261*, E261A, E261D, E261R, E261W, Q262*, Q262F, Q262H, Q262W, Q262Y, M263K, M263L, M263Q, D264*, D264C, D264E, D264N, Y265F, N267S, N267T, W268C, W268E, W268M, W268R, Y270F, A271D, A271G, H272D, H272I, H272M, H272P, H272V, H272W, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y281R, Y282E, Y282N, H283I, A284I, A284L, A284N, A284P, A284T, A284V, T287N, S288P, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308E, K308G, K308I, K308L, K308Q, K308S, K308T, K308V, K308Y, K309A, K309C, K309D, K309E, K309G, K309H, K309L, K309M, K309N, K309Q, K309S, K309T, K309I, K312A, K312E, K312L, K312M, K312N, K312Q, K312S, K312W, E314I, E314L, E314V, L315I, L315V, R319A, Y321F and N323R; and b) recovering the variant, wherein the variant has hexosaminidase, preferably beta-1,6 N-acetylglucosaminidase activity.

One aspect of the invention relates to method for obtaining a dispersin variant, comprising;

a) introducing into a parent dispersin one or more substitutions selected from the group consisting of: D2V, Q3F, Q3I, S12A, H15Y, T17W, T17E, V18L, K22M, S23I, S23C, S23A, S23T, S23L, S23V, S23E, L24I, V25R, Y30A, Y30L, A49W, A49Y, S56T, N59D, N59C, N59E, N59R, N59F, N59W, N59V, N62C, N62D, T63C, N68Q, S72D, S72E, I74L, S77A, I82V, L90F, E99Q, L100S, T114S, T114C, Y123W, Y124I, Y124M, Y124H, Y124R, Y124V, Y124Q, Y124T, Y124K, D125R, D125C, D125G, D125H, D125K, D125Q, Q135M, D138R, D138K, D138N, D138Q, V140I, S163P, L170D, L170K, L170S, L170H, D171E, D171K, D171Y, D171M, D171Q, D171L, I173C, D174W, D174H, D174M, D174N, F175Y, Q178K, I179T, S181T, S181F, S181Q, S181G, S181N, S181C, S181K, E185A, E185R, E185M, E185V, S186K, S186M, S186R, S186H, K187G, Y188P, E189V, S199C, S199L, A203G, A203E, A203V, N204L, N204Y, N204V, L205I, D207N, D207S, D207C, D207G, S210T, Q215K, Q215R, T218Q, S221N, S225G, N227T, N227K, E232D, G235W, S237W, Y244M, Y244C, N252P, N252C, Q256E, Q256D, N260Q, Q262H, M263Q, D264E, Y265F, N267T, N267S, Y270F, H272M, H272P, H272I, H272V, N273I, N273W, K274H, F276A, F276N, F276K, F276C, I278V, S279N, S279D, S279G, D280E, D280C, Y281P, Y282F, Y282N, H283I, A284T, A284L, A284I, S288P, S288K, V290I, K291R, T296C, T303Q, D304M, D304C, L305M, L305N, S306C, K308D, K308E, K308A, K308V, K308Q, K308S, K308Y, K308G, K308L, K308T, K308I, K309E, K309G, K309C, K309L, K309D, K309Q, K309N, K309T, K309A, K309S, K309M, K309H, K312E, K312A, K312Q, K312S, K312W, K312L, K312N, E314L, E314V, E314I, L315I, R319A, Y321F, and N323R; and b) recovering the variant, wherein the variant has hexosaminidase, preferably beta-1,6 N-acetylglucosaminidase activity.

The method preferably comprises introduction of 2-20, e.g. 2-10 and 2-5, such as 2, 3, 4, 5, 6, 7, 8, 9, 10, 11, 12, 13, 14, 15, 16, 17, 18, 19 or 20 alterations compared to the polypeptide shown in SEQ ID NO: 1.

Some aspects of the invention relate to a method for obtaining a dispersin variant, comprising introducing into a parent dispersin an alteration at one or more positions, wherein the dispersin parent belongs to the *Terribacillus* clade and wherein the parent dispersin comprises one or more of the motifs: GXDE (SEQ ID NO:8), [EQ][NRSHA][YVFL][AGSTC][IVLF][EAQYN][SN] (SEQ ID NO:9), [VIM][LIV]G[GAV]DE[VI][PSA] (SEQ ID NO: 10), WND[SQR][IVL][TLVM] (SEQ ID NO: 11), QSTL (SEQ ID NO: 12), NKFFY (SEQ ID NO: 13) or NLD[DR]S (SEQ ID NO: 14).

Some aspects of the invention relate to a method for obtaining a dispersin variant, comprising introducing into a parent dispersin an alteration at one or more positions, wherein the parent dispersin is selected from the group of polypeptides:

a) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 1, b) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 2, c) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 3, d) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 4, e) a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 5, Some aspect relates to a method of obtaining a dispersin variant wherein the parent dispersin is obtained from *Terribacillus* genus.

Some aspect relates to a method of obtaining a dispersin variant wherein the dispersin parent has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 1.

The variants of the invention may be prepared by procedures such as those mentioned below.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966. Site-directed mutagenesis can also be accomplished in vivo by methods known in the art.

See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

The variants of the applications may be prepared and identified by site saturated library methods, such described in: "Methods and applications in protein engineering", Rodrigo M. P. Siloto, Randall J. Weselake. *Biocatalysis and Agricultural Biotechnology* 1 (2012) 181-189.

Stabilization of an enzyme may entail running a site saturation library (SSL) screening campaign. A SSL library allows all 20 amino acids at the given amino acid position and a library is normally constructed for each amino acid position in the protein. The number of SSL libraries are thus typically counted in the hundreds for a typical enzyme molecule. The entire campaign tends to be very time consuming and resource demanding. The process will typically require construction of libraries, plating, colony picking, sequencing, re-gridding and high-throughput screening (HTS).

The screening itself is based on the principle that an exponential decay is observed for degradation of a protein when exposed to stress conditions, e.g. elevated temperature, proteases, surfactant. A stability improved variant can be found in a screening situation regardless of its initial concentration, as the stable variant after sufficient stress will always surpass the concentration of a reference sample by comparison, given a sufficiently sensitive detection method is available. The concentration may be reflected in e.g. an activity measurement.

Surprisingly, the principle of screening described above can successfully be extended to screening multiple variants for increased half-life in one go, i.e. screened as a single library pool or a mixture of variants. The first round of screening will not identify the stabilizing substitution itself, but it will enable a prioritization of the many libraries according to likelihood of containing variant(s) of interest based on selected parameters (e.g. thermostability, stability in presence of surfactant).

The result of screening could for example be the level of stability described by the ratio in activity between a stressed and an unstressed library. The actual measurement of activity in a stressed pool (and the backbone reference), can be conducted in several ways, spanning from a single end-of-stress activity measurement to multiple measurements characterizing the degradation as a function of time or increasing stress. The presence of improved variant(s) in a library will become increasing profound as the pool (and backbone reference) becomes increasingly degraded. It is therefore advantageous to measure the level of degradation late in the stress process.

Libraries with the highest level of stability, and preferably above that determined for the reference, are selected to be most interesting. The result obtained for a library is the combined effect of all variants it contains and the likelihood of finding improved variants in a specific library therefore increases with the level of its overall stability. Several factors can contribute to a positive screening result for a library, e.g. small sized library, variants having a high half-life, high concentration of stable variants, sensitive detection method to allow high stress conditions. The variants contained in the libraries of the selected amino acid positions are then tested for improved properties as isolated clones. The number of positions selected may in principle range from 1 to the total number of amino acid positions, but it will in practice always be significantly lower than the total number of positions.

In summary, the method of screening mixtures of variants is particularly useful in the context of screening small libraries targeting a single position in the context of protein engineering, e.g. libraries generated using NNS or other degenerate nucleotides at a given codon. The screening principle described can be carried out for multiple different small libraries, each representing e.g. full or partial site saturation of a single position, thus investigating multiple positions in parallel. This enables a quick assessment of the potential for hits in multiple positions in a single step. Promising positions can be prioritized and further investigated, leading to faster identification of hits (stabilizing substitutions). In summary, the method saves time, labour and consumables by significantly reducing the number of clones required to be screened for identification of stabilizing substitutions.

The method of the invention comprises; preparing a library of polypeptide variants ($V_L$), for each position (P) in the polypeptide. Up to all the 20 possible amino acids are introduced by substitution resulting in a specific number of different variants for each position. This can be done by well-known methods of generating diversity in the positions of the polypeptide. Some examples include but are not limited to NNS doping, where the codons comprise all four possible nucleobases A (adenine), C (cytosine), G (guanine), T (thymine) at position 1 and 2, whereas the third position comprises C (cytosine), G (guanine) only. In that way codons encoding all 20 natural amino acids are introduced randomly. The method diverges from traditional way of screening individual clones from the library: The inventors have found that the library $V_L$ could be subjected to measurement directly and from this measurement, libraries including improved variants could be selected directly. This enables selecting a subset library ($V_{LSub}$) containing improved variants. This subset $V_{LSub}$ is subjected to steps 1 to 4:

1. plate clones on agar plates,
2. pick each colony grown on the plates,
3. grow the picked individual colonies in microtiter plates, and
4. screen and sequence grown colonies Unlike the normal procedure these four steps only need to be performed for selected subsets and not for each position e.g. 324 times for a polypeptide having 324 positions. The steps 1-4 are very time consuming. The method of the current invention therefore significantly reduces the amount of time for making improved variants by limiting the number of libraries processed in steps 1 to 4.

One embodiment of the invention relates to a method for finding improved polypeptide variants, comprising the steps of:

a) generate diversity in selected, preferably all, positions of a polypeptide, thereby preparing libraries of polypeptide variants ($V_L$), and b) select subset library ($V_{LSub}$) with improved variants.

The subset library ($V_{LSub}$) may be selected based on different criteria such as improved stability, activity etc. as already described above. Thus, in one embodiment the libraries of polypeptide variants $V_L$ are subjected to a stress condition, e.g. elevated temperature, and a subset library ($V_{LSub}$) is selected from $V_L$.

One embodiment of the invention relates to a method for finding improved polypeptide variants, comprising the steps of:

a) generate diversity in selected, preferably all, positions of a polypeptide, thereby preparing a library of polypeptide variants ($V_L$),
b) expose part of the library of polypeptide variants ($V_L$) to one or more stress conditions suitable for measuring a property of interest, thereby generating a stressed $V_{LS+n}$ and an unstressed $V_{LUS}$ library;
c) compare the stressed $V_{LS}$ and the unstressed $V_{LUS}$ library; and
d) select subset library ($V_{LSub}$) with improved variants. Where $V_{LS+n}$ reflects that any number of library stressed subset could be made i.e. n≥1. Preferably, the subset library is subjected to the steps 1 to 4 as described above. Thus, one embodiment of the invention relates to a method for finding improved polypeptide variants, comprising the steps of:
a) generate diversity in selected, preferably all, positions of a polypeptide, thereby preparing a library of polypeptide variants ($V_L$), and
b) select subset library ($V_{LSub}$) with improved variants,
c) plate selected subset library ($V_{LSub}$) clones on agar plates,
d) pick each colony grown on the plates,
e) grow the picked individual colonies e.g. in microtiter plates
f) select individual improved variants by screening, and
g) sequence selected variants to identify specific mutations.
One embodiment of the invention relates to a method for finding improved polypeptide variants, comprising the steps of:
a) generate diversity in selected, preferably all, positions of a polypeptide, thereby preparing a library of polypeptide variants ($V_L$),
b) grow the individual libraries e.g. in microtiter plates
c) expose part of the library of polypeptide variants ($V_L$) to one or more stress conditions suitable for measuring a property of interest, thereby generating a stressed $V_{LS+n}$ and an unstressed $V_{LUS}$ library;
d) compare the stressed $V_{LS}$ and the unstressed $V_{LUS}$ library; and
e) select subset library ($V_{LSub}$) with improved variants
f) plate selected subset library ($V_{LSub}$) clones on agar plates,
g) pick each colony grown on the plates,
h) grow the picked individual colonies e.g. in microtiter plates
i) select individual improved variants by screening, and
j) sequence selected variants to identify specific mutations.
In one embodiment the number of variants in the subset library ($V_{LSub}$) is in the range of 2-20 polypeptide variants, preferable in the range of 5-20 polypeptide variants, preferable in the range of 5-10 polypeptide variants, preferable in the range of 8-20 polypeptide variants or in the range of 8-15 polypeptide variants.

In one embodiment, the library of polypeptide variants ($V_L$) is generated by using doped primers e.g. using NNS doping as described above. In one embodiment, the library of polypeptide variants ($V_L$) is generated by using doped primers e.g. using NMS, NKS, NRS, NYS, NWS, NSS, MNS, KNS, RNS, YNS, WNS, SNS, NAS, NCS, NGS, NTS, ANS, CNS, GNS, TNS, NNK, RNS, YHS, AYS, WRS (IUPAC nucleotide codes) doping as described above In one embodiment, the library ($V_L$) is sequenced to confirm diversity. The distribution of codon usage in the library may be determined by comparison of sequence reads covering the targeted position using any of the methods known in the art e.g. such as next generation sequencing (NGS) as described in *Ravi R. K., Walton K., Khosroheidari M.* (2018) *MiSeq: A Next Generation Sequencing Platform for Genomic Analysis. In: DiStefano J. (eds) Disease Gene Identification. Methods in Molecular Biology, vol 1706.* Humana Press, New York, NY.

The polypeptide is preferably an enzyme but may be applied to any protein. The enzyme may be selected from any suitable enzymes such as hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, hexosaminidases e.g. dispersins, invertase, laccase, esterases, lipase, mannosidase, mannanases, mutanase, nucleases e.g. DNases or RNases, oxidase, pectate lyase, pectinolytic enzyme, peroxidase, phytase, polyphenoloxidase, proteolytic enzyme proteases, transglutaminase and xylanase. The enzyme is preferably a dispersin and preferably the mixture of variants are variants of the present invention.

The property of interest may be e.g. stability, such as thermo-stability, in-wash stability, detergent stability, storage stability, secondary enzyme e.g. protease stability, sulfide-stability etc. all of which is not mutually exclusive. The improved property may be performance or activity e.g. such as wash performance, increased activity on specific substrate. The property may also be improved or altered substrate specificity.

One embodiment relates to a method for identifying and selecting variants with improved stability comprising the steps of:
a) generate diversity in selected, preferably all, positions of a polypeptide, thereby preparing a library of polypeptide variants ($V_L$),
b) divide the library of polypeptide variants ($V_L$) in two, expose one half of the library of polypeptide variants ($V_L$) to one or more stress conditions suitable for measuring stability, thereby generating a stressed $V_{LS}$ and an unstressed $V_{LUS}$ library;
c) compare the stressed $V_{LS}$ and the unstressed $V_{LUS}$ library; and
d) select subset library ($V_{LSub}$) with stability improved variants.

The stability is preferably measured as Half-life improvement factor (HIF) or residual activity ratio (RAR) as described in the "dispersin variants" section above. The stress condition is preferably elevated temperature such as above 37° C., above 41° C., above 46° C. or above 50° C. The property of interest may also be activity defined as improved substrate turn over. In one embodiment the property of interest is improved dispersin activity, such as increased catalysis of β-1,6-glycosidic linkages of N-acetylglucosamine polymers (poly-N-acetylglucosamine, PNAG) i.e. the dispersin variant display improved activity relative (or compared) to the activity of the parent dispersin, such as compared to a dispersin with SEQ ID NO: 1 or compared to a dispersin having the identical amino acid sequence of said variant but not having the alterations at one or more of said specified positions.

One embodiment relates to a method for identifying and selecting variants with improved beta-1,6 N-acetylglucosaminidase activity comprising the steps of a) generate diversity in selected, preferably all, positions of a polypeptide, thereby preparing a library of polypeptide variants ($V_L$),
b) divide the library of polypeptide variants ($V_L$) in two, expose one half of the library of polypeptide variants ($V_L$) to one or more stress conditions suitable for measuring beta-1,6 N-acetylglucosaminidase activity, thereby generating a stressed $V_{LS}$ and an unstressed $V_{LUS}$ library;
c) compare the stressed $V_{LS}$ and the unstressed $V_{LUS}$ library; and
d) select subset library ($V_{LSub}$) with beta-1,6 N-acetylglucosaminidase activity improved variants. It is clear to the skilled artisan that the term improved refers to the polypeptide variants being improved compared to a reference polypeptide, which may be the parent polypeptide or a polypeptide with SEQ ID NO: 1.

Nucleic Acid Constructs

The present invention also relates to nucleic acid constructs comprising a polynucleotide encoding the dispersin variants of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, Molecular Microbiology 13: 97-107), *E. coli* lac operon, *E. coli* trc promoter (Egon et al., 1988, Gene 69: 301-315), *Streptomyces coelicolor* agarase gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the polynucleotide of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* those phosphate isomerase gene); and mutant, truncated, and hybrid promoters thereof. Other promoters are described in U.S. Pat. No. 6,011,147.

In a yeast host, useful promoters are obtained from the genes for Saccharomyces cerevisiae enolase (ENO: 1), *Saccharomyces cerevisiae* galactokinase (GAL1), *Saccharomyces cerevisiae* alcohol dehydrogenase/glyceraldehyde-3 phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3 phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3' terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase lll, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3 phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* ctyIIIA gene (WO 94/25612) and a *Bacillus subtilis* SP82 gene (Hue et al., 1995, *J. Bacteriol.* 177: 3465-3471).

The control sequence may also be a leader, a nontranslated region of an mRNA that is important for translation by the host cell. The leader is operably linked to the 5' terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N terminus of a polypeptide and directs the polypeptide into the cell's secretory pathway. The 5' end of the coding sequence of the polynucleotide may inherently contain a signal peptide coding sequence naturally linked in translation reading frame with the segment of the coding sequence that encodes the polypeptide. Alternatively, the 5' end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), Rhizomucor miehei aspartic proteinase, and Saccharomyces cerevisiae alpha-factor.

Where both signal peptide and propeptide sequences are present, the propeptide sequence is positioned next to the N terminus of a polypeptide and the signal peptide sequence is positioned next to the N terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide encoding the dispersin variants of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression. In a further aspect, polynucleotide sequence codons have been modified by nucleotide substitutions to correspond to the codon usage of the host organism intended for production of the polypeptide of the present invention. The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In some aspects, the dual selectable marker is an hph-tk dual selectable marker system.

The vector preferably contains an element(s) that permits integration of the vector into the host cell's genome or autonomous replication of the vector in the cell independent of the genome. For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, Gene 98: 61-67; Cullen et al., 1987, Nucleic Acids Res. 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma.*

The bacterial host cell may be any Bacillus cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, Mol. Gen. Genet. 168: 111-115), competent cell transformation (see, e.g., Young and Spizizen, 1961, J. Bacteriol. 81: 823-829, or Dubnau and Davidoff-Abelson, 1971, J. Mol. Biol. 56: 209-221), electroporation (see, e.g., Shigekawa and Dower, 1988, Biotechniques 6: 742-751), or conjugation (see, e.g., Koehler and Thorne, 1987, J. Bacteriol. 169: 5271-5278). The introduction of DNA into an *E. coli* cell may be effected by protoplast transformation (see, e.g., Hanahan, 1983, J. Mol. Biol. 166: 557-580) or electroporation (see, e.g., Dower et al., 1988, Nucleic Acids Res. 16: 6127-6145). The introduction of DNA into a Streptomyces cell may be effected by protoplast transformation, electroporation (see, e.g., Gong et al., 2004, Folia Microbiol. (Praha) 49: 399-405), conjugation (see, e.g., Mazodier et al., 1989, J. Bacteriol. 171: 3583-3585), or transduction (see, e.g., Burke et al., 2001, Proc. Natl. Acad. Sci. USA 98: 6289-6294). The introduction of DNA into a Pseudomonas cell may be effected by electroporation (see, e.g., Choi et al., 2006, J. Microbiol. Methods 64: 391-397) or conjugation (see, e.g., Pinedo and Smets, 2005, Appl. Environ. Microbiol. 71: 51-57). The introduction of DNA into a Streptococcus cell may be effected by natural competence (see, e.g., Perry and Kuramitsu, 1981, Infect. Immun. 32: 1295-1297), protoplast transformation (see, e.g., Catt and Jollick, 1991, Microbios 68: 189-207), electroporation (see, e.g., Buckley et al., 1999, Appl. Environ. Microbiol. 65: 3800-3804), or conjugation (see, e.g., Clewell, 1981, Microbiol. Rev. 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Talaromyces emersonii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a dispersin variant of the present invention, comprising (a) cultivating a cell, under conditions conducive for production of the dispersin variants; and optionally, (b) recovering the dispersin variant. In some aspects, the cell is a *Terribacillus* cell. In another aspect, the cell is a *Terribacillus saccharophilus, Terribacillus goriensis* or *Terribacillus saccharophilus* cell.

The present invention also relates to methods of producing a dispersin variant of the present invention, comprising (a) cultivating a recombinant host cell of the present invention under conditions conducive for production of the dispersin variant; and optionally, (b) recovering the dispersin variant.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermenters in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The dispersin variant may be detected using methods known in the art that are specific for the dispersin variant polypeptide. These detection methods include, but are not limited to, use of specific antibodies, formation of an enzyme product, or disappearance of an enzyme substrate. For example, an enzyme assay may be used to determine the activity of the polypeptide.

The dispersin variant polypeptide may be recovered using methods known in the art. For example, the dispersin variant polypeptide may be recovered from the nutrient medium by conventional procedures including, but not limited to, collection, centrifugation, filtration, extraction, spray-drying, evaporation, or precipitation. In some aspects, a fermentation broth comprising the dispersin variant is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the variant.

Compositions

The present invention further relates to a cleaning e.g. detergent composition comprising at least one dispersin variant according to the invention and preferably a detergent adjunct ingredient. The detergent composition may be used for improving deep-cleaning effect, including but not limited to deep cleaning of an item, for preventing and/or reducing the stickiness of an item, for pretreating stains on the item, for preventing and/or reducing redeposition of soil during a wash cycle, for preventing and/or reducing adherence of soil to an item, for maintaining or improving the whiteness of an item and for preventing and/or reducing malodor from an item. The dispersin variants of the invention are useful in powder and liquid detergent.

In some aspects of the invention, the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.

The detergent adjunct ingredient may be a surfactant. One advantage of including a surfactant in a detergent composition comprising a dispersin variant is that the wash performance is improved. In some aspects, the detergent adjunct ingredient is a builder or a clay soil removal/anti-redeposition agent.

In some aspects, detergent adjunct ingredient is an enzyme. The detergent composition may comprise one or more enzymes, as specified below. The one or more enzymes may be selected from the group consisting of proteases, amylases, lipases, cutinases, cellulases, endoglucanases, xyloglucanases, pectinases, pectin lyases, xanthanases, peroxidaes, haloperoxygenases, catalases, nucleases e.g. DNases and RNases and mannanases. Specific enzymes suitable for the detergent compositions of the invention are described below.

The cleaning composition may be formulated as a bar, a homogenous tablet, and a tablet having two or more layers, a pouch having one or more compartments, a regular or compact powder, a granule, a paste, a gel, or a regular, compact or concentrated liquid. The detergent composition can be a liquid detergent, a powder detergent or a granule detergent.

Some aspects of the present invention relate to laundry or cleaning compositions comprising a dispersin, preferably at a level of from about 0.000001 wt % to about 1 wt %, from about 0.0001 wt % to about 1 wt %, from about 0.0002 wt % to about 1 wt %, from about 0.0005 wt % to about 1 wt %, from about 0.001 wt % to about 1 wt %, from about 0.002 wt % to about 1 wt %, from about 0.005 wt % to about 1 wt %, preferably from about 0.01 wt % to about 0.5 wt %, preferably from 0.0002 wt % to about 1 wt % by weight (wt %) of the composition. The amounts are wt % per unit active enzyme e.g. from about 0.00001 wt % to about 1 wt % of dispersin by weight of the composition.

The concentration of the active enzyme having dispersin activity is preferably at least 0.00001%, preferably at least 0.00002%, preferably at least 0.0001 wt %, preferably at least 0.0002 wt %, preferably at least 0.001 wt %, preferably at least 0.002 wt %, preferably at least 0.005 wt %, preferably at least 0.01 wt %, preferably at least 0.02 wt %, preferably at least 0.05 wt % preferably at least 0.1 wt % of the total detergent concentration.

The amount enzyme may also be in ppm (mg/L) active enzyme protein. Thus, in one aspect the amount of dispersin in the composition is at least 0.00001 ppm, 0.00002 ppm, 0.00005 ppm, 0.0001 ppm, 0.0002 ppm, 0.0005 ppm, 0.001 ppm, 0.002 ppm, 0.005 ppm, 0.01 ppm, 0.02 ppm, 0.05 ppm, 0.1 ppm, 0.2 ppm, 0.5 ppm, 1 ppm, 2 ppm, 5 ppm, 10 ppm or at least 20 ppm dispersin enzymes. In one aspect, the amount of dispersin in the composition is in the range from about 0.00001 ppm to about 10 ppm, or in the range from about 0.0001 ppm to about 2 ppm or in the range from about 0.001 ppm to about 2 ppm dispersin enzymes.

In some aspects, the cleaning composition is a liquid or powder laundry detergent, suitable for e.g. washing at high temperature and/or pH, such as at or above 40° C. and/or at or above pH 8. In some aspects, the detergent composition is a liquid or powder laundry detergent, suitable for e.g. washing at low temperature and/or pH, such as at or below 20° C. and/or pH 6. The cleaning composition may also be formulated as a unit dose detergent and/or compact detergent optionally with minimum or no water. The cleaning composition may also be a dish wash detergent. The laundry and dish wash detergents may be phosphate-free.

Surfactants

A surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and in particular alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diyl-bis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl) ammonium, bis(2-hydroxyethyl) ammonium and tris(2-hydroxyethyl) ammonium salts. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. Commercially available nonionic surfactants include Plurafac™, Lutensol™ and Pluronic™ from BASF, Dehypon™ series from Cognis and Genapol™ series from Clariant.

Builders

A builder is preferably selected among phosphates, sodium citrate builders, sodium carbonate, sodium silicate, sodium aluminosilicate (zeolite). Suitable builders are alkali metal or ammonium phosphates, polyphosphates, phosphonates, polyphosphates, carbonates, bicarbonates, borates, citrates, and polycarboxylates. Citrate builders, e.g., citric acid and soluble salts thereof (particularly sodium salt), are polycarboxylate builders. Citrates can be used in combination with zeolite, silicates like the BRITESIL types, and/or layered silicate builders. The builder is preferably added in an amount of about 0-65% by weight, such as about 5% to about 50% by weight. In a laundry detergent, the level of builder is typically about 40-65% by weight, particularly about 50-65% by weight, particularly from 20% to 50% by weight. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), and (carboxymethyl) inulin (CMI), and combinations thereof. Further non-limiting examples of builders include citrate, chelators such as aminocarboxylates, aminopolycarboxylates and phosphonates, and alkyl- or alkenylsuccinic acid. Additional specific examples include 2,2',2''-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N,N-diacetic acid (MGDA), glutamic acid-N,N-diacetic acid (GLDA), 1-hydroxyethane-1,1-diphosphonic acid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl)aspartic acid (SMAS), N-(2-sulfoethyl)-aspartic acid (SEAS), N-(sulfomethylglutamic acid (SMGL), N-(2-sulfoethyl)-glutamic acid (SEGL), N-methyliminodiacetic acid (MIDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and N'-(2-hydroxyethypethylenediamine-N,N,N'-triacetic acid (HEDTA), diethanolglycine (DEG), and combinations and salts thereof. Phosphonates suitable for use herein include 1-hydroxyethane-1,1-diphosphonic acid (HEDP), ethylenediaminetetrakis (methylenephosphonicacid)

(EDTMPA), diethylenetriaminepentakis (methylenephosphonic acid) (DTMPA or DTPMPA or DTPMP), nitrilotris (methylenephosphonic acid) (ATMP or NTMP), 2-phosphonobutane-1,2,4-tricarboxylic acid (PBTC), hexamethylenediaminetetrakis (methylenephosphonic acid) (HDTMP). The composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly (acrylic acid) (PAA) or copoly (acrylic acid/maleic acid) (PAA/PMA) or polyaspartic acid. Further exemplary builders and/or co-builders are described in, e.g., WO 09/102854, U.S. Pat. No. 5,977,053. In some aspects, the builder is a non-phosphorus based builder such as citric acid and/or methylglycine-N,N-diacetic acid (MGDA) and/or glutamic-N,N-diacetic acid (GLDA) and/or salts thereof. The liquid composition may also be phosphate free in that instance the preferred builders includes citrate and/or methylglycine-N,N-diacetic acid (MGDA) and/or glutamic-N,N-diacetic acid (GLDA) and/or salts thereof.

Bleach Components

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of hydrogen peroxide: Suitable sources of hydrogen peroxide are inorganic persalts, including alkali metal salts such as sodium percarbonate and sodium perborates (usually mono- or tetrahydrate), and hydrogen peroxide-urea (1/1).

Sources of peracids: Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyDoxy]benzene-1-sulfonate (ISONOBS), sodium 4-(dodecanoyloxy)benzene-1-sulfonate (LOBS), sodium 4-(decanoyloxy) benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach catalysts and boosters: The bleaching system may also include a bleach catalyst or booster. Some non-limiting examples of bleach catalysts that may be used in the compositions of the present invention include manganese oxalate, manganese acetate, manganese-collagen, cobalt-amine catalysts and manganese triazacyclononane (Mn-TACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn (Me3-TACN)](PF6)2, and [2,2',2"-nitrilotris(ethane-1,2-diylazanylylidene-κN-methanylylidene)triphenolato-κ3O] manganese(III). The bleach catalysts may also be other metal compounds, such as iron or cobalt complexes.

In some aspects, where a source of a peracid is included, an organic bleach catalyst or bleach booster may be used having one of the following formulae:

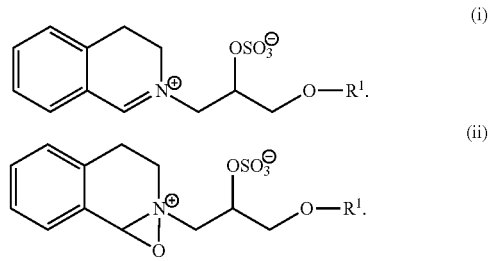

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO 2007/087258, WO 2007/087244, WO 2007/087259, EP 1867708 (Vitamin K) and WO 2007/087242. Suitable photobleaches may for example be sulfonated zinc or aluminium phthalocyanines.

The choice of detergent components may include, for textile care, the consideration of the type of textile to be cleaned, the type and/or degree of soiling, the temperature at which cleaning is to take place, and the formulation of the detergent product. Although components mentioned below are categorized by general header according to a functionality, this is not to be construed as a limitation, as a component may comprise additional functionalities as will be appreciated by the skilled artisan, including the exemplary non-limiting components shown in below.

Hydrotropes

The detergent composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fibre protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent composition of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO 2007/087243.

Enzymes

The detergent composition may comprise one or more additional enzymes such as a protease, lipase, cutinase, amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/001544.

Other cellulases are endo-beta-1,4-glucanase enzyme having a sequence of at least 97% identity to the amino acid sequence of position 1 to position 773 of SEQ ID NO: 2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™(Novozymes A/S), Whitezyme™ (Novozymes A/S), Clazinase™, and Puradax HA™ (Genencor International Inc.), and KAC-500(B)™ (Kao Corporation).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a neutral protease such as a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and *subtilisin lentus, subtilisin Novo, subtilisin Carlsberg, Bacillus licheniformis, subtilisin BPN', subtilisin 309, subtilisin 147* and *subtilisin 168* described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellumonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus lentus* protease shown in SEQ ID NO: 1 of WO 2016/001449. More preferred the protease variants may comprise one or more of the following mutations: S3T, V4I, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A and R269H. The protease variants are preferably variants of the *Bacillus lentus* protease (Savinase®) shown in SEQ ID NO: 1 of WO 2016/001449 or the *Bacillus amylolichenifaciens* protease (BPN') shown in SEQ ID NO: 2 of WO2016/001449. The protease variants preferably have at least 80% sequence identity to the polypeptide shown in SEQ ID NO: 1 or SEQ ID NO: 2 of WO 2016/001449.

A protease variant comprising a substitution at one or more positions corresponding to positions 171, 173, 175, 179, or 180 of SEQ ID NO: 1 of WO2004/067737, wherein said protease variant has a sequence identity of at least 75% but less than 100% to SEQ ID NO: 1 of WO2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases

Suitable amylases which can be used together with the dispersins of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 1 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase obtained from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase obtained from *B. amyloliquefaciens* shown in SEQ ID NO: 6 of WO 2006/066594 and residues 36-483 of SEQ ID NO: 4 are those having the substitutions:
M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID NO: 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Further suitable amylases are alpha-amylase variants comprising a modification in one or more positions corresponding to positions 1, 54, 56, 72, 109, 113, 116, 134, 140, 159, 167, 169, 172, 173, 174, 181, 182, 183, 184, 189, 194, 195, 206, 255, 260, 262, 265, 284, 289, 304, 305, 347, 391, 395, 439, 469, 444, 473, 476, or 477 of SEQ ID NO: 1, wherein the alpha-amylase variant has a sequence identity of at least 75% but less than 100% to SEQ ID NO: 13 or SEQ ID NO: 14 of WO 2016/180748.

Other examples are amylase variants such as those described in WO 2011/098531, WO 2013/001078 and WO 2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment obtained therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an aspect, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In a preferred aspect, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendtyphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment obtained therefrom exhibiting laccase activity, or a compound exhibiting a similar activity, such as a catechol oxidase (EC 1.10.3.1), an o-aminophenol oxidase (EC 1.10.3.4), ora bilirubin oxidase (EC 1.3.3.5).

Preferred laccase enzymes are enzymes of microbial origin. The enzymes may be obtained from plants, bacteria or fungi (including filamentous fungi and yeasts).

Suitable examples from fungi include a laccase derivable from a strain of *Bacillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase obtained from *Coprinopsis* or *Myceliophthora* is preferred; in particular a laccase obtained from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly (ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Dispersants

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent composition may preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxyethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Tinopal CBS-X is a 4.4'-bis-(sulfostyryl)-biphenyl disodium salt also known as Disodium Distyrylbiphenyl Disulfonate. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose derivatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Other Materials

Any detergent components known in the art for use in the cleaning composition of the invention may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in detergents may be utilized. The choice of such ingredients is well within the skill of the artisan.

Formulation of Detergent Products

The detergent composition may be in any convenient form, e.g., a bar, a homogenous tablet, a tablet having two or more layers, a regular or compact powder, a granule, a paste, a gel, or a regular, compact or concentrated liquid.

Detergent formulation forms: Layers (same or different phases), Pouches, versus forms for Machine dosing unit.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US 2009/0011970 A1)

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

Definition/Characteristics of the Forms:

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Granular Detergent Formulations

A granular detergent may be formulated as described in WO 09/092699, EP 1705241, EP 1382668, WO 07/001262, U.S. Pat. No. 6,472,364, WO 04/074419 or WO 09/102854. Other useful detergent formulations are described in WO 09/124162, WO 09/124163, WO 09/117340, WO 09/117341, WO 09/117342, WO 09/072069, WO 09/063355, WO 09/132870, WO 09/121757, WO 09/112296, WO 09/112298, WO 09/103822, WO 09/087033, WO 09/050026, WO 09/047125, WO 09/047126, WO 09/047127, WO 09/047128, WO 09/021784, WO 09/010375, WO 09/000605, WO 09/122125, WO 09/095645, WO 09/040544, WO 09/040545, WO 09/024780, WO 09/004295, WO 09/004294, WO 09/121725, WO 09/115391, WO 09/115392, WO 09/074398, WO 09/074403, WO 09/068501, WO 09/065770, WO 09/021813, WO 09/030632, and WO 09/015951.
WO 2011025615, WO 2011016958, WO 2011005803, WO 2011005623, WO 2011005730, WO 2011005844, WO 2011005904, WO 2011005630, WO 2011005830, WO 2011005912, WO 2011005905, WO 2011005910, WO 2011005813, WO 2010135238, WO 2010120863, WO 2010108002, WO 2010111365, WO 2010108000, WO 2010107635, WO 2010090915, WO 2010033976, WO 2010033746, WO 2010033747, WO 2010033897, WO 2010033979, WO 2010030540, WO 2010030541, WO 2010030539, WO 2010024467, WO 2010024469, WO 2010024470, WO 2010025161, WO 2010014395, WO 2010044905, WO 2010145887, WO 2010142503, WO 2010122051, WO 2010102861, WO 2010099997, WO 2010084039, WO 2010076292, WO 2010069742, WO 2010069718, WO 2010069957, WO 2010057784, WO 2010054986, WO 2010018043, WO 2010003783, WO 2010003792, WO 2011023716, WO 2010142539, WO 2010118959, WO 2010115813, WO 2010105942, WO 2010105961, WO 2010105962, WO 2010094356, WO 2010084203, WO 2010078979, WO 2010072456, WO 2010069905, WO 2010076165, WO 2010072603, WO 2010066486, WO 2010066631, WO 2010066632, WO 2010063689, WO 2010060821, WO 2010049187, WO 2010031607, WO 2010000636.

Formulation of Enzyme in Co-Granule

The dispersin may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink components and the composition additionally comprises from 20 to 80 wt % detergent moisture sink components. WO 2013/188331 also relates to a method of treating and/or cleaning a surface, preferably a fabric surface comprising the steps of (i) contacting said surface with the detergent composition as claimed and described herein aqueous wash liquor, (ii) rinsing and/or drying the surface.

The invention is further described in the following non-limiting paragraphs:

1. A dispersin variant, comprising an alteration, preferably substitution at one or more positions corresponding to positions 2, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 227, 230, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 and 323 of the polypeptide of SEQ ID NO: 1, wherein the dispersin variant has beta-1,6 N-acetylglucosaminidase activity, wherein the dispersin variant has at least 80%, at least 85%, at least 90%, at least 95%, at least 96%, at least 97%, at least 98%, or at least 99%, but less than 100% sequence identity to the polypeptide shown in SEQ ID NO: 1, and wherein the variant has increased stability, preferably thermo stability measured as half-life improvement factor, HIF, compared to the dispersin of SEQ ID NO: 1.

2. The variant of paragraph 1, comprising at least one alteration selected from the group consisting of: D2A, D2L, D2N, D2R, D2V, D2W, Q3I, Q3L, Q3M, Q3P, Q3V, Q3Y, S12A, H15F, H15Y, T17C, T17E, T17F, T17M, T17R, T17V, V18L, E19D, E19N, E19P, K22A, K22M, K22V, S23C, S23E, S23I, S23L, S23R, S23T, S23V, V25R, D26M, Y30*, Y30D, Y30L, Y30M, Y30N, Y30R, Y30T, Y30V, G32L, G32M, G32R, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80V, K80W, D81A, D81G, D81L, D81R, D81S, D81T, D81V, D81W, I82V, L90F, E99Q, E99R, L100S, K103A, K103R, K104N, K104W, D105N, V106A, V106D, V106E, V106H, V106K, V106L, V106M, V106N, V106Q, V106W, V106Y, K107A, K107C, K107L, K107M, K107T, K107V, K107W, N110M, N110R, N110V, D111L, D111E, D111M, D111N, D111Q, D111R, D111V, D111W, V113T, T114C, T114S, Y116D, Y116N, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124I, Y124K, Y124L, Y124M, Y124Q, Y124R, Y124T, Y124V, Y124W, D125C, D125G, D125K, D125Q, D125R, N126V, R127D, R127H, R127K, R127L, R127M, R127Q, R127W, V128C, V128L, V128T, D131V, Q135*, Q135A, Q135D, Q135E, Q135K, Q135M, Q135Y, D138K, D138L, D138M, D138Q, D138R, D138S, D138V, D138W, E139W, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150D, E150H, E150K, E150L, E150M, E150N, E150R, E150V, E150W, E150Y, G151A, G151C, G151D, G151L, G151N, G151P, G151S, G151W, K152D, K152L, K152R, G164D, G164E, G164H, G164S, G164V, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181N, S181P, S181Q, S181T, S181V, S181W, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203R, A203S, A203T, A203V, A203W, N204L, N204M, N204V, N204W, N204Y, L205I, D207A, D207C, D207E, D207G, D207N, D207Q, D207S, D207V, D207W, S208A, S208C, S208D, S208G, S208L, S208Q, S208T, S208V, S208W, S210T, Q215R, Q215M, Q215L, Q215*, S217V, T218A, T218L, T218Q, T218R, T218V, G222D, E224A, E224P, N227A, N227Q, N227R, N227S, N227T, N227K, D230*, D230R, D230T, D230W, N233H, N233Q, N233R, N233W, W234R, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251L, S251N, S251R, S251W, N252P, N252C, G253D, G253W, F254I, F254L, F254M, F254Y, Q256E, Q256R, N260*, N260A, N260C, N260E, N260I, N260K, N260L, N260M, N260Q, N260R, N260V, N260W, N260Y, E261*, E261A, E261D, E261R, E261W, Q262*, Q262F, Q262H, Q262W, Q262Y, M263K, M263L, M263Q, D264*, D264C, D264E, Y265F, N267S, N267T, W268C, W268E, W268M, W268R, Y270F, A271D, A271G, H272D, H272I, H272M, H272P, H272V, N273W, K274R, K274A, K274H, F276A, F276C, F276K, F276N, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y282E, Y282N, H283I, A284I, A284L, A284N, A284P, A284T, A284V, T287N, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308G, K308I, K308L, K308Q, K308S, K308T, K308V, K308Y, K309A, K309C, K309D, K309H, K309L, K309M, K309N, K309Q, K309S, K309T, K312A, K312L, K312M, K312N, K312Q, K312S, K312W, E314I, E314L, E314V, L315I, L315V, R319A, and N323R, wherein the positions correspond to amino acid positions in the amino acid sequence set forth in SEQ ID NO: 1; and wherein the substitution at the one or more positions provides a dispersin variant having an increase in stability, preferably thermo-stability measured as improvement factor, HIF, of at least 1.1, and further wherein the variants have at least 80%, at least 85%, at least 90%, at least 95% identity, at least 96%, at least 97%, at least 98%, or at least 99%, but less than 100%, sequence identity to the polypeptide shown in SEQ ID NO: 1.

3. The dispersin variant according to any of the preceding paragraphs wherein the variant is obtained from *Terribacillus*, preferably *Terribacillus saccharophilus, Terribacillus goriensis* or *Terribacillus saccharophilus*.

4. The dispersin variant according to any of the preceding paragraphs, wherein the variant comprises one or more motifs: GXDE (SEQ ID NO:8), [EQ][NRSHA][YV-FL][AGSTC][IVLF][EAQYN][SN] (SEQ ID NO:9), [VIM][LIV]G[GAV]DE[VI][PSA] SEQ ID NO: 10), [WND[SQR][IVL][TLVM] (SEQ ID NO: 11), QSTL (SEQ ID NO: 12), NKFFY (SEQ ID NO: 13) or NLD[DR]S (SEQ ID NO: 14).

5. The dispersin variant according to any of the preceding paragraphs, wherein the dispersin variant has improved stability, measured as having an improvement factor e.g. RAR or HIF>1.0, compared to the dispersin having the polypeptide sequence shown in SEQ ID NO: 1 or shown in SEQ ID NO: 15.

6. The dispersin variant according to any of the preceding paragraphs, wherein the Half-life Improvement Factor (HIF) is at least 1.2 e.g. 1.5, compared to SEQ ID NO:

1 or compared to SEQ ID NO: 15, wherein HIF is calculated as $T_{1/2 dispersinvariant}T_{1/2reference}$ and the half-life ($T_{1/2}$ in minutes) for the dispersin variants and the dispersin reference (e.g. SEQ ID NO: 1 or 15) is calculated as: 20 minutes× LN(0.5)/LN(RA) and the residual activity (RA) for each dispersin variant and the reference dispersin (e.g. SEQ ID NO: 1 or 15) is calculated as: slope (stress sample, 56° C. for 60 min)/slope(unstressed sample, 21° C. for 60 min), e.g. as described in Example 2b.

7. The dispersin variant of any of the preceding paragraphs, wherein the total number of substitutions compared to SEQ ID NO: 1 is 3-20, e.g. at least 5 to 20, at least 10 to 20 or such as at least 15 to 20 substitutions compared to the dispersin comprising the amino acid sequence shown in SEQ ID NO: 1.

8. A method for obtaining a dispersin variant, comprising;
   a) introducing into a dispersin parent having 1,6-N-acetyl glycosaminidase activity, an alteration, preferably a substitution at one or more positions corresponding to positions 2, 12, 15, 17, 18, 19, 22, 23, 24, 25, 26, 30, 32, 34, 43, 44, 45, 49, 52, 54, 56, 57, 58, 59, 60, 62, 63, 67, 68, 71, 72, 74, 77, 79, 80, 81, 82, 90, 99, 100, 103, 104, 105, 106, 107, 110, 111, 113, 114, 116, 117, 118, 119, 120, 122, 123, 124, 125, 126, 127, 128, 131, 135, 138, 139, 142, 145, 147, 148, 149, 150, 151, 152, 163, 164, 167, 168, 170, 171, 173, 174, 175, 177, 178, 179, 181, 185, 186, 187, 188, 189, 199, 200, 203, 204, 205, 207, 208, 210, 215, 217, 218, 221, 222, 224, 227, 230, 233, 234, 235, 237, 244, 249, 251, 252, 253, 254, 256, 260, 261, 262, 263, 264, 265, 267, 268, 270, 271, 272, 273, 274, 276, 278, 279, 280, 281, 282, 283, 284, 287, 288, 290, 291, 296, 300, 301, 303, 304, 305, 306, 308, 309, 312, 314, 315, 319, 321 and 323 of the polypeptide of SEQ ID NO: 1,
   b) and recovering the variant.

9. The method according to paragraph 8, comprising introducing one or more alteration(s) selected from the group consisting of: D2A, D2L, D2N, D2R, D2V, D2W, Q3I, Q3L, Q3M, Q3P, Q3V, Q3Y, S12A, H15F, H15Y, T17C, T17E, T17F, T17M, T17R, T17V, V18L, E19D, E19K, E19N, E19P, K22A, K22M, K22V, S23A, S23C, S23E, S23I, S23L, S23R, S23T, S23V, L24I, V25R, D26M, Y30*, Y30A, Y30D, Y30L, Y30M, Y30N, Y30R, Y30T, Y30V, G32L, G32M, G32R, N34D, N43*, N43H, N43L, E44*, N45D, N45L, N45V, A49W, A49Y, Y52*, Y52M, G54L, G54M, G54N, S56T, S56W, S57W, E58N, N59A, N59C, N59D, N59E, N59F, N59M, N59R, N59V, N59W, T60V, N62C, N62D, N62H, N62Q, N62W, T63C, T63D, T63L, T63N, T63R, T63V, K67A, K67L, N68L, N68Q, L71H, L71N, L71R, L71V, L71W, S72*, S72C, S72D, S72E, S72F, S72G, S72I, S72M, S72N, S72R, S72T, S72Y, I74L, S77A, D79V, K80*, K80E, K80H, K80L, K80N, K80Q, K80R, K80V, K80W, D81A, D81G, D81L, D81N, D81R, D81S, D81T, D81V, D81W, I82V, L90F, E99Q, E99R, L100S, K103A, K103R, K103V, K104N, K104W, D105N, V106A, V106D, V106E, V106H, V106K, V106L, V106M, V106N, V106Q, V106R, V106W, V106Y, K107A, K107C, K107L, K107M, K107T, K107V, K107W, N110M, N110R, N110V, D111A, D111E, D111M, D111N, D111Q, D111V, D111W, V113T, T114C, T114S, Y116D, Y116N, Y116R, S117*, S117D, S117H, S117N, S117P, E118*, E118A, E118D, E118G, E118L, E119G, E119W, T120I, T120L, T120M, T120V, T120W, D122*, D122H, D122R, Y123W, Y124C, Y124H, Y124I, Y124K, Y124L, Y124M, Y124N, Y124Q, Y124R, Y124T, Y124V, Y124W, D125C, D125G, D125H, D125K, D125Q, D125R, N126V, R127D, R127H, R127K, R127L, R127M, R127Q, R127W, V128A, V128C, V128D, V128L, V128T, D131V, Q135*, Q135A, Q135D, Q135E, Q135K, Q135M, Q135Y, D138K, D138L, D138M, D138N, D138Q, D138R, D138S, D138V, D138W, E139W, D142R, D142W, Y145*, Y145H, Y145L, Y145N, Y145V, P147A, P147C, P147D, P147F, P147G, P147L, P147M, P147R, P147S, P147T, P147V, K148A, K148D, K148L, K148V, F149L, F149M, F149N, E150A, E150D, E150H, E150K, E150L, E150M, E150N, E150R, E150V, E150W, E150Y, G151A, G151C, G151D, G151L, G151N, G151P, G151S, G151W, K152D, K152L, K152R, S163P, G164D, G164E, G164H, G164S, G164V, V167A, V167D, V167E, V167L, V167P, V167Q, V167R, V167W, H168N, L170A, L170D, L170E, L170F, L170H, L170K, L170M, L170N, L170P, L170Q, L170R, L170S, L170V, L170W, L170Y, D171A, D171C, D171E, D171K, D171L, D171M, D171Q, D171R, D171V, D171W, D171Y, I173C, D174H, D174M, D174N, D174V, D174W, F175Y, N177M, Q178*, Q178A, Q178K, Q178R, Q178W, I179T, S181C, S181D, S181F, S181G, S181K, S181N, S181P, S181Q, S181T, S181V, S181W, E185A, E185M, E185R, E185V, E185W, S186D, S186E, S186H, S186I, S186K, S186L, S186M, S186N, S186Q, S186R, S186V, S186W, K187C, K187D, K187G, K187R, K187S, K187V, K187W, Y188P, E189L, E189V, E189W, S199C, S199L, S199M, S199Y, E200D, E200F, E200K, E200L, E200M, E200N, E200R, E200W, A203C, A203D, A203E, A203G, A203L, A203M, A203P, A203Q, A203R, A203S, A203T, A203V, A203W, N204L, N204M, N204V, N204W, N204Y, L205I, D207A, D207C, D207E, D207G, D207K, D207N, D207Q, D207R, D207S, D207V, D207W, S208A, S208C, S208D, S208G, S208L, S208Q, S208T, S208V, S208W, S210T, Q215K, Q215R, Q215M, Q215L, Q215*, S217V, T218A, T218L, T218Q, T218R, T218V, S221N, G222D, E224A, E224P, N227A, N227Q, N227R, N227S, N227T, N227K, D230*, D230N, D230R, D230T, D230W, N233D, N233E, N233H, N233Q, N233R, N233W, W234R, G235A, G235E, G235F, G235H, G235I, G235L, G235M, G235N, G235P, G235S, G235V, S237C, S237G, S237M, S237N, S237W, S237Y, Y244C, Y244E, Y244M, L249H, L249K, L249Q, L249R, L249W, L249Y, S251A, S251L, S251N, S251R, S251W, N252P, N252C, G253D, G253W, F254I, F254L, F254M, F254Y, Q256D, Q256E, Q256R, N260*, N260A, N260C, N260E, N260I, N260K, N260L, N260M, N260Q, N260R, N260T, N260V, N260W, N260Y, E261*, E261A, E261D, E261R, E261W, Q262*, Q262F, Q262H, Q262W, Q262Y, M263K, M263L, M263Q, D264*, D264C, D264E, D264N, Y265F, N267S, N267T, W268C, W268E, W268M, W268R, Y270F, A271D, A271G, H272D, H272I, H272M, H272P, H272V, N273W, K274R, K274A, K274H, F276A, F276C, F276E, F276H, F276G, F276L, F276M, F276P, F276S, F276V, F276W, I278A, I278K, I278N, I278Q, I278V, S279C, S279D, S279E, S279G, S279N, D280C, D280E, Y281*, Y281A, Y281C, Y281H, Y281K, Y281N, Y281P, Y282E, Y282N, H283I, A284I, A284L, A284N, A284P, A284T, A284V, T287N, S288D, S288K, S288N, V290I, K291L, K291R, K291V, T296C, E300A, E300D, H301C, H301N, H301R, T303A, T303C, T303G, T303K, T303Q, T303R, T303W, D304C, D304M, L305M, L305N, S306C, K308A, K308D, K308E, K308G, K308I, K308L, K308Q, K308S, K308T, K308V, K308Y, K309A, K309C, K309D, K309E, K309G, K309H, K309L, K309M, K309N, K309Q, K309S, K309T, K312A, K312E, K312L, K312M, K312N, K312Q, K312S, K312W, E314I, E314L, E314V, L315I, L315V, R319A, Y321F and N323R.

10. The method according to paragraph 8 or 9, wherein the variant comprises 2-20, e.g. 2-10 and 2-5, such as 2, 3, 4, 5, 6, 7, 8, 9, 10, 11, 12, 13, 14, 15, 16, 17, 18, 19 or 20 alterations compared to the polypeptide shown in SEQ ID NO: 1.

11. The method according to any of paragraphs 8 to 10, wherein the dispersin parent obtained from *Terribacillus*, preferably *Terribacillus saccharophilus*, *Terribacillus goriensis* or *Terribacillus saccharophilus*.

12. The method according to any of paragraphs 8 to 11, wherein the dispersin parent comprises one or more motifs: GXDE (SEQ ID NO:8), [EQ][NRSHA][YV-FL][AGSTC][IVLF][EAQYN][SN] (SEQ ID NO:9), [VIM][LIV]G[GAV]DE[VI][PSA] SEQ ID NO: 10), [WND[SQR][IVL][TLVM] (SEQ ID NO: 11), QSTL (SEQ ID NO: 12), NKFFY (SEQ ID NO: 13) or NLD[DR]S (SEQ ID NO: 14).

13. A method according to any of paragraphs 8 to 12, wherein the parent dispersin is selected from the group of polypeptides:
 a) a polypeptide comprising the amino acid sequence shown in SEQ ID NO: 1 or is a polypeptide having at least 60%, at least 65%, at least 70%, at least 75%, at least 80%, at least 85%, at least 90%, at least 95%, such as at least 96%, at least 97%, at least 98% or 100% sequence identity hereto,
 b) a polypeptide comprising the amino acid sequence shown in SEQ ID NO:2 or is a polypeptide having at least 60%, at least 65%, at least 70%, at least 75%, at least 80%, at least 85%, at least 90%, at least 95%, such as at least 96%, at least 97%, at least 98% or 100% sequence identity hereto,
 c) a polypeptide comprising the amino acid sequence shown in SEQ ID NO:3 or is a polypeptide having at least 95%, such as at least 96%, such as at least 60%, at least 65%, at least 70%, at least 75%, at least 80%, at least 85%, at least 90%, at least 95%, such as at least 96%, at least 97%, at least 98% or 100% sequence identity hereto,
 d) a polypeptide comprising the amino acid sequence shown in SEQ ID NO:4 or is a polypeptide having at least 60%, at least 65%, at least 70%, at least 75%, at least 80%, at least 85%, at least 90%, at least 95%, such as at least 96%, at least 97%, at least 98% or 100% sequence identity hereto, and
 e) a polypeptide comprising the amino acid sequence shown in SEQ ID NO:5 or is a polypeptide having at least 60%, at least 65%, at least 70%, at least 75%, at least 80%, at least 85%, at least 90%, at least 95%, such as at least 96%, at least 97%, at least 98% or 100% sequence identity hereto.

14. A composition, preferably a cleaning composition comprising a variant according to any of paragraphs 1 to 7.

15. A method of cleaning an item comprising a) adding a dispersin variant according to any of paragraphs 1 to 7 to a cleaning composition and b) washing item with the composition, wherein the item is a textile or a hard surface.

16. A method for finding improved polypeptide variants, comprising the steps of:
 a) generate diversity in selected, preferably all, positions of a polypeptide, thereby preparing libraries of polypeptide variants ($V_L$), and
 b) select subset library ($V_{LSub}$) with improved variants.

17. A method for finding improved polypeptide variants, comprising the steps of:
 a) generate diversity in selected, preferably all, positions of a polypeptide, thereby preparing a library of polypeptide variants ($V_L$),
 b) expose part of the library of polypeptide variants ($V_L$) to one or more stress conditions suitable for measuring a property of interest, thereby generating a stressed $V_{LS+n}$ and an unstressed $V_{LUS}$ library;
 c) compare the stressed $V_{LS}$ and the unstressed $V_{LUS}$ library; and
 d) select subset library ($V_{LSub}$) with improved variants.

18. The method according to any of paragraphs 16 or 17, wherein the number of variants in the subset library ($V_{LSub}$) is in the range of 2-20 polypeptide variants, preferable in the range of 5-20 polypeptide variants, preferable in the range of 5-10 polypeptide variants, preferable in the range of 8-20 polypeptide variants or in the range of 8-15 polypeptide variants.

19. The method according to any of paragraphs 16 to 18, wherein stress condition is preferably elevated temperature such as above 37° C., above 41° C., above 46° C. or above 50° C.

20. The method according to any of any of paragraphs 16 to 19, wherein the polypeptide variants are selected from the dispersin variants of any of paragraphs 1 to 7.

Methods

Assays and Detergent Compositions

Composition of Model Cetergent A (Liquid)
Ingredients: 12% LAS, 11% AEO Biosoft N25-7 (NI), 7% AEOS (SLES), 6% MPG (monopropylene glycol), 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w (weight percent %))

Unless otherwise mentioned the tested variants were made from a site-saturation library as described below.

Construction of SSL

A site-saturation library was constructed for each amino acid position in the enzyme. The resulting transformants were plated onto LB agar plates containing with 6 μg/ml chloramphenicol and grown overnight at 37° C. The following day 188 individual colonies were picked from each SSL and used to inoculate 200 μl TB-Gly with 6 μg/ml chloramphenicol in 96 well MTPs. The plates were grown overnight, and the mutation contained in each clone was identified by sequencing. A culture representing each of the 20 possible amino acid substitutions at each position in the enzyme was then transferred from the grown MTPs to a new MTP and all these collected variants were for screening.

Growth and Expression

Cultures inoculated from the MTPs of collected variants were grown in deep well plates with 600 µl Cal-18 (Ostergaard P R, Wilting R, Lassen S F. 2010. Identification and characterization of a bacterial glutamic peptidase. BMC Biochem. 11:47) supplemented with 6 µg/ml chloramphenicol at 37° C. for one day with shaking at 700 rpm. The wild type was also inoculated as reference in four wells on each microtiterplate. After growth, the plates were centrifuged to pellet the cells and the variants present in the supernatants were screened for improved stability.

EXAMPLES

Example 1 Growth and Expression

The constructed variants were plated on LB agar supplemented with 6 µg/ml chloramphenicol and grown for 37 'C for one day. After growth, colonies were picked to individual wells of deep well 96-well microtiter plates or standard 96-well microtiter plates containing 600 µl or 200 ul Cal18-2 (Ostergaard P R, Wilting R, Lassen S F. 2010. *Identification and characterization of a bacterial glutamic peptidase. BMC Biochem.* 11:47) broth, respectively, supplemented with 6 µg/ml chloramphenicol. The wild type dispersin (SEQ ID NO: 1), was also inoculated as reference in four wells on each microtiterplate. The deepwell microtiter plates were grown for one day at 37 'C with shaking at 700 rpm and the standard 96-well microtiter plates grown for 3 days at 30° C. with shaking at 225 rpm.

Example 2a Testing the Variants for Stability

Measurement of Thermostability at pH 8

The variants were made as a site-saturation library as described above. Each supernatant sample, grown as stated in example 1, was diluted 20-fold in 50 mM Tris-HCI, pH 8.0. The sample was split in two parts: One part was incubated for 60 minutes at room temperature (21° C., unstressed sample) whereas the second part was incubated in a PCR machine for 60 minutes at 41° C. (stressed sample). After the incubation, 5 µl of the samples was transferred to the 384-well MTP containing 35 pl dispersin assay solution (45 mM citrate buffer pH 5 added 0.5 mg/ml p-nitrophenyl-N-acetyl-β-D-glucosaminide). The 384-well plate was then incubated at room temperature for 3 hours. After incubation, 40 µl stop solution (0.4 M $Na_2CO_3$) was added to the sample and absorbance at 405 nm was read. The measurements were corrected for the background by subtraction of the absorbance measurement obtained for a reference without dispersin. The residual activity (RA) for each dispersin variant and the reference dispersin was calculated as the ratio of background corrected activity between a stressed and an unstressed sample. These values were subsequently used to calculate the residual activity ratio ($RAR=RA_{varinant}/RA_{reference}$), which was used as selection criteria of hits with improved stability. Variants with improved stability will have a RAR>1 as the RAR of the backbone in this setup will by definition be 1.0. The result is shown in Table 1.

TABLE 1

| Variant | RAR | Variant | RAR | Variant | RAR | Variant | RAR |
|---|---|---|---|---|---|---|---|
| D2V | 1.23 | Y124K | 1.22 | S199L | 1.20 | A284T | 3.32 |
| S12A | 2.58 | D125R | 3.36 | A203G | 3.06 | A284L | 3.01 |

TABLE 1-continued

| Variant | RAR | Variant | RAR | Variant | RAR | Variant | RAR |
|---|---|---|---|---|---|---|---|
| T17E | 2.53 | D125C | 2.35 | A203E | 1.36 | A284I | 1.47 |
| V18L | 1.22 | D125G | 2.01 | A203V | 1.10 | S288K | 4.43 |
| K22M | 2.17 | D125H | 1.58 | N204L | 2.02 | V290I | 1.43 |
| S23I | 1.65 | D125K | 1.29 | N204Y | 1.72 | K291R | 1.36 |
| S23C | 1.45 | D125Q | 1.18 | N204V | 1.21 | T296C | 1.18 |
| S23A | 1.45 | Q135M | 1.16 | L205I | 1.78 | T303Q | 4.45 |
| S23T | 1.41 | D138R | 2.44 | D207K | 3.47 | D304M | 2.00 |
| S23L | 1.33 | D138K | 1.57 | D207S | 3.01 | D304C | 1.12 |
| S23V | 1.24 | D138N | 1.32 | D207C | 2.06 | L305M | 4.54 |
| S23E | 1.18 | D138Q | 1.14 | D207G | 1.90 | L305N | 1.19 |
| L24I | 2.68 | S163P | 1.67 | S210T | 1.32 | S306C | 1.48 |
| V25R | 1.31 | L170D | 2.47 | Q215K | 3.95 | K308D | 6.09 |
| Y30A | 3.11 | L170K | 1.78 | Q215R | 2.59 | K308E | 5.11 |
| Y30L | 1.85 | L170S | 1.43 | S221N | 1.22 | K308A | 3.83 |
| A49W | 2.38 | L170H | 1.33 | N227T | 1.99 | K308V | 3.79 |
| A49Y | 1.89 | D171E | 3.61 | N227K | 1.50 | K308Q | 3.73 |
| S56T | 1.18 | D171K | 3.26 | Y244M | 1.47 | K308S | 3.21 |
| N59D | 1.78 | D171Y | 2.33 | Y244C | 1.21 | K308Y | 1.96 |
| N59C | 1.59 | D171M | 2.01 | N252C | 1.15 | K308G | 1.54 |
| N59E | 1.51 | D171Q | 1.57 | Q256E | 1.54 | K308L | 1.50 |
| N59R | 1.29 | D171L | 1.37 | Q256D | 1.31 | K308T | 1.37 |
| N59F | 1.25 | I173C | 1.41 | Q262H | 2.32 | K308I | 1.35 |
| N59W | 1.22 | D174W | 2.05 | M263Q | 1.13 | K309E | 5.27 |
| N59V | 1.20 | D174H | 1.69 | D264E | 1.35 | K309G | 4.86 |
| N62C | 1.69 | D174M | 1.33 | Y265F | 3.45 | K309C | 4.84 |
| N62D | 1.42 | D174N | 1.28 | N267T | 2.40 | K309L | 4.16 |
| T63C | 1.38 | F175Y | 1.39 | N267S | 2.07 | K309D | 3.99 |
| N68Q | 1.11 | Q178K | 1.91 | Y270F | 1.22 | K309Q | 3.97 |
| S72D | 2.10 | I179T | 4.04 | H272M | 3.49 | K309N | 3.71 |
| S72E | 1.69 | S181F | 3.68 | H272P | 2.28 | K309T | 3.60 |
| I74L | 1.11 | S181Q | 3.41 | H272I | 1.87 | K309A | 3.50 |
| S77A | 1.91 | S181G | 2.75 | H272V | 1.57 | K309S | 3.48 |
| I82V | 1.83 | S181N | 2.32 | N273W | 1.13 | K309M | 2.25 |
| L90F | 3.44 | S181C | 1.68 | K274H | 2.27 | K309H | 2.23 |
| E99Q | 1.76 | S181K | 1.59 | F276A | 4.23 | K312E | 3.79 |
| L100S | 2.05 | E185A | 4.31 | F276N | 3.10 | K312A | 3.11 |
| V106Y | 1.53 | E185R | 1.50 | F276K | 2.24 | K312Q | 2.65 |
| T114S | 3.12 | E185M | 1.44 | F276C | 2.03 | K312S | 2.39 |
| T114C | 1.31 | E185V | 1.28 | I278V | 1.59 | K312W | 2.05 |
| Y123W | 1.92 | S186K | 2.88 | S279N | 2.85 | K312L | 1.33 |
| Y124I | 2.48 | S186M | 2.10 | S279D | 1.21 | K312N | 1.22 |
| Y124M | 2.44 | S186R | 1.89 | S279G | 1.17 | E314L | 1.23 |
| Y124H | 2.14 | S186H | 1.84 | D280E | 3.19 | E314V | 1.19 |
| Y124R | 2.09 | K187G | 1.21 | D280C | 1.17 | E314I | 1.14 |
| Y124V | 1.98 | Y188P | 2.71 | Y281P | 4.70 | L315I | 2.42 |
| Y124Q | 1.97 | E189V | 1.12 | Y282N | 1.65 | R319A | 1.21 |
| Y124T | 1.38 | S199C | 1.42 | H283I | 3.92 | Y321F | 1.58 |
| | | | | | | N323R | 1.20 |

Table 1 shows that all the dispersin variants have improved RAR i.e. RAR above 1, and thus are more stable under the tested conditions compared to the dispersin without the above substitutions e.g. compared to the dispersin shown in SEQ ID NO: 1.

Example 2b Testing the Variants for Stability

Growth and Expression

The constructed variants and the backbone used for the variants were grown in standard 96-well microtiter plates (200 ul broth/well). The used broth for growth and expression was Cal18-2 (*Ostergaard P R, Wilting R, Lassen S F. 2010. Identification and characterization of a bacterial glutamic peptidase. BMC Biochem.* 11:47) supplemented with 6 ug/ml chloramphenicol. The microtiter plates were grown for 3 days at 30° C. with shaking at 225 rpm. After growth, the plates were centrifuged, and the supernatants were stressed and assayed for stability. All steps regarding growth, stress and assaying are done in 96- or 384-well format microtiter plates.

Measurement of Stability in the Presence of 80% (v/v) Model A +/−1.0% (v/v) Protease The supernatants were diluted 5-fold in concentrated Model A detergent containing 1.25% (v/v) protease (SEQ ID NO:6). After mixing, the samples were split in two parts. One part was incubated for 60 minutes at room temperature (21° C., unstressed sample) whereas the second part was incubated in a PCR machine for 60 minutes at 56° C. (stressed sample). After incubation, the samples were diluted 8-fold in dilution buffer (100 mM Tris-HCl, 0.01% (v/v) TritonX-100, pH 8.0) before the activity of the unstressed and stressed samples was determined by transferring 5 ul sample to a 384-well microtiter plate containing 35 ul assay solution (45 mM citrate buffer pH 5.0 supplemented with 1.0 mg/ml p-nitrophenyl-N-acetyl-β-D-glucosaminide (Sigma Aldrich). After incubation at room temperature for 12 hours, the reactions were stopped by adding 40 μl stop solution (0.4 M $Na_2CO_3$) and the absorbances at 405 nm (A405) read. For each sample the residual activity (RA) was calculated as: RA=A405(stressed sample)/A405(unstressed sample). All A405 measurements were corrected for the signal of a blank sample (no dispersin present) before calculating the RA. The RA was used to calculate the half-life of the variants and the backbone: Half-life (minutes)=60 (minutes)× Ln(0.5)/Ln (RA) of each variant and the backbone. For each variant the half-life improvement factor (HIF) are calculated as: HIF=Half-life(variant)/Half-life(backbone). Variants with improved stability will have a HIF>1 as the HIF of the backbone in this setup will by definition be 1.0.

TABLE 2

| Variant | HIF | Variant | HIF | Variant | HIF | Variant | HIF |
|---|---|---|---|---|---|---|---|
| D2L | 1.49 | V106M | 1.16 | G164D | 1.39 | D230T | 1.20 |
| D2A | 1.23 | V106D | 1.15 | G164H | 1.26 | N233E | 1.56 |
| D2W | 1.21 | V106K | 1.15 | G164S | 1.25 | N233D | 1.54 |
| D2V | 1.20 | V106A | 1.14 | G164E | 1.24 | N233H | 1.28 |
| D2R | 1.11 | V106Q | 1.13 | G164V | 1.11 | N233Q | 1.25 |
| D2N | 1.11 | K107M | 1.32 | V167Q | 2.66 | N233R | 1.24 |
| Q3L | 3.59 | K107W | 1.30 | V167A | 1.38 | N233W | 1.11 |
| Q3V | 2.75 | K107L | 1.23 | V167W | 1.36 | W234R | 1.36 |
| Q3Y | 2.32 | K107C | 1.21 | V167P | 1.32 | G235A | 1.43 |
| Q3M | 2.13 | K107V | 1.19 | V167D | 1.26 | G235S | 1.42 |
| Q3I | 1.64 | K107A | 1.13 | V167L | 1.22 | G235V | 1.40 |
| Q3P | 1.61 | K107T | 1.12 | V167R | 1.20 | G235L | 1.38 |
| H15Y | 2.20 | N110R | 1.29 | V167E | 1.18 | G235M | 1.33 |
| H15F | 1.27 | N110V | 1.12 | L170N | 1.56 | G235E | 1.25 |
| T17L | 1.55 | N110M | 1.11 | L170R | 1.55 | G235F | 1.24 |
| T17R | 1.31 | D111V | 1.57 | L170D | 1.43 | G235P | 1.14 |
| T17M | 1.30 | D111A | 1.29 | L170E | 1.37 | G235I | 1.12 |
| T17F | 1.30 | D111R | 1.21 | L170K | 1.26 | G235W | 3.10 |
| T17E | 1.28 | D111N | 1.19 | L170F | 1.26 | S237W | 2.68 |
| T17C | 1.20 | D111W | 1.17 | L170M | 1.23 | S237Y | 1.66 |
| T17W | 3.50 | D111M | 1.12 | L170A | 1.23 | S237G | 1.38 |
| E19P | 1.25 | D111Q | 1.11 | L170W | 1.20 | S237M | 1.37 |
| E19N | 1.21 | D111E | 1.11 | L170Y | 1.17 | S237N | 1.33 |
| E19K | 1.10 | V113T | 1.13 | L170V | 1.15 | S237C | 1.25 |
| E19D | 1.10 | Y116R | 1.18 | L170Q | 1.15 | Y244E | 1.59 |
| K22A | 1.31 | Y116D | 1.14 | L170P | 1.12 | L249Q | 2.38 |
| K22V | 1.22 | Y116N | 1.14 | D171L | 1.35 | L249R | 1.65 |
| S23V | 1.53 | S117N | 1.27 | D171V | 1.31 | L249W | 1.60 |
| S23R | 1.40 | S117H | 1.21 | D171A | 1.18 | L249H | 1.41 |
| S23T | 1.34 | S117D | 1.18 | D171W | 1.13 | L249K | 1.14 |
| S23A | 1.22 | S117P | 1.14 | D171R | 1.11 | L249Y | 1.11 |
| D26M | 1.13 | S117* | 1.12 | D171C | 1.10 | S251A | 1.41 |
| Y30* | 1.60 | E118G | 1.32 | D174V | 1.43 | S251L | 1.30 |
| Y30R | 1.43 | E118* | 1.18 | N177M | 1.12 | S251R | 1.22 |
| Y30V | 1.39 | E118A | 1.17 | Q178R | 1.26 | S251W | 1.14 |
| Y30D | 1.31 | E118L | 1.14 | Q178* | 1.23 | S251N | 1.12 |
| Y30A | 1.24 | E118D | 1.12 | Q178W | 1.23 | G253D | 1.48 |
| Y30T | 1.20 | E119W | 1.71 | Q178K | 1.16 | G253W | 1.16 |
| Y30N | 1.16 | E119G | 1.22 | Q178A | 1.15 | F254I | 2.61 |
| Y30L | 1.15 | T120W | 1.76 | S181W | 1.24 | F254L | 2.27 |

TABLE 2-continued

| Variant | HIF | Variant | HIF | Variant | HIF | Variant | HIF |
|---|---|---|---|---|---|---|---|
| Y30M | 1.14 | T120M | 1.55 | S181C | 1.23 | F254M | 1.60 |
| G32R | 1.70 | T120V | 1.24 | S181V | 1.21 | F254Y | 1.52 |
| G32M | 1.32 | T120L | 1.16 | S181D | 1.18 | Q256R | 1.15 |
| G32L | 1.23 | T120I | 1.14 | S181T | 1.15 | N260Q | 2.39 |
| N34D | 1.45 | D122* | 1.26 | S181P | 1.12 | N260L | 1.80 |
| N43* | 1.24 | D122R | 1.22 | G235N | 1.32 | N260C | 1.68 |
| N43L | 1.20 | H168N | 1.22 | G235H | 1.31 | N260R | 1.60 |
| N43H | 1.13 | D122H | 1.13 | E185W | 1.40 | N260M | 1.55 |
| E44* | 1.24 | Y124L | 1.33 | S186R | 1.81 | N260K | 1.51 |
| N45D | 1.19 | Y124N | 1.21 | S186D | 1.29 | N260A | 1.47 |
| N45L | 1.19 | Y124W | 1.19 | S186E | 1.23 | N260V | 1.41 |
| N45V | 1.10 | Y124C | 1.18 | S186N | 1.22 | N260* | 1.37 |
| Y52M | 1.13 | Y124R | 1.16 | S186Q | 1.18 | N260I | 1.26 |
| Y52* | 1.12 | D125H | 1.42 | S186L | 1.15 | N260T | 1.23 |
| G54N | 1.17 | N126V | 1.11 | S186K | 1.13 | N260E | 1.23 |
| G54L | 1.13 | R127L | 1.26 | S186W | 1.12 | N260W | 1.18 |
| G54M | 1.12 | R127W | 1.25 | S186V | 1.12 | N260Y | 1.14 |
| S56W | 1.11 | R127Q | 1.22 | S186I | 1.10 | E261A | 1.34 |
| S57W | 1.21 | R127M | 1.20 | K187R | 1.31 | E261D | 1.21 |
| E58N | 1.30 | R127D | 1.15 | K187W | 1.25 | E261R | 1.15 |
| N59R | 1.43 | R127H | 1.15 | K187V | 1.24 | E261W | 1.12 |
| N59A | 1.43 | R127K | 1.14 | K187C | 1.22 | E261* | 1.11 |
| N59C | 1.39 | V128L | 1.22 | K187D | 1.20 | Q262F | 2.05 |
| N59M | 1.38 | V128D | 1.15 | K187S | 1.14 | Q262W | 1.28 |
| N59D | 1.30 | V128A | 1.14 | K187G | 1.12 | Q262Y | 1.26 |
| N59W | 1.14 | V128C | 1.14 | E189L | 1.23 | Q262* | 1.22 |
| N59F | 1.11 | V128T | 1.12 | E189W | 1.13 | M263L | 1.12 |
| T60V | 1.19 | D131V | 1.15 | S199Y | 1.27 | M263K | 1.11 |
| N62D | 1.38 | Q135M | 1.37 | S199M | 1.19 | D264* | 1.27 |
| N62W | 1.17 | Q135* | 1.29 | S199C | 1.16 | D264C | 1.17 |
| N62Q | 1.14 | Q135Y | 1.15 | S199L | 1.14 | D264N | 1.16 |
| N62H | 1.10 | Q135A | 1.14 | E200W | 1.53 | W268E | 1.79 |
| T63V | 1.34 | Q135D | 1.13 | E200D | 1.20 | W268R | 1.26 |
| T63L | 1.32 | Q135E | 1.13 | E200K | 1.18 | W268C | 1.26 |
| T63N | 1.31 | Q135K | 1.11 | E200R | 1.13 | W268M | 1.10 |
| T63R | 1.23 | D138M | 1.30 | E200M | 1.12 | A271G | 1.27 |
| T63D | 1.13 | D138V | 1.28 | E200F | 1.11 | A271D | 1.16 |
| K67L | 1.17 | D138R | 1.27 | E200N | 1.10 | H272M | 3.24 |
| K67A | 1.15 | D138L | 1.27 | E200L | 1.10 | H272V | 1.85 |
| N68L | 1.14 | D138W | 1.25 | A203V | 1.37 | H272D | 1.84 |
| L71R | 1.25 | D138S | 1.14 | A203R | 1.33 | K274R | 1.24 |
| L71H | 1.22 | E139W | 1.18 | A203G | 1.31 | K274A | 1.14 |
| L71N | 1.20 | D142W | 1.48 | A203W | 1.26 | I278V | 2.28 |
| L71W | 1.20 | D142R | 1.24 | A203P | 1.25 | I278Q | 1.41 |
| L71V | 1.11 | Y145V | 1.51 | A203C | 1.21 | I278A | 1.40 |
| S72T | 1.39 | Y145N | 1.34 | A203L | 1.20 | I278N | 1.37 |
| S72G | 1.34 | Y145* | 1.22 | A203S | 1.17 | I278K | 1.17 |
| S72C | 1.30 | Y145H | 1.14 | A203M | 1.17 | S279D | 3.41 |
| S72M | 1.30 | Y145L | 1.11 | A203Q | 1.14 | S279C | 1.52 |
| S72F | 1.24 | P147L | 1.36 | A203T | 1.13 | S279N | 1.51 |
| S72N | 1.24 | P147D | 1.27 | A203D | 1.12 | S279G | 1.46 |
| S72Y | 1.23 | P147A | 1.26 | N204V | 1.25 | S279E | 1.19 |
| S72* | 1.23 | P147V | 1.25 | N204W | 1.19 | Y281P | 4.46 |
| S72R | 1.17 | P147G | 1.21 | N204M | 1.15 | Y281H | 2.40 |
| S72E | 1.16 | P147R | 1.17 | D207N | 1.72 | Y281A | 1.45 |
| S72I | 1.14 | P147S | 1.17 | D207V | 1.54 | Y281K | 1.34 |
| D79V | 1.11 | P147M | 1.15 | D207R | 1.33 | Y281N | 1.28 |
| K80N | 1.36 | P147T | 1.14 | D207Q | 1.27 | Y281C | 1.16 |
| K80R | 1.31 | P147C | 1.14 | D207E | 1.15 | Y281* | 1.13 |
| K80W | 1.23 | P147F | 1.11 | D207W | 1.14 | Y282E | 1.10 |
| K80E | 1.23 | K148L | 1.20 | D207K | 1.13 | A284V | 1.95 |
| K80* | 1.21 | K148D | 1.19 | D207A | 1.12 | A284N | 1.29 |
| K80L | 1.14 | K148A | 1.18 | S208A | 1.59 | A284P | 1.16 |
| K80V | 1.11 | K148V | 1.16 | S208V | 1.35 | A284T | 1.12 |
| K80Q | 1.10 | F149N | 1.26 | S208C | 1.26 | T287N | 1.15 |
| K80H | 1.10 | F149M | 1.25 | S208W | 1.23 | S288D | 1.56 |
| D81G | 1.44 | F149L | 1.18 | S208D | 1.20 | S288N | 1.49 |
| D81A | 1.36 | E150N | 1.48 | S208T | 1.18 | K291L | 1.13 |
| D81L | 1.33 | E150R | 1.35 | S208Q | 1.13 | K291R | 1.12 |
| D81W | 1.29 | E150D | 1.31 | S208G | 1.12 | K291V | 1.11 |
| D81T | 1.27 | E150K | 1.27 | S208L | 1.12 | E300D | 1.45 |
| D81V | 1.26 | E150M | 1.21 | Q215L | 1.24 | E300A | 1.17 |
| D81R | 1.19 | E150H | 1.20 | Q215R | 1.17 | H301N | 1.95 |
| D81S | 1.19 | E150W | 1.18 | Q215M | 1.16 | H301C | 1.66 |
| D81N | 1.14 | E150V | 1.14 | Q215* | 1.11 | H301R | 1.46 |
| E99R | 1.12 | E150Y | 1.17 | S217V | 1.84 | T303A | 1.71 |
| K103R | 1.45 | E150L | 1.15 | T218Q | 1.83 | T303C | 1.29 |
| K103V | 1.35 | E150A | 1.12 | T218R | 1.27 | T303K | 1.24 |

TABLE 2-continued

| Variant | HIF | Variant | HIF | Variant | HIF | Variant | HIF |
|---|---|---|---|---|---|---|---|
| K103A | 1.20 | G151A | 1.45 | T218A | 1.25 | T303G | 1.24 |
| K104N | 1.29 | G151P | 1.45 | T218V | 1.20 | T303Q | 1.22 |
| K104W | 1.22 | G151W | 1.27 | T218L | 1.10 | T303W | 1.21 |
| D105N | 1.11 | G151D | 1.25 | S221N | 1.17 | T303R | 1.18 |
| V106L | 1.36 | G151L | 1.22 | G222D | 1.16 | K312M | 1.26 |
| V106Y | 1.28 | G151S | 1.21 | E224A | 1.44 | K312W | 1.10 |
| V106H | 1.26 | G151N | 1.16 | E224P | 1.28 | L315V | 1.85 |
| V106E | 1.25 | G151C | 1.15 | D230N | 1.71 | L315I | 1.36 |
| V106W | 1.24 | K152D | 1.15 | D230R | 1.53 | | |
| V106N | 1.23 | K152L | 1.12 | D230* | 1.42 | | |
| V106R | 1.20 | K152R | 1.10 | D230W | 1.28 | | |

Table 2 shows that all the dispersin variants have improved HIF i.e. HIF above 1, and thus are more stable under the tested conditions compared to the dispersin without the above alterations e.g. compared to the dispersin shown in SEQ ID NO: 1.

Example 3 Generation of SSLs and Screening Resulting Libraries as Pools

Construction of SSL

A site-saturation library was constructed for each amino acid position in the enzyme and the expected diversity was confirmed by sequencing of the pools of transformants. The pools of grown transformants were stored at −80° C. until use.

Growth and Expression

Cultures inoculated from the pools of transformants were grown in deep well plates with 600 µl Cal-18 (Ostergaard P R, Wilting R, Lassen S F. 2010. Identification and characterization of a bacterial glutamic peptidase. BMC Biochem. 11:47) supplemented with 6 µg/ml chloramphenicol at 37° C. for one day with shaking at 700 rpm. The wild type was also inoculated as reference in four wells on each microtiterplate. After growth, the plates were centrifuged to pellet the cells and the variants present in the supernatants were screened for improved stability.

Testing Dispersin Variants for Stability

Each supernatant sample was diluted 20-fold in 50 mM Tris-HCI, pH 8.0. The sample was split in two: 5 µl is transferred to a 384-well MTP (unstressed reference) and 10 µl is transferred to 384-well PCR plate. The PCR plate was stressed in a PCR machine at 47° C. for 30 min, while the unstressed reference plate was kept at room temperature (21° C.). After the incubation, 5 µl of the stressed sample was transferred to the 384-well MTP before assaying the activity in all samples by usage of p-nitrophenyl-N-acetyl-β-D-glucosaminide (pNP-NAG).

Dispersin Activity Assay

For the dispersin activity measurement, the prepared 384-well microtiter plate containing 5 µl samples was added 35 µl dispersin assay solution (45 mM citrate buffer pH 5 added 0.5 mg/ml p-nitrophenyl-N-acetyl-β-D-glucosaminide). The 384-well plate was then incubated at room temperature for 3 hours. After incubation, 40 µl stop solution (0.4 M $Na_2CO_3$) was added to the sample and absorbance at 405 nm was measured. The obtained activity values were corrected for the background by subtraction of the absorbance measurement obtained for a reference without dispersin. The residual activity (RA) for each pool of dispersin variants and the reference dispersin was calculated as the ratio of background corrected activity between a stressed and an unstressed sample. These values were subsequently used to calculate the residual activity ratio ($RAR_{pool}=RA_{pool}/RA_{reference}$), which was used to prioritize of libraries in terms of likelihood of containing stabilized variant(s).

SSL Hit Selection

The result obtained for the pool will be the average of all variants contained in the pool and the likelihood of finding improved candidates therefore increase significantly the higher the value of the ratio ($RAR_{pool}$). SSLs with highest ratio and above that determined for the reference (i.e. $RAR_{pool}>1$) are deemed to be most interesting. In this particular example, six SSL pools with $RAR_{pool}>2$ were selected to screen for improved properties amongst isolated clones represented therein.

Plating, Regrow, Rescreen and Sequence

The selected variant pools (hits) were plated on LB agar supplemented with 6 µg/ml chloramphenicol and grown for 37° C. for one day. After growth, colonies were picked to individual wells of 96-well deep well plates containing 600 µl Cal18-2 (Ostergaard P R, Wilting R, Lassen S F. 2010. Identification and characterization of a bacterial glutamic peptidase. BMC Biochem. 11:47) broth supplemented with 6 µg/ml chloramphenicol. Dispersin (SEQ ID NO: 1), was also inoculated as reference in four wells on each microtiterplate. The microtiter plates were grown for one day at 37° C. with shaking at 700 rpm. After growth, the supernatants were screened for residual activity after stressing them for 30 minutes at 47° C. in 50 mM Tris-HCl, pH 8.0. The following criteria was used for qualification of the collected data. The background corrected activity obtained for the unstressed reference should be at least 0.25. The criteria for selection of hits was based upon the RA obtained for WT, which was determined to 0.1. A sample was considered a hit if its $RA_{varinant}/RA_{reference}$ equal to RAR>1.

TABLE 3a

| Mutations of position in SEQ ID NO: 1 | $RA_{pool}$: 30 min. 47° C. 50 mM Tris-HCl. pH 8.0 | $RAR_{pool}$ |
|---|---|---|
| SEQ ID NO: 1 | 0.12 | 1.00 |
| 2 | 0.13 | 1.11 |
| 3 | 0.24 | 1.98 |
| 20 | 0.21 | 1.74 |
| 23 | 0.13 | 1.09 |
| 24 | 0.16 | 1.37 |
| 29 | 0.15 | 1.26 |
| 30 | 0.15 | 1.25 |
| 31 | 0.22 | 1.82 |
| 33 | 0.25 | 2.11 |
| 36 | 0.15 | 1.26 |
| 42 | 0.19 | 1.58 |
| 43 | 0.20 | 1.64 |
| 45 | 0.22 | 1.82 |
| 59 | 0.27 | 2.27 |
| 72 | 0.12 | 1.03 |
| 73 | 0.17 | 1.41 |
| 114 | 0.12 | 0.98 |
| 124 | 0.31 | 2.55 |
| 125 | 0.13 | 1.09 |
| 134 | 0.14 | 1.13 |
| 135 | 0.13 | 1.04 |
| 138 | 0.21 | 1.77 |
| 171 | 0.15 | 1.27 |
| 174 | 0.17 | 1.39 |
| 181 | 0.26 | 2.18 |
| 185 | 0.16 | 1.31 |
| 186 | 0.18 | 1.49 |
| 199 | 0.14 | 1.17 |
| 207 | 0.20 | 1.66 |
| 215 | 0.15 | 1.26 |
| 216 | 0.17 | 1.39 |
| 225 | 0.23 | 1.89 |
| 227 | 0.25 | 2.10 |

TABLE 3a-continued

| Mutations of position in SEQ ID NO: 1 | RA$_{pool}$: 30 min. 47° C. 50 mM Tris-HCl. pH 8.0 | RAR$_{pool}$ |
|---|---|---|
| 230 | 0.18 | 1.52 |
| 243 | 0.15 | 1.22 |
| 244 | 0.22 | 1.80 |
| 249 | 0.16 | 1.30 |
| 252 | 0.15 | 1.21 |
| 253 | 0.21 | 1.79 |
| 254 | 0.12 | 0.98 |
| 256 | 0.12 | 0.97 |
| 261 | 0.12 | 1.03 |
| 262 | 0.12 | 0.96 |
| 265 | 0.16 | 1.36 |
| 272 | 0.22 | 1.85 |
| 276 | 0.31 | 2.56 |
| 294 | 0.12 | 0.99 |
| 303 | 0.12 | 1.01 |
| 308 | 0.37 | 3.05 |
| 309 | 0.55 | 4.59 |
| 312 | 0.40 | 3.36 |
| 322 | 0.15 | 1.25 |

Table 3a shows the subset of SSL libraries having improved RAR$_{pool}$ i.e. RAR$_{pool}$ above 1, and thus contain a mixture of substitutions giving more stability on average under the tested conditions compared to the dispersin without the substitutions e.g. compared to the dispersin shown in SEQ ID NO: 1

The experiment above was repeated by screening pools made using a stabilized enzyme variant (SEQ ID NO: 17) as template during SSL construction but the residual activity ratio (RAR) was measured in model detergent A, with the presence of a protease (SEQ ID NO: 16). The results are shown in table 3a* below.

TABLE 3a*

| Mutations compared to SEQ ID NO: 17 | RAR$_{pool}$: 60 min. 64° C. 10 g/L model A detergent added 1 v/v % protease |
|---|---|
| SEQ ID NO: 17 | 1.00 |
| 1 | 1.54 |
| 3 | 8.53 |
| 6 | 1.33 |
| 57 | 1.21 |
| 73 | 1.76 |
| 75 | 1.30 |
| 90 | 1.86 |
| 94 | 2.14 |
| 116 | 1.40 |
| 141 | 1.11 |
| 142 | 1.10 |
| 144 | 1.07 |
| 147 | 1.84 |
| 149 | 1.34 |
| 169 | 1.35 |
| 170 | 1.14 |
| 193 | 6.30 |
| 205 | 1.94 |
| 217 | 1.71 |
| 225 | 5.32 |
| 232 | 6.95 |
| 233 | 1.17 |
| 241 | 1.96 |
| 243 | 1.73 |
| 253 | 1.39 |
| 254 | 3.15 |
| 261 | 1.29 |
| 267 | 2.61 |
| 272 | 33.88 |
| 276 | 1.53 |
| 277 | 6.31 |
| 278 | 1.17 |
| 279 | 1.98 |
| 281 | 4.19 |

TABLE 3a*-continued

| Mutations compared to SEQ ID NO: 17 | RAR$_{pool}$: 60 min. 64° C. 10 g/L model A detergent added 1 v/v % protease |
|---|---|
| 284 | 1.34 |
| 289 | 3.89 |
| 296 | 1.30 |
| 297 | 1.67 |
| 299 | 1.60 |
| 301 | 1.09 |

The experiment above was repeated by screening pools made using (SEQ ID NO: 1) as template during SSL construction and the residual activity ratio (RAR) was measured in model detergent A. The results are shown in table 3b below.

TABLE 3b

| Mutations compared to SEQ ID NO: 1 | RA: 30 min, 47° C., 50 mM Tris-HCl, pH 8.0 | RAR |
|---|---|---|
| SEQ ID NO: 1 | 0.13 | 1.00 |
| Y124A | 0.22 | 1.70 |
| Y124C | 0.63 | 4.82 |
| Y124F | 0.44 | 3.38 |
| Y124K | 0.41 | 3.13 |
| Y124L | 0.44 | 3.39 |
| Y124M | 0.66 | 5.06 |
| Y124R | 0.66 | 5.03 |
| Y124S | 0.16 | 1.25 |
| Y124V | 0.59 | 4.52 |
| Y124W | 0.37 | 2.82 |
| N227A | 0.80 | 6.09 |
| N227K | 0.92 | 7.04 |
| N227Q | 0.93 | 7.11 |
| N227R | 1.11 | 8.49 |
| N227S | 0.79 | 6.02 |
| N227T | 1.23 | 9.43 |
| F276A | 0.90 | 6.86 |
| F276C | 0.93 | 7.14 |
| F276G | 0.24 | 1.85 |
| F276K | 0.44 | 3.35 |
| F276L | 0.17 | 1.31 |
| F276M | 0.39 | 2.97 |
| F276P | 0.38 | 2.94 |
| F276S | 0.35 | 2.67 |
| F276V | 0.23 | 1.74 |
| F276W | 0.38 | 2.88 |

Table 3b shows dispersin variants having improved RAR i.e. RAR above 1, and thus are more stable under the tested conditions compared to the dispersin without the above substitutions e.g. compared to the dispersin shown in SEQ ID NO: 1

The experiment above was repeated by screening selected positions from SSLs made using a stabilized enzyme variant (SEQ ID NO: 17) as template but the residual activity ratio (RAR) was measured in model detergent A, with the presence of a protease (SEQ ID NO: 16). The results are shown in table 3b* below.

TABLE 3b*

| Mutations compared to SEQ ID NO: 17 | RAR: 60 min. 63° C. 10 g/L model A detergent added 1 v/v % protease |
|---|---|
| SEQ ID NO: 17 | 1 |
| Q3F | 9.72 |
| Q3I | 8.24 |
| Q3L | 8.80 |
| Q3T | 8.03 |
| Q3V | 5.89 |
| S225G | 6.79 |

TABLE 3b*-continued

| Mutations compared to SEQ ID NO: 17 | RAR: 60 min. 63° C. 10 g/L model A detergent added 1 v/v % protease |
|---|---|
| E232D | 9.03 |
| E232V | 9.90 |
| H272M | 16.45 |
| H272P | 11.91 |
| H272V | 12.48 |
| H272W | 9.03 |
| S279G | 3.60 |
| Y281K | 7.64 |
| Y281P | 11.25 |
| Y281R | 5.80 |

The experiment above was repeated by screening pools made using SEQ ID NO: 1 as template during SSL construction and the residual activity ratio (RAR) was measured in model detergent A. The results are shown in table 3c below.

TABLE 3c

| Mutations compared to SEQ ID NO: 1 | RA: 30 min, 47° C., 50 mM Tris-HCl, pH 8.0 | RAR |
|---|---|---|
| SEQ ID NO: 1 | 0.17 | 1.00 |
| K308A | 0.38 | 2.23 |
| K308D | 0.54 | 3.19 |
| K308E | 0.62 | 3.64 |
| K308G | 0.26 | 1.53 |
| K308S | 0.34 | 2.02 |
| K308T | 0.28 | 1.63 |
| K308V | 0.17 | 1.02 |
| K308Y | 0.17 | 1.01 |
| K309A | 0.35 | 2.07 |
| K309C | 0.53 | 3.10 |
| K309E | 0.56 | 3.30 |
| K309G | 0.49 | 2.88 |
| K309H | 0.23 | 1.38 |
| K309I | 0.18 | 1.07 |
| K309L | 0.19 | 1.11 |
| K309N | 0.35 | 2.08 |
| K309Q | 0.47 | 2.78 |
| K309S | 0.35 | 2.06 |
| K309T | 0.34 | 1.98 |
| K312A | 0.43 | 2.52 |
| K312E | 0.66 | 3.93 |
| K312L | 0.27 | 1.59 |
| K312N | 0.31 | 1.85 |
| K312Q | 0.48 | 2.85 |
| K312S | 0.45 | 2.65 |

Table 3c shows dispersin variants having improved RAR i.e. RAR above 1, and thus are more stable under the tested conditions compared to the dispersin without the above substitutions e.g. compared to the dispersin shown in SEQ ID NO: 1

Example 4 Combination Variants with 1-3 Mutations

Growth and Expression

The constructed variants and the backbone used for the variants were grown in standard 96-well microtiter plates 200 ul Cal18-2 broth (Ostergaard P R, Wilting R, Lassen S F. 2010. Identification and characterization of a bacterial glutamic peptidase. BMC Biochem. 11:47) supplemented with 6 ug/ml chloroampenicol broth/well. The microtiter plates were grown for 3 days at 30° C. with shaking at 225 rpm. After growth, the plates were centrifuged, and the supernatants were stressed and assayed for stability. All steps regarding growth, stress and assaying are done in 96- or 384-well format microtiter plates.

Measuring Stability at Elevated Temperature

Each supernatant sample was diluted 10-fold in stress buffer (100 mM Tris-HCl, 0.01% (v/v) TritonX-100, pH 8.0. After mixing, the samples were split in four and two samples incubated at room temperature (21° C., unstressed samples) and the other two samples (stressed samples) incubated in a PCR machine for 120 minutes at 41° C. and 46° C., respectively. After incubation, the activity of the un-stressed and stressed samples was determined by transferring 5 ul of each sample to a 384-well microtiter plate containing 35 ul assay solution (45 mM citrate buffer pH 5.0 supplemented with 1.0 mg/ml p-nitrophenyl-N-acetyl-β-D-glucosaminide (Sigma Aldrich). After incubation at room temperature for 3 hours, the reactions were stopped by adding 40 μl stop solution (0.4 M $Na_2CO_3$) and the absorbances at 405 nm (A405 nm) read. For each sample the residual activity (RA) was calculated as: RA=A405(stressed sample)/A405(un-stressed sample). All A405 nm measurements were corrected for the signal of a blank sample (no dispersin present) before calculating the RA. A variant is improved in stability if RA(variant)>RA(backbone).

TABLE 4

| Number of substitutions | Mutations | RA (residual activity) 41° C., 120 min | 46° C., 120 min |
|---|---|---|---|
| 0 | SEQ ID NO: 1 | 0.07 | 0.01 |
| 1 | F276A | 0.90 | 0.17 |
| 1 | K308E | 0.92 | 0.10 |
| 1 | K309E | 0.94 | |
| 1 | K312E | 0.91 | 0.13 |
| 1 | N227T | 0.78 | 0.05 |
| 1 | N252P | 0.45 | 0.02 |
| 1 | N267T | 0.56 | 0.01 |
| 1 | Q215K | 0.63 | 0.03 |
| 1 | S163P | 0.48 | 0.02 |
| 2 | F276A + K308E | 0.98 | 0.98 |
| 2 | F276A + K309E | 1.00 | 1.00 |
| 2 | K308E + K309E | 0.97 | 0.97 |
| 2 | K308E + K312E | 0.99 | 0.88 |
| 2 | K309E + K312E | 1.00 | 0.93 |
| 2 | N227T + F276A | 1.00 | 0.98 |
| 2 | N227T + K308E | 0.97 | 0.94 |
| 2 | N227T + K312E | 0.99 | 0.94 |
| 2 | N227T + N252P | 1.00 | 0.15 |
| 2 | N227T + N267T | 0.94 | 0.40 |
| 2 | N252P + F276A | 0.98 | 0.97 |
| 2 | N252P + K308E | 1.00 | 0.26 |
| 2 | N252P + K309E | 0.99 | 0.81 |
| 2 | N252P + N267T | 0.75 | 0.02 |
| 2 | N267T + F276A | 0.97 | 0.63 |
| 2 | N267T + K308E | 1.00 | 0.32 |
| 2 | N267T + K309E | 0.98 | 0.79 |
| 2 | N267T + K312E | 0.97 | 0.59 |
| 2 | Q215K + F276A | 1.00 | 0.79 |
| 2 | Q215K + K308E | 0.94 | 0.62 |
| 2 | Q215K + K309E | 0.98 | 0.75 |
| 2 | Q215K + K312E | 0.97 | 0.71 |
| 2 | Q215K + N227T | 0.98 | 0.60 |
| 2 | Q215K + N252P | 0.83 | 0.03 |
| 2 | Q215K + N267T | 0.96 | 0.05 |
| 2 | S163P + F276A | 0.97 | 0.79 |
| 2 | S163P + K308E | 0.96 | 0.75 |
| 2 | S163P + K309E | 0.96 | 0.83 |
| 2 | S163P + K312E | 0.97 | 0.88 |
| 2 | S163P + N252P | 0.96 | 0.05 |
| 2 | S163P + N267T | 0.64 | 0.03 |
| 2 | S163P + Q215K | 0.91 | 0.14 |
| 3 | F276A + K308E + K309E | 0.97 | 0.96 |
| 3 | F276A + K308E + K312E | 0.99 | 1.00 |
| 3 | F276A + K309E + K312E | 1.00 | 1.00 |
| 3 | K308E + K309E + K312E | 1.00 | 0.99 |
| 3 | N227T + F276A + K309E | 0.99 | 0.97 |

TABLE 4-continued

| Number of substitutions | Mutations | RA (residual activity) 41° C., 120 min | 46° C., 120 min |
|---|---|---|---|
| 3 | N227T + F276A + K312E | 0.99 | 0.98 |
| 3 | N227T + K308E + K309E | 0.99 | 1.00 |
| 3 | N227T + K308E + K312E | 1.00 | 1.00 |
| 3 | N227T + K309E + K312E | 1.00 | 0.99 |
| 3 | N227T + N252P + K308E | 1.00 | 1.00 |
| 3 | N227T + N252P + K309E | 0.99 | 0.99 |
| 3 | N227T + N252P + K312E | 1.00 | 1.00 |
| 3 | N227T + N252P + N267T | 1.00 | 1.00 |
| 3 | N227T + N267T + F276A | 1.00 | 0.99 |
| 3 | N227T + N267T + K308E | 0.99 | 0.97 |
| 3 | N227T + N267T + K309E | 0.97 | 0.96 |
| 3 | N227T + N267T + K312E | 1.00 | 0.89 |
| 3 | N252P + F276A + K308E | 0.96 | 0.97 |
| 3 | N252P + F276A + K309E | 1.00 | 0.99 |
| 3 | N252P + F276A + K312E | 0.98 | 0.97 |
| 3 | N252P + K308E + K309E | 0.99 | 0.93 |
| 3 | N252P + K308E + K312E | 0.97 | 0.95 |
| 3 | N252P + N267T + F276A | 1.00 | 0.97 |
| 3 | N252P + N267T + K308E | 1.00 | 1.00 |
| 3 | N252P + N267T + K309E | 1.00 | 1.00 |
| 3 | N252P + N267T + K312E | 0.99 | 0.98 |
| 3 | N267T + F276A + K308E | 1.00 | 1.00 |
| 3 | N267T + F276A + K309E | 0.99 | 1.00 |
| 3 | N267T + F276A + K312E | 0.98 | 0.97 |
| 3 | N267T + K308E + K309E | 1.00 | 1.00 |
| 3 | N267T + K308E + K312E | 0.97 | 0.98 |
| 3 | N267T + K309E + K312E | 1.00 | 0.98 |
| 3 | Q215K + F276A + K308E | 0.98 | 0.92 |
| 3 | Q215K + F276A + K312E | 1.00 | 1.00 |
| 3 | Q215K + K308E + K312E | 0.99 | 0.94 |
| 3 | Q215K + K309E + K312E | 0.98 | 0.98 |
| 3 | Q215K + N227T + F276A | 1.00 | 1.00 |
| 3 | Q215K + N227T + K308E | 0.99 | 0.99 |
| 3 | Q215K + N227T + K309E | 0.97 | 0.97 |
| 3 | Q215K + N227T + K312E | 0.96 | 0.96 |
| 3 | Q215K + N227T + N252P | 0.96 | 0.78 |
| 3 | Q215K + N227T + N267T | 0.96 | 0.86 |
| 3 | Q215K + N252P + F276A | 1.00 | 0.96 |
| 3 | Q215K + N252P + K309E | 0.98 | 0.93 |
| 3 | Q215K + N252P + K312E | 0.99 | 0.95 |
| 3 | Q215K + N267T + F276A | 0.97 | 0.23 |
| 3 | Q215K + N267T + K312E | 0.99 | 0.97 |
| 3 | Q215K + N267T + K312E | 1.00 | 0.96 |
| 3 | S163P + F276A + K308E | 1.00 | 1.00 |
| 3 | S163P + F276A + K312E | 0.98 | 0.96 |
| 3 | S163P + K308E + K309E | 0.98 | 0.97 |
| 3 | S163P + K308E + K312E | 1.00 | 1.00 |
| 3 | S163P + K309E + K312E | 0.99 | 1.00 |
| 3 | S163P + N227T + F276A | 0.96 | 0.96 |
| 3 | S163P + N227T + K309E | 1.00 | 1.00 |
| 3 | S163P + N227T + N252P | 1.00 | 0.98 |
| 3 | S163P + N227T + N267T | 0.97 | 0.86 |
| 3 | S163P + N252P + F276A | 1.00 | 0.99 |
| 3 | S163P + N252P + K308E | 0.97 | 0.91 |
| 3 | S163P + N252P + K309E | 0.99 | 0.98 |
| 3 | S163P + N252P + K312E | 0.98 | 0.96 |
| 3 | S163P + N252P + N267T | 0.97 | 0.57 |
| 3 | S163P + N267T + K308E | 0.91 | 0.90 |
| 3 | S163P + N267T + K309E | 0.99 | 0.99 |
| 3 | S163P + N267T + K312E | 0.98 | 0.96 |
| 3 | S163P + Q215K + F276A | 0.99 | 0.95 |
| 3 | S163P + Q215K + K308E | 1.00 | 0.94 |
| 3 | S163P + Q215K + K309E | 0.63 | 0.95 |
| 3 | S163P + Q215K + K312E | 0.94 | 0.95 |
| 3 | S163P + Q215K + N227T | 0.95 | 0.90 |
| 3 | S163P + Q215K + N252P | 0.94 | 0.38 |

Table 4 shows the effect of adding several substitutions compared to SEQ ID NO: 1. It is shown that the single stabilizing substitutions can be combined to generate a variant which is more stable or on par to the corresponding variant with one less substitution.

Example 5 Combination Variants with 4-9 Mutations

Growth and Expression

The constructed variants and the backbone used for the variants were grown in either 96-deep-Well (600 ul broth/well) or standard 96-well microtiter plates (200 ul broth/well). The used broth for growth and expression was Cal18-2 (Ostergaard P R, Wilting R, Lassen S F. 2010. *Identification and characterization of a bacterial glutamic peptidase. BMC Biochem.* 11:47) supplemented with 6 ug/ml chloramphenicol. The plates were grown for 1 day at 37° C. with shaking at 700 rpm (96-well deepwell plates) or for 3 days at 30° C. with shaking at 225 rpm (standard 96-well microtiter plates). After growth, the plates were centrifuged, and the supernatants were stressed and assayed for stability. All steps regarding growth, stress and assaying are done in 96- or 384-well format microtiter plates.

Measurement of Stability in the Presence of 0.9 g/L Model A +/−0.9% (v/v) Protease Each supernatant sample was diluted 10-fold in stress buffer (100 mM Tris-HCl, 0.01% (v/v) TritonX-100, pH 8.0 supplemented with 1 g/L Model A detergent). In the cases with applied protease stress, the stress buffer was also added 1% (v/v) protease (SEQ ID NO:7). After mixing, the sample was split into an unstressed sample which was incubated at room temperature (21° C.) and a stressed sample which was incubated in a PCR machine for 30 minutes at the selected stress temperatures (50° C., 51° C., 54° C., 57° C. and/or 60° C.). After the incubation, the activity of the un-stressed and stressed sample was determined by transferring 5 ul of each sample to a 384-well microtiter plate containing 35 ul assay solution (45 mM citrate buffer pH 5.0 supplemented with 1.0 mg/ml p-nitrophenyl-N-acetyl-β-D-glucosaminide (Sigma Aldrich). After 3 hour incubation at room temperature, the reactions were stopped by adding 40 μl stop solution (0.4 M $Na_2CO_3$) and the absorbances at 405 nm (A405) read. For each sample the residual activity (RA) was calculated as: RA=A405(stressed sample)/A405(unstressed sample). All A405 measurements were corrected for the signal of a blank sample (no dispersin present) before calculating the RA. A variant stabilized at the tested stress conditions is defined as a variant having a RA higher than the used backbone. All variants were tested in 30 min in 0.9 g/L Model A detergent.

TABLE 5

| Number of substitutions | Substitutions compared to SEQ ID NO: 1 | RA (residual activity) 50° C. | RA (residual activity) 50° C. + 0.9% Protease |
|---|---|---|---|
| 0 | SEQ ID NO: 1 | <0.05 | <0.05 |
| 4 | N227T + F276A + K308E + K309E | 0.78 | 0.37 |

TABLE 5-continued

| Number of substitutions | Substitutions compared to SEQ ID NO: 1 | RA (residual activity) 50° C. | RA (residual activity) 50° C. + 0.9% Protease |
|---|---|---|---|
| 4 | N227T + F276A + K308E + K312E | 0.87 | 0.44 |
| 4 | N227T + F276A + K309E + K312E | 0.89 | 0.42 |
| 4 | N227T + N267T + F276A + K308E | 0.76 | 0.38 |
| 4 | N227T + N267T + F276A + K309E | 0.86 | 0.45 |
| 4 | N227T + N267T + F276A + K312E | 0.82 | 0.45 |
| 4 | S163P + N227T + F276A + K308E | 0.55 | 0.39 |
| 5 | N227T + N267T + F276A + K308E + K309E | 0.92 | 0.54 |
| 5 | N227T + N267T + F276A + K308E + K312E | 0.94 | 0.51 |
| 5 | N227T + N267T + F276A + K309E + K312E | 0.92 | 0.50 |
| 5 | S163P + N227T + F276A + K308E + K312E | 0.90 | 0.74 |
| 5 | N227T + F276A + K308E + K309E + K312E | 0.92 | 0.53 |
| 6 | N227T + N267T + F276A + K308E + K309E + K312E | 0.94 | 0.53 |

TABLE 6

| Number of substitutions | Substitutions compared to SEQ ID NO: 1 | RA (residual activity) 51° C. 0.9% Protease | RA (residual activity) 54° C. 0.9% Protease |
|---|---|---|---|
| 5 | N227T + F276A + K308E + K309E + K312E | 0.36 | 0.24 |
| 6 | N227T + N267T + F276A + K308E + K309E + K312E | 0.35 | 0.18 |
| 6 | N227T + N252P + F276A + K308E + K309E + K312E | 0.49 | 0.25 |
| 6 | Q215K + N227T + F276A + K308E + K309E + K312E | 0.50 | 0.36 |
| 6 | S163P + N227T + F276A + K308E + K309E + K312E | 0.71 | 0.63 |
| 7 | N227T + N252P + N267T + F276A + K308E + K309E + K312E | 0.41 | 0.26 |
| 7 | Q215K + N227T + N252P + F276A + K308E + K309E + K312E | 0.45 | 0.31 |
| 7 | Q215K + N227T + N267T + F276A + K308E + K309E + K312E | 0.51 | 0.32 |
| 7 | S163P + N227T + N252P + F276A + K308E + K309E + K312E | 0.80 | 0.74 |
| 7 | S163P + N227T + N267T + F276A + K308E + K309E + K312E | 0.75 | 0.72 |
| 7 | S163P + Q215K + N227T + F276A + K308E + K309E + K312E | 0.76 | 0.72 |
| 8 | Q215K + N227T + N252P + N267T + F276A + K308E + K309E + K312E | 0.41 | 0.31 |
| 8 | S163P + N227T + N252P + N267T + F276A + K308E + K309E + K312E | 1.02 | 0.81 |
| 8 | S163P + Q215K + N227T + N252P + F276A + K308E + K309E + K312E | 0.81 | 0.77 |
| 8 | S163P + Q215K + N227T + N267T + F276A + K308E + K309E + K312E | 0.81 | 0.72 |
| 9 | S163P + Q215K + N227T + N252P + N267T + F276A + K308E + K309E + K312E | 0.81 | 0.78 |

TABLE 7

| Number of substitutions | Substitutions compared to SEQ ID NO: 1 | RA (residual activity) 57° C. 0.9% Protease | RA (residual activity) 60° C. 0.9% Protease |
|---|---|---|---|
| 5 | N227T + F276A + K308E + K309E + K312E | 0.09 | |
| 6 | N227T + N267T + F276A + K308E + K309E + K312E | 0.09 | |
| 6 | N227T + N252P + F276A + K308E + K309E + K312E | 0.13 | 0.11 |
| 6 | Q215K + N227T + F276A + K308E + K309E + K312E | 0.16 | 0.10 |
| 6 | S163P + N227T + F276A + K308E + K309E + K312E | 0.30 | 0.11 |
| 7 | N227T + N252P + N267T + F276A + K308E + K309E + K312E | 0.10 | 0.08 |

TABLE 7-continued

| Number of substitutions | Substitutions compared to SEQ ID NO: 1 | RA (residual activity) 57° C. 0.9% Protease | RA (residual activity) 60° C. 0.9% Protease |
|---|---|---|---|
| 7 | Q215K + N227T + N252P + F276A + K308E + K309E + K312E | 0.20 | 0.17 |
| 7 | Q215K + N227T + N267T + F276A + K308E + K309E + K312E | 0.14 | 0.10 |
| 7 | S163P + N227T + N252P + F276A + K308E + K309E + K312E | 0.54 | 0.37 |
| 7 | S163P + N227T + N267T + F276A + K308E + K309E + K312E | 0.44 | 0.27 |
| 7 | S163P + Q215K + N227T + F276A + K308E + K309E + K312E | 0.50 | 0.30 |
| 8 | Q215K + N227T + N252P + N267T + F276A + K308E + K309E + K312E | 0.15 | 0.11 |
| 8 | S163P + N227T + N252P + N267T + F276A + K308E + K309E + K312E | 0.60 | 0.40 |
| 8 | S163P + Q215K + N227T + N252P + F276A + K308E + K309E + K312E | 0.66 | 0.46 |
| 8 | S163P + Q215K + N227T + N267T + F276A + K308E + K309E + K312E | 0.57 | 0.45 |
| 9 | S163P + Q215K + N227T + N252P + N267T + F276A + K308E + K309E + K312E | 0.58 | 0.46 |

Table 5, 6 and 7 shows the effect of adding several substitutions compared to SEQ ID NO: 1. It is shown that the single stabilizing substitutions can be combined to generate a variant which is more or on par in stability as the corresponding variant with one less substitution.

Example 6 Testing for Thermostability

Growth and Expression

The variants were grown and expressed as described in the previous examples and purified as described below.

Purification

The culture broth was centrifuged (26000×g, 20 min) and the supernatant was carefully decanted from the precipitate. The supernatant was filtered through a Nalgene 0.2 μm filtration unit to remove the rest of the *Bacillus* host cells. The 0.2 μm filtrate was transferred to 20 mM MES/NaOH, pH 6.0 on a G25 sephadex column (from GE Healthcare). The G25 transferred solution was applied to a SOURCE Q column (from GE Healthcare) equilibrated in 20 mM MES/NaOH, pH 6.0. After washing the column extensively with the equilibration buffer, the protease was eluted with a linear NaCl gradient (0→1.0 M NaCl) in the same buffer over five column volumes. Fractions were collected during elution and the collected fractions were analysed by SDS-PAGE. Fractions, where only one band was seen after coomassie staining, were pooled as the purified preparation and was used for further experiments.

Measurement of Stability

Nano differential scanning fluorimetry (nDSF) was utilized to determine thermal stability. Dispersin variants for nDSF were diluted to ~0.2 mg/mL (>10-fold dilution) in 50 mM 2-(N-Morpholin)ethansulfonsyre (MES), 50 mM glycine, 50 mM acetic acid, pH 7 or 50 mM MES, 50 mM glycine, 50 mM acetic acid, pH 7 and x (x=2 or 50) g/L Model A (model detergent A). Sample dilution was made in 96-well microtiter plates and transferred to 384-well microplates. The instruments utilized for nDSF experiments, were either a Prometheus NT.48 or Prometheus NT.Plex with autosampler from Nanotemper. With the Prometheus NT.48, the samples were loaded manually using single capillaries (PR-0002), while samples were loaded in the Prometheus NT.Plex using capillary chips (PR-AC002). The experiments were conducted from 20 to 95° C. with a temperature gradient of 3.3° C./min. The melting temperatures (Tm-values) were obtained from peak values derived from the first-derivative of the signal trace (350/330 nm fluorescence ratio or 330 nm fluorescence) using PR.ThermControl software.

TABLE 8

Thermostability for variants

| | Tm-values (° C.) | | |
|---|---|---|---|
| Substitutions compared to SEQ ID NO: 1 | 0 g/L Model A | 2 g/L Model A | 50 g/L Model A |
| SEQ ID NO: 1 | 50.53 | 40.94 | |
| F276A | 55.22 | 53.86 | 52.36 |
| K308E | 54.14 | | |
| K309E | 55.48 | 52.75 | 46.62 |
| K312E | 54.96 | 52.23 | |
| N227T | 53.11 | 41.30 | |
| N227T + F276A | 58.00 | 55.99 | 49.87 |
| N227T + F276A + K308E | 63.38 | 62.25 | 58.99 |
| N227T + F276A + K309E | 64.28 | 64.05 | 60.35 |
| N227T + F276A + K312E | 63.71 | 63.78 | 60.70 |

TABLE 8-continued

Thermostability for variants

| Substitutions compared to SEQ ID NO: 1 | Tm-values (° C.) | | |
|---|---|---|---|
| | 0 g/L Model A | 2 g/L Model A | 50 g/L Model A |
| N227T + F276A + K308E + K309E | 68.45 | 67.73 | 65.24 |
| N227T + F276A + K308E + K312E | 67.19 | 66.32 | 63.88 |
| N227T + F276A + K309E + K312E | 67.37 | 66.9 | 64.57 |
| N227T + N267T + F276A + K308E | 64.71 | 55.32 | 63.10 |
| N227T + N267T + F276A + K309E | 66.45 | 66.79 | 64.72 |
| N227T + N267T + F276A + K312E | 65.86 | 66.59 | 65.07 |
| N227T + F276A + K308E + K309E + K312E | 68.42 | 67.96 | 66.06 |
| N227T + N267T + F276A + K308E + K309E | 70.36 | 69.86 | 68.2 |
| N227T + N267T + F276A + K308E + K312E | 69.33 | 68.89 | 66.83 |
| S163P + N227T + F276A + K308E + K312E | 67.59 | 66.78 | 63.81 |
| N227T + N267T + F276A + K308E + K309E + K312E | 70.53 | 70.54 | 68.88 |
| S163P + Q215K + N227T + N252P + N267T + F276A | 76.12 | 75.87 | 73.98 |
| S163P + N227T + N252P + F276A + K308E + K309E + K312E | 72.74 | 72.69 | 70.67 |
| S163P + N227T + N267T + F276A + K308E + K309E + K312E | 71.27 | 71.04 | 68.87 |
| S163P + Q215K + N227T + F276A + K308E + K309E + K312E | 71.42 | | 68.59 |
| S163P + Q215K + N227T + N252P + N267T + F276A + K308E | 70.63 | 69.74 | 66.42 |
| S163P + Q215K + N227T + N252P + N267T + F276A + K309E | 73.46 | 73.41 | 69.96 |
| S163P + Q215K + N227T + N252P + N267T + F276A + K312E | 72.49 | 71.59 | 69.04 |
| Q215K + N227T + N252P + N267T + F276A + K308E + K309E + K312E | 75.79 | 75.53 | 74.29 |
| S163P + N227T + N252P + N267T + F276A + K308E + K309E + K312E | 74.87 | 74.82 | 73.40 |
| S163P + Q215K + N227T + N252P + F276A + K308E + K309E + K312E | 75.10 | 75.02 | 73.01 |
| S163P + Q215K + N227T + N252P + N267T + F276A + K308E + K309E | 76.61 | 75.93 | 73.57 |
| S163P + Q215K + N227T + N252P + N267T + F276A + K309E + K312E | 75.74 | 75.5 | 73.56 |
| S163P + Q215K + N227T + N252P + N267T + F276A + K308E + K309E + K312E | 72.05 | 71.6 | 68.52 |
| S163P + Q215K + N227T + N267T + F276A + K308E + K309E + K312E | 73.07 | 72.92 | 70.98 |
| S163P + Q215K + N252P + N267T + F276A + K308E + K309E + K312E | 72.68 | 72.66 | 70.85 |
| S163P + Q215K + N227T + N252P + N267T + F276A + K308E + K309E + K312E | 76.77 | 76.72 | 75.07 |

TABLE 8a

| Substitutions compared to SEQ ID NO: 1 | Tm-values (° C.) | | |
|---|---|---|---|
| | 0 g/L Model A | 2 g/L Model A | 50 g/L Model A |
| SEQ ID NO: 1 | 50.53 | 40.94 | N.D. |
| S186R + N227T + E232D + K308E | 59.60 | 57.39 | 50.18 |
| S163P + Q215K + N227T + N252P + N267T + F276A + K308Q + K309E + K312E | 65.25 | 65.08 | 59.92 |
| S163P + Q215K + N227T + N252P + N267T + F276A + K308E + K309E + K312Q | 76.80 | 76.42 | 74.66 |
| Q3F + A49W + N59E + S163P + S186R + N227T + E232D + N252P + F276A + S279G + K308E + K309E + K312E | 77.70 | 77.49 | 76.00 |
| A49W + N59E + S163P + S186R + S225G + N227T + E232D + N252P + F276A + S279G + K308E + K309E + K312E | 77.84 | 77.93 | 76.16 |
| Q3F + T17W + A49W + N59E + S163P + S186R + S225G + N227T + G235W + N252P + H272P + Y281P + K308Q + K309E + K312Q | 78.25 | 77.67 | 74.95 |
| A49W + N59E + S163P + S186R + N227T + E232D + N252P + H272V + F276A + S279G + K308E + K309E + K312E | 78.39 | 78.31 | 76.49 |
| Q3F + A49W + N59E + S163P + S186R + S225G + N227T + N252P + F276A + S279G + K308E + K309E + K312E | 78.65 | 78.33 | 76.84 |
| A49W + N59E + S163P + S186R + N227T + E232D + N252P + F276A + S279G + Y281P + K308E + K309E + K312E | 78.68 | 78.13 | 76.54 |
| A49W + N59E + S163P + S186R + S225G + N227T + N252P + F276A + S279G + Y281P + K308E + K309E + K312E | 79.16 | 79.12 | 77.89 |

TABLE 8a-continued

| Substitutions compared to SEQ ID NO: 1 | Tm-values (° C.) | | |
|---|---|---|---|
| | 0 g/L Model A | 2 g/L Model A | 50 g/L Model A |
| Q3F + A49W + N59E + S163P + S186R + S225G + N227T + E232D + N252P + F276A + S279G + K308E + K309E + K312E | 79.71 | 79.56 | 78.05 |
| Q3F + S163P + S186R + Q215K + N227T + E232D + N252P + N267T + F276A + S279G + K308E + K309E + K312E | 80.17 | 79.52 | 78.43 |
| H15Y + A49W + N59E + S163P + S186R + S225G + N227T + E232D + G235W + N252P + N260Q + H272P + S279D + Y281P + K308Q + K309E + K312Q | 80.19 | 80.20 | 78.91 |
| Q3F + S163P + S186R + Q215K + S225G + N227T + N252P + N267T + F276A + S279G + K308E + K309E + K312E | 80.36 | 79.76 | 78.52 |
| H15Y + A49W + N59E + S163P + S186R + S225G + N227T + E232D + N252P + N260Q + H272P + S279D + Y281P + S288P + K308Q + K309E + K312Q | 80.42 | 81.57 | 78.94 |
| A49W + N59E + S163P + S186R + S225G + N227T + E232D + N252P + H272V + F276A + S279G + K308E + K309E + K312E | 80.76 | 80.61 | 79.42 |
| H15Y + A49W + N59E + S163P + S186R + S225G + N227T + E232D + G235W + N252P + N260Q + H272V + S279D + Y281P + K308Q + K309E + K312Q | 80.94 | 81.12 | 79.29 |
| S163P + S186R + Q215K + N227T + E232D + N252P + N267T + F276A + S279G + Y281P + K308E + K309E + K312E | 80.97 | 80.09 | 79.23 |
| Q3F + A49W + N59E + S163P + S186R + N227T + E232D + N252P + F276A + S279G + Y281P + K308E + K309E + K312E | 80.99 | 80.56 | 79.67 |
| H15Y + A49W + N59E + S163P + S186R + S225G + N227T + E232D + N252P + N260Q + H272P + S279D + Y281P + K308Q + K309E + K312Q | 81.15 | 81.32 | 79.56 |
| A49W + N59E + S163P + S186R + S225G + N227T + E232D + N252P + F276A + S279G + Y281P + K308E + K309E + K312E | 81.16 | 81.06 | 79.84 |
| H15Y + A49W + N59E + S163P + S186R + S225G + N227T + E232D + N252P + N260Q + H272V + Y281P + K308Q + K309E + K312Q | 81.17 | 80.92 | 77.86 |
| Q3F + T17W + A49W + N59E + S163P + S186R + D207N + T218Q + S225G + N227T + G235W + N252P + H272P + Y281P + K308Q + K309E + K312Q | 81.18 | 80.71 | 78.60 |
| H15Y + T17W + A49W + N59E + S163P + S186R + S225G + N227T + E232D + G235W + N252P + N260Q + H272V + S279D + Y281P + K308Q + K309E + K312Q | 81.24 | 81.19 | 77.87 |
| Q3F + A49W + N59E + S163P + S186R + S225G + N227T + N252P + F276A + S279G + Y281P + K308E + K309E + K312E | 81.76 | 81.55 | 80.60 |
| Q3F + A49W + N59E + S163P + S186R + S225G + N227T + E232D + N252P + H272V + F276A + S279G + K308E + K309E + K312E | 81.81 | 81.59 | 80.51 |
| A49W + N59E + S163P + S186R + N227T + E232D + N252P + H272V + F276A + S279G + Y281P + K308E + K309E + K312E | 81.87 | 81.46 | 80.62 |
| S163P + S186R + S225G + N227T + E232D + N252P + N267T + F276A + S279G + Y281P + K308E + K309E + K312E | 81.93 | 83.27 | 81.14 |
| H15Y + T17W + A49W + N59E + S163P + S186R + S225G + N227T + E232D + N252P + N260Q + H272V + S279D + Y281P + K308Q + K309E + K312Q | 81.96 | 81.81 | 79.45 |
| Q3F + S163P + S186R + Q215K + N227T + E232D + N252P + N267T + H272V + F276A + S279G + K308E + K309E + K312E | 82.12 | 81.36 | 80.19 |
| Q3I + H15Y + A49W + N59E + S163P + S186R + S225G + N227T + E232D + G235W + N252P + N260Q + H272V + S279D + Y281P + K308Q + K309E + K312Q | 82.13 | 81.51 | 79.96 |
| S163P + S186R + Q215K + S225G + N227T + E232D + N252P + N267T + F276A + S279G + Y281P + K308E + K309E + K312E | 82.15 | 81.36 | 80.60 |
| S163P + Q215K + S225G + N227T + E232D + N252P + N267T + F276A + S279G + Y281P + K308E + K309E + K312E | 82.16 | 81.33 | 80.43 |
| S163P + S186R + Q215K + S225G + N227T + E232D + N252P + N267T + H272V + F276A + S279G + K308E + K309E + K312E | 82.28 | 81.08 | 79.79 |
| S163P + Q215K + S225G + N227T + E232D + N252P + N267T + H272V + F276A + S279G + K308E + K309E + K312E | 82.39 | 81.76 | 80.60 |
| A49W + N59E + S163P + S186R + S225G + N227T + N252P + H272V + F276A + S279G + Y281P + K308E + K309E + K312E | 82.60 | 82.50 | 81.14 |
| Q3F + S163P + S186R + Q215K + N227T + E232D + N252P + N267T + F276A + S279G + Y281P + K308E + K309E + K312E | 82.61 | 83.55 | 81.68 |
| Q3F + S163P + Q215K + N227T + E232D + N252P + N267T + F276A + S279G + Y281P + K308E + K309E + K312E | 82.69 | 81.60 | 80.72 |
| Q3F + H15Y + T17W + A49W + N59E + S163P + S186R + T218Q + S225G + N227T + G235W + S237W + N252P + H272P + Y281P + K308Q + K309E + K312Q | 82.78 | 83.35 | 80.07 |
| S163P + Q215K + N227T + E232D + N252P + N267T + H272V + F276A + S279G + Y281P + K308E + K309E + K312E | 82.84 | 84.19 | 82.34 |
| Q3F + S163P + Q215K + S225G + N227T + E232D + N252P + N267T + H272V + F276A + S279G + K308E + K309E + K312E | 82.91 | 81.69 | 80.47 |
| Q3F + A49W + N59E + S163P + S186R + N227T + E232D + N252P + H272V + F276A + S279G + Y281P + K308E + K309E + K312E | 82.94 | 82.48 | 81.61 |
| Q3F + S163P + S186R + Q215K + S225G + N227T + N252P + N267T + F276A + S279G + Y281P + K308E + K309E + K312E | 83.18 | 82.41 | 81.62 |
| Q3F + H15Y + T17W + A49W + N59E + S163P + S186R + D207N + T218Q + S225G + N227T + G235W + S237W + N252P + H272P + Y281P + K308Q + K309E + K312Q | 83.42 | 84.07 | 80.61 |
| S163P + S186R + Q215K + S225G + N227T + N252P + N267T + H272V + F276A + S279G + Y281P + K308E + K309E + K312E | 83.47 | 84.70 | 83.22 |

TABLE 8a-continued

| Substitutions compared to SEQ ID NO: 1 | Tm-values (° C.) | | |
|---|---|---|---|
| | 0 g/L Model A | 2 g/L Model A | 50 g/L Model A |
| S163P + Q215K + S225G + N227T + N252P + N267T + H272V + F276A + S279G + Y281P + K308E + K309E + K312E | 83.50 | 82.53 | 81.62 |
| Q3F + S163P + Q215K + N227T + E232D + N252P + N267T + H272V + F276A + S279G + Y281P + K308E + K309E + K312E | 83.62 | 82.52 | 82.27 |
| Q3F + A49W + N59E + S163P + S186R + S225G + N227T + E232D + N252P + F276A + S279G + Y281P + K308E + K309E + K312E | 83.65 | 82.73 | 81.76 |
| Q3F + A49W + N59E + S163P + S186R + S225G + N227T + N252P + H272V + F276A + S279G + Y281P + K308E + K309E + K312E | 83.85 | 83.63 | 82.18 |
| A49W + N59E + S163P + S186R + S225G + N227T + E232D + N252P + H272V + F276A + S279G + Y281P + K308E + K309E + K312E | 83.97 | 83.44 | 82.73 |
| S163P + Q215K + S225G + N227T + E232D + N252P + N267T + H272V + F276A + S279G + Y281P + K308E + K309E + K312E | 84.12 | 82.91 | 82.08 |
| Q3F + S163P + S186R + Q215K + S225G + N227T + E232D + N252P + N260Q + N267T + H272V + S279D + Y281P + K308Q + K309E + K312Q | 84.21 | 84.61 | 82.56 |
| Q3F + S163P + S186R + Q215K + N227T + E232D + N252P + N267T + H272V + F276A + S279G + Y281P + K308E + K309E + K312E | 84.33 | 83.00 | 82.34 |
| S163P + S186R + Q215K + S225G + N227T + E232D + N252P + N267T + H272V + F276A + S279G + Y281P + K308E + K309E + K312E | 84.55 | 85.90 | 84.65 |
| Q3F + S163P + S186R + Q215K + S225G + N227T + N252P + N267T + H272V + F276A + S279G + Y281P + K308E + K309E + K312E | 84.62 | 83.59 | 82.73 |
| Q3F + H15Y + V140I + S163P + S186R + Q215K + S225G + N227T + E232D + G235W + N252P + N260Q + N267T + H272V + S279D + Y281P + K308Q + K309E + K312Q | 84.79 | 83.58 | 82.43 |
| Q3F + T17W + S163P + S186R + Q215K + S225G + N227T + E232D + G235W + N252P + N267T + H272V + F276A + S279G + Y281P + K308E + K309E + K312Q | 84.80 | 84.93 | 83.17 |
| Q3F + S163P + S186R + Q215K + S225G + N227T + E232D + N252P + N267T + H272V + F276A + S279G + Y281P + K308E + K309E + K312Q | 85.08 | 85.62 | 83.87 |
| Q3F + A49W + N59E + S163P + S186R + S225G + N227T + E232D + N252P + H272V + F276A + S279G + Y281P + K308E + K309E + K312E | 85.15 | 84.60 | 83.54 |
| Q3F + S163P + S186R + Q215K + S225G + N227T + E232D + N252P + N267T + H272V + F276A + S279G + Y281P + K308E + K309E + K312E | 85.19 | 84.99 | 83.88 |
| Q3F + H15Y + T17W + S163P + S186R + Q215K + S225G + N227T + E232D + G235W + N252P + N260Q + N267T + H272V + S279D + Y281P + K308Q + K309E + K312Q | 85.20 | 85.06 | 83.15 |
| Q3F + S163P + Q215K + S225G + N227T + E232D + N252P + N267T + H272V + F276A + S279G + Y281P + K308E + K309E + K312E | 85.34 | 86.79 | 84.79 |
| Q3F + H15Y + S163P + S186R + Q215K + S225G + N227T + E232D + G235W + N252P + N260Q + N267T + H272V + S279D + Y281P + K308Q + K309E + K312Q | 85.53 | 85.89 | 84.59 |
| Q3F + A49W + N59E + S163P + S186R + S225G + N227T + E232D + G235W + N252P + N260Q + H272P + F276A + S279D + Y281P + K308E + K309E + K312Q | 85.71 | 87.50 | 86.35 |
| Q3F + H15Y + T17W + S163P + S186R + Q215K + S225G + N227T + E232D + N252P + N260Q + N267T + H272V + S279D + Y281P + K308Q + K309E + K312Q | 86.24 | 86.09 | 83.78 |
| Q3F + H15Y + S163P + S186R + Q215K + S225G + N227T + E232D + N252P + N260Q + N267T + H272P + S279D + Y281P + K308Q + K309E + K312Q | 86.42 | 87.01 | 85.52 |
| Q3F + H15Y + S163P + S186R + Q215K + S225G + N227T + E232D + G235W + N252P + N267T + H272V + F276A + S279G + Y281P + K308Q + K309E + K312Q | 86.61 | 86.96 | 85.35 |
| Q3F + H15Y + T17W + S163P + S186R + Q215K + S225G + N227T + E232D + N252P + N267T + H272V + F276A + S279G + Y281P + K308Q + K309E + K312Q | 86.96 | 86.83 | 84.64 |
| Q3F + H15Y + A49W + N59E + V140I + S163P + S186R + Q215K + S225G + N227T + E232D + G235W + N252P + N260Q + N267T + H272V + S279D + Y281P + K308Q + K309E + K312Q | 87.16 | 85.92 | 84.43 |

Table 8+8A show that adding substitutions mentioned in this invention to SEQ ID NO: 1 generally increase the Tm (melting temperature) value both in a buffer system and in buffer supplemented with the detergent Model A. A Tm increase is here used as evaluation for increased stability of the variants.

TABLE 9

Thermostability for variants comprising di-sulphide bridges

| | | | nDSF | | Effect of A269C – Y282C | |
|---|---|---|---|---|---|---|
| | | | | | Delta | Delta |
| Substitution | Base Substitution | Di-sulphide Bridge | Tm (° C.) 0 g/L Model A | Tm (° C.) 2 g/L ModelA | Tm 0 g/L Model A | Tm 2 g/L Model A |
| A49W + F276A + K308E | A49W + F276A + K308E | No Disulfide Bridge | 58.79 | 58.14 | 5.30 | 5.59 |

TABLE 9-continued

Thermostability for variants comprising di-sulphide bridges

| | | | nDSF | | Effect of A269C – Y282C | |
|---|---|---|---|---|---|---|
| | | | Tm (° C.) | Tm (° C.) | Delta Tm | Delta Tm |
| Substitution | Base Substitution | Di-sulphide Bridge | 0 g/L Model A | 2 g/L ModelA | 0 g/L Model A | 2 g/L Model A |
| A49W + A269C + F276A + Y282C + K308E | A49W + F276A + K308E | A269C + Y282C | 64.09 | 63.73 | | |
| A49W + N227T + F276A | A49W + N227T + F276A | No Disulfide Bridge | 58.97 | 56.27 | 5.73 | 7.01 |
| A49W + N227T + A269C + F276A + Y282C | A49W + N227T + F276A | A269C + Y282C | 64.70 | 63.28 | | |
| A49W + N227T + F276A + K308E | A49W + N227T + F276A + K308E | No Disulfide Bridge | 63.06 | 63.21 | 5.66 | 4.83 |
| A49W + N227T + A269C + F276A + Y282C + K308E | A49W + N227T + F276A + K308E | A269C + Y282C | 68.72 | 68.04 | | |
| A49W + N227T + A269C + Y282C + K308E | A49W + N227T + K308E | A269C + Y282C | 64.5 | 63.08 | ND | ND |
| A49W + S186R + N227T + F276A | A49W + S186R + N227T + F276A | No Disulfide Bridge | 60.13 | 56.72 | 4.32 | 6.39 |
| A49W + S186R + N227T + A269C + F276A + Y282C | A49W + S186R + N227T + F276A | A269C + Y282C | 64.45 | 63.11 | | |
| A49W + S186R + N227T + F276A + K308E | A49W + S186R + N227T + F276A + K308E | No Disulfide Bridge | 63.55 | 62.46 | 5.20 | 6.18 |
| A49W + S186R + N227T + A269C + F276A + Y282C + K308E | A49W + S186R + N227T + F276A + K308E | A269C + Y282C | 68.75 | 68.64 | | |
| A49W + S186R + N227T + K308E | A49W + S186R + N227T + K308E | No Disulfide Bridge | 59.72 | 54.84 | 4.88 | 9.24 |
| A49W + S186R + N227T + A269C + Y282C + K308E | A49W + S186R + N227T + K308E | A269C + Y282C | 64.60 | 64.08 | | |
| A49W + Y124R + N227T + F276A + K308E | A49W + Y124R + N227T + F276A + K308E | No Disulfide Bridge | 63.30 | 62.69 | 5.25 | 5.54 |
| A49W + Y124R + N227T + A269C + F276A + Y282C + K308E | A49W + Y124R + N227T + F276A + K308E | A269C + Y282C | 68.55 | 68.23 | | |
| A49W + Y124R + S186R + N227T + F276A | A49W + Y124R + S186R + N227T + F276A | No Disulfide Bridge | 61.89 | 57.85 | 2.76 | 6.66 |
| A49W + Y124R + S186R + N227T + A269C + F276A + Y282C | A49W + Y124R + S186R + N227T + F276A | A269C + Y282C | 64.65 | 64.51 | | |
| A49W + Y124R + S186R + N227T + F276A + K308E | A49W + Y124R + S186R + N227T + F276A + K308E | No Disulfide Bridge | 64.61 | 62.60 | 4.17 | 5.86 |
| A49W + Y124R + S186R + N227T + A269C + F276A + Y282C + K308E | A49W + Y124R + S186R + N227T + F276A + K308E | A269C + Y282C | 68.78 | 68.46 | | |
| A49W + Y124R + S186R + N227T + K308E | A49W + Y124R + S186R + N227T + K308E | No Disulfide Bridge | 61.72 | 56.68 | 4.02 | 7.91 |
| A49W + Y124R + S186R + N227T + A269C + Y282C + K308E | A49W + Y124R + S186R + N227T + K308E | A269C + Y282C | 65.74 | 64.59 | | |
| N227T + F276A + K308E | N227T + F276A + K308E | No Disulfide Bridge | 63.38 | 62.25 | 4.86 | 5.91 |

TABLE 9-continued

Thermostability for variants comprising di-sulphide bridges

| | | | nDSF | | Effect of A269C – Y282C | |
|---|---|---|---|---|---|---|
| | | | Tm (° C.) | Tm (° C.) | Delta Tm | Delta Tm |
| Substitution | Base Substitution | Di-sulphide Bridge | 0 g/L Model A | 2 g/L ModelA | 0 g/L Model A | 2 g/L Model A |
| N227T + A269C + F276A + Y282C + K308E | N227T + F276A + K308E | A269C + Y282C | 68.24 | 68.16 | | |
| S186R + F276A + K308E | S186R + F276A + K308E | No Disulfide Bridge | 59.16 | 58.33 | 4.88 | 4.81 |
| S186R + A269C + F276A + Y282C + K308E | S186R + F276A + K308E | A269C + Y282C | 64.04 | 63.14 | | |
| S186R + N227T + F276A | S186R + N227T + F276A | No Disulfide Bridge | 59.58 | 57.18 | 5.17 | 6.47 |
| S186R + N227T + A269C + F276A + Y282C | S186R + N227T + F276A | A269C + Y282C | 64.75 | 63.65 | | |
| S186R + N227T + A269C + F276A + Y282C + K308E | S186R + N227T + F276A + K308E | A269C + Y282C | 68.74 | 68.43 | ND | ND |
| S186R + N227T + K308E | S186R + N227T + K308E | No Disulfide Bridge | 58.87 | 54.49 | 5.55 | 8.88 |
| S186R + N227T + A269C + Y282C + K308E | S186R + N227T + K308E | A269C + Y282C | 64.42 | 63.37 | | |
| Y124R + S186R + N227T + F276A + K308E | Y124R + S186R + N227T + F276A + K308E | No Disulfide Bridge | 63.60 | 62.60 | 4.88 | 5.71 |
| Y124R + S186R + N227T + A269C + F276A + Y282C + K308E | Y124R + S186R + N227T + F276A + K308E | A269C + Y282C | 68.48 | 68.31 | | |

Table 9 shows, that addition of the disulfide bride A269C+Y282 increases the Tm (melting temperature) values both in a buffer system and in buffer supplemented with the detergent Model A (approx. 2-10° C.=Delta Tm) for all the tested variants (Base mutation +/−Disulfide bridge). A Tm increase are here used as evaluation for increased stability of the variants.

The invention claimed is:

1. A dispersin variant, comprising one or more substitutions selected from the group consisting of:
D2A, D2L, D2N, D2R, D2V, or D2W,
Q3F, Q3I, Q3L, Q3M, Q3P, Q3V, Q3Y, or Q3T,
S12A,
H15F or H15Y,
T17W, T17C, T17E, T17F, T17M, T17R, or T17V,
V18L,
E19D, E19K, E19N, or E19P,
K22A, K22M, or K22V,
S23A, S23C, S23E, S23I, S23L, S23R, S23T, or S23V,
L24I,
V25R,
D26M,
Y30A, Y30D, Y30L, Y30M, Y30N, Y30R, Y30T, or Y30V,
G32L, G32M, or G32R,
N34D,
N43H or N43L,
N45D, N45L, or N45V,
A49W or A49Y,
Y52M,
G54L, G54M, or G54N,
S56T, S56W, or S57W,
E58N,
N59A, N59C, N59D, N59E, N59F, N59M, N59R, N59V, or N59W,
T60V,
N62C, N62D, N62H, N62Q, or N62W,
T63C, T63D, T63L, T63N, T63R, or T63V,
K67A or K67L,
N68L or N68Q,
L71H, L71N, L71R, L71V, or L71W,
S72C, S72D, S72E, S72F, S72G, S72I, S72M, S72N, S72R, S72T, or S72Y,
I74L,
S77A,
D79V,
K80E, K80H, K80L, K80N, K80Q, K80R, K80V, or K80W,
D81A, D81G, D81L, D81N, D81R, D81S, D81T, D81V, or D81W,
I82V,
L90F,
E99Q or E99R,
L100S,
K103A, K103R, or K103V,
K104N or K104W,
D105N,
V106A, V106D, V106E, V106H, V106K, V106L, V106M, V106N, V106Q, V106R, V106W, or V106Y,
K107A, K107C, K107L, K107M, K107T, K107V, or K107W,
N110M, N110R, or N110V,
D111A, D111E, D111M, D111N, D111Q, D111R, D111V, or D111W,
V113T,
T114C or T114S,
Y116D, Y116N, or Y116R,
S117D, S117H, S117N, or S117P,
E118A, E118D, E118G, or E118L,
E119G or E119W,
T120I, T120L, T120M, T120V, or T120W,
D122H or D122R,
Y123W,
Y124C, Y124H, Y124I, Y124K, Y124L, Y124M, Y124N, Y124Q, Y124R, Y124T, Y124V, or Y124W,
D125C, D125G, D125H, D125K, D125Q, or D125R,
N126V,
R127D, R127H, R127K, R127L, R127M, R127Q, or R127W,
V128A, V128C, V128D, V128L, or V128T,
D131V,
Q135A, Q135D, Q135E, Q135K, Q135M, or Q135Y,
D138K, D138L, D138M, D138N, D138Q, D138R, D138S, D138V, or D138W,
E139W,
V140I,
D142R or D142W,
Y145H, Y145L, Y145N, or Y145V,
P147A, P147C, P147D, P147F, P147G, P147L, P147M, P147R, P147S, P147T, P147V,
K148A, K148D, K148L, or K148V,
F149L, F149M, or F149N,
E150A, E150D, E150H, E150K, E150L, E150M, E150N, E150R, E150V, E150W, E150Y,
G151A, G151C, G151D, G151L, G151N, G151P, G151S, or G151W,
K152D, K152L, or K152R,
S163P,
G164D, G164E, G164H, G164S, or G164V,
V167A, V167D, V167E, V167L, V167P, V167Q, V167R, or V167W,
H168N,
L170A, L170D, L170E, L170F, L170H, L170K, L170M, L170N, L170P, L170Q, L170R, L170S, L170V, L170W, or L170Y, D171A, D171C, D171E, D171K, D171L, D171M, D171Q, D171R, D171V, D171W, or D171Y,
I173C,
D174H, D174M, D174N, D174V, or D174W,
F175Y,
N177M,
Q178A, Q178K, Q178R, or Q178W,
I179T,
S181C, S181D, S181F, S181G, S181K, S181N, S181P, S181Q, S181T, S181V, or S181W,
E185A, E185M, E185R, E185V, or E185W,
S186D, S186E, S186H, S186I, S186K, S186L, S186M, S186N, S186Q, S186R, S186V, or S186W,
K187C, K187D, K187G, K187R, K187S, K187V, or K187W,
Y188P,
E189L, E189V, or E189W,
S199C, S199L, S199M, or S199Y,
E200D, E200F, E200K, E200L, E200M, E200N, E200R, or E200W,
A203C, A203D, A203E, A203G, A203L, A203M, A203P, A203Q, A203R, A203S, A203T, A203V, or A203W,
N204L, N204M, N204V, N204W, or N204Y,
L205I,
D207A, D207C, D207E, D207G, D207K, D207N, D207Q, D207R, D207S, D207V, or D207W,
S208A, S208C, S208D, S208G, S208L, S208Q, S208T, S208V, or S208W,
S210T,
Q215K, Q215R, Q215M, or Q215L,
S217V,
T218A, T218L, T218Q, T218R, or T218V,
S221N,
G222D,
E224A or E224P,
S225G,
N227A, N227Q, N227R, N227S, N227T, or N227K,
D230N, D230R, D230T, or D230W,
E232D or E232V,
N233D, N233E, N233H, N233Q, N233R, or N233W,
W234R,
G235A, G235W, G235E, G235F, G235H, G235I, G235L, G235M, G235N, G235P, G235S, or G235V,
S237C, S237G, S237M, S237N, S237W, or S237Y,
Y244C, Y244E, or Y244M,
L249H, L249K, L249Q, L249R, L249W, or L249Y,
S251A, S251L, S251N, S251R, or S251W,
N252P or N252C,
G253D or G253W,
F254I, F254L, F254M, or F254Y,
Q256D, Q256E, or Q256R,
N260A, N260C, N260E, N260I, N260K, N260L, N260M, N260Q, N260R, N260T, N260V, N260W, or N260Y,
E261A, E261D, E261R, or E261W,
Q262F, Q262H, Q262W, or Q262Y,
M263K, M263L, or M263Q,
D264C, D264E, or D264N,
Y265F,
N267S or N267T,
W268C, W268E, W268M, or W268R,
Y270F,
A271D or A271G,
H272D, H272I, H272M, H272P, H272V, or H272W,
N273W,
K274R, K274A, or K274H,
F276A, F276C, F276K, F276N, F276G, F276L, F276M, F276P, F276S, F276V, or F276W,
I278A, I278K, 1278N, 1278Q, or I278V,
S279C, S279D, S279E, S279G, or S279N,
D280C or D280E,
Y281A, Y281C, Y281H, Y281K, Y281N, Y281P, or Y281R,
Y282E or Y282N,
H283I,
A284I, A284L, A284N, A284P, A284T, or A284V,
T287N,
S288P, S288D, S288K, or S288N,
V290I,
K291L, K291R, or K291V,
T296C,
E300A or E300D,
H301C, H301N, or H301R,
T303A, T303C, T303G, T303K, T303Q, T303R, or T303W,
D304C or D304M,
L305M or L305N,
S306C,
K308A, K308D, K308E, K308G, K308I, K308L, K308Q, K308S, K308T, K308V, or K308Y,
K309A, K309C, K309D, K309E, K309G, K309H, K309L, K309M, K309N, K309Q, K309S, K309T, or K309I,
K312A, K312E, K312L, K312M, K312N, K312Q, K312S, or K312W,
E314I, E314L, or E314V,
L315I or L315V,
R319A,
Y321F and
N323R,
wherein the dispersin variant has at least 80% sequence identity to SEQ ID NO: 1, hexosaminidase activity, and increased stability compared to the polypeptide of SEQ ID NO: 1.

2. The dispersin variant of claim 1, comprising one or more substitutions selected from the group consisting of:
Q3F, Q3I, Q3L, Q3M, Q3P, Q3V, Q3Y, or Q3T,
H15F or H15Y,
A49W or A49Y,
N59A, N59C, N59D, N59E, N59F, N59M, N59R, N59V, or N59W,
S163P,
S186D, S186E, S186H, S186I, S186K, S186L, S186M, S186N, S186Q, S186R, S186V, or S186W,
S225G,
N227A, N227Q, N227R, N227S, N227T, or N227K,
E232D or E232V,
G235A, G235W, G235E, G235F, G235H, G235I, G235L, G235M, G235N, G235P, G235S, or G235V,
N252P or N252C,
N260A, N260C, N260E, N260I, N260K, N260L, N260M, N260Q, N260R, N260T, N260V, N260W, or N260Y,
H272D, H272I, H272M, H272P, H272V, or H272W,
S279C, S279D, S279E, S279G, or S279N,
Y281A, Y281C, Y281H, Y281K, Y281N, Y281P, or Y281R,
K308A, K308D, K308E, K308G, K308I, K308L, K308Q, K308S, K308T, K308V, or K308Y,
K309A, K309C, K309D, K309E, K309G, K309H, K309L, K309M, K309N, K309Q, K309S, K309T, or K309I, and K312A, K312E, K312L, K312M, K312N, K312Q, K312S, or K312W.

3. The dispersin variant of claim 2, comprising three or more substitutions selected from the group consisting of:
Q3F, Q3I, Q3L, Q3M, Q3P, Q3V, Q3Y, or Q3T,
H15F or H15Y,
A49W or A49Y,
N59A, N59C, N59D, N59E, N59F, N59M, N59R, N59V, or N59W,
S163P,
S186D, S186E, S186H, S186I, S186K, S186L, S186M, S186N, S186Q, S186R, S186V, or S186W,
S225G,
N227A, N227Q, N227R, N227S, N227T, or N227K,
E232D or E232V,
G235A, G235W, G235E, G235F, G235H, G235I, G235L, G235M, G235N, G235P, G235S, or G235V,
N252P or N252C,
N260A, N260C, N260E, N260I, N260K, N260L, N260M, N260Q, N260R, N260T, N260V, N260W, or N260Y,
H272D, H272I, H272M, H272P, H272V, or H272W,
S279C, S279D, S279E, S279G, or S279N,
Y281A, Y281C, Y281H, Y281K, Y281N, Y281P, or Y281R,
K308A, K308D, K308E, K308G, K308I, K308L, K308Q, K308S, K308T, K308V, or K308Y,
K309A, K309C, K309D, K309E, K309G, K309H, K309L, K309M, K309N, K309Q, K309S, K309T, or K309I, and
K312A, K312E, K312L, K312M, K312N, K312Q, K312S, or K312W.

4. The dispersin variant of claim 2, comprising one or more substitutions selected from the group consisting of Q3I, H15Y, A49W, N59E, S163P, S186R, S225G, N227T, E232D, G235W, N252P, N260Q, H272V, S279D, Y281P, K308Q, K309E and K312Q.

5. The dispersin variant of claim 2, comprising two or more substitutions selected from the group consisting of Q3I, H15Y, A49W, N59E, S163P, S186R, S225G, N227T, E232D, G235W, N252P, N260Q, H272V, S279D, Y281P, K308Q, K309E and K312Q.

6. The dispersin variant of claim 2, comprising three or more substitutions selected from the group consisting of Q3I, H15Y, A49W, N59E, S163P, S186R, S225G, N227T, E232D, G235W, N252P, N260Q, H272V, S279D, Y281P, K308Q, K309E and K312Q.

7. The dispersin variant of claim 2, comprising four or more substitutions selected from the group consisting of Q3I, H15Y, A49W, N59E, S163P, S186R, S225G, N227T, E232D, G235W, N252P, N260Q, H272V, S279D, Y281P, K308Q, K309E and K312Q.

8. The dispersin variant of claim 2, comprising five or more substitutions selected from the group consisting of Q3I, H15Y, A49W, N59E, S163P, S186R, S225G, N227T, E232D, G235W, N252P, N260Q, H272V, S279D, Y281P, K308Q, K309E and K312Q.

9. The dispersin variant of claim 2, comprising six or more substitutions selected from the group consisting of Q3I, H15Y, A49W, N59E, S163P, S186R, S225G, N227T, E232D, G235W, N252P, N260Q, H272V, S279D, Y281P, K308Q, K309E and K312Q.

10. The dispersin variant of claim 2, comprising the substitutions K308Q+K309E+K312Q.

11. The dispersin variant of claim 2, which has increased thermostability, measured as half-life improvement factor (HIF), of at least 1.1 compared to the polypeptide shown in SEQ ID NO: 1, wherein HIF is calculated as the half-life of the dispersin variant divided by the half-life of the polypeptide of SEQ ID NO: 1.

12. The dispersin variant of claim 2, which has at least 85%, but less than 100% sequence identity to the polypeptide of SEQ ID NO: 1.

13. The dispersin variant of claim 2, which has at least 90%, but less than 100% sequence identity to the polypeptide of SEQ ID NO: 1.

14. The dispersin variant of claim 2, which is a variant of a parent dispersin having the amino acid sequence of SEQ ID NO: 1.

15. The dispersin variant of claim 2, comprising one or more motifs: GXDE (SEQ ID NO 8), [EQ][NRSHA][YV-FL][AGSTC][IVLF][EAQYN][SN] (SEQ ID NO 9), [VIM][LIV]G[GAV]DE[VI][PSA] SEQ ID NO 10), [WND[SQR][IVL][TLVM] (SEQ ID NO 11), QSTL (SEQ ID NO 12), NKFFY (SEQ ID NO 13) or NLD [DR]S (SEQ ID NO 14).

16. The dispersin variant of claim 2, which has improved thermostability, measured as a residual activity ratio (RAR), greater than 1.0, compared to the dispersin having the polypeptide sequence shown in SEQ ID NO: 1, wherein RAR is calculated as the residual activity of the variant divided by the residual activity of the polypeptide of SEQ ID NO: 1.

17. The dispersin variant of claim 2, which has a half-life improvement factor (HIF) of at least 1.2 compared to the polypeptide of SEQ ID NO: 1.

18. The dispersin variant of claim 2, which has beta-1,6 N-acetylglucosaminidase activity.

19. A composition comprising a dispersin variant of claim 1 and a surfactant.

20. A method of cleaning a textile or a hard surface, comprising washing the textile or the hard surface with the composition of claim 19.

* * * * *

SEQUENCE LISTING

<160> NUMBER OF SEQ ID NOS: 17

<210> SEQ ID NO 1
<211> LENGTH: 324
<212> TYPE: PRT
<213> ORGANISM: Terribacillus saccharophilus

<400> SEQUENCE: 1

Gln Asp Gln Glu Lys Gly Ile Thr Ile Asp Ile Ser Arg Lys His Tyr
1               5                   10                  15

Thr Val Glu Thr Leu Lys Ser Leu Val Asp Glu Ile Ser Tyr Asn Gly
            20                  25                  30

Gly Asn Tyr Val Gln Leu His Phe Ser Asp Asn Glu Asn Tyr Ala Ile
        35                  40                  45

Ala Ser Glu Tyr Leu Gly Gln Ser Ser Glu Asn Thr Asn Asn Thr Tyr
    50                  55                  60

Leu Thr Lys Asn Glu Leu Leu Ser Leu Ile Ala Tyr Ser Asn Asp Lys

```
                65                  70                  75                  80
Asp Ile Leu Val Ile Pro Asp Ile Asp Leu Pro Ala His Ser Lys Gly
                    85                  90                  95

Trp Leu Glu Leu Ile Lys Lys Lys Asp Val Lys Leu Tyr Asn Asp Ile
                100                 105                 110

Val Thr Asp Tyr Ser Glu Glu Thr Leu Asp Tyr Tyr Asp Asn Arg Val
                115                 120                 125

Ala Leu Asp Thr Val Asn Gln Leu Leu Asp Glu Val Leu Asp Leu Phe
130                 135                 140

Tyr Gln Pro Lys Phe Glu Gly Lys Gln Arg Ile Val Leu Gly Gly Asp
145                 150                 155                 160

Glu Val Ser Gly Ser Glu Val His Gln Leu Asp Phe Ile Asp Phe Met
                165                 170                 175

Asn Gln Ile Ala Ser Thr Val Lys Glu Ser Lys Tyr Glu Pro Gln Met
                180                 185                 190

Trp Asn Asp Ser Ile Thr Ser Glu Gly Ile Ala Asn Leu Asp Asp Ser
                195                 200                 205

Phe Ser Ile Leu Tyr Trp Gln Gln Ser Thr Leu Ser Ser Gly Glu Glu
210                 215                 220

Ser Leu Asn Val Glu Asp Phe Glu Asn Trp Gly Phe Ser Val Tyr Asn
225                 230                 235                 240

Tyr Asn Ala Tyr Ser Leu Tyr Phe Leu Pro Ser Asn Gly Phe Thr Gln
                245                 250                 255

Glu Asp Ile Asn Glu Gln Met Asp Tyr Met Asn Trp Ala Tyr Ala His
                260                 265                 270

Asn Lys Phe Phe Tyr Ile Ser Asp Tyr Tyr His Ala Val Glu Thr Ser
                275                 280                 285

Asn Val Lys Gly Ser Ser Leu Thr Phe Trp Gly Glu His Ala Thr Asp
                290                 295                 300

Leu Ser Gln Lys Lys Leu Leu Lys Gln Glu Leu Pro Leu Ile Arg His
305                 310                 315                 320

Tyr Leu Asn Leu

<210> SEQ ID NO 2
<211> LENGTH: 324
<212> TYPE: PRT
<213> ORGANISM: Terribacillus saccharophilus

<400> SEQUENCE: 2

Gln Asp Gln Glu Lys Gly Ile Thr Ile Asp Ile Ser Arg Lys Tyr Tyr
1               5                   10                  15

Ser Ile Lys Thr Leu Lys Ala Ile Val Asp Glu Ile Ser Ala Asn Gly
                20                  25                  30

Gly Asp Tyr Leu Gln Leu His Phe Ser Asp Asn Glu Ser Tyr Ala Ile
                35                  40                  45

Ala Ser Glu Phe Leu Gly Gln Asn Ser Glu Asn Pro Asn Ser Ala Tyr
                50                  55                  60

Leu Thr Lys Lys Glu Leu Leu Ser Leu Ala Tyr Ser Asn Asp Arg
65                  70                  75                  80

Asn Ile Met Val Ile Pro Asp Ile Asp Leu Pro Ala His Ser Lys Gly
                    85                  90                  95

Trp Leu Asn Ile Met Lys Glu Lys Asp Ser Gly Leu Tyr Thr Asp Ile
                100                 105                 110

Val Thr Asp Tyr Ser Glu Asp Thr Leu Asp Tyr His Asn Asn Ala Val
```

```
                    115                 120                 125
Ala Leu Tyr Thr Ala Asn Gln Leu Leu Asp Glu Val Leu Asp Leu Phe
    130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Ala Lys Thr Ala Lys Ala Ser Asn Tyr Glu Pro Gln Met
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Asn Gly Ala Gln
    210                 215                 220

Ser Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Pro
        275                 280                 285

Asn Val Lys Gly Ser Ser Leu Val Phe Trp Gly Glu His Ala Asn Asp
    290                 295                 300

Leu Ser Gln Glu Gly Leu Leu Lys Gln Glu Lys Pro Leu Ile Gln Asn
305                 310                 315                 320

Phe Leu Gly Leu

<210> SEQ ID NO 3
<211> LENGTH: 324
<212> TYPE: PRT
<213> ORGANISM: Terribacillus goriensis

<400> SEQUENCE: 3

Gln Asp Gln Glu Lys Gly Ile Thr Ile Asp Ile Ser Arg Lys Tyr Tyr
1               5                   10                  15

Ser Ile Glu Thr Leu Lys Ser Ile Ile Asp Glu Ile Ser Ala Asn Gly
            20                  25                  30

Gly Asp Tyr Leu Gln Leu His Phe Ser Asp Asn Glu Arg Tyr Ala Ile
        35                  40                  45

Ala Ser Glu Phe Leu Gly Gln Asn Gly Glu Asn Pro Asn Ser Thr Tyr
    50                  55                  60

Leu Thr Lys Lys Glu Leu Leu Ser Leu Ile Ala Tyr Ser Asn Asp Arg
65                  70                  75                  80

Asp Ile Met Val Ile Pro Asp Ile Asp Leu Pro Ala His Ser Arg Gly
                85                  90                  95

Trp Leu Asn Ile Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Val
        115                 120                 125

Ala Leu Tyr Thr Ala Asn Gln Leu Leu Asp Glu Val Leu Asp Leu Phe
    130                 135                 140

Tyr Gln Pro Lys Phe Ala Gly Lys Gln Arg Ile Val Leu Gly Gly Asp
145                 150                 155                 160

Glu Val Pro Gly Ser Gly Val His Gln Thr Asp Phe Ile Arg Phe Met
```

-continued

```
                165                 170                 175
Asn Gln Ile Ala Glu Thr Ala Lys Ala Ser Asn Tyr Lys Pro Gln Met
                    180                 185                 190

Trp Asn Asp Ser Ile Thr Pro Glu Gly Ile Gln Asn Leu Asp Arg Ser
            195                 200                 205

Phe Ser Ile Leu Tyr Trp Lys Gln Ser Thr Leu Ser Asn Gly Ala Gln
        210                 215                 220

Gly Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ala Thr Arg Phe Thr Gln
                245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Ser
        275                 280                 285

Asn Val Lys Gly Ser Ser Leu Val Phe Trp Gly Glu His Ala Asn Asp
290                 295                 300

Leu Ser Gln Glu Gly Leu Leu Lys Gln Glu Lys Pro Leu Ile Gln Asn
305                 310                 315                 320

Phe Leu Gly Leu

<210> SEQ ID NO 4
<211> LENGTH: 324
<212> TYPE: PRT
<213> ORGANISM: Terribacillus saccharophilus

<400> SEQUENCE: 4

Lys Asp Gln Glu Lys Gly Ile Thr Ile Asp Ile Ser Arg Lys Tyr Tyr
1               5                   10                  15

Ser Ile Gly Thr Leu Lys Ala Ile Val Asp Glu Ile Asn Ala Asn Gly
                20                  25                  30

Gly Asp Tyr Leu Gln Leu His Phe Ser Asp Asn Glu Ser Tyr Ala Ile
            35                  40                  45

Ala Ser Glu Phe Leu Gly Gln Asn Ser Glu Asn Pro Asn Ser Thr Tyr
        50                  55                  60

Leu Thr Lys Lys Glu Leu Leu Ser Leu Ile Ala Tyr Ser Asn Asp Arg
65                  70                  75                  80

Asn Ile Met Val Ile Pro Asp Ile Asp Leu Pro Ala His Ser Lys Gly
                85                  90                  95

Trp Leu Asn Val Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Ala
        115                 120                 125

Ala Leu Tyr Thr Ala Asn Gln Leu Leu Asp Glu Val Leu Asp Leu Phe
130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Asp Glu Thr Ala Lys Ala Ser Asn Tyr Glu Pro Gln Met
                    180                 185                 190

Trp Asn Asp Ser Ile Thr Pro Glu Gly Ile Gln Asn Leu Asp Arg Ser
            195                 200                 205

Phe Ser Ile Leu Tyr Trp Lys Gln Ser Thr Leu Ser Ser Gly Ala Gln
```

```
      210                 215                 220
Gly Leu Asp Val Gln Asn Phe Glu Glu Lys Gly Phe Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Ala Tyr Ala Tyr
                260                 265                 270

Asn Lys Phe Phe Tyr Ile Ser Asp Tyr Tyr Lys Gln Val Asp Thr Ser
                275                 280                 285

Asn Val Lys Gly Ser Ser Leu Val Phe Trp Gly Glu His Ala Asn Asp
                290                 295                 300

Leu Ser Gln Glu Gly Leu Leu Glu Gln Glu Lys Pro Leu Ile Gln Asn
305                 310                 315                 320

Phe Leu Ser Leu

<210> SEQ ID NO 5
<211> LENGTH: 324
<212> TYPE: PRT
<213> ORGANISM: Terribacillus saccharophilus

<400> SEQUENCE: 5

Lys Asp Gln Glu Lys Gly Ile Ser Ile Asp Ile Ser Arg Lys Tyr Tyr
1               5                   10                  15

Ser Ile Gly Thr Leu Lys Ala Ile Ile Asp Glu Ile Ser Ala Asn Gly
                20                  25                  30

Gly Asp Tyr Leu Gln Leu His Phe Ser Asp Asn Glu Ser Tyr Ala Ile
                35                  40                  45

Ala Ser Asp Tyr Leu Gly Gln Ile Ser Asp Thr Pro Asn Asn Thr Tyr
50                  55                  60

Leu Thr Lys Asn Asp Leu Leu Ser Leu Ile Ala Tyr Ser Asn Asp Arg
65                  70                  75                  80

Asn Ile Leu Ile Ile Pro Asp Met Asp Leu Pro Ala His Ser Arg Gly
                85                  90                  95

Trp Leu Glu Leu Met Lys Val Lys Asp Arg Glu Leu Tyr Thr Asp Ile
                100                 105                 110

Val Thr Asp Tyr Ser Asn Glu Thr Leu Asp Tyr His Asn Asn Thr Asp
                115                 120                 125

Ala Leu Asn Thr Ala Asn Gln Leu Leu Asn Glu Ile Leu Glu Leu Phe
130                 135                 140

Tyr Gln Pro Lys Phe Ala Gly Lys Gln Arg Ile Val Leu Gly Gly Asp
145                 150                 155                 160

Glu Val Pro Gly Ser Glu Ile His Gln Leu Asp Phe Ile Arg Phe Ile
                165                 170                 175

Asn Gln Ile Ala Ser Thr Ala Lys Ala Ser Asn Tyr Ala Pro Gln Met
                180                 185                 190

Trp Asn Asp Ser Ile Thr Ala Glu Gly Ile Gln Asn Leu Asp Lys Ser
                195                 200                 205

Phe Ser Ile Leu Tyr Trp Lys Gln Ser Thr Leu Ser Asn Gly Ala Gln
                210                 215                 220

Ser Leu Glu Val Gln Asp Phe Glu Asp Trp Asp Phe Pro Val Tyr Asn
225                 230                 235                 240

Tyr Asn Ala Tyr Ser Leu Tyr Phe Leu Pro Ser Ile Arg Phe Thr Asp
                245                 250                 255

Glu Asp Ile Thr Glu Gln Met Asn Tyr Met Lys Trp Ala Tyr Ala Tyr
```

```
                260             265             270
Asn Lys Phe Phe Tyr Ile Ser Asp Tyr Tyr Lys Ser Val Asp Ala Ser
            275                 280                 285

Asn Val Lys Gly Ser Ser Leu Thr Phe Trp Gly Glu His Ala Thr Asp
        290                 295                 300

Leu Ser Gln Glu Glu Leu Leu Glu Gln Glu Leu Pro Leu Ile Lys Lys
305                 310                 315                 320

Phe Leu Ser Leu

<210> SEQ ID NO 6
<211> LENGTH: 269
<212> TYPE: PRT
<213> ORGANISM: Bacillus clausii

<400> SEQUENCE: 6

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Glu Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Asp Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Glu
                245                 250                 255

Tyr Gly Ser Gly Leu Val Asn Ala Glu Ala Ala Thr Arg
            260                 265

<210> SEQ ID NO 7
<211> LENGTH: 269
<212> TYPE: PRT
<213> ORGANISM: Bacillus Lentus

<400> SEQUENCE: 7
```

```
Ala Gln Ser Val Pro Trp Gly Ile Glu Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Arg Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asp Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Ile Leu Ser Thr Trp Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Asp Thr Trp Glu
                245                 250                 255

Tyr Gly Ser Gly Leu Val Asn Ala Glu Ala Ala Thr Arg
            260                 265

<210> SEQ ID NO 8
<211> LENGTH: 4
<212> TYPE: PRT
<213> ORGANISM: Artificial
<220> FEATURE:
<223> OTHER INFORMATION: Artificial synthetic peptide
<220> FEATURE:
<221> NAME/KEY: Misc
<222> LOCATION: (2)..(2)
<223> OTHER INFORMATION: X = any natural amino acid

<400> SEQUENCE: 8

Gly Xaa Asp Glu
1

<210> SEQ ID NO 9
<211> LENGTH: 7
<212> TYPE: PRT
<213> ORGANISM: Artificial
<220> FEATURE:
<223> OTHER INFORMATION: Artificial synthetic peptide
<220> FEATURE:
<221> NAME/KEY: Misc
<222> LOCATION: (1)..(1)
```

```
<223> OTHER INFORMATION: X=Glu(E) or Gln(Q)
<220> FEATURE:
<221> NAME/KEY: Misc
<222> LOCATION: (2)..(2)
<223> OTHER INFORMATION: X=Asn(N) or Arg(R) or Ser(S) or His(H) or
      Ala(A)
<220> FEATURE:
<221> NAME/KEY: Misc
<222> LOCATION: (3)..(3)
<223> OTHER INFORMATION: X=Tyr(Y) or Val(V) or Phe(F) or Leu(L)
<220> FEATURE:
<221> NAME/KEY: Misc
<222> LOCATION: (4)..(4)
<223> OTHER INFORMATION: X=Ala(A) or Gly(G) or Ser(S) or Thr(T) or
      Cys(C)
<220> FEATURE:
<221> NAME/KEY: Misc
<222> LOCATION: (5)..(5)
<223> OTHER INFORMATION: X=Ile(I) or Val(V) or Leu(L) or Phe(F)
<220> FEATURE:
<221> NAME/KEY: Misc
<222> LOCATION: (6)..(6)
<223> OTHER INFORMATION: X=Glu(E) or Ala(A) or Gln(Q) or Tyr(Y) or
      Asn(N)
<220> FEATURE:
<221> NAME/KEY: Misc
<222> LOCATION: (7)..(7)
<223> OTHER INFORMATION: X= Ser(S) or Asn(N)

<400> SEQUENCE: 9

Xaa Xaa Xaa Xaa Xaa Xaa Xaa
1               5

<210> SEQ ID NO 10
<211> LENGTH: 8
<212> TYPE: PRT
<213> ORGANISM: Artificial
<220> FEATURE:
<223> OTHER INFORMATION: Artificial synthetic peptide
<220> FEATURE:
<221> NAME/KEY: Misc
<222> LOCATION: (1)..(1)
<223> OTHER INFORMATION: X=Val(V) or Ile(I) or Met(M)
<220> FEATURE:
<221> NAME/KEY: Misc
<222> LOCATION: (2)..(2)
<223> OTHER INFORMATION: X=Leu(L) or Ile(I) or Val(V)
<220> FEATURE:
<221> NAME/KEY: Misc
<222> LOCATION: (4)..(4)
<223> OTHER INFORMATION: X=Gly(G) or Ala(A) or Val(V)
<220> FEATURE:
<221> NAME/KEY: Misc
<222> LOCATION: (7)..(7)
<223> OTHER INFORMATION: X=Val(V) or Ile(I)
<220> FEATURE:
<221> NAME/KEY: Misc
<222> LOCATION: (8)..(8)
<223> OTHER INFORMATION: X=Phe(P) or Ser(S) or Ala(A)

<400> SEQUENCE: 10

Xaa Xaa Gly Xaa Asp Glu Xaa Xaa
1               5

<210> SEQ ID NO 11
<211> LENGTH: 6
<212> TYPE: PRT
<213> ORGANISM: Artificial
<220> FEATURE:
<223> OTHER INFORMATION: Artificial synthetic peptide
<220> FEATURE:
<221> NAME/KEY: Misc
<222> LOCATION: (4)..(4)
<223> OTHER INFORMATION: X=Ser(S) or Gln(Q) or Arg(R)
<220> FEATURE:
```

```
<221> NAME/KEY: Misc
<222> LOCATION: (5)..(5)
<223> OTHER INFORMATION: X=Ile(I) or Val(V) or Leu(L)
<220> FEATURE:
<221> NAME/KEY: Misc
<222> LOCATION: (6)..(6)
<223> OTHER INFORMATION: X=Thr(T) or Leu(L) or Val(V) or Met(M)

<400> SEQUENCE: 11

Trp Asn Asp Xaa Xaa Xaa
1               5

<210> SEQ ID NO 12
<211> LENGTH: 4
<212> TYPE: PRT
<213> ORGANISM: Artificial
<220> FEATURE:
<223> OTHER INFORMATION: Artificial synthetic peptide

<400> SEQUENCE: 12

Gln Ser Thr Leu
1

<210> SEQ ID NO 13
<211> LENGTH: 5
<212> TYPE: PRT
<213> ORGANISM: Artificial
<220> FEATURE:
<223> OTHER INFORMATION: Artificial synthetic peptide

<400> SEQUENCE: 13

Asn Lys Phe Phe Tyr
1               5

<210> SEQ ID NO 14
<211> LENGTH: 5
<212> TYPE: PRT
<213> ORGANISM: Artificial
<220> FEATURE:
<223> OTHER INFORMATION: Artificial synthetic peptide
<220> FEATURE:
<221> NAME/KEY: Misc
<222> LOCATION: (4)..(4)
<223> OTHER INFORMATION: X = Asp(D) or Arg(R)

<400> SEQUENCE: 14

Asn Leu Asp Xaa Ser
1               5

<210> SEQ ID NO 15
<211> LENGTH: 324
<212> TYPE: PRT
<213> ORGANISM: Terribacillus saccharophilus

<400> SEQUENCE: 15

Gln Asp Gln Glu Lys Gly Ile Thr Ile Asp Ile Ser Arg Lys His Tyr
1               5                   10                  15

Thr Val Glu Thr Leu Lys Ser Leu Val Asp Glu Ile Ser Tyr Asn Gly
            20                  25                  30

Gly Asn Tyr Val Gln Leu His Phe Ser Asp Asn Glu Asn Tyr Ala Ile
        35                  40                  45

Ala Ser Glu Tyr Leu Gly Gln Ser Ser Glu Asn Thr Asn Asn Thr Tyr
    50                  55                  60

Leu Thr Lys Asn Glu Leu Leu Ser Leu Ile Ala Tyr Ser Asn Asp Lys
65                  70                  75                  80
```

Asp Ile Leu Val Ile Pro Asp Ile Asp Leu Pro Ala His Ser Lys Gly
                85                  90                  95

Trp Leu Glu Leu Ile Lys Lys Lys Asp Val Lys Leu Tyr Asn Asp Ile
            100                 105                 110

Val Thr Asp Tyr Ser Glu Glu Thr Leu Asp Tyr Tyr Asp Asn Arg Val
            115                 120                 125

Ala Leu Asp Thr Val Asn Gln Leu Leu Asp Glu Val Leu Asp Leu Phe
            130                 135                 140

Tyr Gln Pro Lys Phe Glu Gly Lys Gln Arg Ile Val Leu Gly Gly Asp
145                 150                 155                 160

Glu Val Pro Gly Ser Glu Val His Gln Leu Asp Phe Ile Asp Phe Met
                165                 170                 175

Asn Gln Ile Ala Ser Thr Val Lys Glu Ser Lys Tyr Glu Pro Gln Met
            180                 185                 190

Trp Asn Asp Ser Ile Thr Ser Glu Gly Ile Ala Asn Leu Asp Asp Ser
            195                 200                 205

Phe Ser Ile Leu Tyr Trp Lys Gln Ser Thr Leu Ser Ser Gly Glu Glu
            210                 215                 220

Ser Leu Thr Val Glu Asp Phe Glu Asn Trp Gly Phe Ser Val Tyr Asn
225                 230                 235                 240

Tyr Asn Ala Tyr Ser Leu Tyr Phe Leu Pro Ser Pro Gly Phe Thr Gln
            245                 250                 255

Glu Asp Ile Asn Glu Gln Met Asp Tyr Met Thr Trp Ala Tyr Ala His
            260                 265                 270

Asn Lys Phe Ala Tyr Ile Ser Asp Tyr Tyr His Ala Val Glu Thr Ser
            275                 280                 285

Asn Val Lys Gly Ser Ser Leu Thr Phe Trp Gly Glu His Ala Thr Asp
            290                 295                 300

Leu Ser Gln Glu Glu Leu Leu Glu Gln Glu Leu Pro Leu Ile Arg His
305                 310                 315                 320

Tyr Leu Asn Leu

<210> SEQ ID NO 16
<211> LENGTH: 271
<212> TYPE: PRT
<213> ORGANISM: Bacillus clausii

<400> SEQUENCE: 16

Ala Gln Ser Val Pro Trp Gly Ile Glu Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Arg Ile Arg Gly Gly Ala Ser
            35                  40                  45

Phe Val Pro Gly Glu Pro Ser Thr Gln Asp Gly Asn Gly His Gly Thr
            50                  55                  60

His Val Ala Gly Thr Ile Ala Ala Leu Asp Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

```
Pro Ser Ala Thr Leu Glu Gln Ala Val Asn Ser Ala Thr Ser Arg Gly
        130                 135                 140

Val Leu Val Val Ala Ala Ser Gly Asn Ser Gly Glu Pro Glu Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Val Ala Pro Gly Val Asp Ile Leu Ser Thr Trp Pro Gly Gly Thr Tyr
        195                 200                 205

Ala Val Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Glu
                245                 250                 255

Tyr Gly Ser Gly Leu Val Asn Ala Glu Ala Ala Thr Arg His His
            260                 265                 270

<210> SEQ ID NO 17
<211> LENGTH: 324
<212> TYPE: PRT
<213> ORGANISM: Bacillus subtilis

<400> SEQUENCE: 17

Gln Asp Gln Glu Lys Gly Ile Thr Ile Asp Ile Ser Arg Lys His Tyr
1               5                   10                  15

Thr Val Glu Thr Leu Lys Ser Leu Val Asp Glu Ile Ser Tyr Asn Gly
            20                  25                  30

Gly Asn Tyr Val Gln Leu His Phe Ser Asp Asn Glu Asn Tyr Ala Ile
        35                  40                  45

Trp Ser Glu Tyr Leu Gly Gln Ser Ser Glu Gly Thr Asn Asn Thr Tyr
    50                  55                  60

Leu Thr Lys Asn Glu Leu Leu Ser Leu Ile Ala Tyr Ser Asn Asp Lys
65                  70                  75                  80

Asp Ile Leu Val Ile Pro Asp Ile Asp Leu Pro Ala His Ser Lys Gly
                85                  90                  95

Trp Leu Glu Leu Ile Lys Lys Lys Asp Val Lys Leu Tyr Asn Asp Ile
            100                 105                 110

Val Thr Asp Tyr Ser Glu Glu Thr Leu Asp Tyr Tyr Asp Asn Arg Val
        115                 120                 125

Ala Leu Asp Thr Val Asn Gln Leu Leu Asp Glu Val Leu Asp Leu Phe
130                 135                 140

Tyr Gln Pro Lys Phe Glu Gly Lys Gln Arg Ile Val Leu Gly Gly Asp
145                 150                 155                 160

Glu Val Pro Gly Ser Glu Val His Gln Leu Asp Phe Ile Asp Phe Met
                165                 170                 175

Asn Gln Ile Ala Ser Thr Val Lys Glu Arg Lys Tyr Glu Pro Gln Met
            180                 185                 190

Trp Asn Asp Ser Ile Thr Ser Glu Gly Ile Ala Asn Leu Asp Asp Ser
        195                 200                 205

Phe Ser Ile Leu Tyr Trp Gln Gln Ser Thr Leu Ser Ser Gly Glu Glu
    210                 215                 220

Ser Leu Thr Val Glu Asp Phe Glu Asn Trp Gly Phe Ser Val Tyr Asn
225                 230                 235                 240
```

```
Tyr Asn Ala Tyr Ser Leu Tyr Phe Leu Pro Ser Pro Gly Phe Thr Gln
            245             250             255

Glu Asp Ile Asn Glu Gln Met Asp Tyr Met Asn Trp Ala Tyr Ala His
            260             265             270

Asn Lys Phe Ala Tyr Ile Ser Asp Tyr Tyr His Ala Val Glu Thr Ser
        275             280             285

Asn Val Lys Gly Ser Ser Leu Thr Phe Trp Gly Glu His Ala Thr Asp
        290             295             300

Leu Ser Gln Glu Glu Leu Leu Glu Gln Glu Leu Pro Leu Ile Arg His
305             310             315             320

Tyr Leu Asn Leu
```